United States Patent
Obika et al.

(10) Patent No.: US 10,961,269 B2
(45) Date of Patent: Mar. 30, 2021

(54) BRIDGED NUCLEIC ACID GUNA, METHOD FOR PRODUCING SAME, AND INTERMEDIATE COMPOUND

(71) Applicants: MITSUBISHI TANABE PHARMA CORPORATION, Osaka (JP); OSAKA UNIVERSITY, Suita (JP)

(72) Inventors: Satoshi Obika, Minoo (JP); Eiji Kawanishi, Osaka (JP); Hiroaki Sawamoto, Osaka (JP); Shuhei Yamakoshi, Osaka (JP); Yuuki Arai, Osaka (JP); Shinji Kumagai, Osaka (JP)

(73) Assignees: MITSUBISHI TANABE PHARMA CORPORATION, Osaka (JP); OSAKA UNIVERSITY, Suita (JP)

( * ) Notice: Subject to any disclaimer, the term of this patent is extended or adjusted under 35 U.S.C. 154(b) by 0 days.

(21) Appl. No.: 15/760,513

(22) PCT Filed: Sep. 20, 2016

(86) PCT No.: PCT/JP2016/077748
§ 371 (c)(1),
(2) Date: Mar. 15, 2018

(87) PCT Pub. No.: WO2017/047816
PCT Pub. Date: Mar. 23, 2017

(65) Prior Publication Data
US 2018/0251488 A1    Sep. 6, 2018

(30) Foreign Application Priority Data

Sep. 18, 2015 (JP) .............. JP2015-185730
Mar. 1, 2016 (JP) .............. JP2016-039351

(51) Int. Cl.
| | | |
|---|---|---|
| *C07H 19/06* | (2006.01) | |
| *C07H 9/06* | (2006.01) | |
| *C07H 21/00* | (2006.01) | |
| *C07H 19/16* | (2006.01) | |
| *C07H 1/00* | (2006.01) | |
| *C07C 279/16* | (2006.01) | |
| *C07D 498/04* | (2006.01) | |
| *C07D 498/08* | (2006.01) | |

(52) U.S. Cl.
CPC .............. *C07H 19/06* (2013.01); *C07H 1/00* (2013.01); *C07H 9/06* (2013.01); *C07H 19/16* (2013.01); *C07H 21/00* (2013.01); *C07C 279/16* (2013.01); *C07D 498/04* (2013.01); *C07D 498/08* (2013.01)

(58) Field of Classification Search
CPC .......... C07H 1/00; C07H 19/06; C07H 21/00; C07H 19/16; C07D 498/08; C07D 498/04; C07C 279/16
See application file for complete search history.

(56) References Cited

U.S. PATENT DOCUMENTS

| | | | |
|---|---|---|---|
| 6,268,490 B1 | 7/2001 | Imanishi et al. | |
| 6,670,461 B1 * | 12/2003 | Wengel | C07H 21/00 536/22.1 |

(Continued)

FOREIGN PATENT DOCUMENTS

| | | |
|---|---|---|
| JP | 09-328497 A | 12/1997 |
| JP | 2002-521310 A | 7/2002 |

(Continued)

OTHER PUBLICATIONS

Barman et al., "2'-N-Guanidino, 4'-C-ethylene bridged thymidine (GENA-T) modified oligonucleotide exhibits triplex formation with excellent enzymatic stability", RSC Advances 2015, 5, Jan. 14, 2015, pp. 12257-12260.

(Continued)

*Primary Examiner* — Lawrence E Crane
(74) *Attorney, Agent, or Firm* — Birch, Stewart, Kolasch & Birch, LLP

(57) ABSTRACT

A method for preparing a compound represented by general formula I:

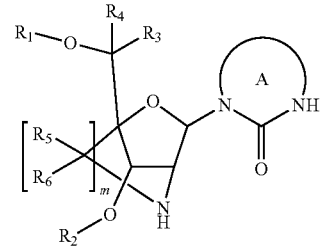

or a salt thereof includes a step of reacting a compound represented by formula II:

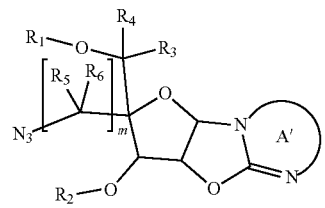

with a reducing agent to cleave an oxazolidine ring fused to a cycle A'. The reducing agent includes at least one of phosphines, metal hydrides, or transition metal catalysts in the presence of hydrogen gas.

25 Claims, No Drawings
Specification includes a Sequence Listing.

(56) References Cited

U.S. PATENT DOCUMENTS

| | | | | |
|---|---|---|---|---|
| 6,794,499 | B2* | 9/2004 | Wengel | C07H 21/00 536/22.1 |
| 7,034,133 | B2* | 4/2006 | Wengel | C07H 21/00 536/22.1 |
| 7,427,672 | B2* | 9/2008 | Imanishi | C07H 19/04 536/22.1 |
| 7,615,619 | B2* | 11/2009 | Imanishi | C07H 19/06 536/23.1 |
| 8,541,562 | B2* | 9/2013 | Obika | C07H 19/06 536/23.1 |
| 10,377,789 | B2* | 8/2019 | Obika | C07H 19/10 |
| 2002/0068708 | A1 | 6/2002 | Wengel et al. | |
| 2006/0166908 | A1 | 7/2006 | Imanishi et al. | |
| 2007/0167387 | A1 | 7/2007 | Imanishi et al. | |
| 2012/0208991 | A1 | 8/2012 | Obika et al. | |
| 2015/0266917 | A1 | 9/2015 | Obika et al. | |

FOREIGN PATENT DOCUMENTS

| | | |
|---|---|---|
| WO | WO 98/39352 A1 | 9/1998 |
| WO | WO 99/14226 A2 | 3/1999 |
| WO | WO 03/068795 A1 | 8/2003 |
| WO | WO 03/095467 A1 | 11/2003 |
| WO | WO 2005/021570 A1 | 3/2005 |
| WO | WO 2007/145593 A1 | 12/2007 |
| WO | WO 2011/052436 A1 | 5/2011 |
| WO | WO 2011/156202 A1 | 12/2011 |
| WO | WO 2013/013068 A1 | 1/2013 |
| WO | WO 2014/046212 A1 | 3/2014 |
| WO | WO 2014/109384 A1 | 7/2014 |
| WO | WO 2014/124952 A1 | 8/2014 |
| WO | WO 2015/054465 A1 | 4/2015 |
| WO | WO 2016/100569 A1 | 6/2016 |
| WO | WO 2016/145142 A1 | 9/2016 |

OTHER PUBLICATIONS

Hanessian et al., "A Constrained Tricyclic Nucleic Acid Analogue of α-L-LNA: Investigating the Effects of Dual Conformational Restriction on Duplex Thermal Stability", The Journal of Organic Chemisty, 2013, vol. 78, pp. 9064-9075.

Hari et al., "Synthesis and properties of 2'-O,4'-C-methyleneoxymethylene bridged nucleic acid", Bioorganic & Medicinal Chemistry 14 (2006), pp. 1029-1038.

International Preliminary Report on Patentability (PCT/IB/373), issued in the corresponding application No. PCT/JP2016/077748, dated Mar. 20, 2018, with an English translation thereof.

International Search Report (PCT/ISA/210) issued in the corresponding Application No. PCT/JP2016/077748, dated Dec. 20, 2016, with an English translation thereof.

Kitano et al., "Synthesis of 4'-C-Fluoromethylnucleosides as Potential Antineoplastic Agents", Tetrahedron, 1997, vol. 53, No. 39, pp. 13315-13322.

Kuwahara et al., "Systematic analysis of enzymatic DNA polymerization using oligo-DNA templates and triphosphate analogs involving 2',4'-bridged nucleosides", Nuceleic Acids Research, 2008, vol. 36, No. 13, Jun. 26, 2008, pp. 4257-4265.

Madsen et al., "Large Scale Synthesis of 2'-Amino-LNA Thymine and 5-Methylcytosine Nucleosides", The Journal of Organic Chemisty, 2012, vol. 77, Nov. 12, 2012, pp. 10718-10728.

Miyashita et al., "N-Methyl substituted 2', 4'—BNANC: a highly nuclease-resistant nucleic acid analogue with high-affinity RNA selective hybridization", Chem. Commun. 2007, pp. 3765-3767.

Obika et al., "2'-O,4'-C-Methylene Bridged Nucleic Acid (2',4'-BNA): Synthesis and Triplex-Forming Properties", Bioorganic & Medicinal Chemistry 9 (2001), Nov. 21, 2000, pp. 1001-1011.

Rahman et al., "Design, Synthesis, and Properties of 2',4'-BNANC: A Bridged Nucleic Acid Analogue", JACS, Mar. 15, 2008, vol. 130, No. 14, 2008, pp. 4886-4896.

Rosenbohm et al., "Synthesis of 2'-amino-LNA: a new strategy", Org. Biomol. Chem., 2003,1, Jan. 21, 2003, pp. 655-663.

Salinas et al., "Alternative Synthesis of (S)-cEt-BNA: A Key Constrained Nucleoside Component of Bioactive Antisense Gapmer Sequences", The Journal of Organic Chemistry 2014, vol. 79, pp. 11651-11660.

Shrestha et al., "Guanidine bridged nucleic acid (GuNA): an effect of a cationic bridged nucleic acid on DNA binding affinity", Chem. Commun., 2014, 50, pp. 575-577.

Singh et al., "Synthesis of Novel Bicyclo[2.2.1] Ribonucleosides: 2'-Amino- and 3'-Thio-LNA Monomeric Nucleosides", J. Org. Chem. 1998, 63, Apr. 13, 1998, pp. 6078-6079.

Varghese et al., "Conformationally Constrained 2'-N,4'-C-Ethylene-Bridged Thymidine (Aza-ENA-T): Synthesis, Structure, Physical, and Biochemical Studies of Aza-ENA-T-Modified Oligonucleotides", J. Am, Chem. Soc. 2006, 128, Nov. 8, 2006, pp. 15173-15187.

Wahlestedt et al., "Potent and nontoxic antisense oligonucleotides containing Icoked nucleic acis", PNAS, May 9, 2000, vol. 97, No. 10, pp. 5633-5638.

Blade et al., "Molecular Synthesis of Constrained Ethyl (cEt) Purine and Pyrimidine Nucleosides," J. Org. Chem (2015), vol. 80, pp. 5337-5343.

Office Action dated Apr. 10, 2019, in Singapore Patent Application No. 11201802190U.

European Search Report dated May 15, 2019, in European Patent Application No. 16846687.8.

* cited by examiner

BRIDGED NUCLEIC ACID GuNA, METHOD FOR PRODUCING SAME, AND INTERMEDIATE COMPOUND

CROSS-REFERENCE TO RELATED APPLICATIONS

The present application is a national phase under 35 U.S.C. § 371 of PCT International Application No. PCT/JP2016/077748 which has an International filing date of Sep. 20, 2016, which claims priority under 35 U.S.C. § 119 to Application No. 2015-185730 filed in Japan on Sep. 18, 2015, and Application No. 2016-039351 filed in Japan on Mar. 1, 2016, the entire contents of which are hereby incorporated by reference.

TECHNICAL FIELD

The present invention relates to monomer or oligomer of bridged nucleic acid GuNA, a method for preparing the same, as well as an intermediate compound for preparing the same.

BACKGROUND ART

Examples of methods for treating diseases using nucleic acid drugs include antisense therapies, antigen therapies, aptamer-based therapies, siRNA-based therapies, and the like. Among these therapies, the antisense therapies are approaches for treating or preventing diseases, involving inhibiting a translation process of pathogenic RNAs by externally introducing oligonucleotides (antisense strands) that are complementary to disease-associated mRNAs to form double strands. The siRNA-based therapies are similar to the antisense therapies, involving inhibiting translation from mRNAs to proteins by administering double-stranded RNAs into a living body. Meanwhile, the antigen therapies suppress transcription from DNAs to RNAs by externally introducing triplex-forming oligonucleotides corresponding to DNA sites that are to be transcribed into pathogenic RNAs. Also, aptamers exert their function by binding specifically to biological components such as disease-associated proteins and thereby adjusting the protein activity.

Although various artificial nucleic acids have been developed as materials for such the nucleic acid drugs, no ideal molecule has been found yet. Examples of the materials developed for nucleic acid drugs to date include phosphorothioate (S—$PO_3$) oligonucleotide (S-oligo), 2',4'-bridged nucleic acid (BNA)/2',4'-locked nucleic acid (LNA) (see Patent Documents 1 to 4 and Non-Patent Documents 1 to 6), and the like. S-oligo is commercially available in the United States as an antisense drug for cytomegalovirus. S-oligo has a high nuclease resistance, but is problematic and needs improvement in that its binding affinity to the target nucleic acid strands is low. 2',4'-BNA/LNA developed to date has a high binding affinity to the target nucleic acid strands, and provides the most promising molecules as the materials for the future nucleic acid drugs. However, there is still room for improvement in that the nuclease resistance is not sufficient and the stability in a living body is poor.

As one of artificial nucleic acid, 2'-amino LNA has been reported (see Non-Patent Document 7. It has a nuclease resistance, and has a high binding affinity to a target nucleic acid strand, and thus is the most expected molecule to be a material for nucleic acid drugs like the above-mentioned LNA. However, for the nucleotide with appropriate substituents that can be a starting material for synthesizing oligonucleotide, only nucleotides containing thyminyl or 5-methyl-cytosinyl have been known (see Non-patent document 8).

Also, as another artificial nucleic acid, Aza-ENA has been reported (see Non-Patent Document 9). The Aza-ENA has a structure in which the number of the carbon atom that is composed of the bridging is one more than the 2'-amino LNA, and only the nucleic acid in which the base moiety thereof is thyminyl has been known.

As further artificial nucleic acid, a guanidine bridged artificial nucleic acid (GuNA) is included. Hitherto, for the guanidine bridged artificial nucleic acid (GuNA), GuNA that contains thyminyl as a base moiety of nucleic acid has been known (see Non-Patent Document 5). However, GuNA that contains the base moiety of nucleic acid other than thyminyl has never been known. Also, since the preparation of GuNA requires multi steps, it has not been easy to prepare GuNA effectively. Also, as artificial nucleic acid being analogous to GuNA, GENA has been reported (see Non-Patent Document 10). The GENA has a structure in which the number of the carbon atom that is composed of the bridging is one more than GuNA, and only the nucleic acid in which the base moiety thereof is thyminyl has been known.

Though the preparation method of GuNA that has been known so far is described in Non-Patent document 11, the method needs multi steps, and the production yields was not sufficient.

The preparation route is shown below.

[chem.1]

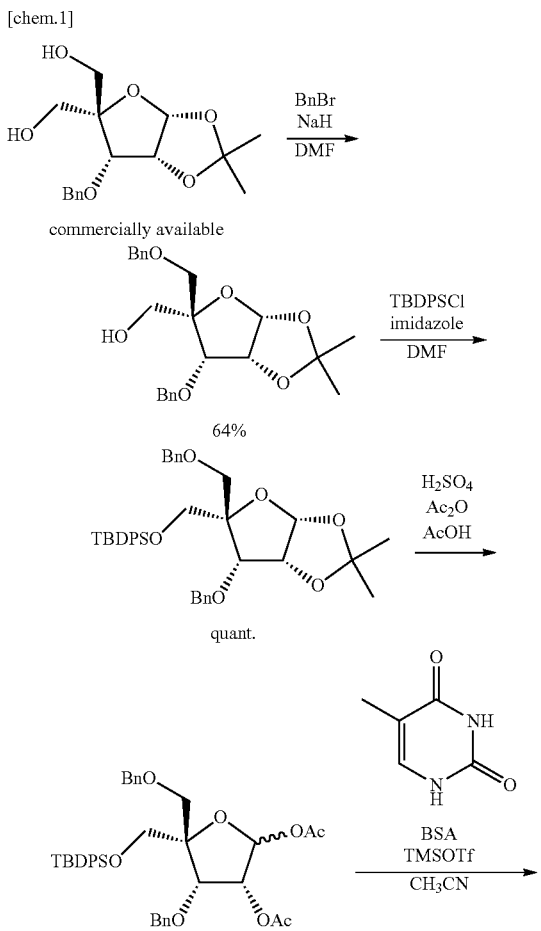

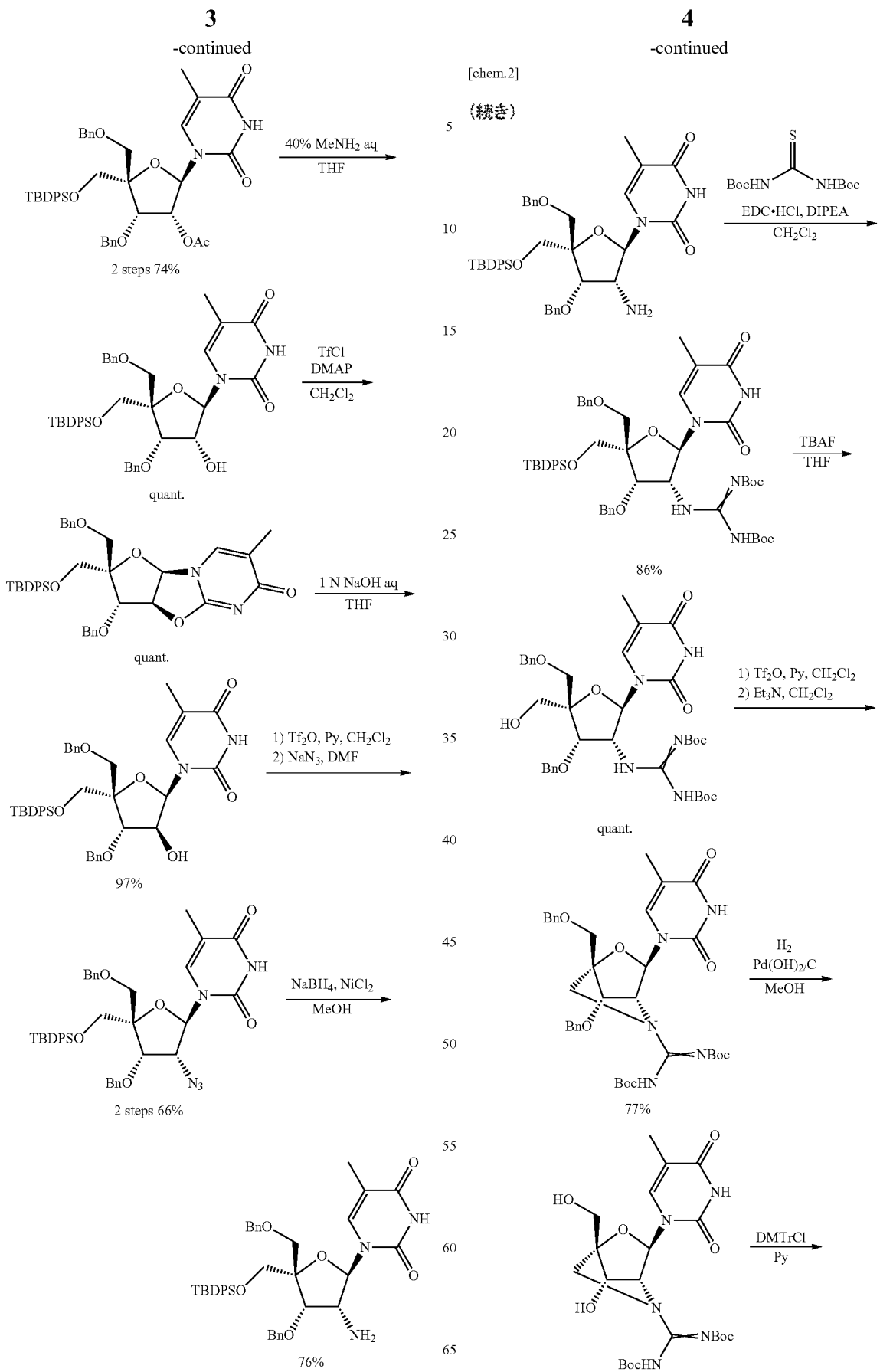

-continued

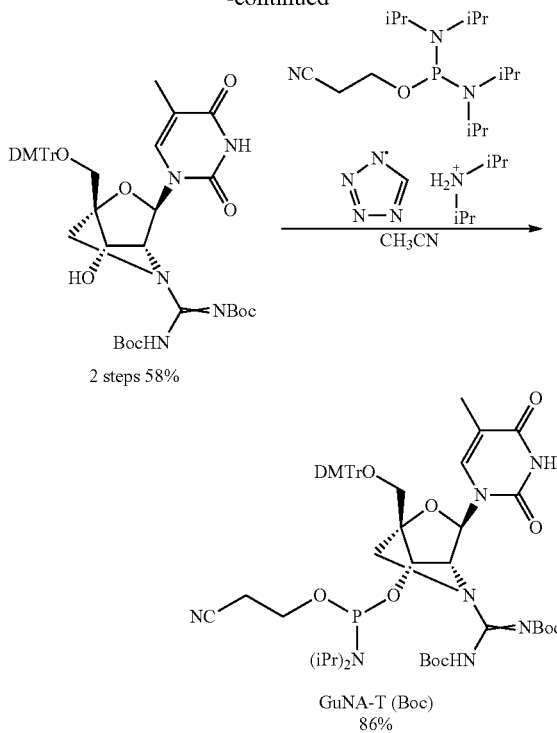

2 steps 58%

GuNA-T (Boc)
86%

CITATION LIST

Patent Document

Patent Document 1: WO 98/39352 pamphlet
Patent Document 2: WO 2005/021570 pamphlet
Patent Document 3: WO 2003/068795 pamphlet
Patent Document 4: WO 2011/052436 pamphlet
Patent Document 5: WO 2014/046212 pamphlet Non-Patent Document Non-Patent Document 1: C. Wahlestedt et al., Proc. Natl. Acad. Sci. USA, 2000, 97, 10, 5633-5638

Non-Patent Document 2: Y. Hari et al., Bioorg. Med. Chem., 2006, 14, 1029-1038

Non-Patent Document 3: K. Miyashita et al., Chem. Commun., 2007, 3765-3767

Non-Patent Document 4: S. M. A. Rahman et al., J. Am. Chem. Soc., 2008, 130, 14, 4886-4896

Non-Patent Document 5: M. Kuwahara et al., Nucleic Acids Res., 2008, 36, 13, 4257-4265

Non-Patent Document 6: S. Obika et al., Bioorg. Med. Chem., 2001, 9, 1001-1011

Non-Patent Document 7: S. K. Singh et al., J. Org. Chem. 1998, 63, 6078-6079

Non-Patent Document 8: Christoph Rosenbohm et al., Org. Biomol. Chem., 2003, 1, 655-663

Non-Patent Document 9: Oommen P. Varghese et al., J. AM. CHEM. SOC. 2006, 128, 15173-15187

Non-Patent Document 10: Jharna Barman et al., RSC Advances 2015, 16, 12257-12260

Non-Patent Document 11: Ajaya R. Shrestha et al., Chem. Commun. 2014, 50, 575-577

SUMMARY OF INVENTION

Problems to be Solved by Invention

The present invention relates to a method for preparing a guanidine bridged artificial nucleic acid (hereinafter, abbreviated as "GuNA"), and intermediate compound for preparing the same, and monomer or oligomer of GuNA.

Means to Solve Problems

In order to solve the above-mentioned problems to be solved, the inventors have intensively studied to find out a novel method for preparing GuNA, which has lower steps as the number of steps compared to the conventional method and has the improved yield of GuNA, and novel intermediate compound for preparing GuNA, thereby completed the present invention as follows.

That is, the present invention includes the following Items [1] to [89], and should not be limited thereto.

Item [1]

A method for preparing a compound represented by general formula I:

[chem. 3]

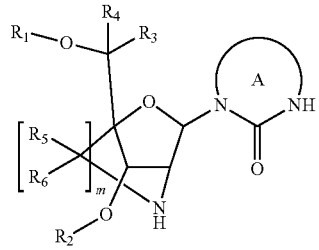

[wherein
$R_1$ and $R_2$ represent independently of each other a protecting group for hydroxy group, $R_3$ and $R_4$ represent independently of each other a hydrogen atom or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and a cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]
or salts thereof,
said method comprising a step of reacting a compound represented by formula II:

[chem. 4]

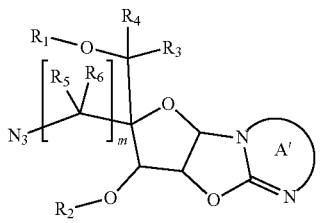

[wherein, each of $R_1$, $R_2$, $R_3$, $R_4$, $R_5$, $R_6$ and m is the same as defined in the above-mentioned general formula I, a cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]

with a reducing agent to cleave an oxazolidine ring fused to a cycle A'.

Item [2]

The method according to Item [1] wherein each of $R_1$ and $R_2$ represents a Bn group, each of $R_3$, $R_4$, $R_5$, and $R_6$ represents a hydrogen atom, cycle A represents a thyminyl group or an uracinyl group, and cycle A' represents the following structural formula II-1 or II-2:

[chem. 5]

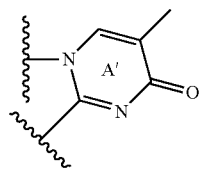
(II-1)

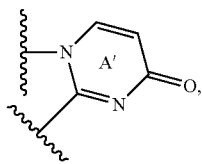
(II-2)

and the reducing agent is $Ph_3P$.

Item [3]

A method for preparing a compound represented by general formula VII:

[chem. 6]

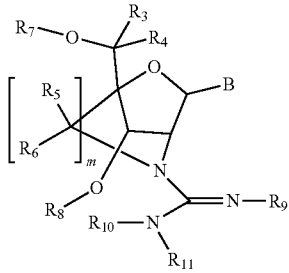

[wherein,
B represents a base moiety of nucleic acid wherein said base moiety may be optionally substituted with one or more substituents, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-8}$ alkyl group which may be optionally substituted with one or more substituents, each $R_6$ represents independently a hydrogen atom, or a $C_{1-6}$ alkyl group which may be optionally substituted with one or more substituents, $R_7$ represents a hydrogen atom or a protecting group for hydroxy group, $R_8$ represents a hydrogen atom, a phosphate group which may be optionally substituted with one or more substituents, a thiophosphate group which may be optionally substituted with one or more substituents, $R_9$, $R_{10}$, and $R_{11}$ represent independently of each other a hydrogen atom, a $C_{1-6}$ alkyl group which may be optionally substituted with one or more substituents, or a protecting group for amino group, and m is an integer of 1 to 3.]

, said method comprising the step according to Item [1] or [2].

Item [4]

A compound represented by formula I:

[chem. 7]

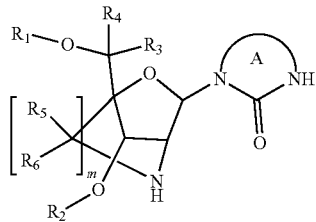

[wherein,
$R_1$ and $R_2$ represent independently of each other a benzyl (Bn) group, a 2-naphthylmethyl group, a p-methoxybenzyl group, a 3,4-dimethoxybenzyl group, a 2,6-dimethoxybenzyl group, or a p-phenylbenzyl group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and a cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]

or salts thereof.

Item [5]

The compound according to Item [4] or salts thereof wherein each of $R_1$ and $R_2$ represents a Bn group, each of $R_3$, $R_4$, $R_5$, and $R_6$ represents a hydrogen atom, and the cycle A represents a thyminyl group or an uracinyl group.

Item [6]

A compound represented by general formula II:

[chem. 8]

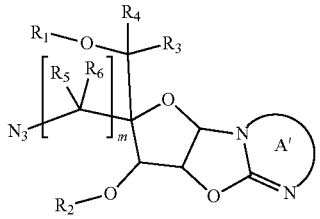

[wherein, $R_1$ and $R_2$ represent independently of each other a protecting group for hydroxy group, $R_3$ and $R_4$ represent independently of each other a hydrogen atom or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and a cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]

or salts thereof.

Item [7]

The compound according to Item [6] or salts thereof wherein $R_1$ and $R_2$ represent a Bn group, each of $R_3$, $R_4$, $R_5$, and $R_6$ represents a hydrogen atom, and cycle A' represents the following structural formula II-1 or II-2:

[chem. 9]

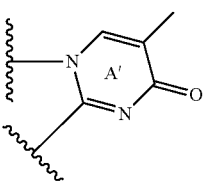

(II-1)

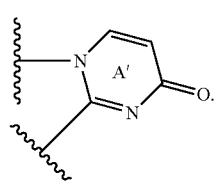

(II-2)

Item [8]

A method for preparing a compound represented by general formula II:

[chem. 10]

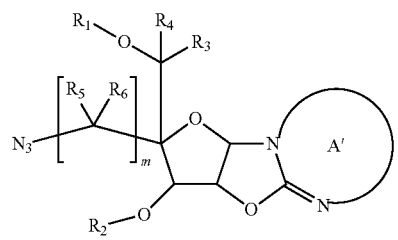

[wherein, $R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]

, said method comprising a step of reacting a compound represented by general formula III:

[chem. 11]

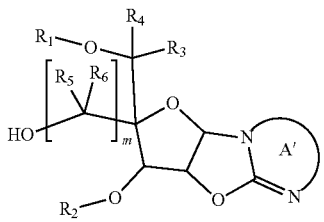

[wherein, each of $R_1$, $R_2$, $R_3$, $R_4$, $R_5$, $R_6$, m and cycle A' is the same as defined in the above-mentioned general formula II.]
with an azide agent.
Item [9]

The method according to Item [8] wherein each of $R_1$ and $R_2$ represents a Bn group, each of $R_3$, $R_4$, $R_5$, and $R_6$ is a hydrogen atom, cycle A' represents the following structural formula II-1 or II-2:

[chem. 12]

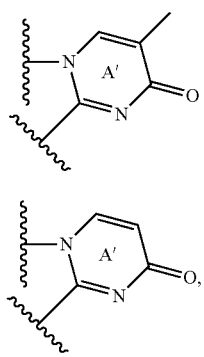

(II-1)

(II-2)

and the azide agent is DPPA.
Item [10]

A method for preparing a compound represented by general formula VII:

[chem. 13]

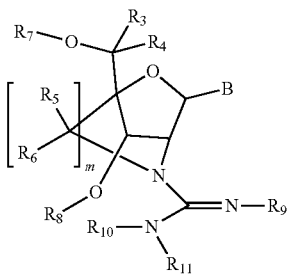

[wherein,
B represents a base moiety of nucleic acid wherein said base moiety may be optionally substituted with one or more substituents, $R_3$ and $R_4$ represents independently of each other a hydrogen atom or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_7$ represents a hydrogen atom or a protecting group for hydroxy group, $R_8$ represents a hydrogen atom, a phosphate group which may be optionally substituted with one or more substituents, or a thiophosphate group which may be optionally substituted with one or more substituents, $R_9$, $R_{10}$, and $R_{11}$ represent independently of each other a hydrogen atom, a $C_{1-6}$ alkyl group which may be optionally substituted with one or more substituents, or a protecting group for amino group, and m is an integer of 1 to 3.]
or salts thereof, the method comprising the steps according to Item [8] or [9].
Item [11]

A compound represented by general formula III:

[chem. 14]

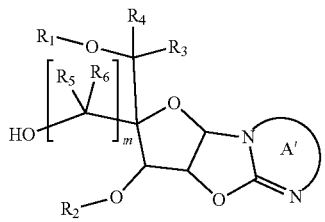

[wherein,
$R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A' represents a five to seven membered unsaturated heterocyclic group which may be optionally substituted with one or more substituent selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]
or salts thereof.
Item [12]

The compound according to Item [11] or salts thereof wherein each of $R_1$ and $R_2$ represents a Bn group, each of $R_3$, $R_4$, $R_5$, and $R_6$ represents a hydrogen atom, and cycle A' represents the following structural formula II-1 or II-2:

[chem. 15]

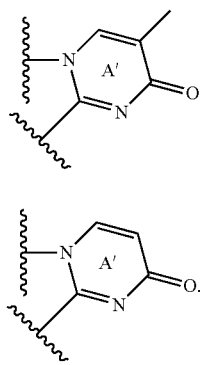

(II-1)

(II-2)

Item [13]

A method for preparing a compound represented by general formula IV:

[chem. 16]

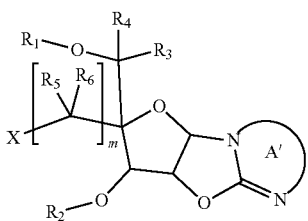

[wherein, $R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]

, the method comprising a step of reacting a compound represented by general formula V:

[chem. 17]

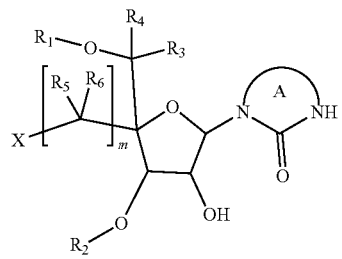

[wherein, each of $R_1$, $R_2$, $R_3$, $R_4$, $R_5$, $R_5$, X and m is the same as defined in the above-mentioned general formula IV, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]

with an activating agent for hydroxy group to activate an unprotected hydroxy group which is substituted on a tetrahydrofuran ring in the general formula V.

Item [14]

The method according to Item [13] wherein each of $R_1$ and $R_2$ represents a Bn group, each of $R_3$, $R_4$, $R_5$ and $R_6$ represents a hydrogen atom, X represents a mesyloxy group (Ms-O—), cycle A represents a thyminyl group or an uracinyl group, cycle A' represents the following structural formula II-1 or II-2:

[chem. 18]

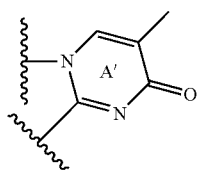

(II-1)

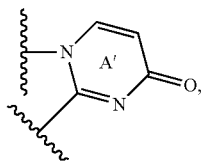

(II-2)

and the activating agent for hydroxy group represents a trifluoromethanesulfonyl chloride.

Item [15]

A method for preparing a compound represented by general formula VII:

[chem. 19]

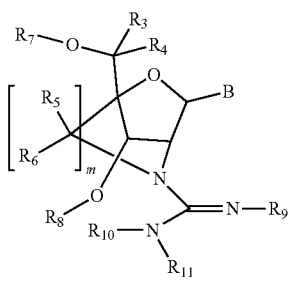

[wherein,

B represents a base moiety of nucleic acid wherein said base moiety may be optionally substituted with one or more substituents, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_7$ represents a hydrogen atom, or a protecting group for hydroxy group, $R_8$ represents a hydrogen atom, a phosphate group which may be optionally substituted with one or more substituents, or a thiophosphate group which may be optionally substituted with one or more substituents, and $R_9$, $R_{10}$ and $R_{11}$ represent independently of each other a hydrogen atom, a C1-6 alkyl group which may be optionally substituted with one or more substituents, or a protecting group for amino group, and m is an integer of 1 to 3.]
, the method comprising the step according to Item [13] or [14].

Item [16]

A compound represented by general formula IV:

[chem. 20]

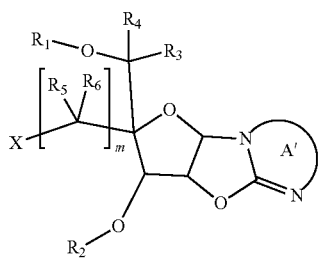

[wherein, $R_1$ and $R_2$ represents independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]
or salts thereof.

Item [17]

The compound according to Item [16] or salts thereof wherein each of $R_1$ and $R_2$ represents a En group, and each of $R_3$, $R_4$, $R_5$, and $R_6$ represents a hydrogen atom, X represents a mesyloxy group (Ms-O—), and cycle A' represents the following structural formula II-1 or II-2:

[chem. 21]

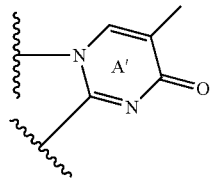

(II-1)

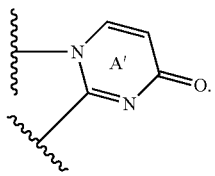

(II-2)

Item [18]

A compound represented by general formula V:

[chem. 22]

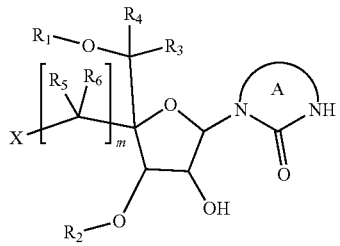

[wherein, $R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]
or salts thereof.

Item [19]

The compound according to Item [18] or salts thereof wherein each of $R_1$ and $R_2$ represents a Bn group, each of $R_3$, $R_4$, $R_5$ and $R_6$ represents a hydrogen atom, X represents a mesyloxy group (Ms-O—), and cycle A represents a thyminyl group or an uracinyl group.

Item [20]

A method for preparing a compound represented by general formula II:

[chem. 23]

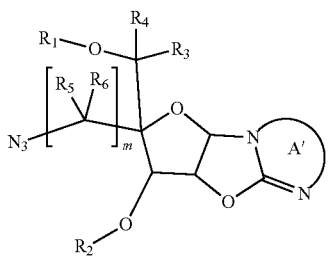

[wherein, $R_1$ and $R_2$ represents independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]

, the method comprising a step of reacting a compound represented by formula IV:

[chem. 24]

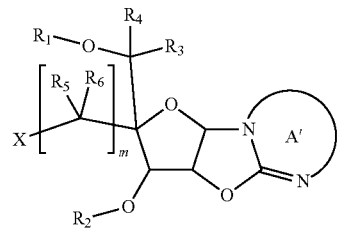

[wherein,

X represents a leaving group, and each of $R_1$, $R_2$, $R_3$, $R_4$, $R_5$, $R_6$, m and cycle A' is the same as defined in the above-mentioned general formula II.]
with an azide agent.

Item [21]

The method according to the Item [20] wherein each of $R_1$ and $R_2$ represent a Bn group, each of $R_3$, $R_4$, $R_5$, and $R_6$ represents a hydrogen atom, and X represents a mesyloxy group (Ms-O—), cycle A7 represents the following structural formula II-1 or II-2:

[chem. 25]

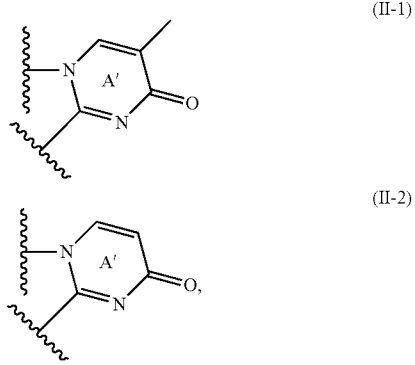

and the azide agent represents $NBu_4NN_3$ or sodium azide.

Item [22]

A method for preparing a compound represented by general formula VII:

[chem. 26]

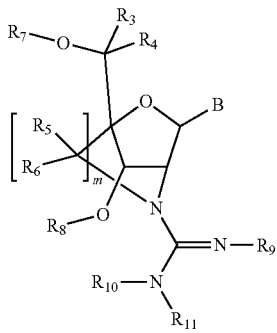

[wherein,

B represents a base moiety of nucleic acid wherein said base moiety may be optionally substituted with one or more substituents, R$_3$ and R$_4$ represents independently of each a hydrogen atom, or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, R$_7$ represents a hydrogen atom, or a protecting group for hydroxy group, R$_8$ represents a hydrogen atom, a phosphate group which may be optionally substituted with one or more substituents, or a thiophosphate group which may be optionally substituted with one or more substituents, R$_9$, R$_{10}$ and R$_{11}$ represent independently of each other a hydrogen atom, a C$_{1-6}$ alkyl group which may be optionally substituted with one or more substituents, or a protecting group for amino group, and m is an integer of 1 to 3.]
, the method comprising the step according to Item [20] or [21].

Item [23]

A method for preparing a compound represented by general formula II:

[chem. 27]

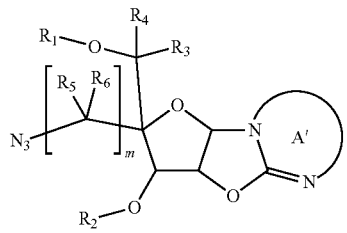

[wherein,

R$_1$ and R$_2$ represent independently of each other a protecting group for hydroxy group, R$_3$ and R$_4$ represent independently of each other a hydrogen atom, or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, m is an integer of 1 to 3, and cycle A' represents a five to seven membered unsaturated heterocyclic group which may be optionally substituted with one or more substituents selected from the group consisting of a C$_{1-6}$ alkyl group which may be optionally substituted with one or more substituents, a C$_{2-6}$ alkenyl group which may be optionally substituted with one or more substituents, a C$_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]

or salts thereof, the method comprising a step of reacting a compound represented by general formula VI:

[chem. 28]

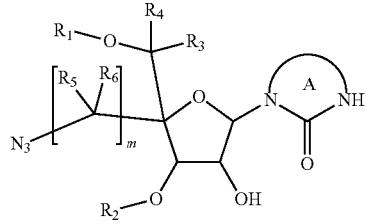

[wherein, each of R$_1$, R$_2$, R$_3$, R$_4$, R$_5$, R$_6$ and m is the same as defined in the above-mentioned general formula II, and cycle A represents a five to seven membered unsaturated heterocyclic group which may be optionally substituted with one or more substituents selected from the group consisting of a C$_{1-6}$ alkyl group which may be optionally substituted with one or more substituents, a C$_{2-6}$ alkenyl group which may be optionally substituted with one or more substituents, a C$_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]

with an activating agent for hydroxy group to activate an unprotected hydroxy group which is substituted on a tetrahydrofuran ring in the general formula VI.

Item [24]

The method according to Item [23] wherein each of R$_1$ and R$_2$ represents a Bn group, each of R$_3$, R$_4$, R$_5$ and R$_6$ represents a hydrogen atom, cycle A represents a thyminyl group or an uracinyl group, cycle A' represents the following structural formula II-1 or the II-2:

[chem. 29]

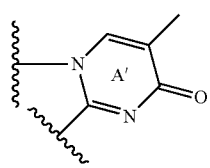
(II-1)

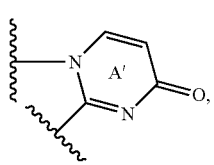
(II-2)

and the activating agent for hydroxy group represents a trifluoromethanesulfonyl chloride.

Item [25]

A method for preparing a compound represented by general formula VII:

[chem. 30]

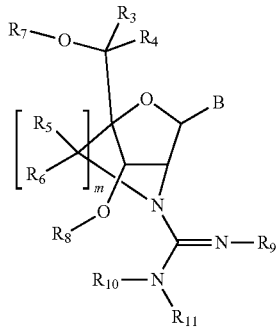

[wherein,

B represents a base moiety of nucleic acid wherein said base moiety may be optionally substituted with one or more substituents, $R_3$ and $R_4$ represents independently of each other a hydrogen atom or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_7$ represents a hydrogen atom or a protecting group for hydroxy group, $R_8$ represents a hydrogen atom, a phosphate group which may be optionally substituted with one or more substituents, or a thiophosphate group which may be optionally substituted with one or more substituents, and $R_9$, $R_{10}$ and $R_{11}$ represent independently of each other a hydrogen atom, a $C_{1-6}$ alkyl group which may be optionally substituted with one or more substituents, or a protecting group for amino group, and m is an integer of 1 to 3.]
, the method comprising the step according to Item [23] or [24].

Item [26]

A compound represented by general formula VII:

[chem. 31]

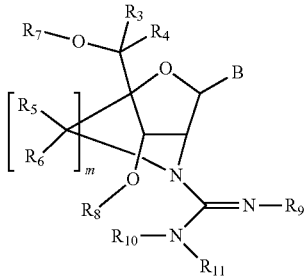

[wherein,

B represents a base moiety of nucleic acid wherein said base moiety may be optionally substituted with one or more substituents, $R_3$ and $R_4$ represents independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_7$ represents a hydrogen atom, or a protecting group for hydroxy group, $R_8$ represents a hydrogen atom, a phosphate group which may be optionally substituted with one or more substituents, or a thiophosphate group which may be optionally substituted with one or more substituents, and $R_9$, $R_{10}$ and represent independently of each other a hydrogen atom, a $C_{1-6}$ alkyl group which may be optionally substituted with one or more substituents, or a protecting group for amino group, and m is an integer of 1 to 3 (with the proviso that the following cases are excluded:

the case where m is 1, B represents a thyminyl group, each of $R_3$, $R_4$, $R_5$ and $R_6$ represents a hydrogen atom, $R_7$ represents a DMTr group, $R_8$ represents a hydrogen atom or a —P(O(CH$_2$)$_2$CN)(N(iPr)$_2$) group, $R_9$ represents a Boc group, $R_{10}$ represents a Boc group, and $R_{11}$ represents a hydrogen atom, and the case where m is 2, B represents a thyminyl group, each of $R_3$, $R_4$, $R_5$ and $R_6$ represents a hydrogen atom, $R_7$ represents a DMTr group, $R_8$ represents a hydrogen atom or a —P(O(CH$_2$)$_2$CN)(N(iPr)$_2$) group, $R_9$ represents a Ceoc group, $R_{10}$ represents a Ceoc group, and $R_{11}$ represents a hydrogen atom.)]
or salts thereof.

Item [27]

The compound according to Item [26] or salts thereof wherein B represents an adeninyl group which may optionally have one or more protecting groups, a guaninyl group which may optionally have one or more protecting groups, a cytosinyl group which may optionally have one or more protecting groups, a 5-methylcytosinyl group which may optionally have one or more protecting groups, or an uracinyl group which may optionally have one or more protecting groups, each of $R_3$, $R_4$, $R_5$ and $R_6$ represents a hydrogen atom, $R_7$ represents a DMTr group, $R_8$ represents a hydrogen atom or a —P(O(CH$_2$)$_2$CN)(N(iPr)$_2$) group, $R_9$ represents a Teoc group or a Boc group, $R_{10}$ represents a Teoc group or a Boc group, and $R_{11}$ represents a hydrogen atom.

Item [28]

The compound according to Item [26] or salts thereof wherein B represents a thyminyl group which may optionally have one or more protecting groups, each of $R_3$, $R_4$, $R_5$ and $R_6$ represents a hydrogen atom, $R_7$ represents a DMTr group, $R_8$ represents a hydrogen atom or a —P(O(CH$_2$)$_2$CN)(N(iPr)$_2$) group, $R_9$ represents a Teoc group, $R_{10}$ represents a Teoc group, and $R_{11}$ represents a hydrogen atom.

Item [29]

A method for preparing a compound represented by general formula VIII:

[chem. 32]

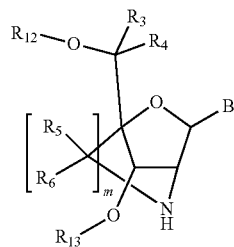

[wherein,

B represents a base moiety of nucleic acid wherein said base moiety may be optionally substituted with one or more substituents, $R_3$ and $R_4$ represents independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, and $R_{12}$ and $R_{13}$ represents independently of each other a hydrogen atom or a protecting group for hydroxy group, and m is an integer of 1 to 3.]
, the method comprising a step of substituting a cycle A in a compound represented by a general formula IX:

[chem. 33]

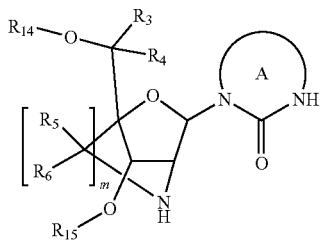

[wherein,
each of $R_3$, $R_4$, $R_5$, $R_6$, and m is the same as defined in the above-mentioned general formula VIII, each of $R_{14}$ and $R_{15}$ represents independently of each other a hydrogen atom, or a protecting group for hydroxy group, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]
with a B.
Item [30]
The method according to Item [29] wherein B represents an adeninyl group which may optionally have one or more protecting groups, a guaninyl group which may optionally have one or more protecting groups, a cytosinyl group which may optionally have one or more protecting groups, a 5-methylcytosinyl group which may optionally have one or more protecting groups, a thyminyl group which may optionally have one or more protecting groups, or an uracinyl group which may optionally have one or more protecting groups, each of $R_{12}$, $R_{13}$, $R_{14}$, and $R_{15}$ represents a Bn group, and cycle A represents a thyminyl group or an uracinyl group.
Item [31]
The method according to Item [29] wherein B represents an adeninyl group which may optionally have one or more protecting groups, a guaninyl group which may optionally have one or more protecting groups, a cytosinyl group which may optionally have one or more protecting groups, a 5-methylcytosinyl group which may optionally have one or more protecting groups, a thyminyl group which may optionally have one or more protecting groups, or an uracinyl which may optionally have one or more protecting groups, $R_{12}$ represents a DMTr group, $R_{13}$ represents a TMS group, $R_{14}$ represents a DMTr group, $R_{15}$ represents a hydrogen atom, and cycle A represents a thyminyl group or an uracinyl group.
Item [32]
The method according to Item [29] wherein B represents an adeninyl group which may optionally have one or more protecting groups, a guaninyl group which may optionally have one or more protecting groups, a cytosinyl group which may optionally have one or more protecting groups, a 5-methylcytosinyl group which may optionally have one or more protecting groups, a thyminyl group which may optionally have one or more protecting groups, or an uracinyl group which may optionally have one or more protecting groups, $R_{12}$ represents a TMS group, $R_{13}$ represents a TMS group, $R_{14}$ represents a hydrogen atom, $R_{15}$ represents a hydrogen atom, and the cycle A represents a thyminyl group or an uracinyl group.
Item [33]
A method for preparing a compound represented by general formula VII:

[chem. 34]

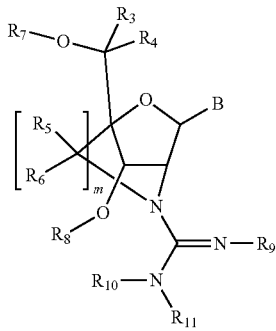

[wherein,
B represents a base moiety of nucleic acid wherein said base moiety may be optionally substituted with one or more substituents, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_7$ represents a hydrogen atom or a protecting group for hydroxy group, $R_8$ represents a hydrogen atom, a phosphate group which may be optionally substituted with one or more substituents, or a thiophosphate group which may be optionally substituted with one or more substituents, and $R_9$, $R_{10}$ and $R_{11}$ represent independently of each other a hydrogen atom, a $C_{1-6}$ alkyl group which may be optionally substituted with one or more substituents, or a protecting group for amino group, and m is an integer of 1 to 3.]
, the method comprising the step according to any one of Item [29] to [32].

Item [34]

A compound represented by general formula VIII:

[chem. 35]

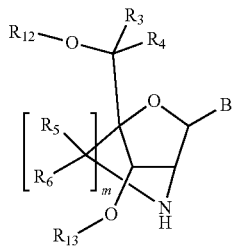

[wherein,

B represents a base moiety of nucleic acid wherein said base moiety may be optionally substituted with one or more substituents, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_{12}$ represents a Bn group, a DMTr group, or a TMS group, and $R_{13}$ represents a Bn group, a hydrogen atom, or a TMS group, and m is an integer of 1 to 3.]

or salts thereof.

Item [35]

The compound according to Item [34] or salts thereof wherein B represents an adeninyl group which may optionally have one or more protecting groups, a guaninyl group which may optionally have one or more protecting groups, a cytosinyl group which may optionally have one or more protecting groups, a 5-methylcytosinyl group which may optionally have one or more protecting groups, a thyminyl group which may optionally have one or more protecting groups, or an uracinyl group which may optionally have one or more protecting groups, each of $R_3$, $R_4$, $R_5$, and $R_6$ represents a hydrogen atom, and each of $R_{12}$ and $R_{13}$ represents a Bn group.

Item [36]

The compound according to Item [34] or salts thereof wherein B represents an adeninyl group which may optionally have one or more protecting groups, a guaninyl group which may optionally have one or more protecting groups, a cytosinyl group which may optionally have one or more protecting groups, a 5-methylcytosinyl group which may optionally have one or more protecting groups, a thyminyl group which may optionally have one or more protecting groups, or an uracinyl group which may optionally have one or more protecting groups, and each of $R_3$, $R_4$, $R_5$ and $R_6$ represents a hydrogen atom, $R_{12}$ represents a DMTr group, and $R_{13}$ represents a hydrogen atom.

Item [37]

A method for preparing an oligonucleotide containing one or more nucleosides represented by general formula X:

[chem. 36]

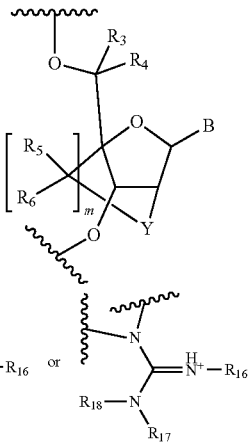

[wherein, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, B represents a base moiety of nucleic acid wherein said base moiety may be optionally substituted with one or more substituents, $R_{16}$, $R_{17}$ and $R_{18}$ represent independently of each other a hydrogen atom, a $C_{1-6}$ alkyl group which may be optionally substituted with one or more substituents, or a protecting group for amino group, and m is an integer of 1 to 3.]

or salts thereof, (with the proviso that when m=1 or 2, the oligonucleotide containing as a bridged nucleic acid only the nucleoside wherein B represents a thyminyl group, each of $R_3$, $R_4$, $R_5$, $R_6$, $R_{16}$, $R_{17}$ and $R_{18}$ represents a hydrogen atom, is excluded), said method comprising a preparation of the same by a phosphoramidite method from a compound represented by general formula XI:

[chem. 37]

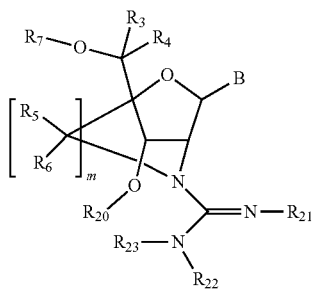

[wherein, each of B, $R_3$, $R_4$, $R_5$, $R_6$ and m is the same as defined in the above-mentioned general formula X, $R_7$ represents a hydrogen atom, or a protecting group for hydroxy group, $R_{20}$ represents a phosphate group which may be optionally substituted with one or more substituents or a thiophosphate group which may be optionally substituted with one or more substituents, and $R_{21}$, $R_{22}$ and $R_{23}$ represents independently of each other a hydrogen atom, a $C_{1-6}$ alkyl group which may be optionally substituted with one or more substituents, or a protecting group for amino group, and m is an integer of 1 to 3.]

Item [38]

The method according to Item [37] wherein B represents an adeninyl group which may optionally have one or more protecting groups, a guaninyl group which may optionally have one or more protecting groups, a cytosinyl group which may optionally have one or more protecting groups, a 5-methylcytosinyl group which may optionally have one or more protecting groups, or an uracinyl group which may optionally have one or more protecting groups, $R_7$ represents a protecting group for hydroxy group, each of $R_{16}$, $R_{17}$ and $R_{18}$ represents a hydrogen atom, $R_{20}$ represents a —P(O(CH$_2$)$_2$CN)(N(iPr)$_2$) group, and each of $R_{21}$, $R_{22}$ and $R_{23}$ represent a protecting group for amino group.

Item [39]

An oligonucleotide containing one or more nucleosides represented by general formula X:

[chem. 38]

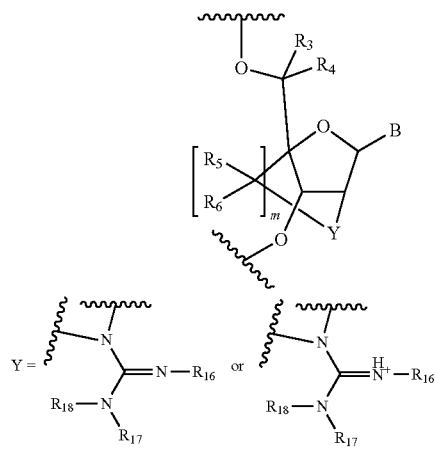

[wherein, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, B represents a base moiety of nucleic acid wherein said base moiety may be optionally substituted with one or more substituents, $R_{16}$, $R_{17}$ and $R_{18}$ represent independently of each other a hydrogen atom, a $C_{1-6}$ alkyl group which may be optionally substituted with one or more substituents, or a protecting group for amino group, and m is an integer of 1 to 3.]

(with the proviso that when m=1 or 2, the oligonucleotide containing as a bridged nucleic acid only the nucleoside wherein B represents a thyminyl group, each of $R_3$, $R_4$, $R_5$, $R_6$, $R_{16}$, $R_{17}$ and $R_{18}$ represents a hydrogen atom is excluded).

Item [40]

The oligonucleotide according to Item [39] or salts thereof wherein B represents an adeninyl group, a guaninyl group, a cytosinyl group, a 5-methylcytosinyl group, a thyminyl group, or an uracinyl group, and each of $R_{16}$, $R_{17}$ and $R_{18}$ represents a hydrogen atom].

Item [41]

A compound represented by general formula XII:

[chem. 39]

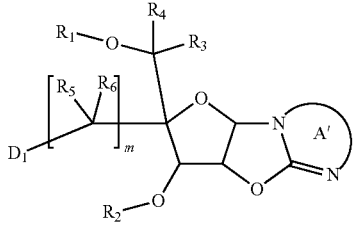

[wherein, $R_1$ and $R_2$ represents independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $D_1$ represents $N_3$, a hydroxy group, or —X (wherein —X represents a leaving group, preferably a leaving group for hydroxy group, and exemplifies a methanesulfonyloxy (mesyloxy; Ms-O—) group, a trifluoromethanesulfonyloxy group, a p-toluenesulfonyloxy group and the like, which should not be limited thereto), m is an integer of 1 to 3, and cycle A' represents a five to seven membered unsaturated heterocyclic group which may be optionally substituted with one or more substituents, and the unsaturated heterocycle may be fused with another cycle to form the cycle A' (wherein, the substituents for "five to seven membered unsaturated heterocycle" represent preferably a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, or a halogen atom.)], or salts thereof.

Item [42]

The compound according to Item [41] or salts thereof wherein $R_3$, $R_4$, $R_5$ and $R_6$ represent independently of each other a hydrogen atom, or a $C_{1-6}$ alkyl group.

Item [43]

The compound according to Item [41] or [42] or salts thereof wherein each of $R_3$, $R_4$, $R_5$ and $R_6$ represents a hydrogen atom.

Item [44]

The compound according to any one of Items [41] to [43] or salts thereof wherein $R_1$ and $R_2$ represent independently of each other a Bn group, a 4,4'-dimethoxytrityl (DMTr) group, a t-butyldimethylsilyl group, a t-butyldiphenylsilyl group, a trifluoromethansulfonyl group, a trimethylsilyl group, or a methanesulfonyl group, or the like.

Item [45]
The compound according to any one of Items [41] to [44] or salts thereof wherein cycle A' represents a 6 membered unsaturated heterocyclic group which may be optionally substituted with one or more substituents, preferably a heterocyclic group having the following structural formula II-1 or II-2:

[chem. 40]

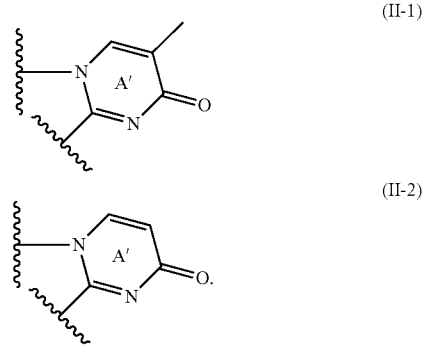

Item [46]
The compound according to any one of Items [41] to [45] wherein $D_1$ represents $N_3$.

Item [47]
The compound according to any one of Items [41] to [45] wherein $D_1$ represents a hydroxy group.

Item [48]
The compound according to any one of Items [41] to [45] wherein $D_1$ represents —X (a leaving group), and the leaving group represents preferably a leaving group for hydroxy group, and exemplifies a methanesulfonyloxy (mesyloxy; Ms-O—) group, a trifluoromethanesulfonyloxy group, or a p-toluenesulfonyloxy group and the like, which should not be limited thereto.

Item [49]
A method for preparing a compound represented by general formula I:

[chem. 41]

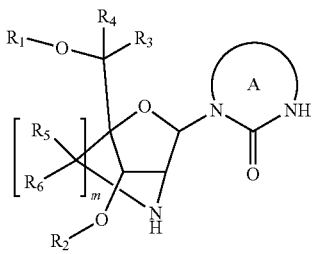

[wherein,
$R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocycle may be fused with another cycle to form the cycle A.]
, said method comprising a step of reacting the compound according to Item [46] with a reducing agent, and the reducing agent used in the present preparation method includes phosphines, preferably $Ph_3P$, and the cycle A includes preferably a thyminyl group or an uracinyl group.

Item [51]
A method preparing the compound according to Item [46] or salts thereof, said method comprising reacting the compound according to Item [47] with an azide agent to prepare the same, and the azide agent used in the present preparation method includes hydrazoic acid, sodium azide, lithium azide, tetrabutylammonium azide, trimethylsilyl azide, diphenylphosphoryl azide (DPPA), nicotinyl azide, zinc azide ($Zn(N_3)_2$), and preferably DPPA.

Item [52]
A method for preparing the compound according to Item [46] or salts thereof, said method comprising reacting the compound according to Item [48] or salts thereof with an azide agent to prepare the same, and the azide agent used in the present preparation method includes $nBu_4NN_3$ or sodium azide, which should not be limited thereto.

Item [53]
A method for preparing the compound according to Item [46] or salts thereof, said method comprising reacting the compound represented by general formula VI:

[chem. 42]

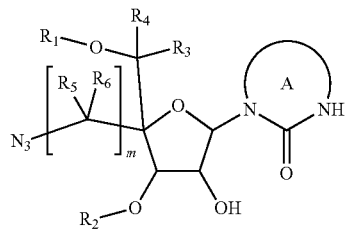

[wherein,
$R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and cycle A represents a five to seven membered unsaturated heterocyclic group which may be optionally substituted with one or more substituents selected from the group consisting of a $C_{1-6}$ alkyl group which may be optionally substituted with one or more substituents, a C$_{2-6}$ alkenyl group which may be optionally substituted with one or more substituents, a C$_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.] with an activating agent for hydroxy group to prepare the compound according to Item [46] or salts thereof, and the activating agent for hydroxy group used in the present preparation method includes, for example, trifluoromethanesulfonyl chloride, methanesulfonyl chloride, and trifluoromethanesulfonic anhydride, which should not be limited thereto.

Item [54]

A method for preparing the compound according to Item [48] or salts thereof, said method comprising reacting a compound represented by general formula V:

[chem. 43]

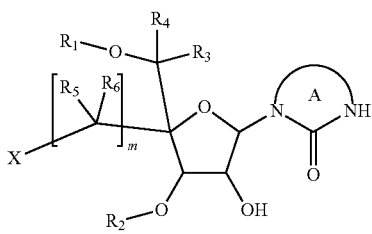

[wherein,

R$_1$ and R$_2$ represent independently of each other a protecting group for hydroxy group, R$_3$ and R$_4$ represent independently of each other a hydrogen atom, or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, X represents a leaving group, m is an integer of 1 to 3, and cycle A represents a five to seven membered unsaturated heterocyclic group which may be optionally substituted with one or more substituents selected from the group consisting of a C$_{1-6}$ alkyl group which may be optionally substituted with one or more substituents, a C$_{2-6}$ alkenyl group which may be optionally substituted with one or more substituents, a C$_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocycle may be further fused with another cycle to form a cycle A.] with an activating agent for hydroxy group to prepare the compound according to Item [48], and the activating agent for hydroxy group used in the present preparation method includes, for example, methanesulfonyl chloride, which should not be limited thereto.

Item [55]

A method for preparing a compound represented by general formula VII:

[chem. 44]

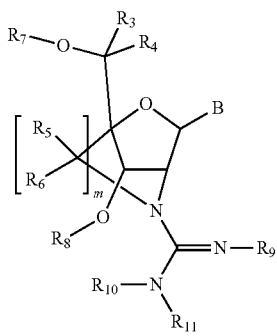

[wherein,

B represents a base moiety of nucleic acid wherein said base moiety may be optionally substituted with one or more substituents, R$_3$ and R$_4$ represent independently of each other a hydrogen atom, or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, R$_7$ represents a hydrogen atom or a protecting group for hydroxy group, R$_8$ represents a hydrogen atom, a phosphate group which may be optionally substituted with one or more substituents, or a thiophosphate group which may be optionally substituted with one or more substituents, and R$_9$, R$_{10}$, and R$_{11}$ represent independently of each other a hydrogen atom, a C$_{1-6}$ alkyl group which may be optionally substituted with one or more substituents, or a protecting group for amino group, and m is an integer of 1 to 3.]
or salts thereof, said method comprising the preparation method according to any one of Items [49] to [54].

Item [56]

A method for preparing guanidine bridged artificial nucleic acid, said method comprising the preparation method according to any one of Items [49] to [55], wherein the guanidine bridged artificial nucleic acid represents an oligonucleotide containing one or more nucleosides represented by general formula X:

[chem. 45]

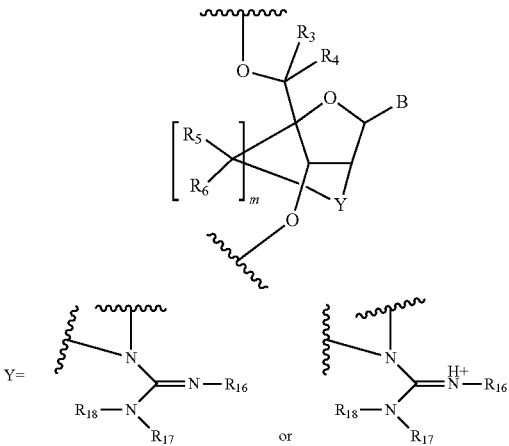

[wherein,

R$_3$ and R$_4$ represent independently of each other a hydrogen atom, or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, B represents a base moiety of nucleic acid wherein said base moiety may be optionally substituted with one or more substituents, R$_{16}$, R$_{17}$ and R$_{18}$ represent independently of each other a hydrogen atom, a C$_{1-6}$ alkyl group which may be optionally substituted with one or more substituents, or a protecting group for amino group, and m is an integer of 1 to 3.]
, and the nucleic acid is a nucleic acid which may be prepared by a phosphoramidite method from the compound represented by general formula XI:

[chem. 46]

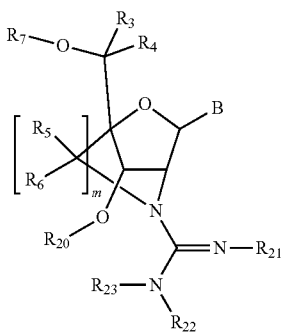

[wherein,
each of B, R$_3$, R$_4$, R$_5$, R$_6$ and m is the same as defined in the above-mentioned general formula X, R$_7$ represents a hydrogen atom, or a protecting group for hydroxy group, R$_{20}$ represents a phosphate group which may be optionally substituted with one or more substituents or a thiophosphate group which may be optionally substituted with one or more substituents, R$_{21}$, R$_{22}$ and R$_{23}$ represent independently of each other a hydrogen atom, a C$_{1-6}$ alkyl group which may be optionally substituted with one or more substituents or a protecting group for amino group.].

Item [57]

A compound represented by general formula XIII:

[chem. 47]

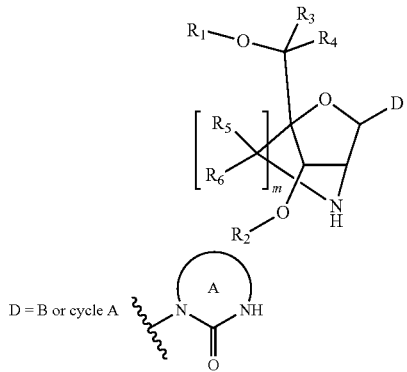

[wherein,

R$_1$ and R$_2$ represent independently of each other a hydrogen atom, or a protecting group for hydroxy group, R$_3$ and R$_4$ represent independently of each other a hydrogen atom, or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, m is an integer of 1 to 3, and D represents a cycle A (wherein the cycle A represents a five to seven membered unsaturated heterocyclic group which may be optionally substituted with one or more substituents selected from the group consisting of a C$_{1-6}$ alkyl group which may be optionally substituted with one or more substituents, a C$_{2-6}$ alkenyl group which may be optionally substituted with one or more substituents, a C$_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.) or
a B (said B represents a base moiety of nucleic acid wherein said base moiety may be optionally substituted with one or more substituents).]
or salts thereof.

Item [58]

The compound according to Item [57] or salts thereof wherein each of R$_3$, R$_4$, R$_5$ and R$_6$ represents a hydrogen atom.

Item [59]

The compound according to Item [57] or [58] or salts thereof wherein D represents a cycle A.

Item [60]

The compound according to Item [59] or salts thereof wherein cycle A represents a thyminyl group or an uracinyl group.

Item [61]

The compound according to Item [59] or [60] or salts thereof wherein each of R$_1$ and R$_2$ represents a protecting group for hydroxy group.

Item [62]

The compound according to Item [61] or salts thereof wherein R$_1$ and R$_2$ represent independently of each other a Bn group, a 2-naphthylmethyl group, a p-methoxybenzyl group, a 3,4-dimethoxybenzyl group, a 2,6-dimethoxybenzyl group, or a p-phenylbenzyl group.

Item [63]

The compound according to any one of Items [59] to [62] selected from the group consisting of 1-{(1R, 3R, 4R, 7S)-7-(benzyloxy)-1-[(benzyloxy)methyl]-2-oxa-5-azabicyclo[2.2.1]hepta-3-yl}-5-methylpyrimidine-2,4(1H,3H)-dione, and 1-{(1R, 3R, 4R, 7S)-7-(benzyloxy)-1-[(benzyloxy)methyl]-2-oxa-5-azabicyclo[2.2.1]hepta-3-yl}-pyrimidine-2,4(1H,3H)-dione, or salts thereof.

Item [64]

The compound according to Item [57] or [58] wherein D represents B (said B represents a base moiety of nucleic acid wherein said base moiety may be optionally substituted with one or more substituents).

Item [65]

The compound according to Item [64] or salts thereof wherein B represents an adeninyl group which may be optionally substituted with one or more substituents, a guaninyl group which may be optionally substituted with one or more substituents, a cytosinyl group which may be optionally substituted with one or more substituents, a 5-methylcytosinyl group which may be optionally substituted with one or more substituents, a thyminyl group which may be optionally substituted with one or more substituents, or an uracinyl group which may be optionally substituted with one or more substituents.

Item [66]

The compound according to Item [64] or [65] wherein $R_1$ represents a protecting group for hydroxy group.

Item [67]

The compound according to Item [66] or salts thereof wherein $R_1$ represents a Bn group, a DMTr group, or a TMS group.

Item [68]

The compound according to any one of Item [64] to [67] wherein $R_2$ represents a protecting group for hydroxy group.

Item [69]

The compound according to Item [68] or salts thereof wherein $R_2$ represents a Bn group.

Item [70]

The compound according to Item [68] or salts thereof wherein $R_2$ represents a TMS group.

Item [71]

The compound according to any one of Items [64] to [67] wherein $R_2$ represents a hydrogen atom.

Item [72]

The compound according to any one of Items [64] to [71] selected from

1-{(1R, 3R, 4R, 7S)-7-(benzyloxy)-1-[(benzyloxy)methyl]-2-oxa-5-azabicyclo[2.2.1]hepta-3-yl}-5-methylpyrimidine-2,4(1H,3H)-dione.

Item [73]

A method for preparing the compound according to Item [64] or salts thereof, said method comprising a replacement of a cycle A in a compound represented by general formula IX:

[chem. 48]

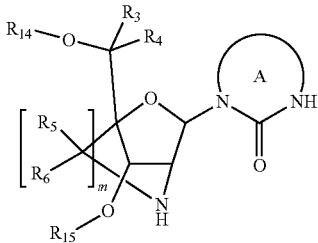

[wherein, $R_3$ and $R_4$ represents independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_{14}$ and $R_{15}$ represents independently of each other a hydrogen atom, or a protecting group for hydroxy group, m is an integer of 1 to 3, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.], in the present preparation method, the B represents preferably an adeninyl group which may optionally have one or more protecting groups, a guaninyl group which may optionally have one or more protecting groups, a cytosinyl group which may optionally have one or more protecting groups, a 5-methylcytosinyl group which may optionally have one or more protecting groups, a thyminyl group which may optionally have one or more protecting groups, or an uracinyl group which may optionally have one or more protecting groups; the cycle A represents preferably a thyminyl group or an uracinyl group; all of the $R_{14}$, $R_{15}$ and $R_{16}$ represent a Bn group, alternatively the $R_{14}$ represents a DMTr group, the $R_{15}$ represents a TMS group, and the $R_{16}$ represents a hydrogen atom, which should not be limited thereto. In the present preparation method, the replacement method of the cycle A includes, for example, a method using a Lewis acid, preferably, a method using a Lewis acid and a silylating agent, which should not be limited thereto.

Item [74]

A method for preparing a compound represented by general formula VII:

[chem. 49]

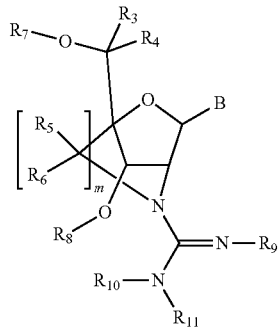

[wherein,

B represents a base moiety of nucleic acid wherein said base moiety may be optionally substituted with one or more substituents, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_7$ represents a hydrogen atom or a protecting group for hydroxy group, $R_8$ represents a hydrogen atom, a phosphate group which may be optionally substituted with one or more substituents, or a thiophosphate group which may be optionally substituted with one or more substituents, and R$_9$, R$_{10}$ and R$_{11}$ represent independently of each other a hydrogen atom, a C$_{1-6}$ alkyl group which may be optionally substituted with one or more substituents, or a protecting group for amino group, and m is an integer of 1 to 3.]

, said method comprising the preparation method according to Item [73].

Item [75]

A method for preparing a guanidine bridged artificial nucleic acid, said method comprising the preparation method according to Item [62] or [63], wherein the guanidine bridged artificial nucleic acid represents an oligonucleotide containing one or more nucleosides represented by general formula X:

[chem. 50]

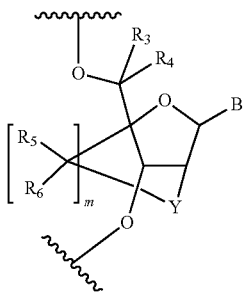

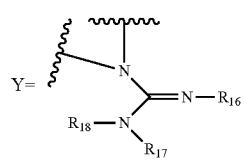 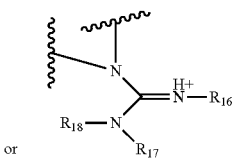

[wherein,

R$_3$ and R$_4$ represent independently of each other a hydrogen atom, or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, B represents a base moiety of nucleic acid wherein said base moiety may be optionally substituted with one or more substituents, and R$_{16}$, R$_{17}$ and R$_{18}$ represent independently of each other a hydrogen atom, a C$_{1-6}$ alkyl group which may be optionally substituted with one or more substituents, or a protecting group for amino group, and m is an integer of 1 to 3.]

, and the nucleic acid is a nucleic acid which may be prepared by a phosphoramidite method from a compound represented by general formula XI:

[chem. 51]

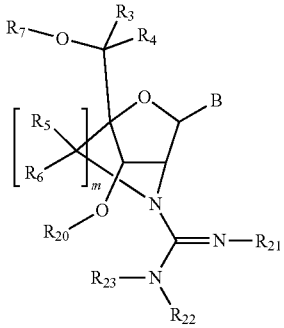

[wherein,
each of B, R$_3$, R$_4$, R$_5$, R$_6$ and m is as the same defined in the above-mentioned general formula X, R$_7$ represents a hydrogen atom or a protecting group for hydroxy group, and R$_{20}$ represents a phosphate group which may be optionally substituted with one or more substituents, or a thiophosphate group which may be optionally substituted with one or more substituents, R$_{21}$, R$_{22}$, and R$_{23}$ represent independently of each other a hydrogen atom, a C$_{1-6}$ alkyl group which may be optionally substituted with one or more substituents, or a protecting group for amino group].

Item [76]

A compound according to general formula VII:

[chem. 52]

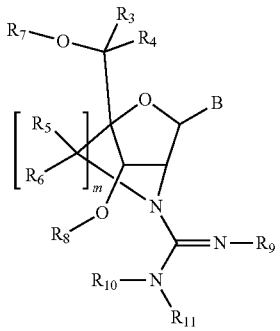

[wherein,
B represents a base moiety of nucleic acid wherein said base moiety may be optionally substituted with one or more substituents, R$_3$ and R$_4$ represent independently of each other a hydrogen atom, or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, R$_7$ represents a hydrogen atom or a protecting group for hydroxy group, R$_8$ represents a hydrogen atom, a phosphate group which may be optionally substituted with one or more substituents, or a thiophosphate group which may be optionally substituted with one or more substituents, and R$_9$, R$_{10}$, and R$_{11}$ represent independently of each other a hydrogen atom, a C$_{1-6}$ alkyl group which may be optionally substituted with one or more substituents, or a protecting group for amino group, and m is an integer of 1 to 3

(with the proviso that the following cases are excluded:

the case where m=1, B represents a thyminyl group, each of $R_3$, $R_4$, $R_5$ and $R_6$ represents a hydrogen atom, $R_7$ represents a DMTr group, $R_8$ represents a hydrogen atom or a —P(O(CH$_2$)$_2$CN)(N(iPr)$_2$) group, $R_9$ represents a Boc group, $R_{10}$ represents a Boc group, and $R_{11}$ represents a hydrogen atom, and the case where m=2, B represents a thyminyl group, each of $R_3$, $R_4$, $R_5$ and $R_6$ represents a hydrogen atom, $R_7$ represents a DMTr group, $R_8$ represents a hydrogen atom or a —P(O(CH$_2$)$_2$CN)(N(iPr)$_2$) group, $R_9$ represents a Ceoc group, $R_{10}$ represents a Ceoc group, and $R_{11}$ represents a hydrogen atom.)]
or salts thereof.

Item [77]

The compound according to Item [76] or salts thereof, wherein B represents an adeninyl group, a guaninyl group, a cytosinyl group, a 5-methylcytosinyl group, or an uracinyl group, each of which may optionally have one or more protecting groups.

Item [78]

The compound according to Item [76] or [77] or salts thereof, wherein each of $R_3$, $R_4$, $R_5$ and $R_6$ represent independently a hydrogen atom.

Item [79]

The compound according to any one of Items [76] to [78] or salts thereof, wherein $R_7$ represents a protecting group for hydroxy group, and the protecting group for hydroxy group as the $R_7$ represents preferably a methyl group which is substituted with one to three aryl groups wherein the aryl group is substituted with an alkyl group having 1 to 6 carbon atoms, an alkoxy group having 1 to 6 carbon atoms, a halogen atom, and/or a cyano group, more preferably a DMTr group, which should not be limited thereto.

Item [80]

The compound according to any one of Item [76] to [79] or salts thereof, wherein $R_8$ represents a hydrogen atom.

Item [81]

The compound according to any one of Items [76] to [79] or salts thereof, wherein $R_8$ represents a phosphate group which may be optionally substituted with one or more substituents, and the phosphate group includes, preferably a —P(O(CH$_2$)$_2$CN)(N(iPr)$_2$) group, which should not be limited thereto.

Item [82]

The compound according to any one of Items [76] to [81] or salts thereof, wherein each of $R_9$ and $R_{10}$ represents independently a protecting group for amino group, and the protecting group for amino group includes, preferably, a Teoc group or a Boc group, which should not be limited thereto.

Item [83]

The compound according to any one of Items [76] to [82] or salts thereof, wherein $R_{11}$ represents a hydrogen atom.

Item [84]

The compound according to Item [76] or salts thereof, wherein B represents a thyminyl group which may optionally have one or more protecting groups.

Item [85]

The compound according to Item [84], wherein each of $R_9$ and $R_{10}$ represents independently a Teoc group.

Item [86]

An oligonucleotide containing one or more nucleosides represented by general formula X:

[chem. 53]

[wherein, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, B represents a base moiety of nucleic acid wherein said base moiety may be optionally substituted with one or more substituents, $R_{16}$, $R_{17}$, and $R_{18}$ represents independently of each other a hydrogen atom, a $C_{1-6}$ alkyl group which may be optionally substituted with one or more substituents, or a protecting group for amino group, and m is an integer of 1 to 3.]

(with the proviso that the oligonucleotide containing as a bridged nucleic acid only nucleoside wherein B represents a thyminyl group, and each of $R_3$, $R_4$, $R_5$, $R_{16}$, $R_{17}$ and $R_n$ represent a hydrogen atom is excluded.), or salts thereof.

Item [87]

The oligonucleotide according to Item [86] or salts thereof, wherein B represents an adeninyl group, a guaninyl group, a cytosinyl group, a 5-methylcytosinyl group, a thyminyl group, or an uracinyl group.

Item [88]

The oligonucleotide according to Item [86] or [87], wherein each of $R_{16}$, $R_{17}$, and $R_{18}$ represent independently a hydrogen atom.

Item [89]

The method for preparing the oligonucleotide according to any one of Items [86] to [89] or salts thereof, said method comprising the preparation of the same by a phosphoramidite method from a compound represented by general formula XI:

[chem. 54]

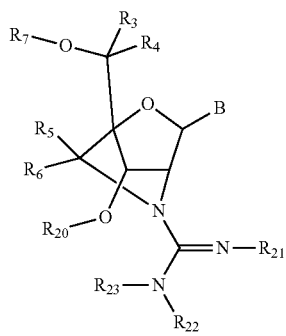

[wherein,
each of B, $R_3$, $R_4$, $R_5$, $R_6$ and m is the same as defined in the above-mentioned general formula X, $R_7$ represents a hydrogen atom, or a protecting group for hydroxy group, $R_{20}$ represents a phosphate group which may be optionally substituted with one or more substituents, or a thiophosphate group which may be optionally substituted with one or more substituents, and $R_{21}$, $R_{22}$ and $R_{23}$ represent independently of each other a hydrogen atom, a $C_{1-6}$ alkyl group which may be optionally substituted with one or more substituents, or a protecting group for amino group.].

Effect of Invention

The preparation method of the present invention can reduce largely the number of steps compared to the conventional method, and also improved the yield of GuNA largely. The replacement method of nucleic acid base of the present invention can prepare GuNA that contains various nucleic acid bases other than a thymine group effectively and also a preferred β-form selectively. The preparation method of the present invention can prepare GuNA oligomer which contains GuNA monomer having various kinds of nucleic acid bases, for example, GuNA monomer having a base moiety of adeninyl, guaninyl, cytosinyl, 5-methylcytosinyl or uracinyl, or GuNA oligomer containing these GuNA monomers. The intermediate compound of the present invention is useful for preparing GuNA of various kinds of nucleic acid base.

The intermediate compound of the present invention includes 2'-amino LNA monomer. The replacement of nucleic acid base of the present invention can prepare 2'-amino LNA having not only adeninyl or thyminyl, but also the other various kinds of nucleic acid base, for example, 2'-amino LNA having a base moiety of guaninyl, cytosinyl, 5-methylcytosinyl or uracinyl.

Using the monomer of the 2'-amino LNA having various kinds of nucleic acid base that is prepared by the present invention, an oligomer of 2'-amino LNA can be prepared. The oligomer of 2'-amino LNA is resistant to nuclease, and also binds strongly to a nucleic acid having a complementary sequence, and accordingly, it can be used as pharmaceuticals containing nucleic acid for treatment, alleviation, prevention, relapse prevention and diagnosis of various diseases, and can be used widely as reagents containing nucleic acid for various inspections or tests.

The GuNA that is prepared by the present invention is remarkably resistant to nuclease, and also binds strongly to nucleic acid having a complementary sequence, and further, migrates effectively into cells, and accordingly, it can be used as pharmaceuticals containing nucleic acid for treatment, alleviation, prevention, relapse prevention and diagnosis for various diseases, and can be used widely as reagents containing nucleic acid for various inspections or tests.

MODE FOR CARRYING OUT THE INVENTION

Hereinafter, the present invention is further explained in details. All of the publications cited herein are incorporated herein by reference.
(Definition)
First, the definitions of the terms as used herein are described.

The term of "$C_{1-6}$ alkyl that may be optionally substituted with one or more substituents" as used herein encompasses any straight chain alkyl group having 1 to 6 carbon atoms ($C_{1-6}$), preferably 1 to 4 carbon atoms ($C_{1-4}$), any branched chain alkyl group having 3 to 6 carbon atoms in which the identical or different branched chains are contained, any cyclic alky group having 3 to 6 carbon atoms, and any combinations thereof which have 4 to 6 carbon atoms. Specific examples of the straight chain alkyl group having 1 to 6 carbon atoms include methyl, ethyl, n-propyl, n-butyl, n-pentyl, and n-hexyl. Specific examples of the branched chain alkyl group having 3 to 6 carbon atoms in which the identical or different branched chains are contained include iso (which is abbreviated as "i")-propyl, isobutyl, tert (which is abbreviated as "t")-butyl, sec (which is abbreviated as "s")-butyl, neopentyl, isopentyl, and the others, and also examples of the cyclic alkyl group having 3 to 6 carbon atoms include preferably a 3 to 6 membered monocyclic cycloalkyl group, and specific examples thereof include cyclopropyl, cyclobutyl, cyclopentyl, cyclohexyl, and the others, which are not limited thereto. Examples of the substituents include one or more (or preferably one to three) identical or different groups selected from the group consisting of a $C_{1-6}$ alkyl group, a $C_{2-6}$ alkenyl group, a $C_{2-6}$ alkynyl group, a $C_{1-6}$ alkoxy group, an amino group, a hydroxy group, an oxo group, a thioxo group, and a halogen atom.

The term of "$C_{2-6}$ alkenyl that may be optionally substituted with one or more substituents" as used herein encompasses any straight chain alkenyl group having 2 to 6 carbon atoms ($C_{2-6}$), preferably having 2 to 4 carbon atoms ($C_{2-4}$), any branched chain alkenyl group having 3 to 6 carbon atoms in which the identical or different branched chains are contained, any cyclic alkenyl group having 3 to 6 carbon atoms, and any combinations thereof that have 4 to 6 carbon atoms. Specific examples of the straight chain alkenyl group having 2 to 6 carbon atoms include ethenyl, 1-propenyl, 2-propenyl, 1-butenyl, 2-butenyl, 1-pentenyl, 2-pentenyl, 3-pentenyl, 4-pentenyl, 1-hexenyl, and the others. Specific examples the branched chain alkenyl group having 3 to 6 carbon atoms in which the identical or different branched chains are contained include isopropenyl, 1-methyl-1-propenyl, 1-methyl-2-propenyl, 2-methyl-1-propenyl, 2-methyl-2-propenyl, 1-methyl-2-butenyl and the others, and also examples of the cyclic alkenyl group having 3 to 6 carbon atoms include a three to six membered monocyclic cycloalkenyl group, and specific examples thereof include cyclopropenyl, cyclobutenyl, cyclopentenyl, cyclohexenyl, and the others. Examples of the substituents include one or more (or preferably one to three) identical or different groups selected from the group consisting of a $C_{1-6}$ alkyl group, a $C_{2-6}$ alkenyl group, a $C_{2-6}$ alkynyl group, a $C_{1-6}$ alkoxy group, an amino group, a hydroxy group, an oxo group, a thioxo group, and a halogen atom.

The term of "a $C_{2-6}$ alkynyl that may be optionally substituted with one or more substituents" as used herein encompasses any straight chain alkynyl group having 2 to 6 carbon atom ($C_{2-6}$), preferably any straight chain alkynyl group having 2 to 4 carbon atoms ($C_{2-4}$), any branched chain alkynyl group having 3 to 6 carbon atoms which have the identical or different branched chains, any cyclic alkynyl group having 3 to 6 carbon atoms, and any combinations thereof which have 4 to 6 carbon atoms. Specific examples of the straight chain alkynyl group having 2 to 6 carbon atoms include ethynyl, 1-propynyl, 2-propynyl, 1-butynyl, 2-butynyl, 1-pentynyl, 2-pentynyl, 3-pentynyl, 4-pentynyl, 1-hexynyl and the others. Specific examples of the branched chain alkynyl group having 3 to 6 carbon atoms in which the identical or different branched chains are contained include isopropynyl, 1-methyl-1-propynyl, 1-methyl-2-propynyl, 2-methyl-1-propynyl, 2-methyl-2-propynyl, 1-methyl-2-butynyl, and the others, and also examples of the cyclic alkynyl group having 3 to 6 carbon atoms include preferably a three to six membered monocyclic cycloalkynyl group, and specific examples thereof include cyclobutynyl, cyclopentynyl, cyclohexynyl and the others, which are not limited thereto. Examples of the substituents include one or more (or preferably one to three) identical or different group selected from the group consisting of a $C_{1-6}$ alkyl group, a $C_{2-6}$ alkenyl group, a $C_{2-6}$ alkynyl group, a $C_{1-6}$ alkoxy group, an amino group, a hydroxy group, an oxo group, a thioxo group, and halogen atom.

The term of "$C_{1-6}$ alkoxy group" as used herein represents a monovalent group in which the $C_{1-6}$ alkyl binds to an oxygen atom, and represents a $C_{1-6}$ alkyl-O group. Specific examples thereof include methoxy, ethoxy, n-propoxy, i-propoxy, n-butoxy, t-butoxy, s-butoxy, 3-methylbutoxy, and the others, which are not limited thereto.

Examples of the term of "halogen (atom)" as used herein include fluorine atom (fluoro), chlorine atom (chloro), bromine atom (bromo), and iodine atom (iodo).

The term of "aryl (group)" as used herein represents a functional group or a substituent group which is derivatized from aromatic hydrocarbon group and encompasses a group composed of a plurality of cycles, and specifically, represents a monovalent group having 6 to 14 carbon atoms in which one hydrogen atom is excluded from aromatic hydrocarbon atom, and include, for example, phenyl, indenyl, naphthyl, phenanthrenyl, anthracenyl and the others. Also the aryl ring may be substituted with one or more groups selected from a halogen atom, a $C_{1-6}$ alkyl group, a $C_{2-6}$ alkenyl group, a $C_{2-6}$ alkynyl group, a hydroxy group, a $C_{1-6}$ alkoxy group, an aryloxy group, an amino group, a nitro group, a trifluoromethyl group, or a phenyl group. Examples of the aryl group which may be optionally substituted include 2-methylphenyl, 3-methylphenyl, 4-methylphenyl, 2,6-dimethylphenyl, 2,4-dimethylphenyl, 2-chlorophenyl, 4-chlorophenyl, 2,4-dichlorophenyl, 2,5-dichlorophenyl, 2,6-dichlorophenyl, 2-bromophenyl, 4-methoxyphenyl, 4-chloro-2-nitrophenyl, 4-nitrophenyl, 2-nitrophenyl, 2,4-dinitrophenyl, biphenyl and the others. Preferred examples of the aryl group include a phenyl group which is substituted with halogen atom, $C_{1-6}$ alkoxy group or nitro group, or an unsubstituted phenyl group.

The term of "heteroaryl (group)" as used herein represents a monovalent group in which one hydrogen atom is excluded from optional heteroaromatic compound containing heteroatoms (such as nitrogen atom, oxygen atom, and/or sulfur atom) in a ring structure and having 3 to 12 carbon atoms, and include, for example, pyridyl, pyrimidinyl, pyridazinyl, pyrrolyl, isoquinolyl, quinolyl, indolyl, imidazolyl, triazolyl, furyl, thienyl and the others. Also, the heteroaryl ring may be optionally substituted with one or more groups selected from a halogen atom, a $C_{1-6}$ alkyl group, a $C_{2-6}$ alkenyl group, a $C_{2-6}$ alkynyl group, a hydroxy group, a $C_{1-6}$ alkoxy group, an aryloxy group, an amino group, a nitro group, a trifluoromethyl group, or a phenyl group and the others.

Herein when the compound of the present invention, an intermediate compound, or a starting material and the others has a functional group (such as, a hydroxy group, an amino group, a carboxyl group and the others), the functional group may be protected with a protecting group that is usually used in an organic synthetic chemistry according to the method described in Theodora W. Greene, Peter G. M. Wuts, "Protective Groups in Organic Synthesis" 4th. ed., John Wiley & Sons, Inc. 1999, and after the reaction, the protecting group may be then removed to obtain the desirable compound. Examples of the protecting group include the protecting group that is usually used in an organic synthetic chemistry as described in the same document, and is also usually used in an organic synthetic chemistry, and examples of each of the protecting group depending on the functional group are described below.

The term of "protecting group" described in terms of "a protecting group for hydroxy group", "a protecting group for amino group", "a protecting group for phosphate group", or "a protecting group for mercapto group" as used herein is not particularly limited to any group as long as it can protect amino group, hydroxy group, phosphate group or mercapto group stably during a nucleic acid synthesis. Specific examples thereof include a protecting group that is stable under acidic or neutral condition and also can be cleaved by a chemical method such as a hydrogenolysis, a hydrolysis, an electrolysis, and a photolysis. Examples of the protecting group includes an alkyl group having 1 to 6 carbon atoms; an alkenyl group having 2 to 6 carbon atoms; an alkynyl group having 2 to 6 carbon atoms; an acyl group; a tetrahydropyranyl group or a tetrahydrothiopyranyl group; a tetrahydrofuranyl group or a tetrahydrothiofuranyl group; a silyl group; a methyl group substituted with alkoxy group having 1 to 6 carbon atoms; a methyl group substituted with alkoxy group having 1 to 6 carbon atoms, said alkoxy group being substituted with alkoxy group having 1 to 6 carbon atoms; a methyl group substituted with alkoxy group having 1 to 6 carbon atoms said alkoxy group being substituted with halogen atom; an ethyl group substituted with alkoxy group having 1 to 6 carbon atoms; an ethyl group substituted with halogen atom; a methyl group substituted with one to three aryl groups; a methyl group substituted with one to three aryl groups, said aryl groups being substituted with alkyl group having 1 to 6 carbon atoms, alkenyl group having 2 to 6 carbon atoms, alkynyl group having 2 to 6 carbon atoms, alkoxy group having 1 to 6 carbon atoms, halogen atom, and/or cyano group; a carbonyl group substituted with alkoxy group having 1 to 6 carbon atoms; an aryl group substituted with halogen atom, alkoxy group having 1 to 6 carbon atoms and/or nitro group; a carbonyl group substituted with alkoxy group having 1 to 6 carbon atoms, said alkoxy group being substituted with halogen atom and/or silyl group substituted with alkyl group having 1 to 6 carbon atoms; an alkenyloxycarbonyl group; an aralkyloxycarbony group which may be optionally substituted with alkoxy group having 1 to 6 carbon atoms and/or aryl group substituted with nitro group; and the others.

The term of "protecting group for hydroxy group" represents a protecting group that is usually used in an organic synthetic chemistry (in particular, nucleic acid synthesis), and includes, for example, an aliphatic acyl group; an aromatic acyl group; an aminocarbonyl group which may be substituted; an alkoxycarboyl group which may be substituted; an aliphatic sulfonyl group; an aromatic sulfonyl group; a methyl group substituted with one to three aryl groups; a methyl group substituted with one to three aryl groups, said aryl group being substituted with alkyl group having 1 to 6 carbon atoms, alkoxy group having 1 to 6 carbon atoms, halogen atom and/or cyano group; or a silyl group. Specific examples thereof include benzyl (Bn), 4,4'-dimethoxytrityl (DMTr), 4-methoxytrityl, triphenylmethyl, 2-naphthylmethyl, diphenylaminocarbonyl (DPC), cyanoethoxycarbonyl, tetrahydropyranyl, trimethylsilyl, triethylsilyl, triisopropylsilyl, t-butyldimethylsilyl, t-butyldiphenylsilyl, triphenylsilyl, 4-methoxybenzyl (p-methoxybenzyl), 3,4-dimethoxybenzyl, 2,6-dimethoxybenzyl, p-phenylbenzyl, methanesulfonyl, trifluoromethansulfonyl, methoxymethyl, benzoyl (Br), and acetyl and the others, which should not be limited thereto. Preferably, benzyl (Bn), 4,4'-dimethoxytrityl (DMTr), t-butyldimethylsilyl, t-butyldiphenylsilyl, trimethylsilyl (TMS), diphenylaminocarbonyl (DPC), methanesulfonyl, and trifluoromethansulfonyl are included.

The term of "hydroxy group which may be optionally substituted with one or more substituents" as used herein encompasses a hydroxy group which may optionally have a protecting group, and examples of the substituents includes the above-mentioned protecting group for hydroxy group, $C_{1-6}$ alkyl group, aryl group which may be optionally substituted, and heteroaryl group which may be optionally substituted. Preferred examples of protecting group for hydroxy group include Bn, DPC, DMTr, 4-methoxytrityl, triphenylmethyl, 2-naphthylmethyl, cyanoethoxycarbonyl, tetrahydropyranyl, trimethylsilyl, triethylsilyl, triisopropylsilyl, t-butyldimethylsilyl, t-butyldiphenylsilyl, trimethylsilyl, 4-methoxybenzyl, 3,4-dimethoxybenzyl, benzoyl (Bz), and acetyl, and preferred examples of $C_{1-6}$ alkyl include methyl, ethyl, propyl, isopropyl, butyl, isobutyl, sec-butyl, t-butyl, pentyl, and isopentyl, and preferred examples of aryl include phenyl, biphenyl, naphthyl, and anthracenyl, and preferred examples of heteroaryl include pyridyl, pyrimidinyl, pyridazinyl, pyrrolyl, isoquinolyl, quinolyl, indolyl, imidazolyl, benzimidazolyl, triazolyl, furyl, thienyl and the others. Also, examples of the substituents of the aryl group which may be optionally substituted or the heteroaryl group which may be optionally substituted include a halogen atom, a $C_{1-6}$ alkyl group, a $C_{2-6}$ alkenyl group, a $C_{2-6}$ alkynyl group, hydroxy group, a $C_{1-6}$ alkoxy group, an aryloxy group, an amino group, a nitro group, a trifluoromethyl group, a phenyl group and the others, which may be further optionally substituted with one or more of these groups.

The term of "protecting group for amino group" represents a protecting group that is usually used in an organic synthetic chemistry (in particular, nucleic acid synthesis), and include, for example, an aliphatic acyl group; an aromatic acyl group; an alkoxycarboyl group which may be optionally substituted; a methyl group substituted with one to three aryl groups; and a methyl group substituted with aryl groups, said aryl group being substituted with halogen atom and/or cyano group. Specific examples thereof include acetyl (Ac), phenoxyacetyl (Pac), propionyl group, isobutyryl, benzoyl (Bz), methoxycarbonyl, ethoxycarbonyl, t-butoxycarbonyl (Boc), trimethylsilylethoxycarbonyl (Teoc), cyanoethoxycarbonyl (Ceoc), benzyloxycarbonyl (Cbz), allyloxycarbonyl, 9-fluorenylmethoxycarbonyl (Fmoc), 2,2,2-trichloroethoxycarbonyl, t-amyloxycarbonyl, 4-methoxybenzyl, triphenylmethyl, 2-nitrobenzenesulfonyl, 2,4-dinitrobenzenesulfonyl or 2-(trimethylsilyl)ethoxymethyl and the others, which are not limited thereto. Preferably, isobutyryl, benzoyl (Bz), t-butoxycarbonyl (Boc), and trimethylsilylethoxycarbonyl (Teoc) are included.

The term of "amino group which may be optionally substituted with one or more substituents" as used herein encompasses an amino group which may optionally have a protecting group, and the examples of substituents include the above-mentioned protecting group for amino group, a $C_{1-6}$ alkyl group, an aryl group which may be optionally substituted, and a heteroaryl group which may be optionally substituted. Preferred examples of the protecting group for amino group include Bn, DPC, CMTr, 4-methoxytrityl, triphenylmethyl, 2-naphthylmethyl, cyanoethoxycarbonyl, tetrahydropyranyl, trimethylsilyl, triethylsilyl, triisopropylsilyl, t-butyldimethylsilyl, t-butyldiphenylsilyl, trimethylsilyl, 4-methoxybenzyl, 3,4-dimethoxybenzyl, benzoyl (Bz), and acetyl, and preferred examples of $C_{1-6}$ alkyl group include methyl, ethyl, propyl, isopropyl, butyl, isobutyl, sec-butyl, t-butyl, pentyl, and isopentyl, and preferred examples of aryl group include phenyl, biphenyl, naphthyl, and anthracenyl, and preferred examples of heteroaryl group include pyridyl, pyrimidinyl, pyridazinyl, pyrrolyl, isoquinolyl, quinolyl, indolyl, imidazolyl, benzimidazolyl, triazolyl, furyl, thienyl and the others. Also, examples of the substituents of the aryl group which may be optionally substituted, or the heteroaryl group which may be optionally substituted include a halogen atom, a $C_{1-6}$ alkyl group, a $C_{2-6}$ alkenyl group, a $C_{2-6}$ alkynyl group, a hydroxy group, a $C_{1-6}$ alkoxy group, an aryloxy group, an amino group, a nitro group, a trifluoromethyl group, and a phenyl group, and the others, which may be further optionally substituted with one or more of these groups.

The term of "protecting group for a phosphate group" represents a protecting group that is usually used in an organic synthetic chemistry (in particularly, nucleic acid synthesis), and examples thereof include an alkyl group having 1 to 6 carbon atoms and/or an alkyl group having 1 to 6 carbon atoms substituted with cyano group; an aralkyl group; an aralkyl group substituted with aryl group, said aryl group being substituted with nitro group and/or halogen atom; an aryl group substituted with alkyl group having 1 to 6 carbon atoms, halogen atom, or nitro group; 2-cyanoethyl group; 2,2,2-trichloroethyl group; benzyl group; 2-chlorophenyl group; and 4-chlorophenyl group, and the others, which are not limited thereto.

The term of "protecting group for mercapto group" represents a protecting group that is usually used in an organic synthetic chemistry (in particularly, nucleic acid synthesis), and includes, for example, an aliphatic acyl group, an aromatic acyl group, a benzoyl group (Bz), and the others, which are not limited thereto.

The term of "leaving group" as used herein represents a partial substrate having electron pairs that is created when the substrate is cleaved by a cleavage of heterolysis during reaction(s), and encompasses a halogen atom (such as fluorine atom, chlorine atom, bromine atom, iodine atom), and "a leaving group for hydroxyl group". Examples of the leaving group for hydroxyl group include a sulfonyloxy group (such as paratolunesulfonyloxy, mesyloxy, and trifluoromethanesulfonyloxy), an acyloxy group (preferably, saturated or unsaturated acyloxy group having 1 to 8 carbon atoms, for example, aryl group represented by $R^L$—C(=O)—O— wherein the $R^L$ represents an aryl group which may be optionally substituted with alkyl group (the total number of carbon atom is preferably 6 to 8, for example, phenyl, or p-tolyl), an aryloxy group which may be optionally substituted with alkyl group (the total number of carbon atom is preferably 6 to 8, for example, phenoxy, or p-tolyloxy), an aralkyl group (the total number of carbon atom is preferably 7 to 9, for example, benzyl), an arylalkenyl group (the total number of carbon atom is preferably 8 or 9, for example, cinnamyl), an aralkyloxy group (the total number of carbon atom is 7 to 15, for example, benzyloxy, or 9-fluorenylmethyloxy), an alkoxy group (a straight chain or branched chain alkoxy group, for example, methoxy, ethoxy, t-butoxy), and specific examples of the leaving group include iodo, bromo, chloro, fluoro, mesyloxy, methanesulfonyloxy, trifluoromethanesulfonyloxy, ethanesulfonyloxy, 2,2,2-trifluoroethanesulfonyloxy, propanesulfonyloxy, iso-propanesulfonyloxy, butanesulfonyloxy, nonafluorobutanesulfonyloxy, heptafluoropropan-1-sulfonyloxy, pentanesulfonyloxy, pentafluoroethanesulfonyloxy, pentanesulfonyloxy, cyclopentanesulfonyloxy, hexanesulfonyloxy, cyclohexanesulfonyloxy, o-toluenesulfonyloxy, m-toluenesulfonyloxy, p-toluenesulfonyloxy, benzenesulfonyloxy, o-bromobenzenesulfonyloxy, m-bromobenzenesulfonyloxy, p-bromobenzenesulfonyloxy, o-nitrobenzenesulfonyloxy, m-nitrobenzenesulfonyloxy, and p-nitrobenzenesulfonyloxy, and the others, which are not limited thereto. Preferred examples of the leaving group include methanesulfonyloxy (mesyloxy; Ms-O—), trifluoromethanesulfonyloxy, and p-toluenesulfonyloxy.

The term of "phosphate group which may be optionally substituted" as used herein represents a phosphate, a phosphite, or a hydrophosphite, each of which may have optionally substituents (which encompasses protecting group). The term encompasses a phosphate group represented by a formula of —P($R^{P1}$)$R^{P2}$, wherein $R^{P1}$ and $R^{P2}$ represent independently of each other a hydroxy group, a hydroxy group that is protected with a protecting group for nucleic acid synthesis, a mercapto group, a mercapto that is protected with a protecting group for nucleic acid synthesis, an amino group, an alkoxy group having 1 to 5 carbon atoms, an alkylthio group having 1 to 6 carbon atoms, a cyanoalkoxy group having 1 to 6 carbon atoms, or an amino group that is substituted with alkyl group having 1 to 6 carbon atoms. Here the groups of the above-mentioned formula wherein $R^{P1}$ represents O$R^{P1a}$ and $R^{P2}$ represents N$R^{P2a}$ is referred to as "phosphoramidite group", which is a preferred example. The $R^{P1a}$ represents an alkyl group having 1 to 5 carbon atoms or a cyanoalkyl group having 1 to 6 carbon atoms, and the $R^{P2a}$ represents an alkyl group having 1 to 6 carbon atoms. Specific examples of "phosphoramidite group" include a group represented by a formula of —P(O(CH$_2$)$_2$CN)(N(iPr)$_2$), or a group represented by a formula of —P(OCH$_3$)(N(iPr)$_2$) and the others, which is not limited thereto. Herein "iPr" represents an isopropyl group.

The term of "thiophosphate group which may be optionally substituted" as used herein encompasses a thiophosphate group which may have optionally substituents (which encompasses protecting group). The term may encompass a phosphate group represented by formula —P(=S)($R^{P3}$)$R^{P4}$, and in the formula, $R^{P3}$ and $R^{P4}$ represent independently of each other a hydroxy group, a hydroxy group that is protected with a protecting group for nucleic acid synthesis, a mercapto group, a mercapto group that is protected with a protecting group for nucleic acid, an amino group, alkoxy group having one to five carbon atoms, an alkylthio group having 1 to 6 carbon atoms, a cyanoalkoxy group having 1 to 6 carbon atoms, or an amino group that is substituted with alkyl group having 1 to 6 carbon atoms.

Examples of the term of "acyl group" as used herein include an aliphatic acyl group and aromatic acyl group. Specific examples of the aliphatic acyl group include an alkylcarbonyl group, such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentdecanoyl, hexadecanoyl, 1-methylpentdecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and henaicosanoyl; an aryloxyalkycarbonyl group such as phenoxyacetyl (pac); a carboxylated alkylcarbonyl group such as succinoyl, glutaroyl, and adipoyl; a carbonyl group that is substituted with alkyl group having 1 to 6 carbon atoms, said alkyl group being substituted with halogen atom, such as chloroacetyl group, dichloroacetyl, trichioroacetyl, trifluoroacetyl; an alkoxyalkylcarbonyl group having 1 to 6 carbon atoms such as methoxyacetyl; and an unsaturated alkylcarbonyl group such as (E)-2-methyl-2-butenoyl. Also, examples of the aromatic acyl group include an arylcarbonyl group such as benzoyl, α-naphthoyl, and β-naphthoyl; a halogenoarylcarbonyl group such as 2-bromobenzoyl and 4-chlorobenzoyl; an arylcarbonyl group that is substituted with alkyl group having 1 to 6 carbon atoms, such as 2,4,6-trimethylbenzoyl, and 4-toluoyl; an arylcarbonyl group that is substituted with alkoxy group having 1 to 6 carbon atoms, such as 4-anisoyl; a carboxylated arylcarbonyl group such as 2-carboxybenzoyl, 3-carboxybezoyl, and 4-carboxybenzoyl; a nitrolated arylcarbonyl group such as 4-nitrobenzolyl and 2-nitrobenzoyl; a carbonylated arylcarbonyl group that is substituted with alkoxy group having 1 to 6 carbon atoms, such as 2-(methoxycarbonyl)benzoyl; and an arylated arylcarbonyl group such as 4-phenylbenzoyl, which are not limited thereto.

The term of "aralkyl group" as used herein represents an alkyl group of 1 to 6 carbon atoms, preferably 1 to 4 carbon atoms, more preferably 1 to 3 carbon atoms, said alkyl group being substituted with aromatic hydrocarbon group (such as, 6 to 14 membered monocyclic, bicyclic, or tricyclic aromatic hydrocarbon group). Specific examples thereof include benzyl, phenethyl, 1-naphthylmethyl, 2-naphthylmethyl, and the others, but which are not limited thereto.

Examples of tetrahydropyranyl group or tetrahydrothiopyranyl group include more specifically, tetrahydropyran-2-yl, 3-bromotetrahydropyran-2-yl, 4-methoxytetrahydropyran-4-yl, tetrahydrothiopyran-4-yl, 4-methoxytetrahydrothiopyran-4-yl, and the others, but which are not limited thereto.

Examples of tetrahydrofuranyl group or tetrahydrothiofuranyl group include more specifically, tetrahydrofuran-2-yl, tetrahydrothiofuran-2-yl, and the others, but which are not limited thereto.

Examples of term of "silyl group" as used herein include a silyl group that is substituted with alkyl group having 1 to 6 carbon atoms, such as trimethylsilyl, triethylsilyl, isopropyldimethylsilyl, t-butyldimethylsilyl, methyldiisopropylsilyl, methyl di-t-butylsilyl, triisopropylsilyl; a silyl group that is substituted with one or two aryl group and also three alkyl groups having 1 to 6 carbon atoms, such as t-butyldiphenylsilyl, diphenylmethylsilyl, butyldiphenylbutylsilyl, diphenylisopropylsilyl, and phenyldiisopropylsilyl; and triphenylsilyl, but which are not limited thereto.

Examples of the term of "methyl group that is substituted with alkoxy group having 1 to 6 carbon atoms" as used herein include methoxymethyl, 1,1-simethyl-1-methoxymethyl, ethoxymethyl, propoxymethyl, isopropoxymethyl, butoxymethyl, t-butoxymethyl and the others, but which are not limited thereto.

Examples of the term of "methyl group that is substituted with alkoxy group having 1 to 6 carbon atoms, said alkoxy group being substituted with alkoxy group having 1 to 6 carbon atoms" as used herein include 2-methoxyethoxymethyl, but which is not limited thereto.

Examples of the term of "methyl group that is substituted with alkoxy group having 1 to 6 carbon atoms, said alkoxy group being substituted with halogen atom" as used herein include 2,2,2-trichloroethoxymethyl, and bis(2-chloroethoxy)methyl and the others, but which are not limited thereto.

Examples of the term of "ethyl group that is substituted with alkoxy group having 1 to 6 carbon atoms" as used herein include 1-ethoxyethyl, 1-(isopropoxy)ethyl and the others, but which are not limited thereto.

Examples of the term of "ethyl group that is substituted with halogen atom" as used herein include 2,2,2-trichloroethyl and the others, but which is not limited thereto.

Examples of the term of "methyl group that is substituted with one to three aryl groups" as used herein include benzyl, α-naphthylmethyl, β-naphthylmethyl, diphenylmethyl, triphenylmethyl, 4,4'-dimethoxytrityl, 4-methoxytrityl, trityl, α-naphthyldiphenylmethyl, 9-anthrylmethyl and the others, but which are not limited thereto.

Examples of the term of "methyl group that is substituted with one to three aryl groups, said aryl groups being substituted with alkyl group having 1 to 6 carbon atoms, alkoxy group having 1 to 6 carbon atoms, halogen atoms and/or cyano groups" as used herein include 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, 4-cyanobenzyl and the others, but which are not limited thereto.

Examples of the term of "carbonyl group that is substituted with alkoxy group having 1 to 6 carbon atoms" as used herein include methoxycarbonyl, ethoxycarbonyl, t-butoxycarbonyl, isobutoxycarbonyl, Teoc, Ceoc, Fmoc and the others, which are not limited thereto.

Examples of the term of "aryl group that is substituted with halogen atoms, alkoxy group having 1 to 6 carbon atoms, and/or nitro group" as used herein include 4-chlorophenyl, 2-fluorophenyl, 4-methoxyphenyl, 4-nitrophenyl, 2,4-dinitrophenyl and the others, which are not limited thereto.

Examples of the term of "carbonyl group that is substituted with alkoxy group having 1 to 6 carbon atoms, said alkoxy group being substituted with silyl group and said silyl group being substituted with halogen atoms and/or three alkyl group having 1 to 6 carbon atoms" as used herein include 2,2,2-trichloroethoxycarbonyl, 2-trimethylsilylethoxycarbonyl and the others, which are not limited thereto.

Examples of the term of "alkenyloxycarbonyl group" as used herein include vinyloxycarbonyl, allyloxycarbonyl and the others, which are not limited thereto.

Examples of the term of "aralkyloxycarbonyl group that is substituted with aryl group, said aryl group being substituted with alkoxy group having 1 to 6 carbon atoms and/or nitro groups" as used herein include benzyloxycarbonyl, 4-methoxybenzyloxycarbonyl, 3,4-dimethoxybenzyloxycarbonyl, 2-nitrobenzyloxycarbonyl, 4-nitrobenzyloxycarbonyl and the others, which are not limited thereto.

The term of "unsaturated heterocycle" as used herein encompasses an unsaturated aliphatic heterocyclic group or an aromatic heterocyclic group. The unsaturated aliphatic heterocyclic group represents an unsaturated aliphatic heterocyclic group in which at least one double bonds are contained in the ring, and one to three identical or different heteroatoms independently selected from oxygen atom, sulfur atom and nitrogen atom are contained, preferably, an unsaturated aliphatic heterocyclic group in which at least one double bonds are contained in the ring, at least one nitrogen atoms is contained, and further at least one (preferably one to two (when two or more thereof are present, they may be the identical or different from each other), particularly preferably one) heteroatoms independently selected from the group consisting of oxygen atom, sulfur atom and nitrogen atom. The unsaturated aliphatic heterocyclic group is, for example, a four to eight membered cycle, preferably a five to seven membered cycle, more preferably a five or six membered cycle, and particularly preferably a six membered cycle. Specific examples thereof include dihydropyrimidinyl, pyrrolidinyl, imidazolidinyl, pyrazolidinyl and the others, which are not limited thereto. Also, the aromatic heterocyclic group represents an aromatic heterocyclic group wherein the heterocyclic moiety contains one to three identical or different heteroatoms independently selected from the group consisting of an oxygen atom, a sulfur atom and a nitrogen atom, preferably an aromatic heterocyclic group wherein the heterocyclic moiety contains at least one nitrogen atoms, and further at least one (preferably one to two (when two or more thereof are present, they are identical or different from each other), particularly preferably one) heteroatoms selected from the group consisting of an oxygen atom, a sulfur atom and a nitrogen atom. The aromatic heterocyclic group is, for example, a four to eight membered cycle, preferably a five to seven membered cycle, more preferably a five or six membered cycle, and particularly preferably a six membered cycle. Specific examples thereof include pyrrolyl, furanyl, thienyl, pyridinyl, pyrimidinyl, pyridazinyl, and the others, which are not limited thereto. Particularly preferably, a pyrimidinyl is included. The unsaturated heterocycle may be optionally substituted with substituent(s), and examples of the substituent include a $C_{1-6}$ alkyl group which may be optionally substituted, a $C_{2-6}$ alkenyl group which may be optionally substituted, a $C_{2-6}$ alkynyl group which may be optionally substituted, an amino group which may be optionally substituted, a hydroxy group which may be optionally substituted, an oxo group, a thioxo group, and a halogen atom, and the others, which are not limited thereto.

The unsaturated heterocycle may be further fused with another cycle. Examples of the another cycle which may be fused include a saturated or unsaturated nonaromatic carbon cycle, an aromatic carbon cycle, a saturated or unsaturated nonaromatic heterocycle, and an aromatic heterocycle, preferably, an aromatic cycle or an aromatic heterocycle. The saturated carbon cycle represents an alkane forming a cycle, for example, the above-mentioned cycloalkane having 3 to 6 carbon atoms. The unsaturated nonaromatic carbon cycle represents an alkene forming a cycle, for example, the above-mentioned cyclic alkene having 3 to 6 carbon atoms. The aromatic carbon cycle (which is referred to as "aryl") encompasses, for example, a six to fourteen membered monocyclic, bicyclic, or tricyclic hydrocarbon group, and specific examples thereof include benzene, naphthalene, phenanthrene, anthracene and the other, which are not limited thereto. The saturated or unsaturated nonaromatic heterocycle represents a saturated five to fourteen monocyclic or bicyclic nonaromatic heterocycle containing one to three heteroatoms independently selected from the group consisting of an oxygen atom, a sulfur atom, and a nitrogen atom, in which at least one double bond may be contained in the ring. Specific examples thereof include azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, dihydrobenzothien, and the others, which are not limited thereto.

Also, the five to seven membered unsaturated heterocycle in "five to seven membered unsaturated heterocycle which may be optionally substituted" as "cycle A" may be a base moiety of nucleic acid in the term of "a base moiety of nucleic acid that may optionally have substituents" as used herein as long as it contains two or more nitrogen atoms and also one or more oxygen atoms are substituted. They may be a cyclic moiety derived from natural nucleic acid base or unnatural nucleic acid base, for example, purine ring derived from adenine or guanine, or derivatives thereof, or mono or di-one ring derived from uracil, cytosine or thymine, or derivatives thereof, preferably thyminyl or uracinyl, which are not limited thereto. The substituent is the same as defined in the above-mentioned unsaturated heterocycle. Preferred substituents for cyclic A include a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, which are not limited thereto.

The "cycle A'" being an unsaturated heterocycle as used herein may be fused with tetrahydrofuran ring or oxazolidine ring to form a polycyclic structure. The cycle A' is not limited to any cycle, as long as it is an unsaturated heterocycle containing two or more nitrogen atoms, however, is preferably "five to seven membered unsaturated heterocycle which may be optionally substituted". The unsaturated heterocycle may be further fused with another cycle. Examples of preferred substituents for cycle A' include a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, which are not limited thereto.

In the preparation method as described herein, when the cycle A is changed into cycle A' by a reaction with an activating agent for hydroxy group, or the fused oxazolidine ring for the cycle A' is cleaved by a reaction with a reducing agent to change into a cycle A, the structurally non-limited moiety that is connected to two nitrogen atoms are identical for the cases of cycle A and cycle A'. The cycle A is not limited to any cycle as long as it is an unsaturated heterocycle containing two or more nitrogen atom, and is preferably a five to seven membered unsaturated heterocycle which may be optionally substituted, more preferably a pyrimidine group which may be optionally substituted, and most preferably a thyminyl group or an uracinyl group. The unsaturated heterocycle may be further fused with another ring.

The "a base moiety of nucleic acid" in the term of "a base moiety of nucleic acid which may optionally have substituents" includes, for example, a base moiety of natural nucleic acid, and a base moiety of unnatural nucleic acid, which contains an aromatic heterocycle, and encompasses a monocyclic ring, a bicyclic ring, and a tricyclic ring. Here it should be clearly understood that base moieties of various nucleic acid that has been now considered "unnatural" to a skilled person in the art, could be found in nature hereafter. Thus "nucleic acid base moiety" includes not only any heterocycle contained in publicly known purine and pyrimidine, but also their heterocyclic analogues and tautomers. Specific examples of the base moiety of nucleic acid include adeninyl, guaninyl, thyminyl, cytosinyl, uracinyl, purinyl, xanthinyl, diaminopurinyl, 8-oxo-$N^6$-methyladeninyl, 7-deazaxanthinyl, 7-deazaguaninyl, $N^4,N^4$-ethanocytosinyl, $N^6,N^6$-ethano-2,6-diaminopurinyl, 5-methylcytosinyl, 5-(C3-C6)-alkynylcytosinyl, 5-fluorocytosinyl, 5-bromoanuracinyl, pseudoisocytosinyl, 2-hydroxy-5-methyl-4-triazolopyridinyl, isocytosinyl, isoguaninyl, inosinyl, $N^6$-arylpurinyl, $N^6$-acylpurinyl, $N^6$-benzylpurinyl, $N^6$-halopurinyl, $N^6$-vinylpurinyl, $N^6$-acetylenic purinyl, $N^6$-acylpurinyl, $N^6$-hydroxyalkylpurinyl, $N^6$-thioalkylpurinyl, $N^2$-alkylpurinyl, $N^6$-alkylpyrimidinyl, $N^4$-acylpyrimidinyl, $N^4$-benzylpurinyl, $N^4$-halopyrimidinyl, $N^4$-vinylpyrimidinyl, $N^4$-acetylenic pyrimidinyl, $N^4$-acetylpyrimidinyl, $N^4$-hydroxyalkylpyrimidinyl, $N^6$-thioalkylpyrimidinyl, 6-azapyrimidinyl, 6-azacytosinyl, 2- and/or 4-mercaptopyrimidinyl, uracinyl, $C^5$-alkylpyrimidinyl, $C^5$-benzylpyrimidinyl, $C^5$-halopyrimidinyl, $C^5$-vinylpyrimidinyl, $C^5$-acetylenicpyrimidinyl, $C^5$-acylpyrimidinyl, $C^5$-hydroxyalkylpurinyl, $C^5$-amidopyrimidinyl, $C^5$-cyanopyrimidinyl, $C^5$-nitropyrimidinyl, $C^5$-aminopyrimidinyl, N2-alkylpurinyl, $N^2$-alkyl-6-thiopurinyl, 5-cytidinyl, 5-azauracinyl, trazolopyridinyl, imidazolopyridinyl, pyrrolopyrimidinyl, pyrazolopyrimidinyl, and the others, which are not limited thereto. Preferred examples of the base moiety of nucleic acid include adeninyl, guaninyl, 2,6-diaminopurinyl, thyminyl, 2-thiothyminyl, cytosinyl, 5-methylcytosinyl, uracinyl, 5-fluorocytosinyl, xanthinyl, 6-aminopurinyl, 2-aminopurinyl, 6-chloro-2-aminopurinyl, and 6-chloropurinyl, and particular preferred examples of the base moiety of nucleic acid include adeninyl, guaninyl, cytosinyl, 5-methylcytosinyl, thyminyl, and uracinyl. These base moieties of nucleic acid may further have one or more substituents, and examples of the substituents include hydroxy group, $C_{1-6}$ alkoxy group, mercapto group, $C_{1-6}$ alkylthio group, amino group, amino group substituted with $C_{1-6}$ alkyl group, $C_{1-6}$ alkyl group, $C_{1-6}$ alkynyl group, oxo group, thioxo group, and halogen atom. If necessary or if desirable, the functional oxygen atom, sulfur atom and nitrogen atom on the base moiety may be protected and/or deprotected. The appropriate protecting group is well known to a skilled person in the art, and encompasses, for example, the above-mentioned protecting group for hydroxy group and protecting group for amino group, and includes diphenylaminocarbonyl group, silyl group (such as trimethylsilyl group, dimethylhexylsilyl group, t-butyldimethylsilyl group, and t-butyldiphenylsilyl group), trityl group, alkyl group, acyl group (such as acetyl group, propionyl group, isobutyryl group, benzoyl group (Bz), phenoxyacetyl group (Pac)), alkoxycarboyl group (such as t-butoxycarbonyl group (Boc), benzyloxycarbonyl group (Cbz), diphenylaminocarbonyl group (DPC), cyanoethoxycarbonyl group (Ceoc)), sulfonyl group (such as methanesulfonyl group, and p-toluenesulfonyl group), and the others, which are not limited thereto.

The term of "azide agent" as used herein represents a reagent for adding an azide group, and for example, includes, preferably hydrazoic acid, sodium azide, lithium azide, tetrabutylammonium azide (Bu$_4$NN$_3$), trimethylsilyl azide, diphenylphosphoryl azide (DPPA), nicotinyl azide, zinc azide (Zn(N$_3$)$_2$), and more preferably tetrabutylammonium azide, sodium azide, and diphenylphosphoryl azide (DPPA).

The term of "activating agent for hydroxy group" as used herein represents a reagent for increasing a leaving ability by activating a non-protected hydroxy group, and includes, for example, methanesulfonylating agent, trifluoromethansulfonylating agent, ethanesulfonylating agent, 2,2,2-trifluoroethanesulfonylating agent, propanesulfonylating agent, isopropanesulfonylating agent, butanesulfonylating agent, nonafluorobutanesulfonylating agent, heptafluoropropane-1-sulfonylating agent, pentanesulfonylating agent, pentafluoroethanesulfonylating agent, cyclopentanesulfonylating agent, hexanesulfonylating agent, cyclohexanesulfonylating agent, o-toluenesulfonylating agent, m-toluenesulfonylating agent, p-toluenesulfonylating agent, benzenesulfonylating agent, o-bromobenzenesulfonylating agent, m-bromobenzenesulfonylating agent, p-bromobenzenesulfonylating agent, o-nitrobenzenesulfonylating agent, m-nitrobenzenesulfonylating agent, and p-nitrobenzenesulfonylating agent, and specific examples thereof include methanesulfonyl chloride, methanesulfonic anhydride, trifluoromethanesulfonyl chloride, trifluoromethanesulfonic anhydride, ethanesulfonylchloride, 2,2,2-trifluoroethanesulfonylchloride, 2,2,2-trifluoroethanesulfonylfluoride, propanesulfonylchloride, propanesulfonylfluoride, isopropylsulfonylchloride, isopropylsulfonylfluoride, butanesulfonylchloride, butanesulfonylfluoride, nonafluorobutanesulfonylchloride, nonafluorobutanesulfonylfluoride, nonafluorobutane sulfonic acid anhydride, heptafluoropropane-1-sulfonylchloride, heptafluoropropane-1-sulfonylfluoride, pentanesulfonylchloride, pentanesulfonylfluoride, pentafluoroethanesulfonylchloride, pentafluoroethanesulfonylfluoride, cyclopentanesulfonylchloride, cyclopentanesulfonylfluoride, hexanesulfonylchloride, hexanesulfonylfluoride, cyclohexanesulfonylchloride, cyclohexanesulfonylfluoride, o-toluenesulfonylchloride, o-toluenesulfonylfluoride, m-toluenesulfonylchloride, m-toluenesulfonylfluoride, p-toluenesulfonylchloride, p-toluenesulfonylfluoride, benzenesulfonylchloride, benzenesulfonylfluoride, o-bromobenzenesulfonylchloride, o-bromobenzenesulfonylfluoride, m-bromobenzenesulfonylchloride, m-bromobenzenesulfonylfluoride, p-bromobenzenesulfonylchloride, p-bromobenzenesulfonylfluoride, o-nitrobenzenesulfonylchloride, o-nitrobenzenesulfonylfluoride, m-nitrobenzenesulfonylchloride, m-nitrobenzenesulfonylfluoride, p-nitrobenzenesulfonylchloride, p-nitrobenzenesulfonylfluoride, and the others, which are not limited thereto. For example, preferably, trifluoromethanesulfonyl chloride, trifluoromethanesulfonic anhydride, methanesulfonyl chloride, methanesulfonic anhydride, p-toluenesulfonyl chloride, nonafluoro-1-butanesulfonylfluoride, heptafluoropropane-1-sulfonylfluoride, 2,2,2-trifluoroethanesulfonylchloride, and pentafluoroethanesulfonylchloride are preferably included, and trifluoromethanesulfonyl chloride, trifluoromethanesulfonic anhydride, methanesulfonyl chloride, methanesulfonic anhydride, and p-toluenesulfonylchloride are more preferably included.

For example, the term of "reducing agent" as used herein includes preferably phosphines such as trialkylphosphine and triarylphosphine, metal hydrides, and transition metal catalysts in the presence of hydrogen gas, and more preferably triphenylphosphine, tributylphosphine, lithium aluminum hydride, sodium borohydride, nickel borohydride, palladium on carbon in the presence of hydrogen gas, and palladium hydroxide in the presence of hydrogen gas.

The term of "a phosphoramidite method" represents a solid-phase synthesis method of nucleic acid using nucleotide monomer, which comprises, for example, a step of coupling the 5' hydroxy group or 3' hydroxy group of a nucleotide, or the amino group of the base moiety of nucleic acid, further, for RNA, a phosphoramidite monomer in which the 2' hydroxy group is protected, with tetrazole type compounds or imidazole type compounds etc., followed by oxidative reaction or oxidative sulfuration reaction to form a phosphodiester bond. The "phosphoramidite method" as used herein is used preferably phosphoramidite monomer, which is at least one kind of bridged nucleic acid, and the bridged nucleic acid is more preferably GuNA.

The "replacement of a cyclic A with a B" represents a phenomenon in which the cycle A that binds to a sugar moiety of nucleic acid is dissociated from the sugar moiety, and is then replaced with a B, which is a base moiety of nucleic acid which may be optionally substituted with one or more substituents, (transglycosylation). Here the cycle A that binds to the sugar moiety of nucleic acid is dissociated by treating with Lewis acid, and a B binds to the sugar moiety of the nucleic acid in which the cycle A is dissociated. Examples of the Lewis acid used for dissociation include TMSOTf, and TBSOTf, which are not limited thereto. Silylating agent can be used to facilitate the transglycosylation. Examples of the silylating agent include BSA, and hexamethyldisilazane, which are not limited thereto. The transglycosylation is preferably conducted in one step.

In the transglycosylation, the B may be provided as any reactant as long as the B is in the form that can be replaced, and the reactant is preferably "nucleic acid base". Said "nucleic acid base" includes not only any heterocycle contained in publicly known purine and pyrimidine, but also their heterocyclic analogues and tautomers. Specific examples of the base moiety of nucleic acid include adenine, guanine, thymine, cytosine, uracine, purine, xanthine, diaminopurine, 8-oxo-N$^6$-methyladenine, 7-deazaxanthine, 7-deazaguanine, N$^4$,N$^4$-ethanocytosine, N$^6$,N$^6$-ethano-2,6-diaminopurine, 5-methylcytosine, 5-(C$^3$-C$^6$)-alkynylcytosine, 5-fluorocytosine, 5-bromoan uracine, pseudoisocytosine, 2-hydroxy-5-methyl-4-triazolopyridine, isocytosine, isoguanine, inosine, N$^6$-arylpurine, N$^6$-acylpurine, N$^6$-benzylpurine, N$^6$-halopurine, N$^6$-vinylpurine, N$^6$-acetylenic purine, N$^6$-acylpurine, N$^6$-hydroxyalkylpurine, N$^6$-thioalkylpurine, N$^2$-alkylpurine, N$^6$-alkylpyrimidine, N$^4$-acylpyrimidine, N$^4$-benzylpurine, N$^4$-halopyrimidine, N$^4$-vinylpyrimidine, N$^4$-acetylenic pyrimidinel, N$^4$-acetylpyrimidine, N$^4$-hydroxyalkylpyrimidine, N$^6$-thioalkylpyrimidine, 6-azapyrimidine, 6-azacytosine, 2- and/or 4-mercaptopyrimidine, uracine, C$^5$-alkylpyrimidine, C$^5$-benzylpyrimidine, C$^5$-halopyrimidine, C$^5$-vinylpyrimidine, C$^5$-acetylenicpyrimidine, C$^5$-acylpyrimidine, C$^5$-hydroxyalkylpurine, C$^5$-amidopyrimidine, C$^5$-cyanopyrimidinyl, C$^5$-nitropyrimidine, C$^5$-aminopyrimidine, N2-alkylpurine, N$^2$-alkyl-6-thiopurine, 5-cytidine, 5-azauracine, trazolopyridine, imidazolopyridine, pyrrolopyrimidine, pyrazolopyrimidine, and the others, which are not limited thereto. Preferred examples of the nucleic acid base include adenine, guanine, 2,6-diaminopurine, thymine, 2-thiothymine, cytosine, 5-methylcytosine, uracine, 5-fluorocytosine, xanthine, 6-aminopurine, 2-aminopurine, 6-chloro-2-aminopurine, and 6-chloropurine, and particular preferred examples of the base moiety of nucleic acid include adenine, guanine, cytosine, 5-methylcytosine, thymine, and uracine. These nucleic acid bases may further have one or more substituents, and examples of the substituents include hydroxy group, $C_{1-6}$ alkoxy group, mercapto group, $C_{1-6}$ alkylthio group, amino group, amino group substituted with $C_{1-6}$ alkyl group, $C_{1-6}$ alkyl group, $C_{1-6}$ alkynyl group, oxo group, thioxo group, and halogen atom. If necessary or if desirable, the functional oxygen atom, sulfur atom and nitrogen atom on the base moiety may be protected and/or deprotected. The appropriate protecting group is well known to a skilled person in the art, and encompasses, for example, the above-mentioned protecting group for hydroxy group and protecting group for amino group, and includes diphenylaminocarbonyl group, silyl group (such as trimethylsilyl group, dimethylhexylsilyl group, t-butyldimethylsilyl group, and t-butyldiphenylsilyl group), trityl group, alkyl group, acyl group (such as acetyl group, propionyl group, isobutyryl group, benzoyl group (Bz), phenoxyacetyl group (Pac)), alkoxycarboyl group (such as t-butoxycarbonyl group (Boc), benzyloxycarbonyl group (Cbz), diphenylaminocarbonyl group (DPC), cyanoethoxycarbonyl group (Ceoc)), sulfonyl group (such as methanesulfonyl group, and p-toluenesulfonyl group), and the others, which are not limited thereto. These nucleic acid bases are commercially available or can be prepared using commercially available starting materials according to organic synthesis methods.

The term of "β form" as used herein represents the a compound having a stereochemistry in which the direction of substituting the substituted base moiety of nucleic acid at 1' position of a (deoxy) ribose of nucleic acid and the direction of substituting the substituted 5'-position side chain at 4' position of a (deoxy) ribose of nucleic acid are the same direction of the substitution. For a bridged artificial nucleic acid 2',4'-LNA, the β form represents the compound having the stereo configuration in which the direction of substituting the substituted base moiety of nucleic acid at 1' position of a (deoxy) ribose of nucleic acid and the direction of substituting the substituted 5'-position side chain that is not used for bridging substituted at 4' position of (deoxy) ribose of nucleic acid are the same direction of the substitution.

The term of "α form" represents the a compound having a stereochemistry in which the direction of substituting the substituted base moiety of nucleic acid at 1' position of a ribose of nucleic acid and the direction of substituting the substituted 5'-position side chain at 4' position of a ribose of nucleic acid are the different direction of the substitution.

The term of "β selective" as used herein represents that a β form can be obtained. It means that the β form is obtained in its contents of preferably 80% or more, more preferably 90% or more, most preferably 99% or more, as opposed to the total contents of the a form and the β form as a product obtained by the transglycosylation The term of "artificial nucleic acid" as used herein encompasses artificial nucleoside, artificial nucleotide (herein, one nucleoside or nucleotide is sometimes referred to as a monomer) or artificial oligonucleotide. These artificial nucleic acids are not natural nucleic acids, but nucleic acids that can be produced only artificially. Examples of these artificial nucleic acids include those in which the nucleic acid base moiety contains an unnatural base, those having a sugar in which the sugar moiety is modified, and/or those containing an unnatural phosphate group as a phosphate moiety, and the artificial nucleic acids as used herein represents those in which the sugar moiety contains an unnatural sugar, in particular, those containing a (deoxy) ribose in which the carbon atoms at 2' position and 4' position are bridged.

The term of "artificial oligonucleotide" as used herein represents a substance in which two or more of the identical or different "artificial nucleotides" are bonded with each other via a phosphodiester bond or a thiophosphodiester bond and the like, and includes a substance in which preferably 2 up to 100, more preferably 5 up to 50, most preferably 10 up to 30 artificial nucleotides are bonded, or a substance in which the nucleotides together with these complementary strands forms a double strand. Herein, an oligonucleotide in which two or more nucleotides are bonded with each other is sometimes referred to as oligomer.

Embodiments of the preparation methods and the compounds of the present invention (including intermediate compounds) are described.

Preparation Method of Compound Represented by General Formula I

According to one aspect of the present application, the present invention provides a method for preparing a compound represented by general formula I:

[chem. 55]

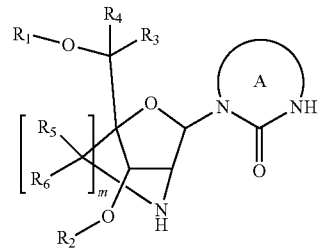

[wherein $R_1$ and $R_2$ represent independently of each other a protecting group for hydroxy group, $R_3$ and $R_4$ represent independently of each other a hydrogen atom or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a 6 alkyl group which may be optionally substituted with one or more substituents, m is an integer of 1 to 3, and a cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]
or salts thereof, said method comprising a step of reacting a compound represented by formula II:

[chem. 56]

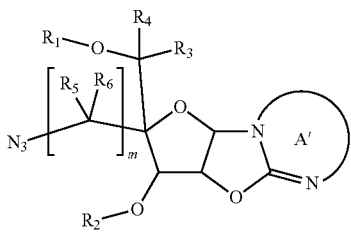

[wherein,
each of $R_1$, $R_2$, $R_3$, $R_4$, $R_5$, $R_6$ and m is the same as defined in the above-mentioned general formula I, a cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]
with a reducing agent to cleave an oxazolidine ring fused to a cycle A'.

According to one embodiment of the present application, the reducing agent is preferably phosphines, more preferably triphenylphosphine ($Ph_3P$).

According to one embodiment, a compound represented by formula I:

[chem. 57]

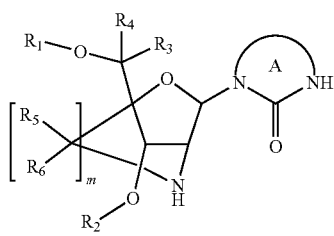

(I)

[wherein,
$R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.

Here, when m=1 or 2, and each of $R_3$, $R_4$, $R_5$ and $R_6$ represents a hydrogen atom, or
when m=1, and each of $R_3$ and $R_5$ represents a methyl group, each of $R_4$ and $R_6$ represents a hydrogen atom, cycle A is preferably not a thyminyl group.]
or salts thereof is included as a novel intermediate compound.

According to one embodiment of the present application, the compound represented by the above-mentioned general formula I, wherein $R_1$ and $R_2$ represent independently of each other a benzyl (Bn) group, a 2-naphthylmethyl group, a 4-methoxybenzyl group, a 3,4-dimethoxybenzyl group, a 2,6-dimethoxybenzyl group, or a p-phenylbenzyl group, $R_3$, $R_4$, $R_5$, and $R_6$ represent independently of each other a hydrogen atom, or a $C_{1-6}$ alkyl group which may be optionally substituted with one or more substituents, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A, or salts thereof is included.

According to one embodiment of the present application, the compound represented by general formula I or salts thereof is preferably a compound represented by general formula I-a:

[chem. 58]

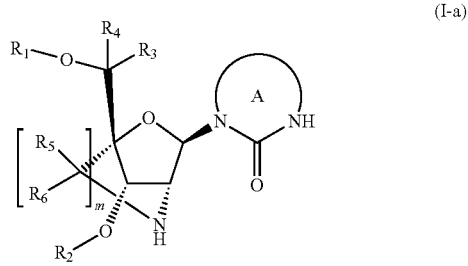

(I-a)

(wherein, $R_1$, $R_2$, $R_3$, $R_4$, $R_5$, $R_6$, m and cycle A are the same as defined in the above-mentioned formula I.

Here, when m=1 or 2, and each of $R_3$, $R_4$, $R_5$ and $R_6$ represents a hydrogen atom, or
when m=1, and each of $R_3$ and $R_5$ represents a methyl group, each of $R_4$ and $R_6$ represents a hydrogen atom, cycle A is preferably not a thyminyl group.

According to one embodiment of the present application, in the general formula I (formula I-a), when each of $R_1$ and $R_2$ represents a protecting group for hydroxy group, the protecting group for hydroxy group includes, for example, a methyl group substituted with one to three aryl group(s), and preferably a benzyl (Bn) group, a 2-naphthylmethyl group, a p-methoxybenzyl group, a 3,4-dimethoxybenzyl group, a 2,6-dimethoxybenzyl group, and a p-phenylbenzyl group, and more preferably a benzyl group.

According to one embodiment of the present application, in the general formula I (formula I-a), each of $R_3$, $R_4$, $R_5$, and $R_6$ represents independently a hydrogen atom.

According to one embodiment of the present application, in the general formula I (formula I-a), when each of $R_3$, $R_4$, $R_5$, and $R_6$ represents a $C_{1-6}$ alkyl group which may be optionally substituted with one or more substituents, the $C_{1-6}$ alkyl group is preferably methyl group, ethyl group, propyl group, isopropyl group, butyl group, isobutyl group, pentyl group, or hexyl group, more preferably methyl group. Examples of the substituents include one or more (or preferably one to three) identical or different groups selected from the group consisting of a $C_{1-6}$ alkyl group, a $C_{2-6}$ alkenyl group, a $C_{2-6}$ alkynyl group, a $C_{1-6}$ alkoxy group, an amino group, a hydroxy group, an oxo group, a thioxo group, and a halogen atom).

According to one embodiment of the present application, in the general formula I (formula I-a), the cycle A is preferably a 6 membered unsaturated heterocyclic group, and examples of the substituents of the cycle A include one or more (preferably 2 or 3) groups selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, a halogen atom, and an oxo group. The cycle A is more preferably a thyminyl group or an uracinyl group. The substituents are preferably a methyl group, a halogen atom (such as fluoro atom, chloro atom, or bromo atom).

According to one embodiment of the present application, the compound represented by general formula I or salts thereof is particular preferably the compound represented by the above-mentioned general formula I (preferably formula I-a) wherein each of $R^1$ and $R^2$ represents a Bn group, each of $R_3$, $R_4$, $R_5$, and $R_6$ represents a hydrogen atom, cycle A represents a thyminyl group or an uracinyl group, and the cycle A' represents the following structure II-1 or II-2:

[chem. 59]

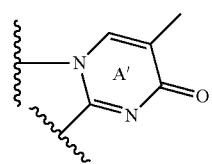
(II-1)

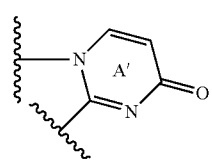
(II-2)

or salts thereof.

As used herein, a wave line:

[chem. 60]

~~~ in the structure II-1 or II-2 represents a binding point to the remaining moiety of the fused tetrahydrofuran ring or oxazolidine ring.

According to one embodiment of the present application, preferred compound represented by general formula II or salts thereof represents the compound represented by general formula II wherein $R_1$, $R_2$, $R_3$, $R_4$, $R_5$ and $R_6$ are the same as defined in the general formula I (formula I-a), and the cycle A' represents an unsaturated heterocyclic group in which the oxazolinone ring fused to the cycle A' is cleaved by the reduction step in the preparation method to form the cycle A represented by general formula I and also two or more nitrogen atoms are contained, and one or more oxygen atom is substituted, or salts thereof.

Preparation Method of Compound Represented by General Formula II

According to one aspect, the present invention provides a method for preparing a compound represented by general formula II:

[chem. 61]

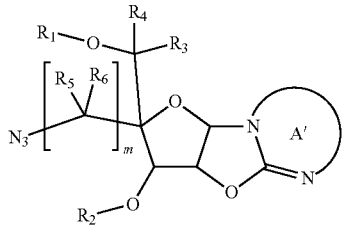
(II)

[wherein, each of $R_1$, $R_2$, $R_3$, $R_4$, $R_5$, $R_6$ and m are the same as defined in the general formula I, and the cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]

or salts thereof,
said method comprising a step of reacting a compound represented by formula III:

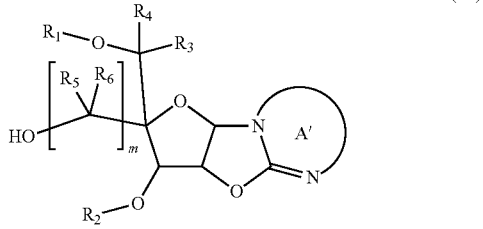

(III)

[wherein,
each of $R_1$, $R_2$, $R_3$, $R_4$, $R_5$, $R_6$, m and cycle A' are the same as defined in general formula II.]
with an azide agent.

According to one embodiment of the present application, the azide agent represents preferably hydrazoic acid, sodium azide, lithium azide, tetrabutylammonium azide, trimethylsilyl azide, diphenylphosphoryl azide (DPPA), nicotinyl azide, and zinc azide ($Zn(N_3)_2$), more preferably diphenylphosphoryl azide (DPPA).

According to one aspect, a compound represented by general formula II:

[chem. 63]

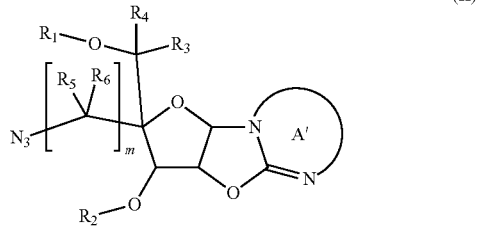

(II)

[wherein,
each of $R_1$ and $R_2$ represents independently a protecting group for hydroxy group, m is an integer of 1 to 3, $R_3$ and $R_4$ represents independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, and cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]
or salts thereof is includes as a novel intermediate compound.

According to one embodiment of the present application, the compound represented by general formula II or salts thereof is preferably a compound represented by general formula II-a:

[chem. 64]

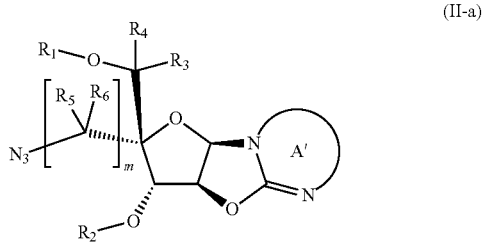

(II-a)

or salts thereof (wherein, each of $R_1$, $R_2$, $R_3$, $R_4$, $R_5$, $R_6$, m and cycle A' is the same as defined in the general formula II).

According to one embodiment of the present application, in the general formula II (formula II-a), when each of R1 and R2 represents a protecting group for hydroxy group, the protecting group for hydroxy group includes, for example, a methyl group substituted with one to three aryl groups, preferably a benzyl group, a 2-naphtylmethyl group, a 4-methoxybenzyl group, more preferably a benzyl group.

According to one embodiment of the present application, in the general formula II (general formula II-a), each of $R_3$, $R_4$, $R_5$, and $R_6$ represents independently a hydrogen atom.

According to one embodiment of the present application, in the general formula II (formula II-a), when each of $R_3$, $R_4$, $R_5$ and $R_6$ represents independently a $C_{1-6}$ alkyl group which may be optionally substituted with one or more substituents, the C1-C6 alkyl group represents preferably methyl group, ethyl group, propyl group, isopropyl group, butyl group, isobutyl group, pentyl group, or hexyl group, more preferably methyl group. Examples of the substituents include one or more (or preferably one to three) identical or different groups selected from the group consisting of a $C_{1-6}$ alkyl group, a $C_{2-6}$ alkenyl group, a $C_{2-6}$ alkynyl group, a $C_{1-6}$ alkoxy group, an amino group, a hydroxy group, an oxo group, a thioxo group, and a halogen atom.

According to one embodiment of the present application, in the general formula II (formula II-a), the cycle A' represents preferably a six membered unsaturated heterocyclic group, and further, the cycle A' represents more preferably the above-mentioned structure II-1 or II-2. The substituents of the cycle A' represents preferably one or more substituents (preferably two or three) groups selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, a halogen atom and an oxo group, and the substituent represents more preferably methyl group, or halogen atom (such as fluoro atom, chloro atom, bromo atom).

According to one embodiment of the present application, the compound represented by general formula II or salts thereof represents particularly preferably a compound represented by the above-mentioned general formula II (preferably the compound represented by general formula II-a or salts thereof, more preferably the compound represented by the above-mentioned general formula II or general formula II-a wherein the cycle A' represents the above-mentioned structure II-1 or II-2) wherein each of $R_1$ and $R_2$ represents a Bn group, each of $R_3$, $R_4$, $R_5$ and $R_6$ represents a hydrogen atom, and the cycle A' represents the following structure II-1 or II-2, or salts thereof.

According to one aspect, a compound represented by general formula III:

[chem. 65]

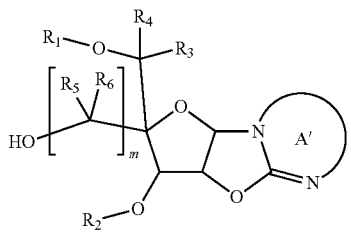
(III)

[wherein,
each of $R_1$ and $R_2$ represents independently a protecting group for hydroxy group, $R_3$ and $R_4$ represent independently of each other a hydrogen atom, or a C1-6 alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and the cycle A' represents a a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-5}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'] or salts thereof is included as intermediate compound.

According to one embodiment of the present application, the compound represented by general formula III or salts thereof represents preferably a compound represented by general formula III-a:

[chem. 66]

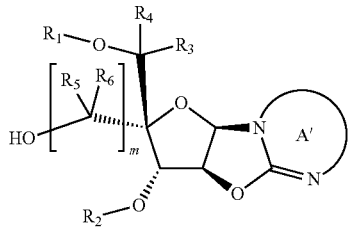
(III-a)

or salts thereof (wherein, each of $R_1$, $R_2$, $R_3$, $R_4$, $R_5$, $R_6$, m and cycle A' is the same as defined in general formula III.).

According to one embodiment of the present application, preferred compound represented by general formula III (or general formula III-a) represents the compound represented by the above-mentioned general formula III (or the above-mentioned general formula III-a) wherein each of $R_1$, $R_2$, $R_3$, $R_4$, $R_5$, $R_6$ and cycle A' is the same as defied in the above-mentioned formula II (or general formula II-a), for example, take the above-mentioned structure II-1 or II-2, or salts thereof.

Preparation Method of a Compound Represented by General Formula IV

According to one aspect, the present invention provides a method for preparing a compound represented by general formula IV:

[chem. 67]

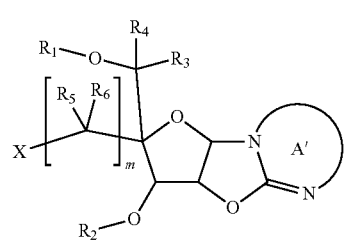
(IV)

[wherein,
each of $R_1$ and $R_2$ represents a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and the cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]

or salts thereof, said method comprising a step of reacting a compound represented by general formula V:

[chem. 68]

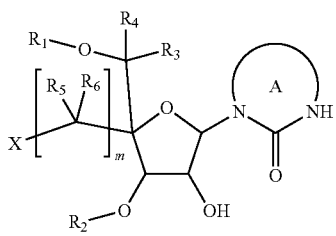

(V)

[wherein, each of $R_1$, $R_2$, $R_3$, $R_4$, $R_5$, $R_6$, m and X is the same as defined in the general formula IV, and the cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]
with an activating agent for hydroxy group to activate an unprotected hydroxy group which is substituted on tetrahydrofuran ring in the general formula V.

According to one embodiment of the present application, the activating agent for hydroxy group represents preferably trifluoromethansulfonylating agent or methanesulfonylating agent, more preferably trifluoromethanesulfonyl chloride, methanesulfonyl chloride, or trifluoromethanesulfonic anhydride, particularly preferably trifluoromethanesulfonyl chloride.

According to one aspect, a compound represented by general formula IV:

[chem. 69]

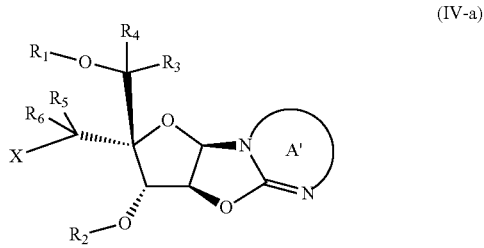

(IV)

[wherein, each of $R_1$ and $R_2$ represents independently a protecting group for hydroxy group, $R_3$ and $R_4$ represents independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A']
or salts thereof is included as intermediate compound.

According to one embodiment of the present application, the compound represented by general formula IV or salts thereof is preferably a compound represented general formula IV-a:

[chem. 70]

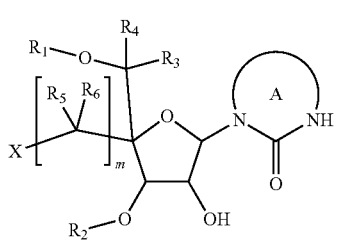

(IV-a)

(wherein, each of $R_1$, $R_2$, $R_3$, $R_4$, $R_5$, $R_6$, X, m and cycle A' is the same as defined in the general formula IV).

According to one embodiment of the present application, the compound represented by general formula IV or salts thereof is preferably a compound represented by the above-mentioned general formula IV (preferably general formula IV-a) wherein more preferably, each of $R_1$ and $R_2$ is a Bn group, each of $R_3$, $R_4$, $R_5$, and $R_6$ is a hydrogen atom, and cycle A' is the cycle A' represented by the above-mentioned structure II-1 or II-2, further preferably, cycle A' may optionally have one or substituents, and said substituents is preferably methyl group, or a halogen atom (fluoro atom, chloro atom, or bromo atom and the like).

According to one embodiment of the present application, in the general formula IV (general formula IV-a), a leaving group as X is preferably mesyloxy group (Ms-O—).

According to one aspect, a compound represented by general formula V:

[chem. 71]

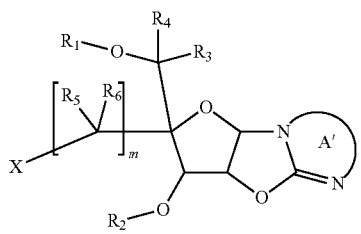

(V)

[wherein, each of $R_1$ and $R_2$ represents independently a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.] is included as a novel intermediate compound.

According to one embodiment of the present application, the compound represented by general formula V or salts thereof represents preferably a compound represented by general formula V-a:

[chem. 72]

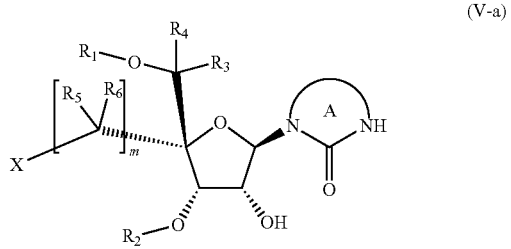

(V-a)

or salts thereof (wherein, each of $R_1$, $R_2$, $R_3$, $R_4$, $R_5$, $R_6$, X, m and cycle A is the same as defined in general formula V.).

According to one embodiment of the present application, when each of $R_1$ and $R_2$ represents independently a protecting group for hydroxy group in a general formula V (a general formula V-a), examples of $R_1$ and $R_2$ include a methyl group substituted with 1 to 3 aryl group(s), and for example, benzyl, 2-naphthylmethyl, or 4-methoxybenzyl is preferred, and benzyl is more preferred.

According to one embodiment of the present application, in a general formula V (a general formula V-a), preferably each of $R_3$, $R_4$, $R_5$ and $R_6$ represents independently a hydrogen atom.

According to one embodiment of the present application, in a general formula V (a general formula V-a), each of $R_3$, $R_4$, $R_5$ and $R_6$ represents a $C_{1-6}$ alkyl group which may be optionally substituted with one or more substituents, examples of the $C_{1-6}$ alkyl group include preferably methyl, ethyl, propyl, isopropyl, butyl, isobutyl, pentyl, and hexyl, and more preferably methyl. Example of the substituents includes one or more (preferably 1 to 3 group(s)) the identical or different groups selected from the group consisting of $C_{1-6}$ alkyl group, $C_{2-6}$ alkenyl group, $C_{2-6}$ alkynyl group, $C_{1-6}$ alkoxy group, amino group, hydroxy group, oxo group, thioxo group, and hydrogen atom.

According to one embodiment of the present application, in a general formula V (a general formula V-a), a leaving group as X group is preferably a mesyloxy group (Ms-O—).

According to one embodiment of the present application, in a general formula V (a general formula V-a), the cycle A is preferably a 6 membered unsaturated heterocycle, and the substituents of the cycle A includes, for example, one or more (preferably 2 or 3) substituents selected from the group consisting of $C_{1-6}$ alkyl group, $C_{2-6}$ alkenyl group, $C_{2-6}$ alkynyl group, halogen atom, and oxo group. The cycle A is more preferably a thymine group or an uracil group. The substituents include preferably methyl group, halogen atom (such as fluoro atom, chloro atom, or bromo atom).

According to one embodiment of the present application, the compound represented by general formula V or salts thereof is particularly preferably a compound represented by the above-mentioned general formula V (preferably a general formula V-a) wherein each of $R_1$ and $R_2$ represents a Bn group, each of $R_3$, $R_4$, $R_5$ and $R_6$ represents a hydrogen atom, and the cycle A represents a thymine group or an uracil group, or salts thereof.

Alternative Method for Preparing a Compound Represented by General Formula II

According to one embodiment of the present application, a method for preparing a compound represented by general formula II:

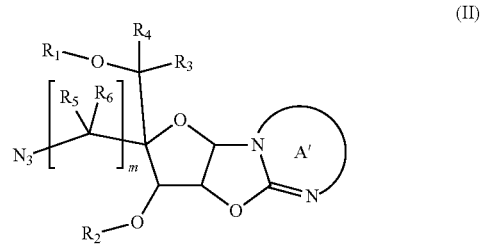

(II)

[wherein, each of $R_1$ and $R_2$ represents independently a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]

or salts thereof is provided, and the method comprising a step of reacting a compound represented by general formula IV:

[chem. 74]

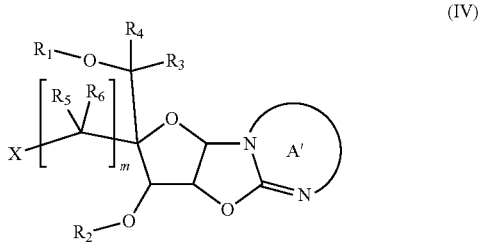

(IV)

[wherein,

X represents a leaving group, and each of $R_1$, $R_2$, $R_3$, $R_4$, $R_5$, $R_6$, m and cycle A' is the same defined in the above-mentioned general formula II]
with an azide agent.

According to one embodiment of the present application, the azide agent for the hydroxy group is preferably $nBu_4NN_3$ or sodium azide.

According to one embodiment of the present application, preferred compound represented by general formula II or salts thereof, and preferred compound represented by general formula IV or salts thereof respectively is as described elsewhere herein.

According to one embodiment of the present application, for a method for preparing the above-mentioned compound represented by general formula II or salts thereof, preferably, each of $R_1$ and $R_2$ represents a Bn group, each of $R_3$, $R_4$, $R_5$ and $R_6$ represents a hydrogen atom, X represents a mesyloxy group (Ms-O—), the cycle A' represents the above-mentioned structure formula II-1 or II-2, and the azide agent represents $nBu_4NN_3$ or sodium azide.

Further Alternative Method for Preparing a Compound Represented by General Formula II According to one aspect, a method for preparing a compound represented by general formula II:

[chem. 75]

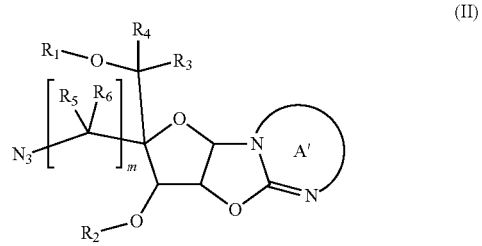

(II)

[wherein, each of $R_1$ and $R_2$ represents independently a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A' represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A'.]

or salts thereof is provided, said method comprising a step of reacting a compound represented by general formula VI:

[chem. 76]

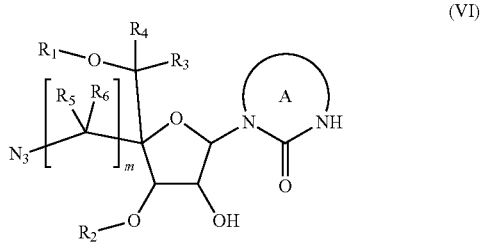

(VI)

[wherein, each of $R_1$, $R_2$, $R_3$, $R_4$, $R_5$, $R_6$ and m is the same defined in the general formula II, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]

with an activating agent for hydroxy group to activate an unprotected hydroxy group that is substituted on tetrahydrofuran ring in a general formula VI.

According to one embodiment of the present application, the activating agent for hydroxy group is preferably a trifluoromethansulfonylating agent or a methanesulfonylating agent, more preferably trifluoromethanesulfonyl chloride, methanesulfonyl chloride, or trifluoromethanesulfonic anhydride, and particularly preferably trifluoromethanesulfonyl chloride.

According to one embodiment of the present application, preferred compound represented by general formula II or salts thereof are as described elsewhere herein.

According to one embodiment of the present application, for a method for preparing a method for preparing the above-mentioned compound represented by general formula II or salts thereof, preferably, each of $R_1$ and $R_2$ represents a Bn group, each of $R_3$, $R_4$, $R_5$ and $R_6$ represents a hydrogen atom, cycle A' represents a thymine group or an uracil group, cycle A' represents the above-mentioned general formula II-1 or II-2, and the activating agent for hydroxy group represents trifluoromethanesulfonyl chloride.

According to one embodiment of the present application, preferred compound represented by general formula VI or salts thereof represents preferably a compound represented by general formula VI-a:

[chem. 77]

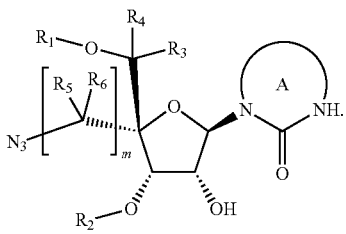

(VI-a)

According to one embodiment of the present application, preferred compound represented by general formula VI (general formula VI-a) or salts thereof represents a compound represented by general formula VI wherein each of $R_1$ and $R_2$ represents a Bn group, each of $R_3$, $R_4$, $R_5$ and $R_6$ represents a hydrogen atom, and cycle A represents a thymine group or an uracil group.]
or salts thereof.

According to one embodiment of the present application, preferred compound represented by general formula II or salts thereof is described elsewhere herein.

Method for Preparing a Compound Represented by General Formula VIII

According to one aspect, a method for preparing a compound represented by general formula VIII:

[chem. 78]

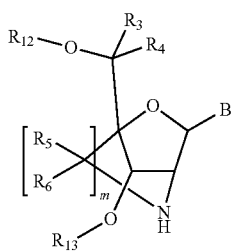

(VIII)

[wherein,
B represents a base moiety of nucleic acid that may be optionally substituted with one or more substituents, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_{12}$ and $R_{13}$ represent independently of each other a hydrogen atom or a protecting group for hydroxy group, and m is an integer of 1 to 3.]
or salts thereof is provided, said method comprising a step of replacing a cycle A in a compound represented by general formula IX:

[chem. 79]

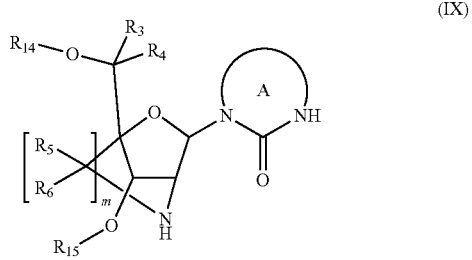

(IX)

[wherein,
each of $R_3$, $R_4$, $R_5$, $R_6$ and m is the same as defined in general formula VIII, and $R_{14}$ and $R_{15}$ represent independently of each other a hydrogen atom or a protecting group for hydroxy group, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.]
wth B.

According to one embodiment of the present application, Lewis acid for use in the replacement reaction of cycle A (transglycosylation) is preferably TMSOTf. Also, in order to facilitate the replacement reaction, a silylating agent may be used, and the silylating agent is preferably BSA.

According to one aspect, a compound represented by general formula VIII:

[chem. 80]

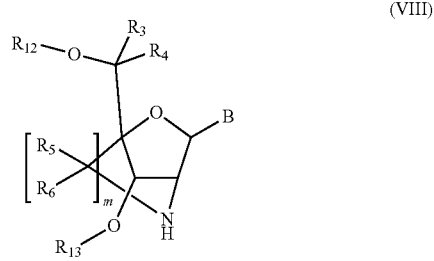

(VIII)

[wherein,
B represents a base moiety of nucleic acid that may be optionally substituted with one or more substituents, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, and $R_{12}$ and $R_{13}$ represent independently of each other a hydrogen atom or a protecting group for hydroxy group, and m is an integer of 1 to 3.

Here, when m=1 or 2, and each of $R_3$, $R_4$, $R_5$ and $R_6$ represents a hydrogen atom, or when m=1, and each of $R_3$ and $R_4$ represents a methyl group, and each of $R_4$ and $R_5$ represent a hydrogen atom, the cycle A is not preferably a thyminyl group.] or salts thereof is included as a novel intermediate compound.

According to one embodiment of the present application, a compound represented by general formula VIII or salts thereof is preferably a compound represented by general formula VIII-a:

[chem. 81]

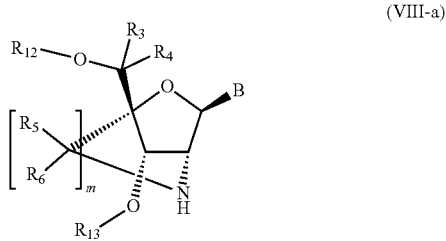

(VIII-a)

or salts thereof.

Here, when m=1 or 2, and each of $R_3$, $R_4$, $R_5$ and $R_6$ represents a hydrogen atom, or when m=1, and each of $R_3$ and $R_4$ represents a methyl group, and each of $R_4$ and $R_5$ represent a hydrogen atom, the cycle A is not preferably a thyminyl group.

According to one embodiment of the present application, a compound represented by a general formula VIII (a general formula VIII-a) wherein B represents a base moiety of nucleic acid that may be optionally substituted with one or more substituents, $R_3$, $R_4$, $R_5$, and $R_6$ represent independently of each other a hydrogen atom or a $C_{1-6}$ alkyl group which may be optionally substituted with one or more substituents, $R_{12}$ represents a Bn group, a DMTr group, or a TMS group, and $R_{13}$ represents a Bn group, a hydrogen atom, or a TMS group, or salts thereof is included.

According to one embodiment of the present application, in general formula VIII (general formula VIII-a), each of $R_3$, $R_4$, $R_5$ and $R_6$ represents independently a hydrogen atom.

According to one embodiment of the present application, in the general formula VIII (formula VIII-a), when each of $R_3$, $R_4$, $R_5$, and $R_6$ represents a $C_{1-6}$ alkyl group which may be optionally substituted with one or more substituents, the $C_{1-6}$ alkyl group represents preferably methyl group, ethyl group, propyl group, isopropyl group, butyl group, isobutyl group, pentyl group, or hexyl group, more preferably methyl group. Examples of the substituents include one or more (or preferably one to three) identical or different groups selected from the group consisting of $C_{1-6}$ alkyl group, $C_{2-6}$ alkenyl group, $C_{2-6}$ alkynyl group, $C_{1-6}$ alkoxy group, amino group, hydroxy group, oxo group, thioxo group, and halogen atom.

According to one embodiment of the present application, in the general formula VIII (formula VIII-a), B represents a base moiety of nucleic acid, preferably a base moiety of natural nucleic acid or a base moiety of unnatural nucleic acid, more preferably a purine ring derived from adenine or guanine or derivatives thereof, or a mono- or di-one ring of pyrimidine derived from uracil, cytosine or thymine or derivatives thereof, particularly preferably adeninyl, guaninyl, cytosinyl, 5-methylcytosinyl, thyminyl or uracinyl. The base moiety of the nucleic acid may optionally have one or more substituents, and the preferred substituents represent preferably hydroxy group, $C_{1-6}$ alkoxy group, mercapto group, $C_{1-6}$ alkylthio group, amino group, amino group substituted with $C_{1-6}$ alkyl group, $C_{1-6}$ alkyl group, $C_{2-6}$ alkenyl group, $C_{2-6}$ alkynyl group, oxo group, thioxo group, or halogen atom, more preferably one or more (preferably two or three) substituents selected from the group consisting of $C_{1-6}$ alkyl group, and oxo group. The base moiety of the nucleic acid may optionally have one or more substituents, and examples of the preferred substituents represents preferably hydroxy group, $C_{1-6}$ alkoxy group, mercapto group, $C_{1-6}$ alkylthio group, amino group, amino group substituted with $C_{1-6}$ alkyl group, $C_{1-6}$ alkyl group, $C_{2-6}$ alkenyl group, $C_{2-6}$ alkynyl group, oxo group, thioxo group, and halogen atom, more preferably one or more (preferably two or three) substituents selected from the group consisting of $C_{1-6}$ alkyl group and oxo group. The hydroxy group, amino group or thiol group of the base moiety of nucleic acid may be optionally protected, and the protecting group represents preferably a protecting group for hydroxy group or a protecting group for amino group, each of which is usually used in nucleic acid synthesis, more preferably acetyl group, phenoxyacetyl group, isobutyryl group, benzoyl group, cyanoethoxycarbonyl group, or diphenylaminocarbonyl group, particularly preferably isobutyryl group, benzoyl group, or diphenylaminocarbonyl group.

According to one embodiment of the present application, the compound represented by general formula VIII or salts thereof represents particularly preferably the compound represented by the above-mentioned general formula VIII (preferably a general formula VIII-a) wherein B represents an adeninyl group which may be optionally substituted with one or more substituents, a guaninyl group which may be optionally substituted with one or more substituents, a cytosinyl group which may be optionally substituted with one or more substituents, or a 5-methylcytosinyl group which may be optionally substituted with one or more substituents, or a thyminyl group which may be optionally substituted with one or more substituents, or an uracinyl group which may be optionally substituted with one or more substituents, each of $R_3$, $R_4$, $R_5$, and $R_6$ represents a hydrogen atom, and each of $R_{12}$ and $R_{13}$ represents a Bn group, or salts thereof.

According to one embodiment of the present application, the compound represented by general formula VIII or salts thereof represents particularly preferably the compound represented by the above-mentioned general formula VIII (preferably, a general formula VIII-a) wherein B represents an adeninyl group which may be optionally substituted with one or more substituents, a guaninyl group which may be optionally substituted with one or more substituents, a cytosinyl group which may be optionally substituted with one or more substituents, a 5-methylcytosinyl group which may be optionally substituted with one or more substituents, a thyminyl group which may be optionally substituted with one or more substituents, or an uracinyl group which may be optionally substituted with one or more substituents, each of $R_3$, $R_4$, $R_5$, and $R_6$ represents a hydrogen atom, $R_{12}$ represents a DMTr group, and $R_{13}$ represents a hydrogen atom, or salts thereof.

According to one aspect, a compound represented by general formula IX:

[chem. 82]

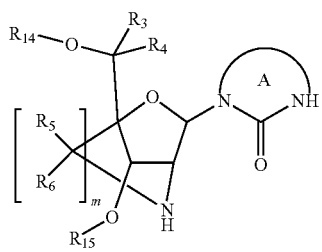

(IX)

[wherein, each of $R_3$, $R_4$, $R_5$, and $R_6$ is the same as defined in the general formula VIII, $R_{14}$ and $R_{15}$ represent independently of each other a hydrogen atom, or a protecting group for hydroxy group, m is an integer of 1 to 3, and cycle A represents a five to seven membered unsaturated heterocyclic group which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, and the unsaturated heterocyclic group may be further fused with another cycle to form a cycle A.

Here, when m=1 or 2, and each of $R_3$, $R_4$, $R_5$ and $R_6$ represents a hydrogen atom, or when m=1, and each of $R_3$ and $R_5$ represents a methyl group, each of $R_4$ and $R_6$ represents a hydrogen atom, cycle A is preferably not a thyminyl group.]
or salts thereof is included as a novel intermediate compound.

According to one embodiment of the present application, the compound represented by general formula IX or salts thereof represents preferably a compound represented by general formula IX-a:

[chem. 83]

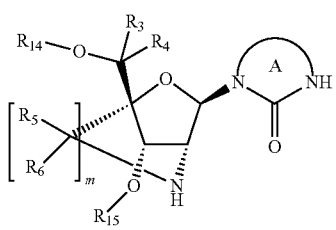

(IX-a)

or salts thereof (wherein, each of $R_3$, $R_4$, $R_5$, $R_6$, $R_{14}$, $R_{15}$, m and cycle A is the same as defined in the general formula IX. Here when m=1 or 2, and each of $R_3$, $R_4$, $R_5$ and $R_6$ represents a hydrogen atom, or when m=1, and each of $R_3$ and $R_5$ represents a methyl group, each of $R_4$ and $R_6$ represents a hydrogen atom, cycle A is preferably not a thyminyl group.)

According to one embodiment of the present application, in the general formula IX (a general formula IX-a), each of $R_3$, $R_4$, $R_5$, and $R_6$ is the same as defined in the general formula VIII (a general formula VIII-a).

According to one embodiment of the present application, in the general formula IX (a general formula IX-a), when $R_{15}$ represents a protecting group for hydroxy group, the protecting group for hydroxy group is preferably the same as defined in the general formula I.

According to one embodiment of the present application, in the general formula IX (a general formula IX-a), the cycle A represents preferably a pyrimidine base moiety of nucleic acid which may be optionally substituted with one or more (preferably two or three) substituents selected from the group consisting of $C_{1-6}$ alkyl group and oxo group.

According to one embodiment of the present application, the compound represented by general formula IX or salts thereof represents particularly preferably a compound represented by general formula IX (a general formula IX-a) wherein B represents an adeninyl group which may be optionally substituted with one or more substituents, a guaninyl group which may be optionally substituted with one or more substituents, a cytosinyl group which may be optionally substituted with one or more substituents, a 5-methylcytosinyl group which may be optionally substituted with one or more substituents, a thyminyl group which may be optionally substituted with one or more substituents, or an uracinyl group which may be optionally substituted with one or more substituents, each of $R_{14}$ and $R_{15}$ represents a Bn group, and the cycle A represents a thyminyl group or an uracinyl group, or salts thereof.

According to one embodiment of the present application, the compound represented by general formula IX or salts thereof represents particularly preferably a compound represented by general formula IX (a general formula IX-a) wherein B represents an adeninyl group which may be optionally substituted with one or more substituents, a guaninyl group which may be optionally substituted with one or more substituents, a cytocinyl group which may be optionally substituted with one or more substituents, a 5-methylcytosinyl group, a thyminyl group which may be optionally substituted with one or more substituents, or an uracinyl group which may be optionally substituted with one or more substituents, $R_{14}$ represents a DMTr group, $R_{15}$ represents a hydrogen atom, and the cycle A represents a thyminyl group or a uracinyl group, or salts thereof.

According to one embodiment of the present application, the compound represented by general formula IX or salts thereof represents particularly preferably a compound represented by general formula IX (a general formula IX-a) wherein B represents an adeninyl group which may be optionally substituted with one or more substituents, a guaninyl group which may be optionally substituted with one or more substituents, a cytocinyl group which may be optionally substituted with one or more substituents, a 5-methylcytosinyl group, a thyminyl group which may be optionally substituted with one or more substituents, or an uracinyl group which may be optionally substituted with one or more substituents, $R^{14}$ represents a hydrogen atom, $R_{15}$ represents a hydrogen atom, and the cycle A represents a thyminyl group or an uracinyl group, or salts thereof.

Method for preparing a compound represented by general formula VII

According to one aspect, a compound represented by general formula VII:

[chem. 84]

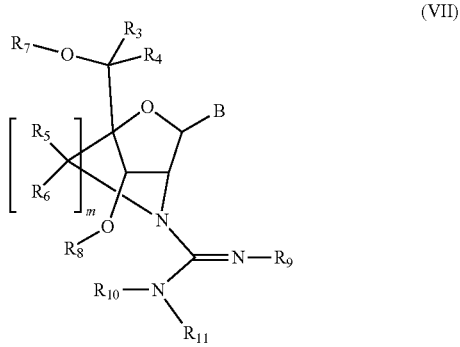

(VII)

[wherein,

B represents a base moiety of nucleic acid that may be optionally substituted with one or more substituents, $R_3$, $R_4$, $R_5$, and $R_6$ represent independently of each other a hydrogen atom, or a $C_{1-6}$ alkyl group which may be optionally substituted with one or more substituents, $R_7$ represents a hydrogen atom or a protecting group for hydroxy group, $R_8$ represents a hydrogen atom, a phosphate group which may be optionally substituted with one or more substituents, or a thiophosphate group which may be optionally substituted with one or more substituents, $R_9$, $R_{10}$ and $R_{11}$ represent independently of each other a hydrogen atom, a $C_{1-6}$ alkyl group which may be optionally substituted with one or more substituents, or a protecting group for amino group, and m is an integer of 1 to 3. (with the proviso that the following cases are excluded:

the case where m is 1, B represents a thyminyl group, each of $R_3$, $R_4$, $R_5$ and $R_6$ represents a hydrogen atom, $R_7$ represents a DMTr group, $R_8$ represents a hydrogen atom or a —P(O(CH$_2$)$_2$CN)(N(iPr)$_2$) group, $R_9$ represents a Boc group, $R_{10}$ represents a Boc group, and $R_{11}$ represents a hydrogen atom, and the case where m is 2, B represents a thyminyl group, each of $R_3$, $R_4$, $R_5$ and $R_6$ represents a hydrogen atom, $R_7$ represents a DMTr group, $R_8$ represents a hydrogen atom or a —P(O(CH$_2$)$_2$CN)(N(iPr)$_2$) group, $R_9$ represents a Ceoc group, $R_{10}$ represents a Ceoc group, and $R_{11}$ represents a hydrogen atom.)]

is included as a novel compound.

According to one embodiment of the present application, the compound represented by general formula VII or salts thereof represents preferably a compound represented by general formula VII-a:

[chem. 85]

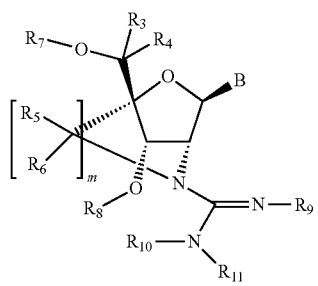

(VII-a)

or salts thereof (wherein, each of B, $R_3$, $R_4$, $R_5$, $R_6$, $R_7$, $R_8$, $R_9$, $R_{10}$, $R_{11}$, and m is the same as defined in general formula VII.).

In the proviso of the general formula VII, the exclusion of the case where B represents a thyminyl group, each of $R_3$, $R_4$, $R_5$ and $R_6$ represents a hydrogen atom, $R_7$ represents a DMTr group, $R_8$ represents a hydrogen atom or —P(O(CH$_2$)$_2$ CN)(N(iPr)$_2$), $R_9$ represents a Boc group, $R_{10}$ represents a Boc group, and $R_{11}$ represents a hydrogen atom is intended to exclude the publicly known compounds described in WO 2014/046212.

According to one embodiment of the present application, in the general formula VII (a general formula VII-a), more preferably, each of $R_3$, $R_4$, $R_5$, and $R_6$ represents independently a hydrogen atom.

According to one embodiment of the present application, in the general formula VII (a general formula VII-a), when each of $R_3$, $R_4$, $R_5$ and $R_6$ represents a $C_{1-6}$ alkyl group which may be optionally substituted with one or more substituents, the $C_{1-6}$ alkyl group represents preferably methyl group, ethyl group, propyl group, isopropyl group, butyl group, isobutyl group, pentyl group, or hexyl group, more preferably methyl group. Examples of the substituents include one or more (or preferably one to three) identical or different groups selected from the group consisting of $C_{1-6}$ alkyl group, $C_{2-6}$ alkenyl group, $C_{2-6}$ alkynyl group, $C_{1-6}$ alkoxy group, amino group, hydroxy group, oxo group, thioxo group, and halogen atom.

According to one embodiment of the present application, in the general formula VII (a general formula VII-a), $R_7$ represents a protecting group for hydroxy group, more preferably trityl type of protecting group, particularly preferably a DMTr.

According to one embodiment of the present application, in the general formula VII (a general formula VII-a), when the compound or salts thereof represents phosphoramidite, $R_8$ represents preferably a formula: —P(O(CH$_2$)$_2$CN)(N(iPr)$_2$).

According to one embodiment of the present application, in the general formula VII (a general formula VII-a), preferably, each of $R_9$ and $R_{10}$ represents a protecting group for amino group, $R_{11}$ represents a hydrogen atom, and more preferably, the protecting group for amino group represents a Teoc group or a Boc group.

According to one embodiment of the present application, in the general formula VII (a general formula VII-a), B represents a base moiety of nucleic acid that may be optionally substituted with one or more substituents, and the preferred substituents represents preferably a hydroxy group, $C_{1-6}$ alkoxy group, mercapto group, $C_{1-6}$ alkylthio group, amino group, amino group substituted with $C_{1-6}$ alkyl group, $C_{1-6}$ alkyl group, $C_{2-6}$ alkenyl group, $C_{2-6}$ alkynyl group, oxo group, thioxo group, halogen atom, more preferably one or more (preferably two or three) substituents selected from the group consisting of $C_{1-6}$ alkyl group and oxo group. The hydroxy group, amino group or thiol group of the base moiety of nucleic acid may be optionally protected, and examples of the protecting group include preferably a protecting group for hydroxy group and a protecting group for amino group, each of which is usually used in a nucleic acid synthesis, more preferably acetyl group, phenoxyacetyl group, isobutyryl group, benzoyl group, cyanoethoxycarbonyl group, and diphenylaminocarbonyl group, more preferably cyanoethoxycarbonyl group and diphenylaminocarbonyl group, and particularly preferably isobutyryl group, benzoyl group, and diphenylaminocarbonyl group. More preferred embodiment of B includes adeninyl, guaninyl, cytosinyl, 5-methylcytosinyl, thyminyl or uracinyl, each of which may optionally have a protecting group.

According to one embodiment of the present application, the compound represented by general formula VII or salts thereof represents preferably a compound represented by general formula VII (a general formula VII-a) wherein B represents an adeninyl which may optionally have one or more protecting groups, a guaninyl which may optionally have one or more protecting groups, a cytosinyl which may optionally have one or more protecting groups, a 5-methylcytosinyl which may optionally have one or more protecting groups, or an uracil which may optionally have one or more protecting groups, each of $R_3$, $R_4$, $R_5$, and $R_6$ represents a hydrogen atom, $R_7$ represents a DMTr group, $R_3$ represents a hydrogen atom or —P(O(CH$_2$)$_2$CN)(N(iPr)$_2$), $R_9$ represents a Teoc group or a Boc group, $R_{10}$ represents a Teoc group or a Boc group, and $R_{11}$ represents a hydrogen atom.

According to one embodiment of the present application, the general formula VII represents preferably a compound represented by general formula VII (general formula VII-a) wherein B represents an adeninyl which may optionally have one or more protecting groups, a guaninyl which may optionally have one or more protecting groups, a cytosinyl which may optionally have one or more protecting groups, a 5-methylcytosinyl which may optionally have one or more protecting groups, or an uracil which may optionally have one or more protecting groups, each of $R_3$, $R_4$, $R_5$ and $R_6$ represents a hydrogen atom, $R_7$ represents DMTr group, $R_8$ represents a hydrogen atom or —P(O(CH$_2$)$_2$CN)(N(iPr)$_2$), $R_9$ represents Teoc group, $R_{10}$ represents Teoc group, and $R_{11}$ represents a hydrogen atom, or salts thereof.

According to one embodiment of the present application, the method for preparing the compound represented by general formula VII or salts thereof may comprise at least one step of the followings among the steps described herein.

According to one embodiment of the present application, the method for preparing the compound represented by general formula VII or salts thereof comprises the step of reacting the compound represented by general formula II with a reducing agent to prepare the compound represented by general formula I or salts thereof.

According to one embodiment of the present application, the method for preparing the compound represented by general formula VII or salts thereof comprises a step of reacting the compound represented by general formula III with an azide agent to prepare the compound represented by general formula II or salts thereof.

According to one embodiment of the present application, the method for preparing the compound represented by general formula VII or salts thereof comprises a step of reacting the compound represented by general formula V with an activating agent for hydroxy group to activate an unprotected hydroxy group which is substituted on tetrahydrofuran ring in the general formula V to prepare the compound represented by general formula IV or salts thereof.

According to one embodiment of the present application, the method for preparing the compound represented by general formula VII or salts thereof comprises a step of reacting the compound represented by general formula IV with an azide agent to prepare the compound represented by general formula II or salts thereof.

According to one embodiment of the present application, the method for preparing the compound represented by general formula VII or salts thereof comprises a step of reacting the compound represented by general formula VI with an activating agent for hydroxy group to activate an unprotected hydroxy group which is substituted on tetrahydrofuran ring in the general formula VI to prepare the compound represented by general formula II or salts thereof.

According to one embodiment of the present application, the method for preparing the compound represented by general formula VII or salts thereof comprises a step of replacing the cycle A in the compound represented by general formula IX with B to prepare the compound represented by general formula VIII or salts thereof.

Method for Preparing Artificial Oligonucleotide Represented by General Formula X According to one aspect, a method for preparing an oligonucleotide containing one or more nucleosides represented by general formula X:

[chem. 86]

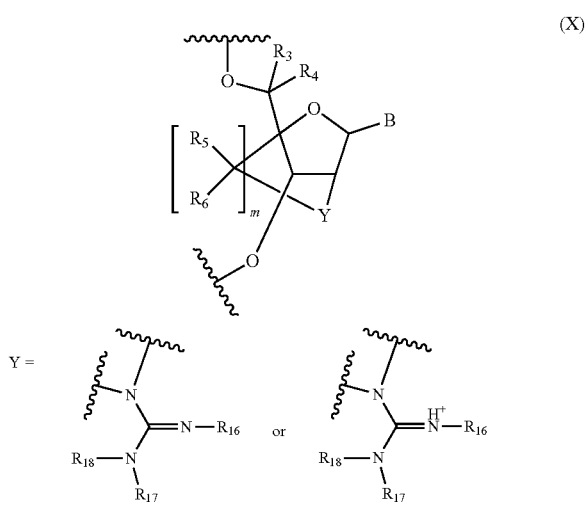

(X)

[wherein, $R_3$, $R_4$, $R_5$, and $R_6$ represent independently of each other a hydrogen atom, or a $C_{1-6}$ alkyl group which may be optionally substituted with one or more substituents, B represents a base moiety of nucleic acid that may be optionally substituted with one or more substituents, $R_{16}$, $R_{17}$ and $R_{18}$ represent independently of each other a hydrogen atom, a $C_{1-6}$ alkyl group which may be optionally substituted with one or more substituents, or a protecting group for amino group, and m is an integer of 1 to 3.]

(with the proviso that when m=1 or 2, the oligonucleotide containing as a bridged nucleic acid only the nucleoside wherein B represents a thyminyl group, each of $R_3$, $R_4$, $R_5$, $R_6$, $R_{16}$, $R_{17}$ and $R_{18}$ represents a hydrogen atom, is excluded), is provided, said method comprising a preparation of the same by a phosphoramidite method from a compound represented by general formula XI:

[chem. 87]

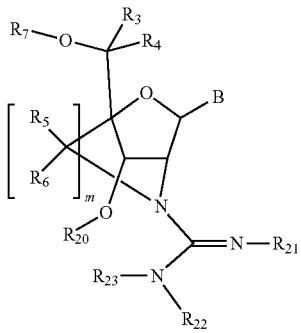

(XI)

[wherein,
each of B, $R_3$, $R_4$, $R_5$, $R_5$, and m is the same as defined in general formula X, $R_7$ represents a hydrogen atom or a protecting group for hydroxy group, $R_{20}$ represents a phosphate group which may be optionally substituted with one or more substituents or a thiophosphate group which may be optionally substituted with one or more substituents, and $R_{21}$, $R_{22}$ and $R_{23}$ represent independently of each other a hydrogen atom, a $C_{1-6}$ alkyl group which may be optionally substituted with one or more substituents, or a protecting group for amino group.].

According to one embodiment of the present application, the phosphoramidite method is preferably conducted according to the method described in WO 2014/046212 A1.

According to one embodiment of the present application, for the preparation method of the oligonucleotide represented by the above-mentioned general formula X, in general formula X or general formula XI, preferably, B represents an adeninyl which may optionally have one or more protecting groups, a guaninyl which may optionally have one or more protecting groups, a cytosinyl which may optionally have one or more protecting groups, a 5-methylcytosinyl which may optionally have one or more protecting groups or an uracinyl which may optionally have one or more protecting groups, $R_7$ represents a protecting group for hydroxy group, each of $R_{16}$, $R_{17}$ and $R_{18}$ represents a hydrogen atom, $R_{20}$ represents —P(O(CH$_2$)$_2$CN)(N(iPr)$_2$), and each of $R_{21}$, $R_{22}$ and $R_{23}$ represents independently a protecting group for amino group.].

According to one aspect, the present invention provides a novel GuNA oligonucleotide or salts thereof, and according to one embodiment of the present application, the present invention provides an oligonucleotide containing one or more nucleosides represented by general formula X:

[chem. 88]

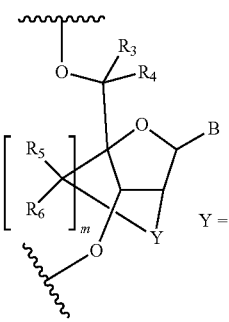

(X)

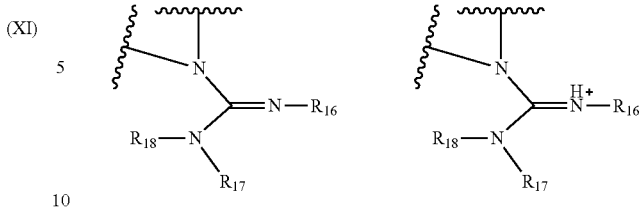

[wherein,
$R_3$, $R_4$, $R_5$, and $R_6$ represent independently of each other a hydrogen atom, or a $C_{1-6}$ alkyl group which may be optionally substituted with one or more substituents, B represents a base moiety of nucleic acid that may be optionally substituted with one or more substituents, $R_{16}$, $R_{17}$ and $R_{18}$ represent independently of each other a hydrogen atom, a $C_{1-6}$ alkyl group which may be optionally substituted with one or more substituents, or a protecting group for amino group, and m is an integer of 1 to 3.]
(with the proviso that the oligonucleotide containing as a bridged nucleic acid only the nucleoside wherein when m=1 or 2, B represents a thyminyl group, each of $R_3$, $R_4$, $R_5$, $R_6$, $R_{16}$, $R_{17}$ and $R_{18}$ represents a hydrogen atom, is excluded), or salts thereof.

According to one embodiment of the present application, the compound represented by general formula X or salts thereof represents preferably an oligonucleotide containing one or more nucleosides represented by general formula X-a:

[chem. 89]

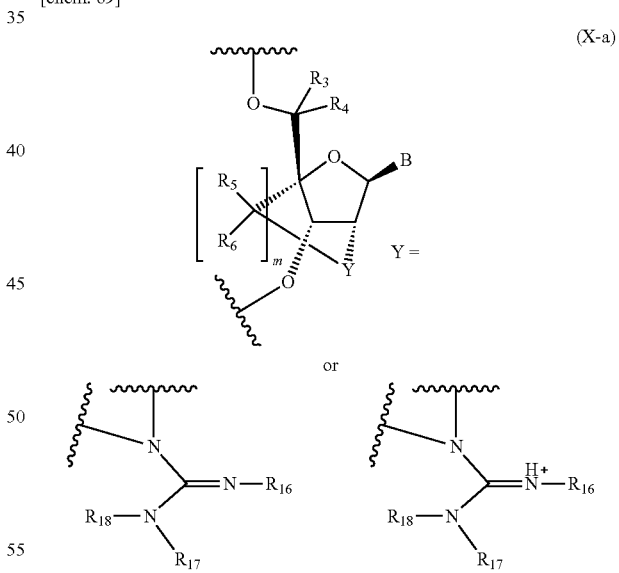

or salts thereof.

According to one embodiment of the present application, in the general formula X (a general formula X-a), each of $R_3$, $R_4$, $R_5$ and $R_6$ represents a hydrogen atom.

According to one embodiment of the present application, in the general formula X (a general formula X-a), when each of $R_3$, $R_4$, $R_5$ and $R_6$ represents a $C_{1-6}$ alkyl group which may be optionally substituted with one or more substituents, the $C_{1-6}$ alkyl group represents preferably methyl group, ethyl group, propyl group, isopropyl group, butyl group, isobutyl group, pentyl group, or hexyl group, more preferably methyl group. Examples of the substituents include one or more (or preferably one to three) groups selected from the group consisting of $C_{1-6}$ alkyl group, $C_{2-6}$ alkenyl group, $C_{2-6}$ alkynyl group, $C_{1-6}$ alkoxy group, amino group, hydroxy group, oxo group, thioxo group, and halogen atom.

According to one embodiment of the present application, in the general formula X (a general formula X-a), each of $R_{16}$, $R_{17}$ and $R_{18}$ represents independently a hydrogen atom.

According to one embodiment of the present application, in the general formula X (a general formula X-a), when each of $R_{16}$, $R_{17}$ and $R_{18}$ represents a $C_{1-6}$ alkyl group which may be branched chain or may be formed to a cycle, and said $C_{1-6}$ alkyl group may be optionally substituted with one or more substituents, the $C_{1-6}$ alkyl group represents preferably methyl group, ethyl group, propyl group, isopropyl group, butyl group, isobutyl group, pentyl group, or hexyl group, more preferably methyl group. Examples of the substituents include one or more (or preferably one to three) identical or different groups selected from the group consisting of $C_{1-6}$ alkyl group, $C_{2-6}$ alkenyl group, $C_{2-6}$ alkynyl group, $C_{1-6}$ alkoxy group, amino group, hydroxy group, an oxo group, a thioxo group, and a halogen atom.

According to one embodiment of the present application, oligonucleotide wherein in the general formula X (the general formula X-a), B represents adeninyl group, guaninyl group, cytosinyl group, 5-methylcytosinyl group, thyminyl group or uracinyl group, and each of $R_{15}$, $R_{17}$ and $R_{18}$ represent a hydrogen atom, or salts thereof is preferred.

According to one embodiment of the present application, the oligonucleotide or salts thereof is made by binding two or more the nucleotides continuously or discontinuously, and preferably contains 2 to 100 nucleotides, more preferably 5 to 50 nucleotides, and particularly preferably those in which 10 to 30 artificial nucleotides are bonded or are combined together with these complementary strands forms a double strand. When the nucleotides are bonded discontinuously, the nucleotide(s) which is/are positioned between the nucleotides is/are not particularly limited, and the nucleotide(s) is/are preferably natural nucleotide(s) without bridged structure.

The term of "salt" in the expression of "salts of compound" used herein includes alkali metal salts such as sodium salt, potassium salt, lithium salt; alkaline earth metal salts such as calcium salt, and magnesium salts; metal salts such as aluminium salt, iron salt, zinc salt, copper salt, nickel salt, and cobalt salt; inorganic salts such as ammonium salt; amine salts, for example, organic salts such as t-octylamine salt, dibenzylamine salt, morpholine salt, glucosamine salt, phenylglysine alkylester salt, etylenediamine salt, N-methylglucamine salt, guanidine salt, diethylamine salt, triethylamine salt, dicyclohexylamine salt, N,N'-dibenzyletylenediamine salt, chloroprocaine salt, procaine salt, diethanolamine salt, N-benzyl phenethylamine salt, piperazine salt, tetramethylammonium salt, and tris(hydroxymethyl)aminomethane salt; inorganic acid salts, for example, hydrohalic acids (such as hydrofluoric acid, hydrochloric acid, hydrobromic acid, and hydroiodic acid), nitrate salt, perchloric acid salt, sulfate salt, and phosphate salt; salts of alkanesulfonic acid having one to six carbon atoms, such as methanesulfonate salt, trifluoro methanesulfonate salt, ethanesulfonate salt; arylsulfonic acid salts such as benzene sulfonate salt, and p-toluene sulfonate salt; organic acid salts such as acetate salt, malate salt, fumarate salt, succinate salt, citrate salt, tartrate salt, oxalate salt, and maleate salt; and amino acid salts such as glycine salt, lysine salt, arginine salt, ornithine salt, glutamic acid salt, and aspartic acid salt, which should not be limited thereto. The salts are encompassed by pharmaceutically acceptable salts.

Each compound represented by general formulae I to XI respectively described herein encompasses enantiomer form, diastereomer form, or mixtures thereof. For example, a stereo configuration of sugar moiety in the structure of each compound encompasses α form and β form, however, β form is preferred. When the above-mentioned compounds represented by formula I to XI is obtained in the form of diastereomer or enantiomer, they can be separated by well-known methods in organic synthesis (for example, sugar synthesis), such as chromatography method or fractional crystallization method. For example, the compound 16a represented by the following formula:

[chem. 90]

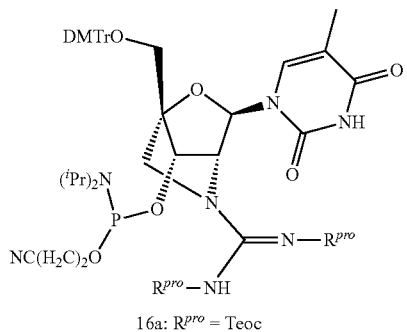

16a: $R^{pro}$ = Teoc has β form as a stereo configuration of sugar moiety.

Each compound represented by general formulae I to XI described herein compases the compounds labeled with isotopes (such as $^3H$, $^{13}C$, $^{14}C$, $^{15}N$, $^{18}F$, $^{32}P$, $^{35}S$ or $^{125}I$) and deuterated transformers.

The oligonucleotide or analogues thereof described herein may be mixed with auxiliary agents that are usually used in the formulation of pharmaceuticals, such as excipients, binders, preservatives, antioxidants, disintegrants, lubricants, and flavors, to make parenterally-administered formulation or liposome formulations. Also, the oligonucleotide or analogues thereof is mixed with pharmaceutical carriers that are usually used in the pharmaceutical arts to formulate into topical formulations such as solutions, creams and ointments.

(Preparation Method)

Hereinafter, the preparation method of bridged nucleic acid GuNA described herein is described. Optically active substances having absolute configuration in each compound represented by general formulae I to XI may be prepared by using as starting material optically active substance(s) or separating the isomers that created in the intermediate stages for synthesis. Also, the below-mentioned replacement reaction of nucleic acid base in which nucleic acid base is replaced may proceed a β-selective transglycosylation effectively, and the obtained compound represented by general formula VIII may be obtained as a desired β former selectively.

The compound of the present invention or pharmaceutically acceptable salts thereof may be prepared according to the following method, but which should not limited thereto.

For starting materials, unless specific processes therefor are stated, they may be used as commercially available ones, or can be prepared according to the publicly known method or a similar method thereto.

The abbreviated symbols as used herein mean the following meanings respectively.

THF: tetrahydrofuran
TBAF: tetra-n-butylammonium fluoride
$Ph_3P$: triphenylphosphine
DMF: N,N-dimethylformamide
MsCl: methanesulfonyl chloride
DMAP: N,N-dimethyl-4-aminopyridine
$iPr_2NEt$, DIPEA: N,N-diisopropylethylamine
$Tf_2O$: trifluoromethanesulfonic anhydride
$NaN_3$: sodium azide
$Bu_4NN_3$: tetrabutylammonium azide
TfCl: trifluoromethanesulfonyl chloride
$Ph_3PO$: triphenylphosphineoxide
BSA: N,O-bis(trimethylsilyl)acetamide
TMSOTf: trifluoro methanesulfonic acid trimethylsilyl
TBSOTf: t-butyldimethylsilyl trifluoro methanesulfonic acid
Bn: benzyl
TMS: trimethylsilyl
TBDPS: tert-butyldiphenylsilyl
Ac: acetyl
Teoc: trimethylsilylethoxycarbonyl
Boc: tert-butoxycarbonyl
$CH_2Cl_2$: dichloroethane
MeCN: acetonitrile
DPPA: diphenylphosphoryl azide
DIAD: diisopropyl azodicarboxylate
DMTr: 4,4'-dimethoxytrityl
BHT: dibutylhydroxytoluene First, the summary of a preparation method for bridged nucleic acid GuNA of the present invention is described.

In the main production route ("A method"), a sugar compound 1 is used as a starting material, and a protecting group for hydroxy group is introduced as $R^1$ variable to prepare a compound 2. Next, multi-step (six steps) reaction routes are carried out using the compound 2 as a starting material to prepare a precursor of a compound represented by general formula III (for example, compound 7). The compound is deprotected to obtain a compound represented by general formula III (for example, compound 8) as a novel intermediate. Successively, Mitsunobu reaction is carried out using an appropriate azidating reagent to obtain a compound represented by general formula II (for example, compound 9 (a derivative on a thymine group) and compound 36 (a derivative on a uracil group) as a novel intermediate.

Further, the resulting compound is reacted with appropriate reducing agent to obtain a compound represented by general formula I (for example, compound 12).

Next, the compound represented by general formula I is deprotected, and is then introduced by novel another protecting group, to obtain a compound represented by general formula IX (for example, compound 14). Successively, the resulting compound is reacted with a guanidination reagent to obtain a compound represented by general formula VII (for example, compound 15) as a novel intermediate, which can be further reacted with a phosphoramidite reagent to obtain a GuNA phosphoramidite compound represented by general formula VII (or general formula XI) (for example, compound 16) as a novel compound. The compounds may be used as a monomer starting material for a preparation of artificial oligonucleotide of bridged nucleic acid GuNA.

Also, in the above-mentioned main production route ("A method"), any alternation may be carried out by adopting another production route. Examples of the alternation method include a mesylation reaction route ("B method"), and an azidation reaction route ("C method"), and a nucleic acid base replacement reaction route ("D method").

A summary of the production route for the preparation method of the present invention is described.

[chem. 91]

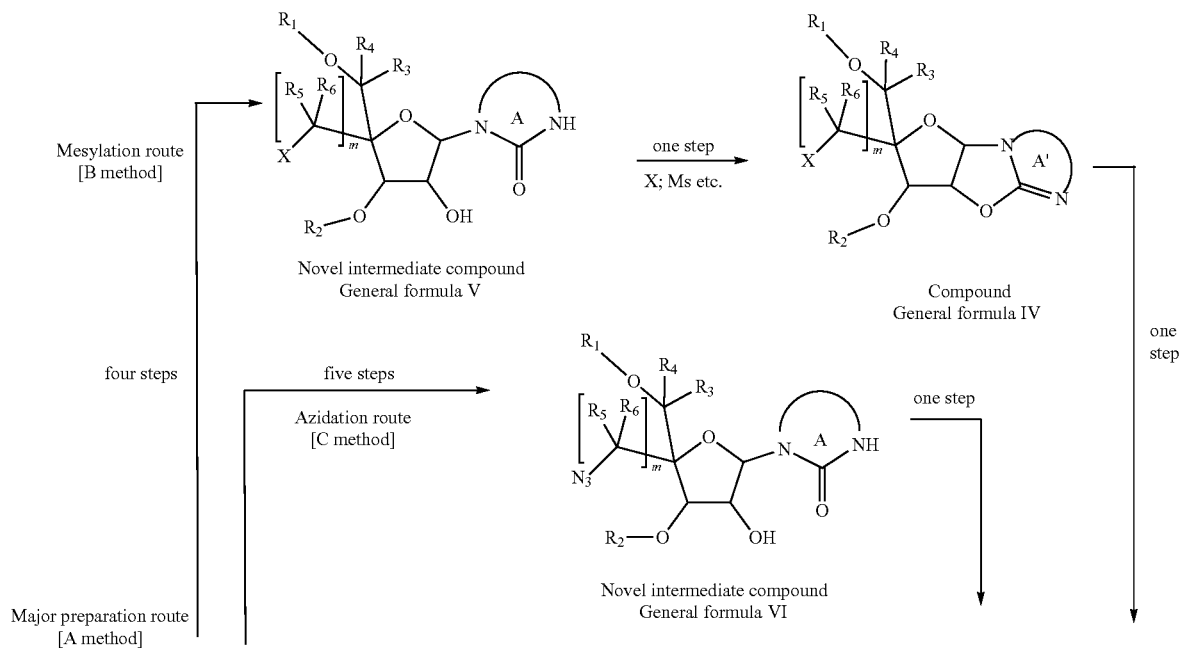

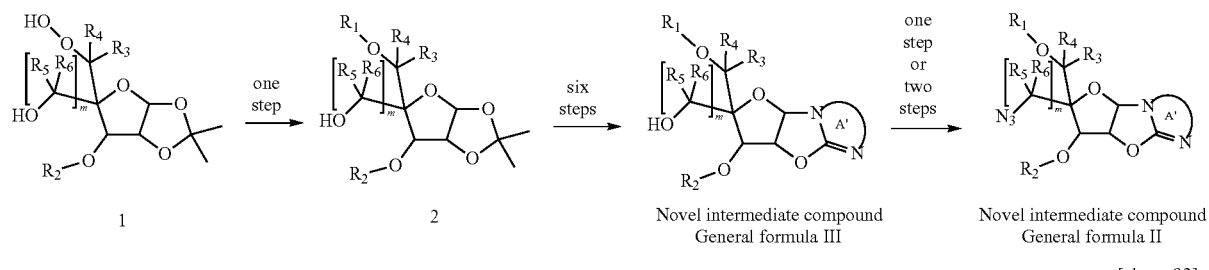
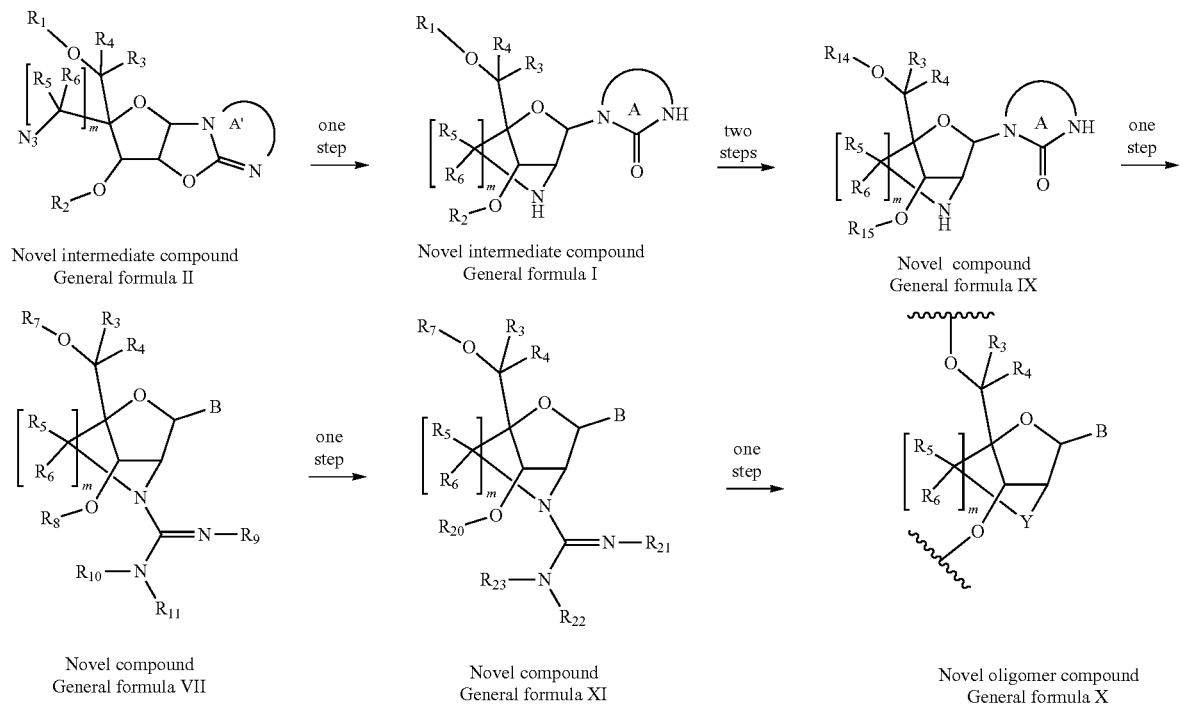
[chem. 93]
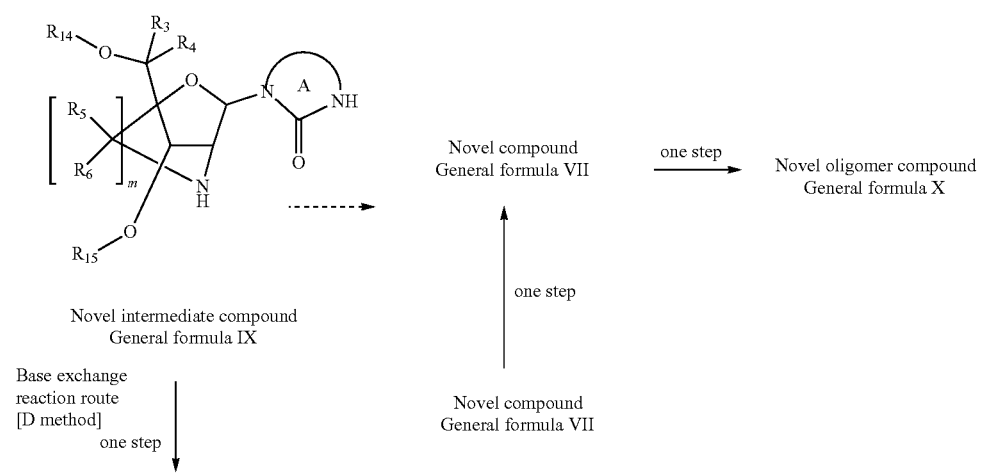

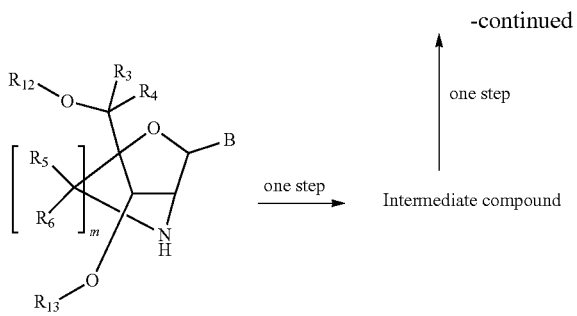

one step → Intermediate compound one step ↑ -continued

[A Method]
A Preparation of Precursors of Novel Intermediate Compound Represented by General Formula III First, a preparation method for precursors of a compound represented by general formula III (for example, compound 7) from a compound 1 as a starting material is carried out via seven steps according to a method known in the reference (for example, described in J. Org. Chem. 2011, 76, 9891-9899).

The representative preparation method is described below.

[chem. 94]

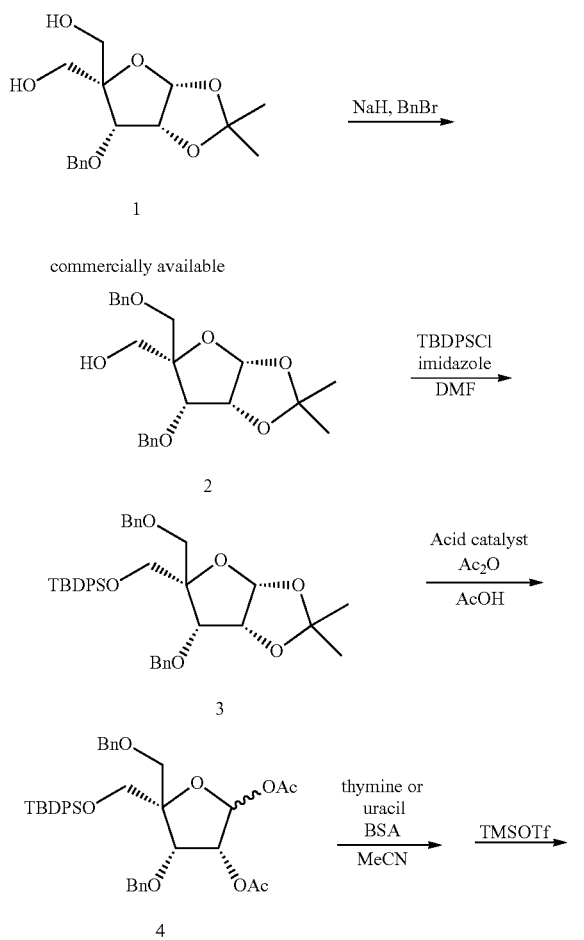

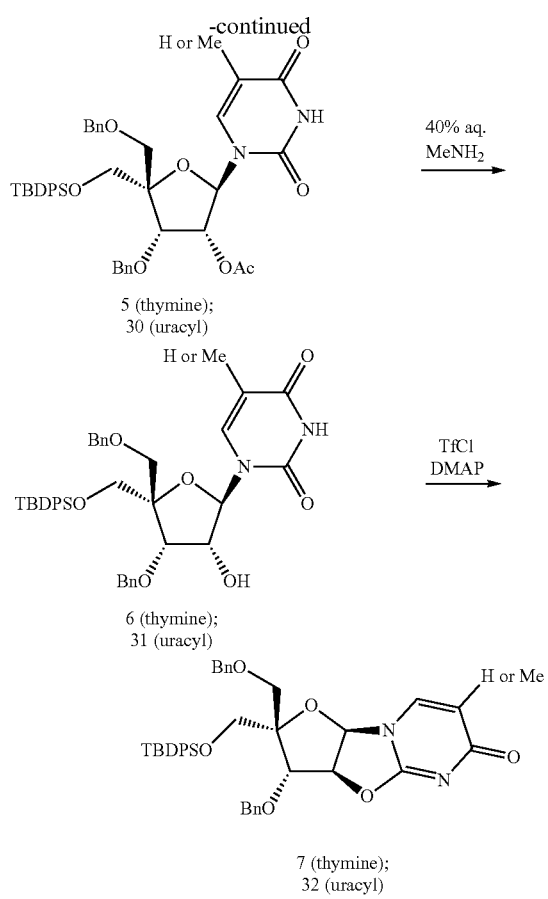

Compound 1 is commercially available or can be prepared using commercially available compounds according to a generally known method in an organic synthetic chemistry (in particular, nucleic acid synthesis). For example, the compound 1 that is described in the above-mentioned reference can be reacted with appropriate reagents according to an organic synthesis to obtain the other compound 1 represented by a general formula.

Each of the preparation steps may be carried out under a reaction condition according to the methods described in J. Org. Chem. 2011, 76, 9891-9899, but the reaction condition of each of the reaction step (for example, reagent to be used, and reaction period) may be varied appropriately depending on kinds of the compound 1 as a starting material. Also, according to the method described in J. Org. Chem. 2011, 76, 9891-9899, the intermediate compound 4 is reacted with the other nucleic acid base (for example, uracil group (U))

as a nucleic acid base as below-mentioned in place of a thymine group (T) in a reaction with a thymine group (T) to prepare some analogues of various kinds of nucleic acid base other than thymine group.

A preparation for novel intermediate compound represented by general formula II using azidating reagent (for example, diphenylphosphoryl azide (DPP)) in the presence of azodicarboxylic acid diester (for example, diethyl azodicarboxylate (DEAD), or diisopropyl azodicarboxylate (DIaD)) or triphenylphosphine ($Ph_3P$)).

[chem. 95]

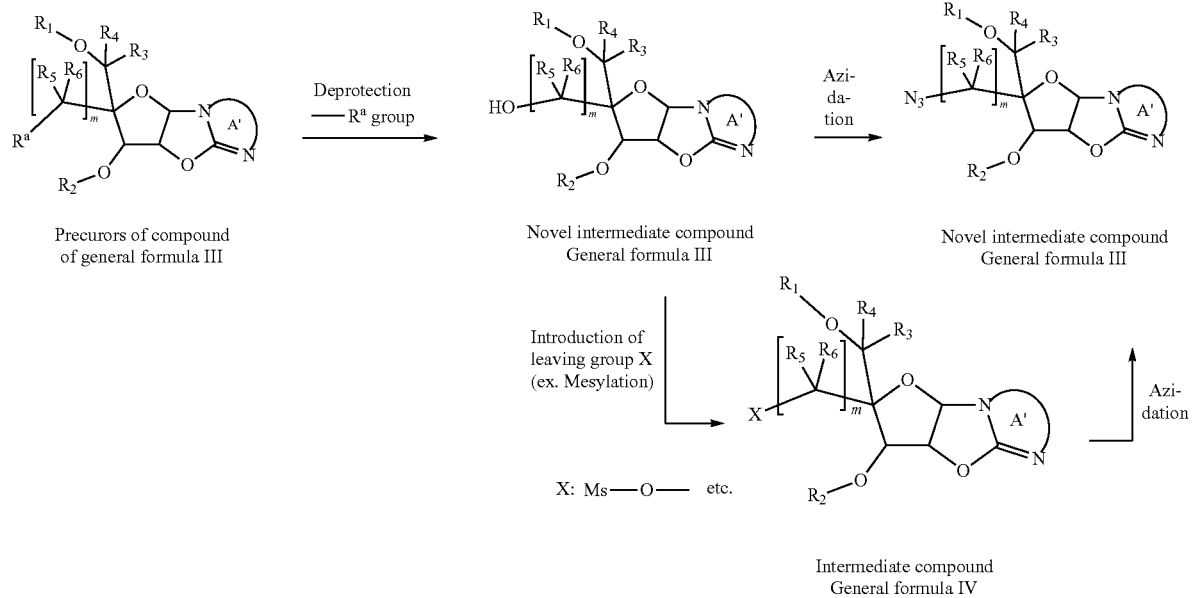

Precursors of compound of general formula III

Novel intermediate compound General formula III

Novel intermediate compound General formula III

Introduction of leaving group X (ex. Mesylation)

X: Ms—O— etc.

Intermediate compound General formula IV (in a general formula of precursors of the compound represented by general formula III, $R^a$ represents a protecting group or hydroxy group.)

Next, the precursors of the above-prepared compound represented by general formula III is deprotected in appropriate solvent to obtain intermediate compounds represented by novel general formula III (for example, compound 8 (for a thymine group) and compound 34 (for an uracil group)). The deprotection reaction may be carried out in appropriate reaction condition (for example, reagents to be used) depending on the kinds of the protecting group. For example, when $R^a$ variable as a protecting group for hydroxy group is a silyl type of protecting group (for example, TBDPS), the deprotection can be carried out by treating the resulting compound with a hydrolysis reaction under acidic condition (for example, acetic acid-THF-water) or a fluoride ion-donating reagent (for example, TBSF). The solvents may be any ones unless they affect the reaction adversely, and the reaction may be carried out in an appropriate solvents (for example, ethers such as THF, halogenated hydrocarbon atoms such as dichloromethane, water, or mixed solvents thereof). The reaction may proceed preferably at 0° C. to 100° C., particularly preferably at 0° C. to 50° C. as a reaction temperature.

Successively, the resulting compound is reacted with an appropriate azidating reagent under Mitsunobu reaction condition to obtain novel intermediate compounds represented by general formula II (for example, compound 9 (for thymine group) and compound 36 (for uracil group)). The azidation reaction may be carried out by reacting the compound represented by general formula III under Mitsunobu reaction condition (for example, which is carried out by The solvents may be any ones unless they affect the reaction adversely, and the reaction may be carried out in appropriate solvent (for example, ethers such as THF, halogenated hydrocarbons such as dichloromethane, hydrocarbons such as toluene, water, or mixed solvents thereof). The reaction may proceed preferably at −78° C. to 100° C., particularly preferably at 0° C. to 50° C. as a reaction temperature.

The progress of the reaction for obtaining azide compound represented by general formula II from the compound represented by general formula III may be easily affected by the degree of purification of the reactant(s) and etc., and the reaction is not easy to handle. Without preparing the compound represented by general formula II directly, once the compound represented by general formula III is converted into an intermediate compound represented by general formula IV in which the hydroxy group is converted into a leaving group) (for example, compound 10 (for a thymine group), compound 35 (for an uracil group)), and thereafter the leaving group is removed and an appropriate azide agent is then introduced to lead easily the compound represented by general formula II.

The leaving groups X are not particularly limited unless they are groups that have been generally known in organic synthesis, and include, for example, methanesulfonyloxy group (mesyloxy; Ms-O—), trifluoromethanesulfonyloxy group, and p-toluenesulfonyloxy group, and mesyloxy group is preferred. Examples of the reagents for introducing a leaving group include trifluoromethanesulfonyl chloride, methanesulfonyl chloride, p-toluenesulfonylchloride, and trifluoromethanesulfonic anhydride, and methanesulfonyl chloride is preferred.

Examples of the azide agent include $NBu_4NN_3$ and sodium azide.

The introduction of the leaving group may be carried out under basic condition (for example, dimethylaminopyridine (DMAP)) using the reaction condition (for example, using a sulfonylating agent (for example, MsCl)) that is well known in organic synthetic chemistry (for example, sugar synthesis).

The solvents may be any ones unless they affect the reaction adversely, and the reaction may be carried out in appropriate solvents (for example, ethers such as THF, halogenated hydrocarbons such as dichloromethane, water, or mixed solvents thereof). The reaction may proceed preferably at −25° C. to room temperature, particularly preferably at 0° C. to room temperature as a reaction temperature.

On the other hand, the reactions associated with a deprotection and an azidation reaction may be carried out using appropriate azidating agent (for example, tetrabutylammonium azide) depending on the kinds of leaving group under the reaction condition that has been well known in organic synthetic chemistry.

b) subjecting the obtained compound represented by general formula III to Mitsunobu reaction using an appropriate azidating reagent to obtaining the compound represented by general formula II.

As an alternative preparation method, the following steps b') and c') comprises in place of the above-mentioned step b);

b') reacting the obtained compound represented by general formula III with an appropriate reagent to introduce the leaving group (X) (on the hydroxy group at 5' position), thereby a compound represented by general formula IV is obtained; and c') reacting the obtained compound represented by general formula IV with an appropriate azidating reagent to obtain a compound represented by general formula II.

Alternative Method for Preparing the Novel Compound Represented by General Formula II An alternative method for preparing a compound represented by general formula II is described.

[chem. 96]

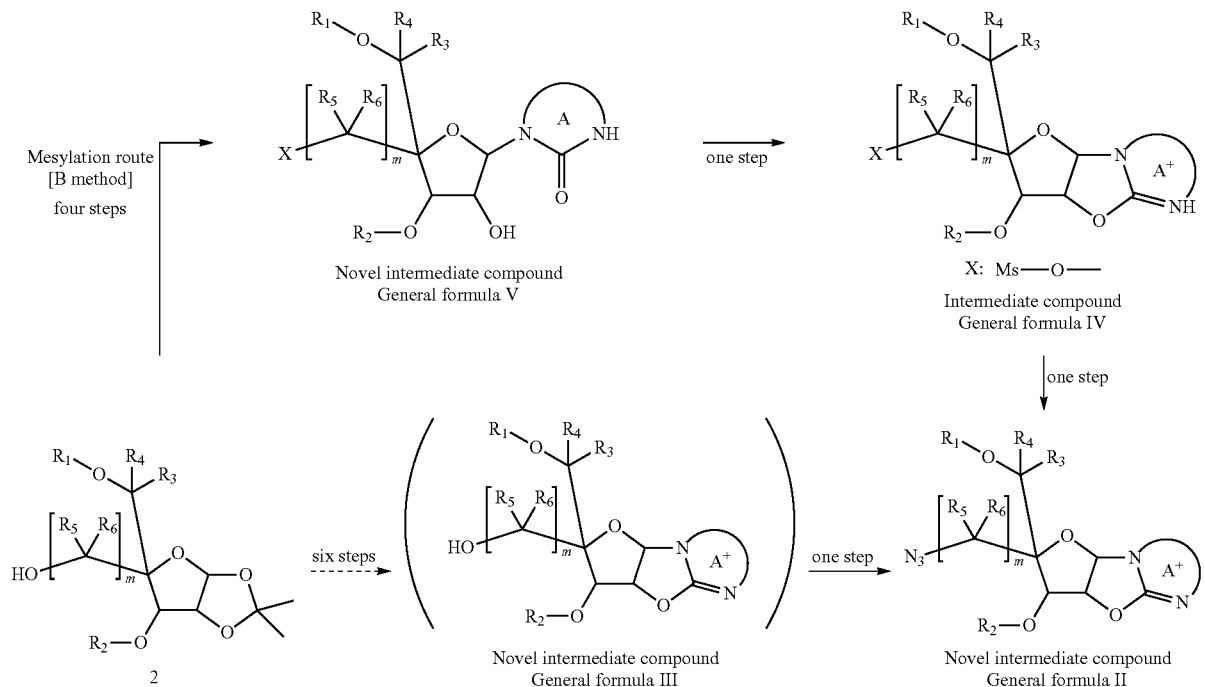

The solvents may be any ones unless they affect the reaction adversely, and the reaction may be conducted in appropriate solvent (for example, ethers such as dioxane, halogenated hydrocarbons such as dichloromethane, water, or mixed solvents thereof). The reaction may proceed preferably at room temperature to a reflux temperature of the used solvents, for example, at 100° C. or more.

That is, the method for preparing the compound represented by general formula II comprises the following steps:

a) deprotecting the precursors of the compound represented by general formula III (that is, deprotecting of the protecting group of the hydroxy group at 5' position) to obtain the compound represented by general formula III; and As aforementioned, first, a hydroxy group is subjected to a mesylation reaction by using the compound 2 that is prepared from the compound 1, successively, the reactions may be carried out via multi-step (four steps) reaction routes according to the method described in the above-mentioned J. Org. Chem. 2011, 76, 9891-9899 (that is, a preparation of the compound 6 from the compound 3) to prepare the novel intermediate compound represented by general formula IV (specifically, compound 25).

The mesylation reaction may be carried out under basic condition (for example, in the presence of triethylamine) using a reaction condition (for example, using a mesylating agent such as methanesulfonyl chloride, and methanesulfonic anhydride) that has been generally known in organic synthetic chemistry (for example, nucleic acid synthesis).

The solvent may be any ones unless they affect the reaction adversely, and the reaction may be conducted in appropriate solvents (for example, ethers such as THF, halogenated hydrocarbons such as dichloromethane, water, or mixed solvents thereof). The reaction may proceed preferably at −25° C. to 100° C., and particularly preferably at 0° C. to room temperature.

That is, the method for preparing a compound represented by general formula IV comprises the following steps:

The compound represented by general formula V as a novel intermediate compound is reacted with an activating agent for hydroxy group (for example, trifluoromethansulfonylating agent) to activate an unprotected hydroxy group that is substituted in a tetrahydrofuran ring in a general formula V, thereby the compound represented by general formula IV is obtained.

As aforementioned, the compound represented by general formula IV (for example, compound 10 (for a thymine group) or compound 35 (for an uracil group)) is reacted with an azide agent (for example, nBu$_4$NN$_3$ or sodium azide) to obtain the compound represented by general formula II.

Alternative Method for Preparing a Novel Intermediate Compound Represented by General Formula II Further alternative method for preparing the compound represented by general formula II is described.

Acta 2000, 83, 128-151) using as a starting material the compound 2 that is prepared from the compound 1 to obtain the azide compound represented by general formula VI (specifically, compound 21) as an intermediate compound.

Next, the resulting compound is reacted with an activating agent for hydroxy group under basic condition (for example, in the presence of DMAP) using a the same reaction condition as those used in the reaction for preparing the compound 7 from the compound 6 (or the compound 10 from the compound 25) to obtain the novel intermediate compound represented by general formula II (specifically, compound 9).

Examples of the activating agent for hydroxy group as used herein include trifluoromethanesulfonyl chloride, methanesulfonyl chloride, and trifluoromethanesulfonic anhydride, and trifluoromethanesulfonyl chloride is preferred.

The solvent may be any ones unless they affect the reaction adversely, and the reaction may be carried out in appropriate solvents (for example, ethers such as THF, halogenated hydrocarbons such as dichloromethane), water, or mixed solvents thereof).

The reaction may proceed preferably at 0° C. to 100° C., and particularly preferably at 0° C. to room temperature.

That is, the method for preparing the compound represented by general formula II as a novel intermediate compound from the compound represented by general formula VI comprises the following steps:

The compound represented by general formula VI is reacted with an activating agent for hydroxy group to activate an unprotected hydroxy group that is substituted to a tetrahydrofuran ring in the general formula VI to obtain the compound represented by general formula II.

[chem. 97]

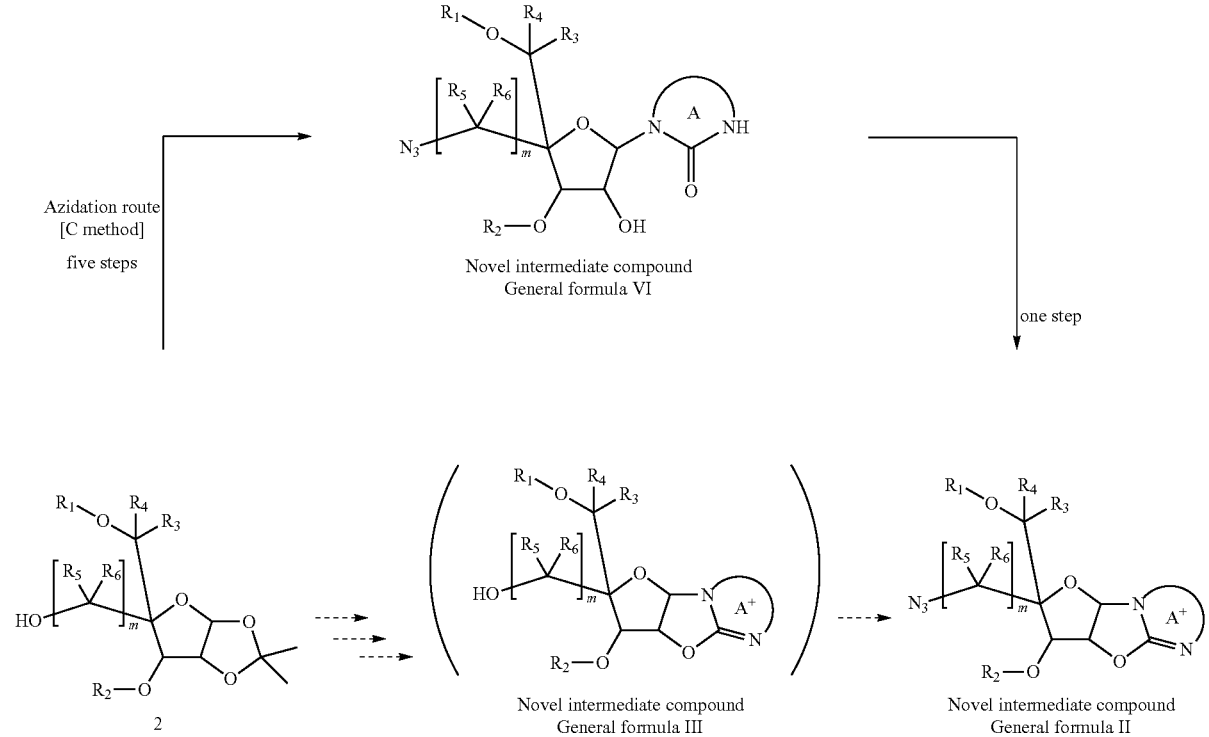

As aforementioned, the reaction may be carried out via multi-steps (five steps) reaction routes according to the method described in the reference (Henrik M. Pfundheller, H. M., Bryld, T., Olsen, C. E., Wengel, J. Helvetica Chimica Preparation of Novel Intermediate Compound Represented by General Formula I

[chem. 98]

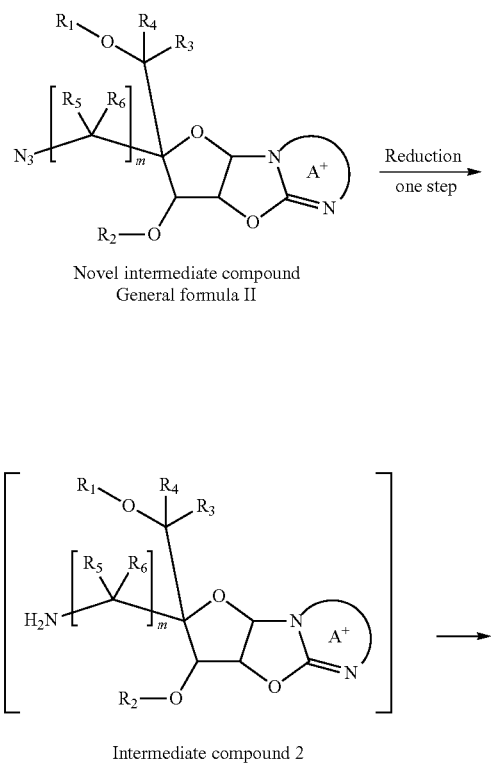

Novel intermediate compound
General formula II

Intermediate compound 2

Novel intermediate compound
General formula I

Further, the obtained compound represented by general formula II may be subjected to a reduction reaction to obtain novel intermediate compound represented by general formula I wherein the azide group is reduced (for example, compound 12 (for a thymine group), compound 37 (for an uracil group)) (herein which referred to as "2'-amino-LNA").

The reduction reaction of the azide group may be carried out in the presence of a reducing agent (for example, phosphines such as triphenylphosphine).

The solvents may be any ones unless they affect the reaction adversely, and the reaction may be carried out in appropriate solvents (for example, ethers such as THF, halogenated hydrocarbons such as dichloromethane, water, or mixed solvents thereof). The reaction may proceed preferably at 0° C. to high temperature, and particularly preferably at room temperature to 100° C. or less.

That is, the method for preparing novel intermediate compound represented by general formula I comprises the following steps:

reacting the above obtained novel intermediate compound represented by general formula II with a reducing agent to prepare the compound represented by general formula I or salts thereof.

Here, the present reaction is novel reaction step comprising introducing 2'-position amino group by expanding an azide methyl group from 4'-position carbon atom and thereby bridging with 2'-position carbon atom.

Preparation of Precursors of Novel Monomer Compound Represented by General Formula VII

[chem. 99]

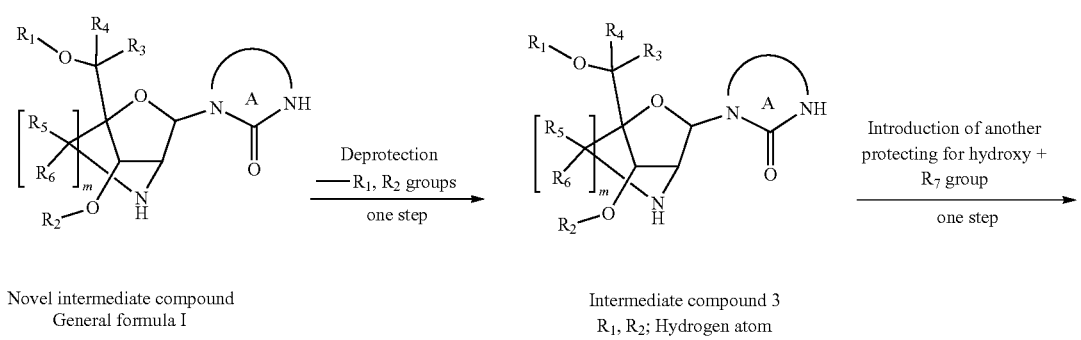

Novel intermediate compound
General formula I

Intermediate compound 3
$R_1$, $R_2$; Hydrogen atom

-continued

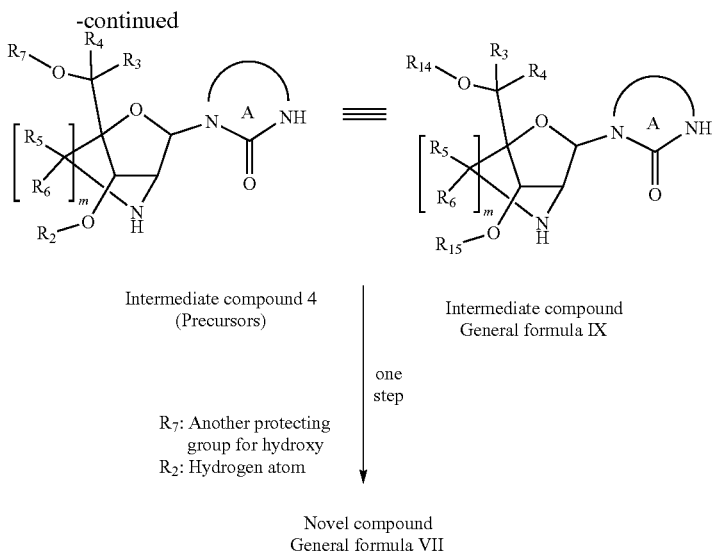

Intermediate compound 4 (Precursors)

Intermediate compound General formula IX one step

R7: Another protecting group for hydroxy
R2: Hydrogen atom

Novel compound General formula VII

The above obtained compound represented by general formula I is deprotected at 5'-position and 3'-position respectively to deprotected $R_1$ variable and $R_2$ variable to obtain an intermediate compound 3 (for example, compound of the example 13). Successively, a new protecting group for hydroxy group having different deprotection condition than the deprotected protecting group is introduced to only 5'-position hydroxy group ($R_7$) to obtain an intermediate compound 4 (for example, compound 14) as a precursor.

Here the deprotection reaction may be carried out under any reaction conditions that have been generally known in organic synthetic chemistry (for example, nucleic acid synthesis) depending on the kinds of the protecting group. For example, when the benzyl type protecting group (for example, Bn group) is used, the deprotection reaction may be carried out by hydrogenation reaction with hydrogen in the presence of organic metallic catalyst (for example, palladium-carbon)

The solvents may be any ones unless they affect the reaction adversely and the reaction may be carried out in appropriate solvents (for example, ethers such as THF, acetates such as ethyl acetate, halogenated hydrocarbons such as dichloromethane, acids such as acetic acid, alcohols such as methanol, water, or mixed solvents thereof) or by using bases itself as solvent. The reaction may proceed preferably at room temperature to high temperature, and particularly preferably at room temperature to 50° C. or less.

Also, examples of the newly introduced protecting group for hydroxy group include trityl type of protecting group (for example, DMTR group). The introduction reaction of the protecting group may be carried out under the reaction condition that has been well known in organic synthetic chemistry (for example, nucleic acid synthesis) depending on the kinds of the protecting group. For when the protecting group for hydroxy group is a trityl type protecting group (for example, DMTr group), he reaction may be carried out under basic condition (for example, in the presence of pyridine).

The solvents may be any ones unless they affect the reaction adversely and the reaction may be carried out in appropriate solvents (for example, ethers such as THF, halogenated hydrocarbons such as dichloromethyl, water, or mixed solvents thereof) or by using bases itself as a solvent.

The reaction may proceed preferably at 0° C. to 50° C., and particularly preferably at room temperature.

That is, the method for preparing the intermediate compound 4 comprises the following steps:
a) subjecting the above obtained compound represented by general formula I (for example, R1 variable and R3 variable at 5'-position and 3'-position) to a deprotection reaction (which provides an intermediate compound 3);
b) introducing a protecting group for hydroxy group into the reaction product (at 5'-position).

As below-mentioned herein, the obtained intermediate compound 4 is carried out by guanidination, followed by phosphoramiditation to obtain a novel compound represented by general formula VII.

Exchange Reaction of Nucleic Acid Base

[chem. 100]

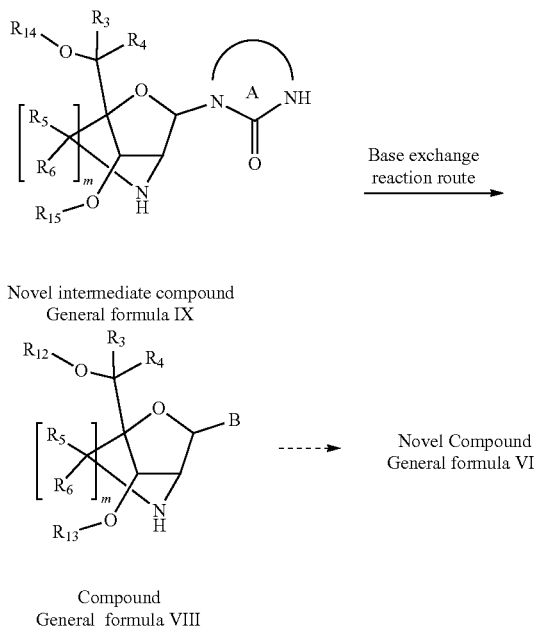

Novel intermediate compound General formula IX

Base exchange reaction route

Compound General formula VIII

Novel Compound General formula VII

According to a nucleic acid exchange reaction (transglycosylation reaction) using as a starting material, the above obtained compound represented by general formula I or the intermediate compound 4 (which collectively referred to as compound represented by general formula IX) (for example, compound 12 and compound 14), a pyrimidine base moiety of nucleic acid base such as thymine group (T) and uracil group (U) may be replaced with another nucleic acid base moiety (for example, adenine (A), guanine (G), uracil (U), thymine (T), cytosine (C), or 5-methylcytosine ($^{Me}$C) to obtain as a novel intermediate compound the compound represented by general formula VIII or salts thereof (for example, compound 26, compound 28 and compound 29).

The base exchange reaction may be carried out, for example, by reacting the compound represented by general formula IX in the presence of Lewis acid, and may be facilitated by reacting with a silylating agent.

Examples of the silylating agent include BSA, and hexamethyldisilazane, and examples of Lewis acid includes TMSOTf, TBSOTf, tin chloride, and the others, which are not limited thereto.

The silylating agent may be used in about 1 to about 20 molar equivalents, and the Lewis acid may be used in a catalytic amount (about 0.05 molar equivalents) to about 2 molar equivalents as opposed to 1 mole of the reaction substrates.

The solvents may be any ones unless they affect the reaction adversely, and the reaction may be carried out in appropriate solvents (for example, ethers such as THF; halogenated hydrocarbons such as dichloromethane, dichloroethane, and chloroform; hydrocarbons such as benzene and toluene; acetonitrile; water; or mixed solvents thereof). The reaction may proceed preferably at 0° C. to high temperature, and particularly preferably at room temperature to about 60° C.

Preparation of Monomer Compound Represented by General Formula VII

[chem. 101]

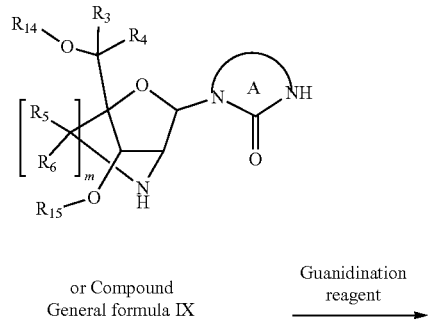

or Compound General formula IX

Guanidination reagent →

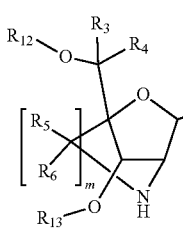

Novel intermediate compound General formula VIII

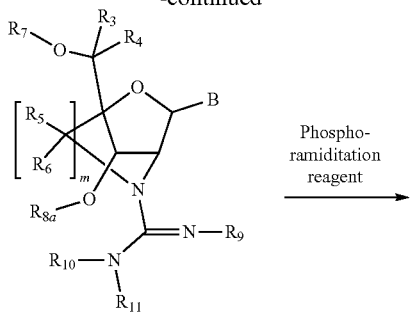

Novel compound General formula VII

R$_{8a}$: Hydrogen atom

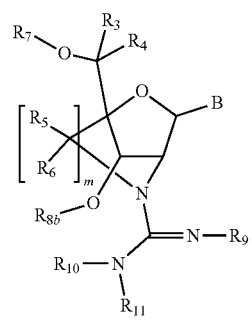

Novel compound General formula VII

R$_{8b}$: Phosphate group which may be optionally substituted

The above obtained compound represented by general formula IX or compound represented by general formula VIII is reacted with guanidination reagent to obtain the guanidinated compound represented by general formula VII (wherein R8a represents a hydrogen atom) (for example, compound 15), which corresponds to the compound wherein a bridged amino group in the compound represented by general formula VIII is guanidine.

Here, the guanidination reaction may be carried out under reaction conditions that have generally known in organic synthesis (in particular, nucleic acid synthesis) (for example, using a reagent). Examples of the guanidination reagent include a compound represented by following formula:

[chem. 102]

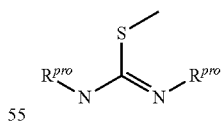

[wherein, R$^{pro}$ represents a protecting group for amino group (for example, Teoc, and Boc)]
, and the reaction may be carried out in appropriate activating reagent (for example, silver triflate (AgOTf)).

Further, the above obtained compound represented by general formula VII may be reacted with phosphoramiditation reagent to obtain a compound represented by general formula VII or salts thereof (which herein referred to as "GuNA phosphoramidite") (for example, compound 16).

Here the phosphoramiditation reaction may be conducted under reaction conditions that have been generally known in organic synthesis (in particular, nucleic acid synthesis) (for example, in terms of reagent(s)). Examples of the phosphoramiditation reagent include agents by the following formula:

[chem. 103]

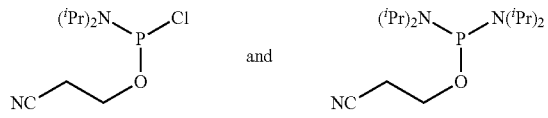

and which should not be limited thereto. The phosphoramiditation reaction may be conducted in the presence of appropriate bases (such as DIPEA) or appropriate acid (such as diisopropyl ammonium tetrafluoride, and 4,5-dicyanoimidazole).

That is, the method for preparing the compound represented by general formula VII or salts thereof may comprise the following steps:

a) a step of guanidination of the compound represented by general formula IX or salts thereof or the compound represented by general formula VIII or salts thereof to prepare the compound represented by general formula VII (wherein, $R_{8a}$ represents a hydrogen atom);

b) a step of phosphoramiditation of the reaction products to prepare the compound represented by general formula VII (wherein, $R_{8b}$ represents a phosphate group which may be optionally substituted).

Also, the method for preparing the compound represented by general formula VII or salts thereof may comprise at least one of the following steps among the steps described herein:

a step of reacting the compound represented by general formula II with a reducing agent to prepare the compound represented by general formula I or salts thereof;

a step of reacting the compound represented by general formula III with an azide agent to prepare the compound represented by general formula II or salts thereof;

a step of reacting the compound represented by general formula V with an activating agent for hydroxy group to prepare the compound represented by general formula IV or salts thereof;

a step of reacting the compound represented by general formula IV with an azide agent to prepare the compound represented by general formula II or salts thereof;

a step of reacting the compound represented by general formula VI with an activating agent for hydroxy group to prepare the compound represented by general formula II or salts thereof;

a step of replacing cycle A in the compound represented by general formula IX to prepare the compounds represented by general formula VIII or salts thereof.

Preparation of GuNA Oligonucleotide Represented by General Formula X

[chem. 104]

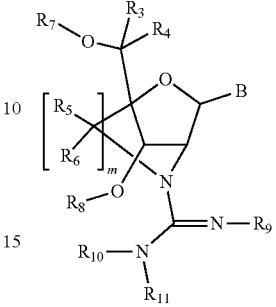

Novel compound
General formula VII or

Amiditation
If necessary,
deprotection

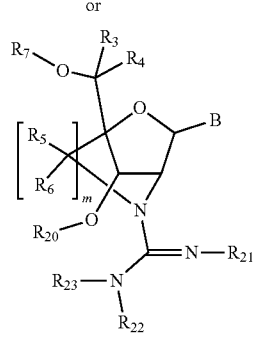

Novel compound
General formula XI

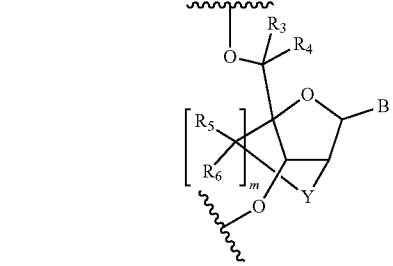

Novel oligomer compound
General formula X

Y =

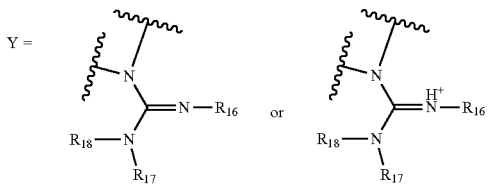

The compound represented by general formula VII or salts thereof can be used as a monomer starting material for preparing GuNA oligonucleotide. The GuNA oligonucleotide can be synthesized by oligomerization of the compound represented by general formula VII or general formula XI or salts thereof, if necessary, followed by deprotecting an amino protecting group.

For example, the oligomerization is not limited to any method as long as it is the method that has been generally known in the synthetic chemistry (in particular, nucleic acid synthesis), and it can be used by an phosphoramidite method. The phosphoramidite method can be conducted, for example, according to the method described in WO 2014/046212 A1.

Using this oligomerization, oligonucleotide containing one or more nucleotides represented by general formula X can be prepared.

That is, the method for preparing oligonucleotide represented by general formula X comprises the following step.
a) a step of oligomerization of the compound represented by general formula VII or general formula XI or salts thereof, if necessary, followed by deprotecting an amino protecting group.

Also, the method for preparing the compound represented by general formula VII or general formula XI or salts thereof may comprise at least one of the following steps among the steps described herein.

a step of reacting the compound represented by general formula II with a reducing agent to prepare the compound represented by general formula I or salts thereof;

a step of reacting the compound represented by general formula III with an azide agent to prepare the compound represented by general formula II or salts thereof;

a step of reacting the compound represented by general formula V with an activating agent for hydroxy group to prepare the compound represented by general formula IV or salts thereof;

a step of reacting the compound represented by general formula IV with an azide agent to prepare the compound represented by general formula II or salts thereof;

a step of reacting the compound represented by general formula VI with an activating agent for hydroxy group to prepare the compound represented by general formula II or salts thereof;

a step of replacing the cycle A in the compound represented by general formula IX to prepare the compound represented by general formula VIII or salts thereof;

a step of guanidination of the compound represented by general formula IX or salts thereof or the compound represented by general formula VIII or salt thereof to prepare the compound represented by general formula VII (wherein $R_{8a}$ represents a hydrogen atom) or salts thereof;

a step of phosphoramiditation of the compound represented by general formula VII (wherein $R_{8a}$ represents a hydrogen atom) or salts thereof to prepare the compound represented by general formula VII (wherein $R_{8b}$ represents a phosphate group which may be optionally substituted) to prepare the compound represented by general formula (wherein $R_{8b}$ represents a phosphate group which may be optionally substituted) or salts thereof;

a step of deprotecting at least one of amino protecting group as $R_9$, $R_{10}$ or $R_{11}$ in the compound represented by general formula VII to prepare the compound represented by general formula XI.

EXAMPLES

Hereinafter, the present invention is further specifically described by Examples, however, the present invention is not limited thereto. The identification of compound was carried out by Elemental analysis, Mass spectrum, High performance liquid chromatography mass spectrometer; LCMS, IR spectrum, NMR spectrum, High-performance liquid chromatography (HPLC) and the like. In NMR spectrum, for proton nuclear magnetic resonance ($^1$H-NMR), an apparatus with 400 MHz of the resonance frequency was used, and for phosphorus nuclear magnetic resonance ($^{31}$P-NMR), an apparatus with 161.8 MHz of the resonance frequency was used. As symbols used in NMR spectrum, "s" is "singlet", "d" is "doublet", "dd" is "double of doublet", "t" is "triplet", "td" is "double of triplet", "q" is "quartet", "quin" is "quintet", "sept" is "septet", "m" is "multiplet", "br" is "broad", "brs" is "broad singlet", "brd" is "broad doublet", "brt" is "broad triplet", and "J" is "coupling constant".

One example of preparation method of compound 12 is described below, however, which is not limited thereto. Specifically, compound 12 was prepared using a commercially available compound 1 as a starting material according to the method described in J. Org. Chem. 2011, 76, 9891-9899.

[chem.105]

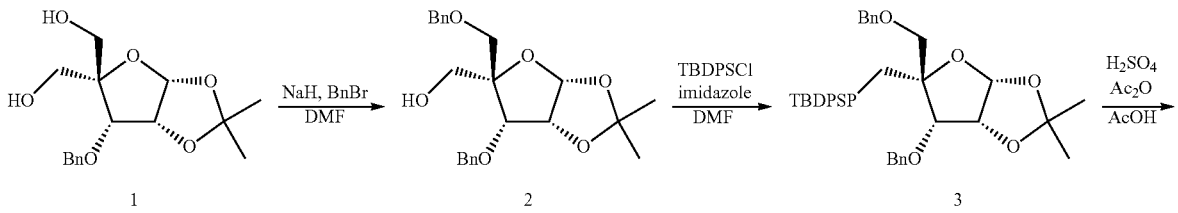

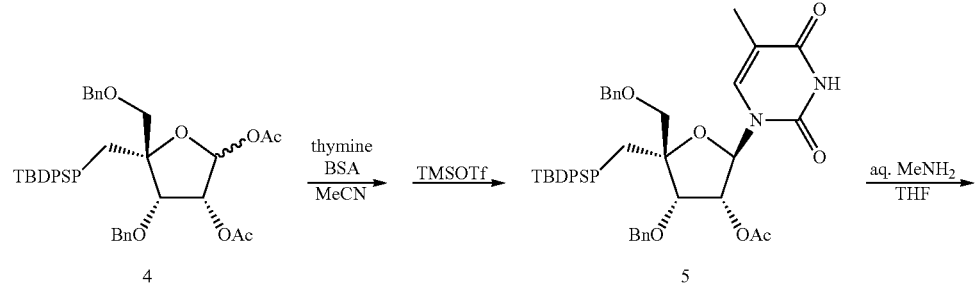

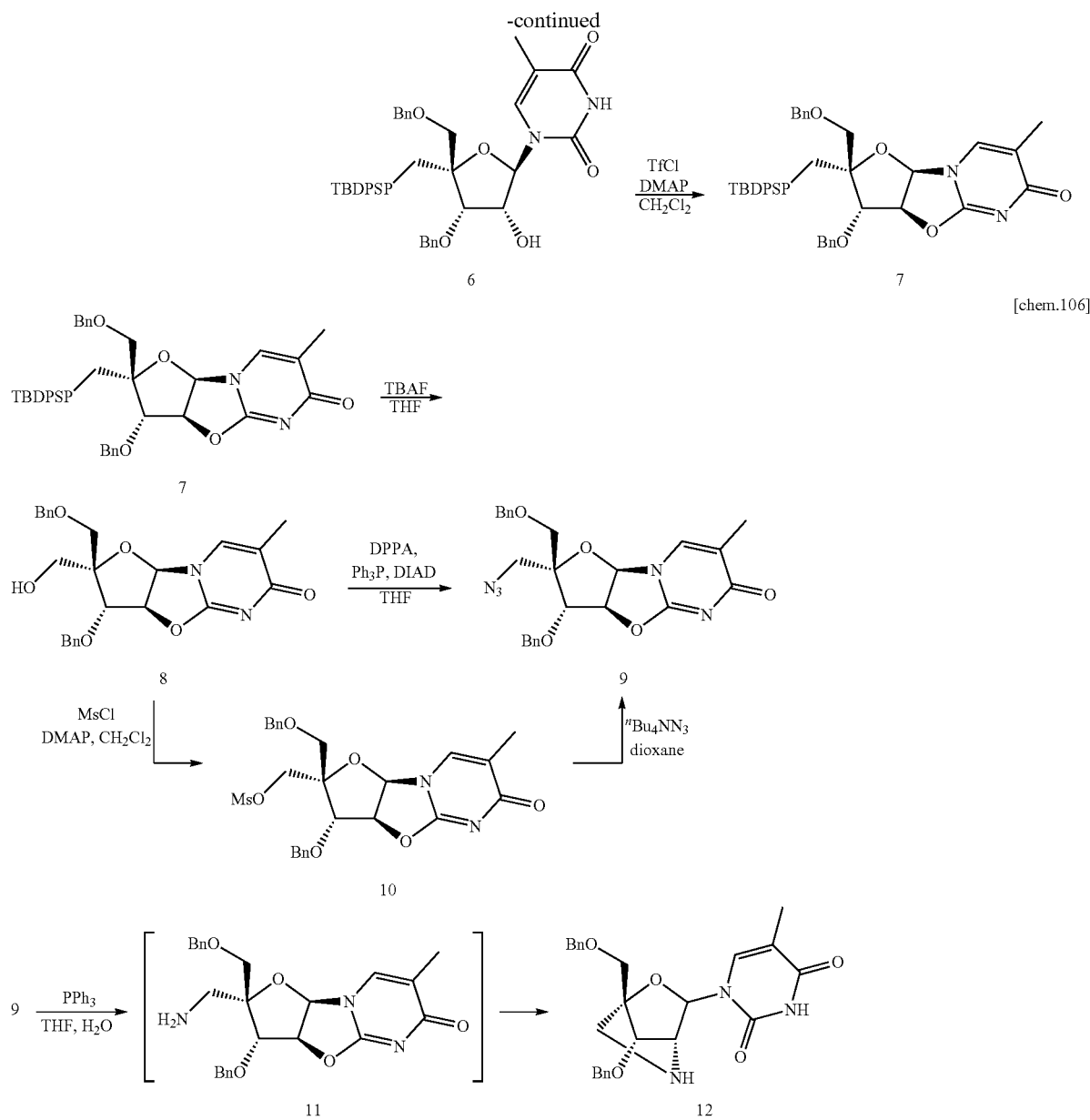

Example 1

((2R,3S,3aS,9aR)-3-(benzyloxy)-2-[(benzyloxy)methyl]-2-(hydroxymethyl)-7-methyl-2,3,3a,9a-tetrahydro-6H-furo[2',3':4,5][1,3]oxazolo[3,2-a]pyrimidine-6-one (Compound 8)

Compound 7 (prepared from 3,5-di-O-benzyl-4-C-hydroxymethyl-1,2-O-isopropylidene-α-D-ribofuranose 2 according to the method described in J. Org. Chem. 2011, 76, 9891) (2.00 g, 2.903 mmol) and THF (14.5 mL) were mixed, and thereto was added TBAF (3.77 mL, 3.774 mmol) dropwise under cooling at 0° C. The mixtures were stirred for 130 minutes at room temperature, and the solvents were evaporated. The resulting residues were purified by silica gel chromatography (chloroform/methanol, 100/0 to 85/15) to obtain compound 8 (1260 mg, yield 96%).

MS (APCI): m/z=451 (M+H)$^+$ $^1$H-NMR (CDCl$_3$) δ: 7.41-7.24 (8H, m), 7.21-7.11 (3H, m), 6.25 (1H, d, J=6.2 Hz), 5.32 (1H, dd, J=6.2, 2.6 Hz), 4.79 (1H, d, J=11.8 Hz), 4.61 (1H, d, J=11.8 Hz), 4.39 (1H, d, J=12.3 Hz), 4.34 (1H, d, J=2.6 Hz), 4.34 (1H, d, J=12.3 Hz), 3.86 (1H, dd, J=12.2, 5.7 Hz), 3.69 (1H, dd, J=12.2, 7.7 Hz), 3.33 (1H, d, J=10.3 Hz), 3.30 (1H, d, J=10.3 Hz), 2.20 (1H, dd, J=7.7, 5.7 Hz), 1.99-1.95 (3H, m)

Example 2

(2R,3S,3aS,9aR)-2-(azidomethyl)-3-(benzyloxy)-2-[(benzyloxy)methyl]-7-methyl-2,3,3a,9a-tetrahydro-6H-furo[2',3':4,5][1,3]oxazolo[3,2-a]pyrimidine-6-one (Compound 9)

Compound 8 (300 mg, 0.6659 mmol) and THF (4.4 mL) were mixed. Thereto were added PPh$_3$ (524 mg, 1.998 mmol) and diisopropyl azodicarboxylate (0.413 mL, 2.098 mmol) under cooling at 0° C., and successively followed by adding diphenylphosphoryl azide (0.431 mL, 1.998 mmol) dropwise. The mixtures were stirred at room temperature for 10 minutes, and stirred under heating at 50° C. as external temperature for 30 minutes. Thereto was added DMF (1.2 mL), and the mixtures were stirred under heating at 50° C. as external temperature for 17 hours. Thereto was added saturated brine at 0° C., and the mixtures were extracted with ethyl acetate. To the resulting organic layers was added anhydrous sodium sulfate, and the mixtures were dried and filtered, and the solvents were then evaporated. The resulting residues were purified by silica gel chromatography (ethyl acetate/methanol, 100/0 to 95/5) to obtain compound 9 (285 mg, yield 90%, containing Ph₃PO as impurities).

MS (APCI): m/z=476 (M+H)⁺

¹H-NMR (CDCl₃) δ: 7.41-7.26 (8H, m), 7.21-7.11 (3H, m), 6.19 (1H, d, J=6.2 Hz), 5.29 (1H, dd, J=6.2, 2.3 Hz), 4.77 (1H, d, J=11.8 Hz), 4.61 (1H, d, J=11.8 Hz), 4.40 (1H, d, J=12.0 Hz), 4.35 (1H, d, J=12.0 Hz), 4.29 (1H, d, J=2.3 Hz), 3.63 (1H, d, J=12.8 Hz), 3.49 (1H, d, J=12.8 Hz), 3.33 (1H, d, J=10.2 Hz), 3.25 (1H, d, J=10.2 Hz), 2.01-1.95 (3H, m)

Example 3

Also, compound 9 can be prepared also from compound 8 according to the following Examples 3 and 4.

{(2S,3S,3aS,9aR)-3-(Benzyloxy)-2-[(benzyloxy) methyl]-7-methyl-6-oxa-2,3,3a,9a-tetrahydro-6H-furo[2',3':4,5][1,3]oxazolo[3,2-a]pyrimidin-2-yl}methyl methanesulfonate (Compound 10)

To the suspension of compound 8 (7.00 g, 15.54 mmol) in methylene chloride (155 mL) were added MsCl (2.05 mL, 26.42 mmol) and DMAP (5695 mg, 46.61 mmol) under ice-cooling, and the mixtures were stirred at room temperature for 1.5 hours. Diisopropyl ether (500 mL) was added thereto to obtain white solids, and the solids were collected by filtration, and washed with diisopropyl ether. The resulting solids were recrystallized from diisopropyl ether (500 mL) and chloroform (100 mL), and the obtained crystals were washed with water (1 L) and dried to obtain compound 10 (8.12 g, 15.4 mmol, yield 98.9%).

MS (APCI): m/z=529 (M+H)⁺

¹H-NMR (CDCl₃) δ: 7.39-7.27 (8H, m), 7.21-7.14 (3H, m), 6.22 (1H, d, J=6.1 Hz), 5.28 (1H, dd, J=6.1, 2.6 Hz), 4.76 (1H, d, J=11.8 Hz), 4.60 (1H, d, J=11.8 Hz), 4.44-4.31 (5H, m), 3.40 (1H, d, J=10.2 Hz), 3.29 (1H, d, J=10.2 Hz), 2.92 (3H, s), 2.00-1.95 (3H, m)

Example 4

(2R,3S,3aS,9aR)-2-(Azidomethyl)-3-(benzyloxy)-2-[(benzyloxy)methyl]-7-methyl-2,3,3a,9a-tetrahydro-6H-furo[2',3':4,5][1,3]oxazolo[3,2-a]pyrimidine-6-one (Compound 9)

To a solution of compound 10 (7.00 g, 13.24 mmol) in 1,4-dioxane (132 mL) was added tetrabutylammonium azide (11.3 g, 39.73 mmol), and the mixtures were stirred at 120° C. as external temperature for 7 hours. The mixtures were cooled under ice-cooling, and thereto was added saturated aqueous sodium bicarbonate solution. The mixtures were extracted with ethyl acetate twice, and the organic layers were washed with saturated brine, and dried over anhydrous sodium sulfate, and the insoluble materials were removed by filtration. The solvents were evaporated from the filtrates, and the resulting residues were purified by silica gel chromatography (ethyl acetate/methanol, 90/10 to 85/15) to obtain compound 9 (5.80 g, 12 mmol, yield 92%).

MS (APCI): m/z=476 (M+H)⁺

¹H-NMR data was identical to those of compound 9 obtained in Examples 2.

Example 5

1-{(1R,3R,4R,7S)-7-(Benzyloxy)-1-[(benzyloxy) methyl]-2-oxa-5-azabicyclo[2.2.1]hepta-3-yl}-5-methylpyrimidine-2,4(1H,3H)-dione (Compound 12)

Compound 9 (1446 mg, 3.041 mmol), THF (20 mL) and water (4 mL) were mixed, and thereto was added Ph₃P (1196 mg, 4.562 mmol), and the mixtures were stirred under heating at 70° C. as external temperature for 17 hours. The solvents were evaporated, and the resulting residues were purified by silica gel chromatography (ethyl acetate/methanol, 95/5 to 85/15) to obtain compound 12 (1267 mg, yield 92%).

MS (APCI): m/z=450 (M+H)⁺

¹H-NMR (CDCl₃) δ: 8.08 (1H, brs), 7.61-7.57 (1H, m), 7.39-7.23 (10H, m), 5.52 (1H, s), 4.65-4.51 (4H, m), 3.91 (1H, s), 3.87 (1H, d, J=10.8 Hz), 3.80 (1H, d, J=10.8 Hz), 3.64 (1H, s), 3.15 (1H, d, J=9.7 Hz), 2.90 (1H, d, J=9.7 Hz), 1.68-1.53 (3H, m)

One example of preparation method of compounds 16a and 15b is described below, however, which is not limited thereto. Specifically, using the above compound 12 as a starting material, compounds 16a and 15b were prepared.

[chem.107]

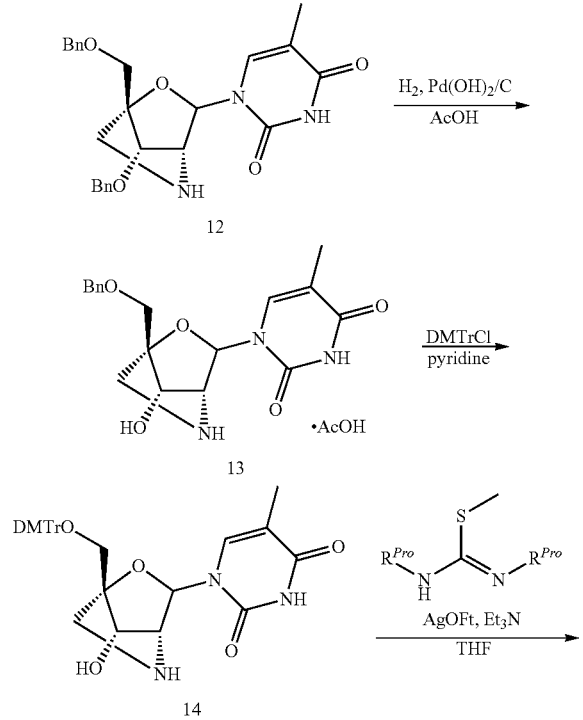

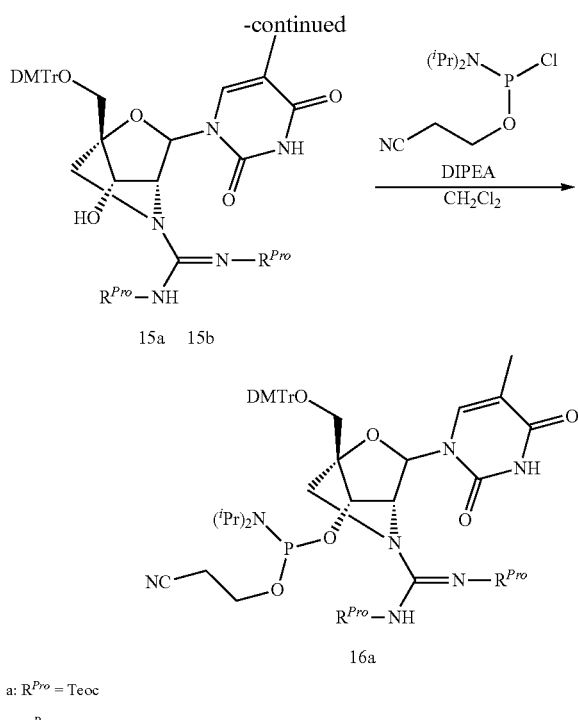

a: $R^{Pro}$ = Teoc
b: $R^{Pro}$ = Boc

Example 6

1-[(1R,3R,4R,7S)-7-Hydroxy-1-(hydroxymethyl)-2-oxa-5-azabicyclo[2.2.1]hepta-3-yl]-5-methylpyrimidine-2,4(1H,3H)-dione acetate salt (Compound 13)

Compound 12 (1.00 g, 2.225 mmol) and acetic acid (6 mL) were mixed, and thereto was added palladium hydroxide (200 mg, 1.425 mmol). The mixtures were stirred under heating at 50° C. as external temperature under hydrogen atmosphere for 6 hours. The reaction solutions were purged with nitrogen, and filtered with a membrane filter using methanol, and the filtrates were concentrated. The residues were azeotroped with toluene, and dried in vacuum to obtain compound 13 (774 mg, containing 9.8 wt % of toluene, yield 100%).

MS (APCI): m/z=270 (M+H)$^+$ $^1$H-NMR (DMSO-d$_6$) δ: 11.31 (1H, brs), 7.75-7.70 (1H, m), 5.33 (1H, s), 3.83 (1H, s), 3.78-3.56 (2H, m), 3.26 (1H, s), 2.90 (1H, d, J=10.2 Hz), 2.58 (1H, d, J=10.2 Hz), 1.91 (3H, s), 1.79-1.75 (3H, m)

Example 7

1-[(1R,3R,4R,7S)-1-{[Bis(4-methoxyphenyl)(phenyl)methoxy]methyl}-7-hydroxy-2-oxa-5-azabicyclo[2.2.1]hepta-3-yl]-5-methylpyrimidine-2,4(1H,3H)-dione (Compound 14)

Under ice-cooling, to the solution of compound 13 (4.00 g, 12.1 mmol) in pyridine (37 mL, 462 mmol) was added 4,4'-dimethoxytrityl chloride (12.4 g, 36.4 mmol), and the mixtures were warmed to room temperature, and stirred for 1.5 hours. The reaction solutions were added dropwise to aqueous acetic acid solution (water 250 mL/acetic acid 69.5 ml), and thereto was added ethyl acetate (300 mL), and the mixtures were stirred for 30 minutes. The mixtures were extracted with ethyl acetate, and the organic layers were then washed with saturated brine, saturated aqueous sodium bicarbonate solution, and saturated brine successively, and dried over anhydrous sodium sulfate, and the insoluble materials were removed by filtration. The solvents were evaporated from the filtrates, and the resulting residues were purified by silica gel chromatography (chloroform/methanol, 100/0 to 90/10) to obtain compound 14 (5.98 g, yield 86%).

MS (APCI): m/z=572 (M+H)$^+$ $^1$H-NMR (DMSO-d$_6$) δ: 11.33 (1H, brs), 7.63-7.59 (1H, m), 7.47-7.21 (9H, m), 6.94-6.86 (4H, m), 5.37 (1H, d, J=5.1 Hz), 5.34 (1H, s), 4.05 (1H, d, J=5.1 Hz), 3.74 (6H, s), 3.39-3.22 (3H, m), 2.84 (1H, d, J=9.8 Hz), 2.63 (1H, d, J=9.8 Hz), 1.53-1.46 (3H, m)

Example 8

Bis[2-(trimethylsilyl)ethyl]{[(1R,3R,4R,7S)-1-{[bis(4-methoxyphenyl)(phenyl)methoxy]methyl}-7-hydroxy-3-(5-methyl-2,4-dioxa-3,4-dihyropyrimidinel(2H)-yl)-2-oxa-5-azabicyclo[2.2.1]hepta-5-yl]methylidene}biscarbamate (Compound 15a)

A solution of compound 14 (1266 mg, 2.215 mmol), THF (7.7 mL), and 2-trimethylsilylethyl N-[methylsulfanyl-(2-trimethylsilylethoxycarbonylamino)methylene]carbamate (1258 mg, 3.322 mmol) in THF (7 mL) was stirred, and thereto were added Et$_3$N (1.23 mL, 8.859 mmol) and AgOTf (854 mg, 3.322 mmol) under ice-cooling successively. The mixtures were warmed to room temperature, and stirred at room temperature for 4 hours. Under ice-cooling, thereto was added saturated brine, and the mixtures were extracted with ethyl acetate. The organic layers were dried over anhydrous sodium sulfate, and the insoluble materials were removed by filtration. The solvents were evaporated from the filtrates, and the resulting residues were purified by silica gel chromatography (hexane/ethyl acetate, 55/45 to 45/55) to obtain compound 15a (1563 mg, containing 1.9 wt % of ethyl acetate, yield 78%).

MS (APCI): m/z=902 (M+H)$^+$ $^1$H-NMR (CDCl$_3$) δ: 10.36 (1H, brs), 8.26 (1H, s), 7.59 (1H, s), 7.49-7.42 (2H, m), 7.39-7.20 (7H, m), 6.89-6.80 (4H, m), 5.62 (1H, s), 4.71 (1H, s), 4.36-4.07 (5H, m), 3.84-3.70 (7H, m), 3.62 (1H, d, J=11.8 Hz), 3.57-3.46 (2H, m), 1.67 (3H, s), 1.11-0.97 (4H, m), 0.04 (18H, s)

Example 9

Bis[2-(trimethylsilyl)ethyl] {[(1R,3R,4R,7S)-1-{[bis(4-methoxyphenyl)(phenyl)methoxy]methyl}-7-{(2-cyanoethoxy)(dipropan-2-ylamino)phosphanyl]oxy}-3-(5-methyl-2,4-dioxo-3,4-dihydropyrimidine-1(2H)-yl)-2-oxa-5-azabicyclo[2.2.1]hepta-5-yl]methylidene}biscarbamate (Compound 16a)

Compound 15a (60.5 mg, 0.0671 mmol) and dichloromethane (1.5 mL) were mixed, and under ice-cooling, thereto were added iPr$_2$NEt (0.0232 mL, 0.134 mmol) and 2-cyanoethyl N,N-diisopropylchlorophosphoramide (0.0224 mL, 0.101 mmol) dropwise successively, and the mixtures were stirred at room temperature for four hours. The mixtures were cooled again under ice-cooling, and thereto were additionally added iPr$_2$NEt (0.0232 mL, 0.134 mmol) and 2-cyanoethyl N,N-diisopropylchlorophosphoramide (0.0224 mL, 0.101 mmol), and the mixtures were stirred at room temperature for 2 hours. Under ice-cooling, thereto was added saturated aqueous sodium bicarbonate solution, and the mixtures were extracted with chloroform. The organic layers were washed with water and saturated brine successively, and dried over anhydrous sodium sulfate, and the insoluble materials were removed by filtration. The solvents were evaporated from the filtrates, and the resulting residues were purified by silica gel chromatography (hexane/ethyl acetate, 65/35 to 50/50) to obtain compound 16a (40.1 mg, yield 54%).

MS (APCI): m/z=1102 (M+H)$^+$ $^{31}$P-NMR (CDCl$_3$) δ: 149.44, 149.31, 148.87, 148.69

Example 10

Di-tert-butyl {[(1R,3R,4R,7S)-1-{([bis(4-methoxyphenyl) (phenyl)methoxy]methyl}-7-hydroxy-3-(5-methyl-2,4-dioxo-3,4-dihydropyrimidin-1(2H)-yl)-2-oxa-5-azabicyclo[2.2.1]hepta-5-yl] methylidene}biscarbamate (Compound 15b)

To a suspension of compound 14 (1.20 g, 2.10 mmol) in THF (21 mL) were added Et$_3$N (1.2 mL, 8.4 mmol), tert-butyl N-[(tert-butoxycarbonylamino)-methylsulfanylmethylene]carbamate (910 mg, 3.1 mmol) and AgOTf (810 mg, 3.1 mmol) successively at room temperature, and the mixtures were stirred at room temperature for 2 hours. To the reaction solution was added saturated brine, and the mixtures were extracted with ethyl acetate. The ethyl acetate layers were washed with saturated brine, and then dried over anhydrous sodium sulfate, and the insoluble materials were removed by filtration. The solvents were evaporated from the filtrates, and the resulting residues were purified by silica gel chromatography (hexane/ethyl acetate, 50/50 to 30/70) to obtain compound 15b (1.44 g, 1.77 mmol, yield 84%).

MS (APCI): m/z=814 (M+H)$^+$ $^1$H-NMR (CDCl$_3$) δ: 10.11 (1H, brs), 8.09 (1H, brs), 7.65-7.57 (1H, m), 7.52-7.41 (2H, m), 7.40-7.19 (7H, m), 6.89-6.78 (4H, m), 5.57 (1H, s), 4.67 (1H, s), 4.32 (1H, s), 4.15 (1H, brs), 3.85-3.72 (7H, m), 3.64-3.40 (3H, m), 1.72-1.65 (3H, m), 1.48 (18H, s)

Another preparation method (hereinafter, sometimes referred to as azidation route) of compound 12 is described.

[chem.108]

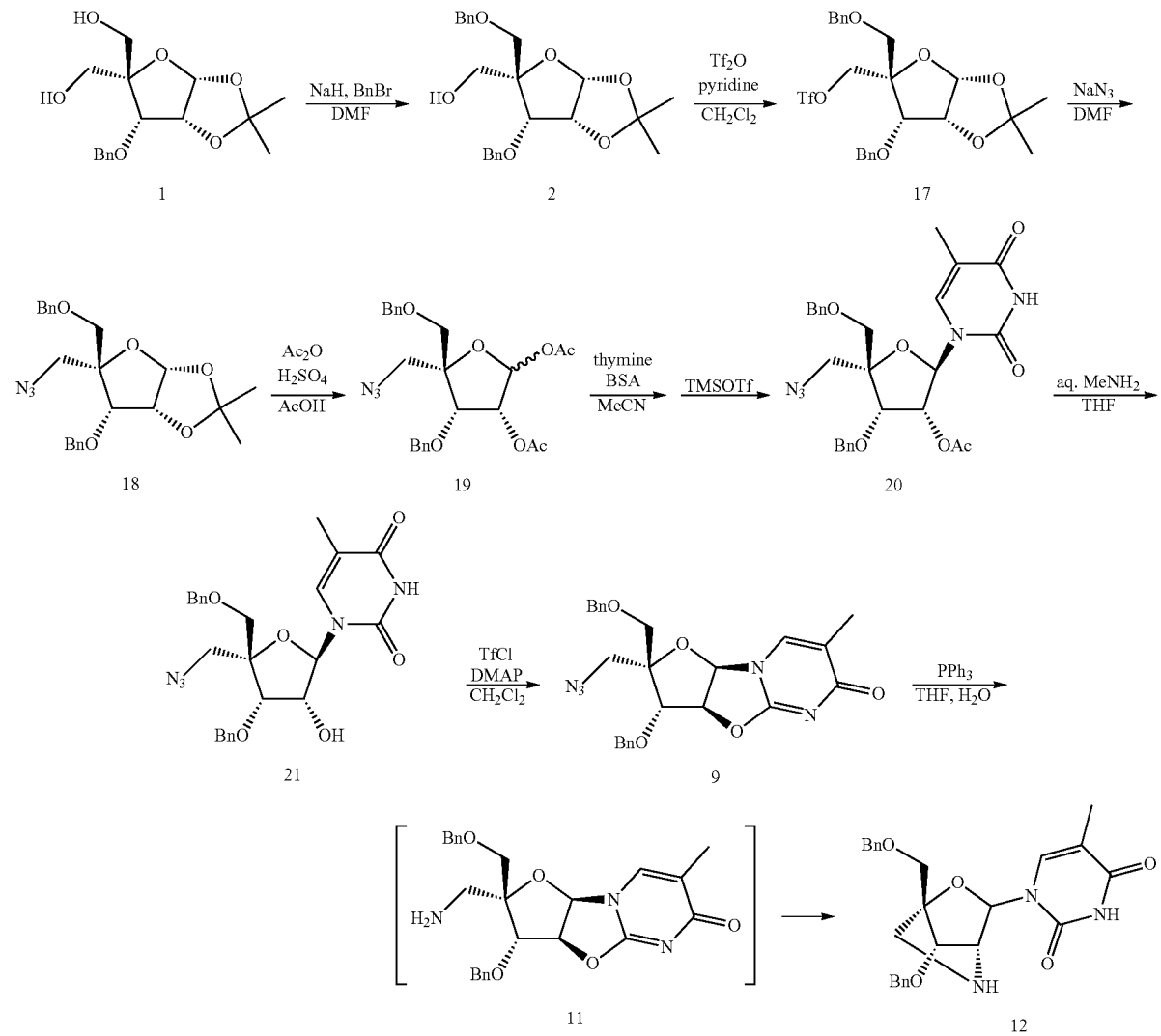

Example 11

Azidation Route

The preparation of compound 20 from compound 2 (3,5-di-O-benzyl-4-C-hydroxymethyl-1,2-O-isopropylidene-α-D-ribofuranose) was carried out according to the known literature (Henrik M. Pfundheller, H. M., Bryld, T., Olsen, C. E., Wengel, J. Helvetica Chimica Acta 2000, 83, 128-151).

3-O-benzyl-4-[(benzyloxy)methyl]-1,2-O-(1-methylethylidene)-5-O-(trifluoromethylsulfonyl)-β-L-lyxofuranose (Compound 17)

Compound 2 (70.10 g, 174 mmol) was dissolved in methylene chloride (700 mL), and thereto was added pyridine (41.51 g, 524 mmol), and the mixtures were cooled to −55° C. as internal temperature. Thereto was added Tf$_2$O (78.93 g, 280 mmol) dropwise at −55 to −48° C. as internal temperature over 30 minutes, and the mixtures were stirred at the same temperature for 1 hour. The cooling bath was replaced with an ice-cooling bath, and the mixtures were stirred for additional 1 hour, and thereto was added 8% aqueous sodium hydrogen carbonate solution, and the organic layers were separated, and washed with 8% aqueous sodium hydrogen carbonate solution and saturated brine successively. Each of aqueous layers was back-extracted with ethyl acetate, and the combined organic layers were dried over anhydrous sodium sulfate, and the insoluble materials were removed by filtration. The solvents were evaporated under reduced pressure to obtain compound 17 (92.96 g).

$^1$H-NMR (CDCl$_3$): the data was identical to that described in the literature.

5-Azido-3-O-benzyl-4-[(benzyloxy)methyl]-5-deoxy-1,2-O-(1-methylethylidene)-β-L-lyxofuranose (Compound 18)

Under nitrogen stream, compound 17 (92.96 g, 174 mmol) was dissolved in DMF (465 mL). Thereto was added NaN$_3$ (45.42 g, 698 mmol) at room temperature, and the mixtures were stirred at 60° C. as external temperature for 4 hours and 30 minutes. After the mixtures were allowed to cool, the mixtures were partitioned between ethyl acetate and water. The organic layers were separated, and washed with 8% aqueous sodium hydrogen carbonate solution and saturated brine successively. Each of the aqueous layers was back-extracted with ethyl acetate, and the combined organic layers were dried over anhydrous sodium sulfate, and the insoluble materials were removed by filtration. The solvents were evaporated under reduced pressure to obtain crude product (75.70 g). The crude product was purified by column chromatography (n-hexane/ethyl acetate, 90/10 to 80/20) to obtain compound 18 (45.70 g, yield 60%).

$^1$H-NMR (CDCl$_3$): the data was identical to that described in the literature.

1,2-Di-O-acetyl-5-azido-3-O-benzyl-4-[(benzyloxy)methyl]-5-deoxy-L-lyxofuranose (Compound 19)

Under nitrogen stream, compound 18 (45.70 g) was dissolved in acetic anhydride (46 mL) and acetic acid (92 mL). Thereto was added concentrated sulfuric acid (280 μL) under ice-cooling, and the mixtures were stirred at room temperature for 2 hours. The mixtures were diluted with ethyl acetate (420 mL), and thereto was added saturated aqueous sodium carbonate solution dropwise under ice-cooling, and the organic layers were separated, and washed with 8% aqueous sodium hydrogen carbonate solution and saturated brine successively. Each of the aqueous layers was back-extracted with ethyl acetate, and the combined organic layers were dried over anhydrous sodium sulfate, and the insoluble materials were removed by filtration. The solvents were evaporated under reduced pressure, and then azeotroped with toluene to obtain compound 19 (50.72 g). The obtained compound was used without purification in next step as quantitative yield.

$^1$H-NMR (CDCl$_3$): the data was identical to that described in the literature.

1-{2-O-Acetyl-5-azido-3-O-benzyl-4-[(benzyloxy)methyl]-5-deoxy-α-L-lyxofuranosyl}-5-methylpyrimidine-2,4(1H,3H)-dione (Compound 20)

Under nitrogen stream, compound 19 (50.72 g) was dissolved in acetonitrile (445 mL), and thereto was added thymine (26.56 g, 210 mmol). Thereto was added BSA (171.86 g, 841 mmol) dropwise over 20 minutes at room temperature, and the mixtures were stirred at 90° C. as external temperature for 1 hour. After the mixtures were allowed to cool, thereto was added TMSOTf (46.96 g, 210 mmol) dropwise over 15 minutes under ice-cooling, and the mixtures were stirred at 90° C. as external temperature for 1 hour. After the mixtures were allowed to cool, thereto was added 8% aqueous sodium hydrogen carbonate solution under ice-cooling, and the participated solids were filtered off, and acetonitrile was evaporated under reduced pressure. Thereto was added ethyl acetate, and the organic layers were separated and washed with saturated brine. Each of the aqueous layers was back-extracted with ethyl acetate, and the combined organic layers were dried over anhydrous sodium sulfate, and the insoluble materials were removed by filtration. The solvents were evaporated under reduced pressure to obtain compound 20 (66.18 g). The obtained compound was used without purification in next step as quantitative yield.

MS (ESI): m/z 536 (M+H)$^+$ $^1$H-NMR (CDCl$_3$): the data was identical to that described in the literature.

1-{5-Azido-3-O-benzyl-4-[(benzyloxy)methyl]-5-deoxy-α-L-lyxofuranosyl}-5-methylpyrimidine-2,4(1H,3H)-dione (Compound 21)

Compound 20 (66.18 g) was dissolved in THF (70 mL), and azeotroped, and was then dissolved in THF (200 mL), and thereto was added 40% aqueous methyl amine solution (132 mL) at room temperature under nitrogen stream. After the mixtures were stirred at room temperature for 1 hour and 30 minutes, the solvents were evaporated under reduced pressure. The concentrated residues were partitioned among ethyl acetate, water, and saturated brine, and the organic layers were separated and washed with saturated brine. Each of the aqueous layers was back-extracted with ethyl acetate, and the combined organic layers were dried over anhydrous sodium sulfate, and insoluble materials were removed by filtration. The solvents were evaporated under reduced pressure to obtain compound 21 (56.26 g). The obtained compound was used without purification in next step as quantitative yield.

MS (ESI): m/z 494 (M+H)$^+$ $^1$H-NMR (CDCl$_3$) δ: 7.40-7.26 (12H, m), 5.88 (1H, d, J=5.1 Hz), 4.74 (1H, d, J=11.3 Hz), 4.64 (1H, d, J=11.3 Hz), 4.55 (2H, s), 4.40 (1H, t, J=5.4 Hz), 4.26 (1H, d, J=5.7 Hz), 3.72 (1H, s), 3.69 (1H, d, J=4.1 Hz), 3.56 (1H, d, J=9.8 Hz), 3.43 (1H, d, J=12.8 Hz), 2.81 (1H, d, J=5.1 Hz), 1.63 (3H, brd)

(2R,3S,3aS,9aR)-2-(Azidomethyl)-3-(benzyloxy)-2-[(benzyloxy)methyl]-7-methyl-2,3,3a,9a-tetrahydro-6H-furo[2',3':4,5][1,3]oxazolo[3,2-a]pyrimidine-6-one (Compound 9)

Under nitrogen stream, compound 21 (56.26 g) was dissolved in methylene chloride (935 mL), and thereto was added DMAP (51.38 g, 420 mmol). The mixtures were stirred for 30 minutes under ice-cooling, and thereto was then added TfCl (51.44 g, 210 mmol) dropwise over 25 minutes. The mixtures were stirred at room temperature for 1 hour, and thereto was then added water under ice-cooling. The organic layers were separated, and washed with water, 0.1 M hydrochloric acid, 4% aqueous sodium hydrogen carbonate solution, and saturated brine successively. Each of the aqueous layers was back-extracted with ethyl acetate and the combined organic layers were dried over anhydrous sodium sulfate, and the insoluble materials were removed by filtration. The solvents were evaporated under reduced pressure to obtain compound 9 (52.10 g). The obtained compound was used without purification in next step as quantitative yield.

MS (ESI): m/z 476 (M+H)$^+$ $^1$H-NMR (CDCl$_3$): the data was identical to that of compound 9 of Examples 2 (DMAP was remained).

1-{(1R,3R,4R,7S)-7-(Benzyloxy)-1-[(benzyloxy)methyl]-2-oxa-5-azabicyclo[2.2.1]hepta-3-yl}-5-methylpyrimidine-2,4(1H,3H)-dione (compound 12)

Under nitrogen stream, compound 9 was dissolved in THF (810 mL), and thereto was added water (160 mL). Thereto was added Ph$_3$P (29.79 g, 113.5 mmol) at room temperature, and the mixtures were stirred at 70° C. as external temperature for 17 hours. After the mixtures were allowed to cool, the solvents were evaporated under reduced pressure, and azeotroped with toluene (200 mL×2) to obtain crude product (167.79 g). The crude product was purified by column chromatography (ethyl acetate/methanol=100/0 to 90/10 to 6/1 to 4/1) to obtain crude compound 12 (42.78 g) containing Ph$_3$PO and ethyl acetate. Under nitrogen stream, the crude compound 12 (42.78 g) was suspended in ethyl acetate (200 mL) in a 1 L egg-plant shaped flask. The mixtures were stirred at 50° C. as external temperature for 1 hour, and thereto was then added diethyl ether (200 mL), and the mixtures were stirred at 50° C. as external temperature for 30 minutes. After the mixtures were allowed to cool overnight, the solids were collected by filtration, and washed with ethyl acetate/diethyl ether=1/1 (100 mL×2), and dried under reduced pressure to obtain compound 12 (30.11 g, yield 70%: on the basis of compound 18).

MS (ESI): m/z 450 (M+H)$^+$

The data of 1H-NMR was identical to that of compound 12 obtained in Example 5 (CDCl$_3$).

One of preparation method (hereinafter, sometimes referred to as mesylation route) of compound 10 is described.

[chem.109]

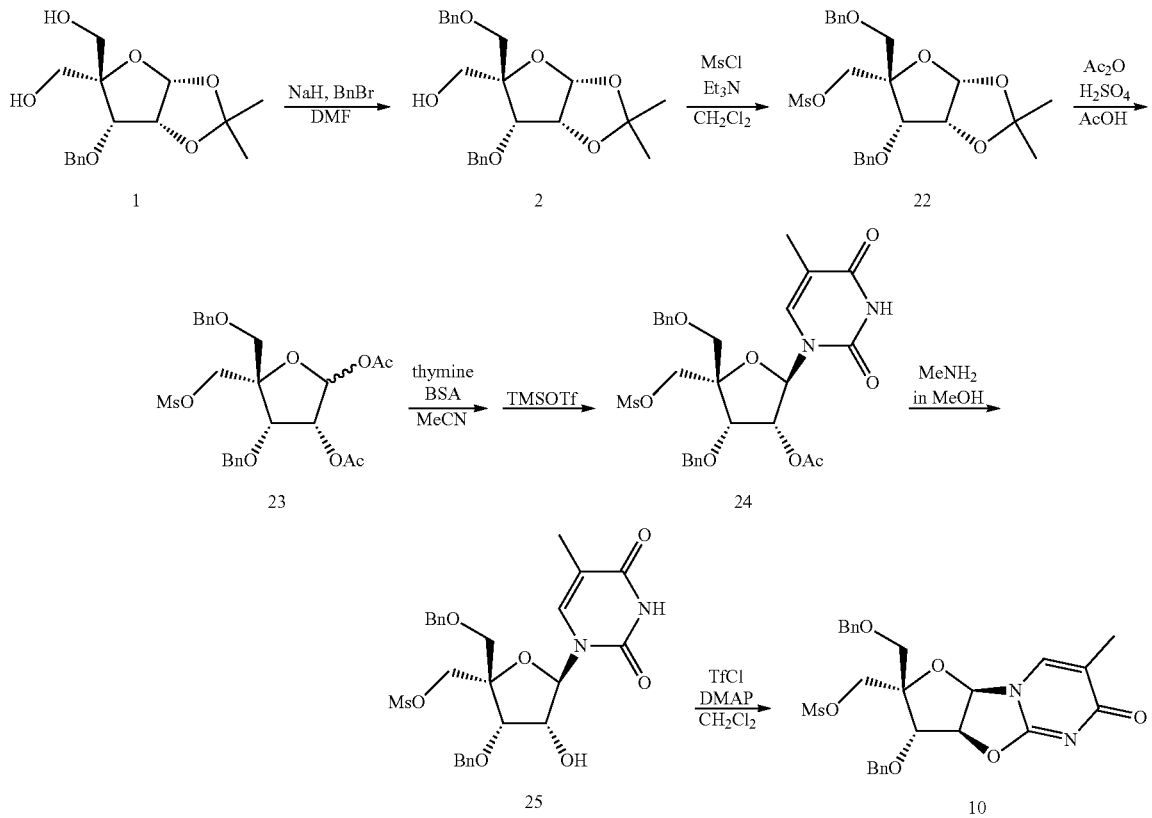

Example 12

Mesylation Route

The preparation of compound 24 from compound 2 was carried out according to the known literature (Henrik M. Pfundheller, H. M., Bryld, T., Olsen, C. E., Wengel, J. Helvetica Chimica Acta 2000, 83, 128-151).

3-O-Benzyl-4-[(benzyloxy)methyl]-1,2-O-(1-methylethylidene)-5-O-(methylsulfonyl)-β-L-lyxofuranose (Compound 22)

Pyridine Method:
Under nitrogen atmosphere, compound 2 (1.00 g, 2.50 mmol) and pyridine (10 mL) were mixed, and thereto was added MsCl (0.23 mL, 2.97 mmol) dropwise at 0° C. After adding dropwise, the mixtures were stirred at the same temperature for 1 hour, and then warmed to room temperature, and stirred for additional 4 hours. To the reaction solutions was added 10% hydrochloric acid, and the mixtures were extracted with ethyl acetate. The organic layers were dried over anhydrous sodium sulfate, and filtered, and then concentrated. The crude product was subjected to column chromatography (n-hexane/ethyl acetate=100/0 to 2/1) to obtain compound 22 (743 mg, yield 62%).

$^1$H-NMR (CDCl$_3$): the data was identical to that described in the literature.

Triethylamine Method
Under nitrogen atmosphere, compound 2 (7.50 g, 18.7 mmol), methylene chloride (150 mL), and Et$_3$N (7.83 mL, 56.2 mmol) were mixed, and thereto was added MsCl (1.74 mL, 22.5 mmol) dropwise at 0° C. After adding dropwise, the mixtures were warmed to room temperature, and the mixtures were stirred for 2 hours. To the reaction solutions was added water, and the mixtures were extracted with methylene chloride. The organic layers were dried over anhydrous sodium sulfate, filtered and concentrated. The crude product was subjected to column chromatography (n-hexane/ethyl acetate=100/0 to 50/50) to obtain compound 22 (8.20 g, yield 92%).

$^1$H-NMR (CDCl$_3$): the data was identical to that described in the literature.

1,2-Di-O-acetyl-3-O-benzyl-4-[(benzyloxy)methyl]-5-O-methylsulfonyl)-L-lyxofuranose (Compound 23)

Under nitrogen atmosphere, compound 22 (8.20 g, 17.1 mmol), acetic acid (140 mL), acetic anhydride (14 mL), and concentrated sulfuric acid (0.14 mL) were mixed, and the mixtures were stirred overnight. To the reaction solutions was added ice water, and the mixtures were extracted with ethyl acetate. The organic layers were washed with saturated aqueous hydrogen carbonate solution, dried over anhydrous sodium sulfate, filtered and concentrated. The crude product was subjected to column chromatography (n-hexane/ethyl acetate=100/0 to 2/1) to obtain compound 23 (5.45 g, yield 61%).

$^1$H-NMR (CDCl$_3$): the data was identical to that described in the literature.

1-{2-O-Acetyl-3-O-benzyl-4-[(benzyloxy)methyl]-5-O-(methylsulfonyl)-α-L-lyxofuranosyl}-5-methylpyrimidine-2,4(1H,3H)-dione (Compound 24)

Under nitrogen atmosphere, compound 23 (5.15 g, 9.86 mmol) and acetonitrile (25 mL) were mixed, and thereto was added thymine (1.67 g, 13.2 mmol) at 0° C., and thereto was added BSA (5.20 mL, 21.3 mmol) dropwise slowly. After adding dropwise, the mixtures were stirred at 50° C. for 3 hours. After the complete dissolution was confirmed, the mixtures were cooled to 0° C., and thereto was added TMSOTf (1.90 mL, 10.5 mmol) slowly. The reaction solutions were stirred at 50° C. overnight. Because the starting materials were not disappeared, the reaction mixtures were cooled to 0° C., and thereto was added TMSOTf (1.90 mL, 10.5 mmol) slowly. After adding dropwise, the mixtures were stirred at 50° C. for 4 hours. To the reaction solutions was added saturated aqueous sodium hydrogen carbonate solution, and the mixtures were extracted with ethyl acetate. The organic layers were saturated aqueous sodium hydrogen carbonate solution, dried over anhydrous sodium sulfate, filtered and concentrated. The crude product was subjected to column chromatography (n-hexane/ethyl acetate=100/0 to 50/50) to obtain compound 24 (5.00 g, yield 86%).

$^1$H-NMR (CDCl$_3$): the data was identical to that described in the literature.

1-{3-O-Benzyl-4-[(benzyloxy)methyl]-5-O-(methylsulfonyl)-α-L-lyxofuranosyl}-5-methylpyrimidine-2,4(1H,3H)-dione (Compound 25)

Under nitrogen atmosphere, compound 24 (5.00 g, 8.49 mmol) and 7N ammonia methanol solution (60 mL) were mixed, and the mixtures were stirred for 4 to 7 hours. The reaction solutions were concentrated, and the crude product was subjected to column chromatography (n-hexane/ethyl acetate 100/0 to 30/70) to obtain compound 25 (4.12 g, yield 89%).

MS (ESI): m/z 547 (M+H)$^+$ $^1$H-NMR (CDCl$_3$) δ: 9.08 (1H, brs), 7.39-7.26 (11H, m), 5.94 (1H, d, J=5.0 Hz), 4.80 (1H, d, J=11.4 Hz), 4.62 (1H, d, J=11.4 Hz), 4.56-4.43 (4H, m), 4.35 (1H, d, J=5.8 Hz), 4.29 (1H, d, J=11.0 Hz), 3.78 (1H, d, J=10.1 Hz), 3.66-3.61 (2H, m), 2.94 (3H, s), 1.59 (3H, d, J=0.8 Hz)

{(2S,3S,3aS,9aR)-3-(Benzyloxy)-2-[(benzyloxy)methyl]-7-methyl-6-oxa-2,3,3a,9a-tetrahydro-6H-furo[2',3':4,5][1,3]oxazolo[3,2-a]pyrimidin-2-yl}methyl methanesulfonate (Compound 10)

Under nitrogen atmosphere, compound 25 (4.10 g, 7.50 mmol), methylene chloride (80 mL) and DMAP (3.67 g, 30.0 mmol) were mixed, and thereto was added TfCl (2.4 mL, 22.5 mmol) dropwise at 0° C. After adding dropwise, the mixtures were warmed to room temperature, and stirred for 2 to 4 hours. To the reaction solutions was added water, and the mixtures were extracted with methylene chloride. The organic layers were dried over anhydrous sodium sulfate, filtered and concentrated. The crude product was subjected column chromatography (chloroform/methanol=90/10) twice repeatedly to obtain compound 10 (3.20 g, yield 81%).

MS (ESI): m/z 529 (M+H)$^+$

The data of $^1$H-NMR was identical to that of compound 10 obtained in the Example 3.

A preparation method of various nucleic acid base compounds from thymine compound (compound 12) using a nucleic acid base replacement method is described.

[chem.110]

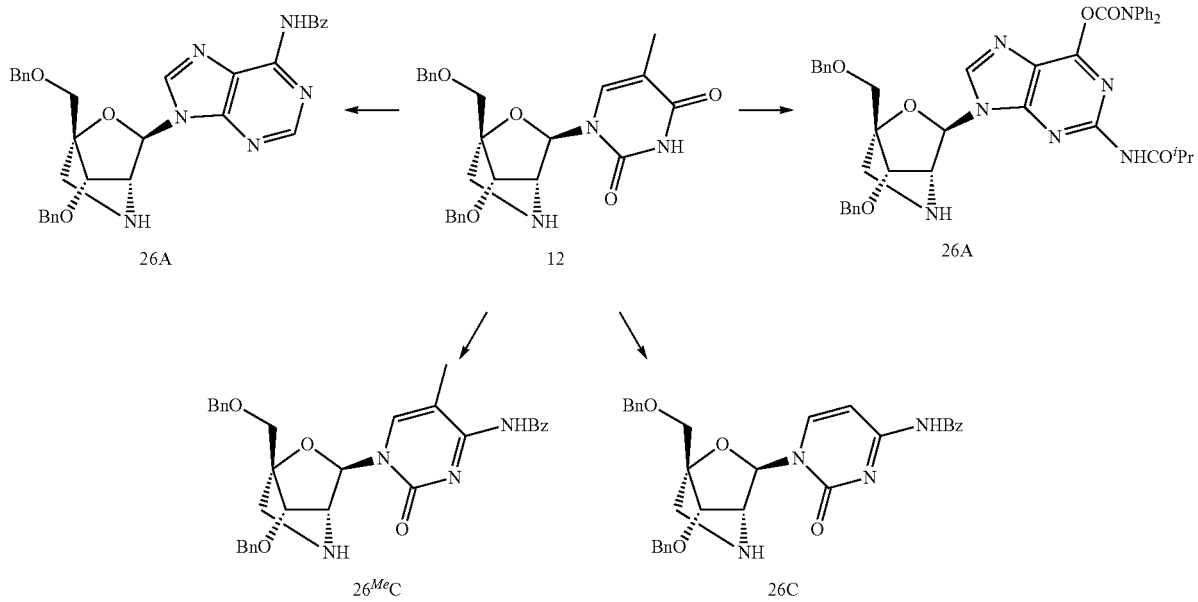

Example 13

Preparation of Adenine (bz) (Compound 26A) from Thymine Compound (Compound 12)

N-(9-{(1R,3R,4R,7S)-7-(Benzyloxy)-1-[(benzyloxy)methyl]-2-oxa-5-azabicyclo[2.2.1]hepta-3-yl)}-9H-purine-6-yl)benzamide (Compound 26A)

To the suspension of compound 12 (100 mg, 0.2225 mmol) and N-(9H-purin-6-yl)benzamide (159 mg, 0.6674 mmol) in 1,2-dichloroethane (2 mL) was added BSA (0.49 mL, 2.002 mmol), and the mixtures were stirred at 60° C. as external temperature for 15 minutes. After the mixtures were allowed to cool at room temperature for 15 minutes, thereto was added TMSOTf (13 µL, 0.067 mmol), and the mixtures were stirred at 60° C. as external temperature again for 15 minutes. To the reaction solutions were added chloroform (10 mL), saturated brine (2 mL), and saturated aqueous sodium bicarbonate solution (2 mL) under ice-cooling, and the mixtures were stirred at room temperature for 10 minutes. The organic layers were passed through a phase separator. After the solvents were evaporated, the resulting residues were purified by silica gel chromatography (chloroform/methanol, 96/4 to 90/10) to obtain compound 26A (119 mg, containing 1.0 wt % of ethyl acetate, yield 95%). Here compound 26A was "β form", and "α form" as an isomer could not be obtained.

MS (APCI): m/z=563 (M+H)$^+$ $^1$H-NMR (CDCl$_3$) δ: 8.91 (1H, s), 8.77 (1H, s), 8.34 (1H, s), 8.06-8.01 (2H, m), 7.65-7.59 (1H, m), 7.57-7.51 (2H, m), 7.40-7.23 (8H, m), 7.22-7.17 (2H, m), 6.02 (1H, s), 4.67 (1H, d, J=12.3 Hz), 4.62 (1H, d, J=12.3 Hz), 4.53 (1H, d, J=11.8 Hz), 4.50 (1H, d, J=11.8 Hz), 4.16 (1H, s), 3.89 (1H, s), 3.84 (1H, d, J=10.8 Hz), 3.79 (1H, d, J=10.8 Hz), 3.22 (1H, d, J=10.3 Hz), 3.02 (1H, d, J=10.3 Hz), 2.21 (1H, brs)

Example 14

Preparation of Guanine (ib, dpc) (Compound 26G) from Thymine Compound (Compound 12)

9-{(1R,3R,4R,7S)-7-(Benzyloxy)-1-[(benzyloxy)methyl]-2-oxa-5-azabicyclo[2.2.1]hepta-3-yl}-2-[(2-methylpropanoyl)amino]-9H-purin-6-yl diphenylcarbamate (Compound 26G)

Similarly to Example 13 using compound 12 (1000 mg, 2.225 mmol) and [2-(2-methylpropanoylamino)-9H-purin-6-yl] N,N-diphenylcarbamate (2779 mg, 6.674 mmol) (the preparation method follows the method described in J. Org. Chem. 1996, 61, 9207), compound 26G (1353 mg, yield 82%) was prepared. Here compound 26G was "β form", and "α form" as an isomer could not be obtained.

MS (APCI): m/z=740 (M+H)$^+$ $^1$H-NMR (CDCl$_3$) δ: 8.26 (1H, s), 7.90 (1H, s), 7.52-7.13 (20H, m), 5.92 (1H, s), 4.65 (1H, d, J=12.3 Hz), 4.61 (1H, d, J=12.3 Hz), 4.50 (2H, s), 4.10 (1H, s), 3.89 (1H, s), 3.81 (1H, d, J=10.8 Hz), 3.76 (1H, d, J=10.8 Hz), 3.19 (1H, d, J=10.3 Hz), 3.04 (1H, brd), 2.98 (1H, d, J=10.3 Hz), 1.26 (6H, d, J=6.7 Hz)

Example 15

Preparation of Methylcytosine (bz) (Compound 26$^{Me}$C) from Thymine Compound (Compound 12)

N-(1-{(1R,3R,4R,7S)-7-(Benzyloxy)-1-[(benzyloxy)methyl]-2-oxa-5-azabicyclo[2.2.1]hepta-3-yl}-5-methyl-2-oxo-1,2-dihydropyrimidin-4-yl)benzamide (Compound 26mC)

To a solution of compound 12 in acetonitrile (6.7 mL) were added N-(5-methyl-2-oxo-1H-pyrimidin-4-yl)benzamide (the preparation method follows the method described in European Journal of Organic Chemistry, 2006, 3152; 431 mg, 2.002 mmol) and BSA (1.47 mL, 6.00 mmol), and the mixtures were stirred at 60° C. as external temperature for 15 minutes. After the mixtures were allowed to cool to room temperature, thereto was added TMSOTf (39 μL, 0.200 mmol) dropwise, and the mixtures were stirred at 60° C. as external temperature again for 150 minutes. The mixtures were cooled under ice-cooling, and thereto were added saturated aqueous sodium bicarbonate solution and chloroform successively, and the mixtures were separated by a separatory funnel. The aqueous layers were extracted with chloroform twice, and the organic layers were washed with saturated brine, and dried over sodium sulfate. The insoluble materials were removed by filtration, and the solvents were removed by filtration, and the solvents were evaporated, and the resulting residues were purified by silica gel chromatography (chloroform/methanol, 100/0 to 95/5) to obtain compound 26$^{Me}$C (71 mg, yield 19%).

Here compound 26$^{Me}$C was "β form", and "α form" as an isomer could not be obtained.

MS (APCI): m/z=553 (M+H)$^+$ $^1$H-NMR (CDCl$_3$) δ: 13.38 (1H, brs), 8.36-8.27 (2H, m), 7.81-7.75 (1H, m), 7.58-7.21 (13H, m), 5.57 (1H, s), 4.68-4.50 (4H, m), 3.92 (1H, s), 3.89 (1H, d, J=11.3 Hz), 3.81(1H, d, J=11.3 Hz), 3.71 (1H, s), 3.16 (1H, d, J=9.8 Hz), 2.91 (1H, d, J=9.8 Hz), 1.80-1.75 (3H, m)

Example 16

N-(1-{(1R,3R,4R,7S)-7-(Benzyloxy)-1-[(benzyloxy) methyl]-2-oxa-5-azabicyclo[2.2.1]hepta-3-y}-2-oxo-1,2-dihydropyrimidin-4-yl)benzamide (Compound 26C)

Similarly to Example 13 from compound 12 (20.0 mg, 0.0445 mmol) and N-(2-oxo-1H-pyrimidin-4-yl)benzamide (28.7 mg, 0.134 mmol), compound 26C (10.4 mg, yield 43%) was prepared. Here compound 26C was "β form", and "α form" as an isomer could not be obtained.

MS (APCI): m/z=539 (M+H)$^+$ $^1$H-NMR (CDCl$_3$) δ: 8.64 (1H, brs), 8.28 (1H, d, J=7.2 Hz), 7.90 (2H, d, J=7.7 Hz), 7.62 (1H, m), 7.53 (2H, m), 7.45-7.20 (11H, m), 5.66 (1H, s), 4.66 (1H, d, J=11.8 Hz), 4.62 (1H, d, J=11.8 Hz), 4.55 (1H, d, J=11.8 Hz), 4.47 (1H, d, J=11.8 Hz), 3.87 (2H, s), 3.84 (1H, d, J=10.8 Hz), 3.79 (1H, d, J=10.8 Hz), 3.16 (1H, d, J=9.8 Hz), 2.95 (1H, d, J=9.8 Hz)

The preparation method of various nucleic acid base compounds from thymine compound (compound 14) using a nucleic acid base replacement method is described.

[chem. 111]

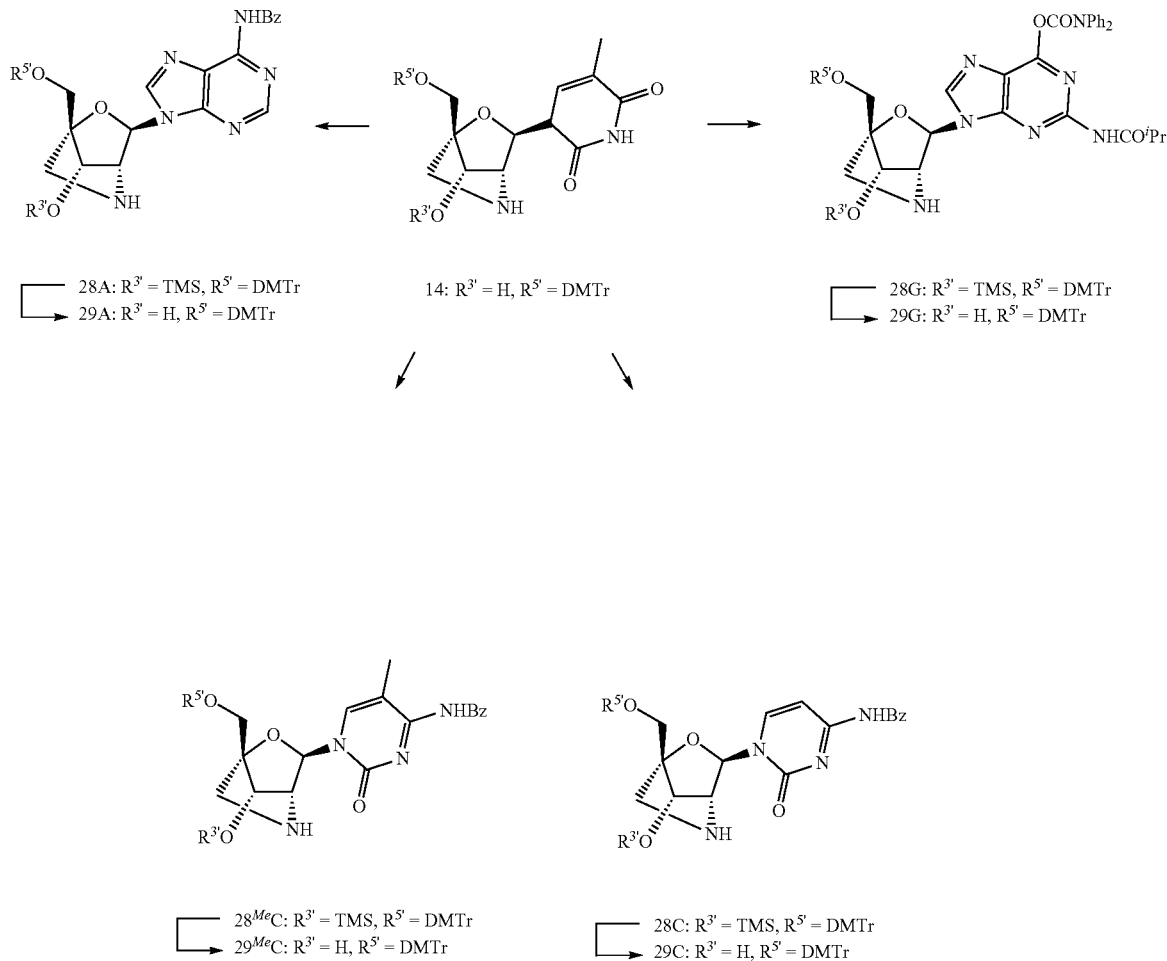

Example 17

Preparation of Adenine (bz) (Compound 28A) from Thymine Compound (Compound 14)

N-(9-{(1R,3R,4R,7S)-1-{[Bis(4-methoxyphenyl)(phenyl)methoxy]methyl}-7-[(trimethylsilyl)oxy]-2-oxa-5-azabicyclo[2.2.1]hepta-3-yl}-9H-purin-6-yl)benzamide (Compound 28A)

Similarly to Example 13 using compound 14 (1.50 g, 2.60 mmol) and BSA (6.40 mL, 26.0 mmol), compound 28A (1.92 g, yield 97%) was obtained. Here compound 28A was "β form", and "α form" as an isomer could not be obtained.

MS (APCI): m/z=757 (M+H)$^+$ $^1$H-NMR (CDCl$_3$) δ: 9.07(1H, s), 8.82 (1H, s), 8.42 (1H, s), 8.09-8.01 (2H, m), 7.66-7.19 (12H, m), 6.90-6.80 (4H, m), 6.05 (1H, s), 4.40 (1H, s), 3.89 (1H, s), 3.80 (6H, s), 3.46 (1H, d, J=10.8 Hz), 3.32 (1H, d, J=10.8 Hz), 3.11 (1H, d, J=10.3 Hz), 2.99 (1H, d, J=10.3 Hz), −0.02 (9H, s)

Example 18

Desilylation of Adenine (bz): (Compound 29A)

N-(9-{(1R,3R,4R,7S)-1-{[Bis(4-methoxyphenyl)(phenyl)methoxy]methyl}-7-hydroxy-2-oxa-5-azabicyclo[2.2.1]hepta-3-yl}-9H-purin-6-yl)benzamide (Compound 29A)

Compound 28A (110 mg, 0.1453 mmol) and THF (2 mL) were mixed, and thereto was added TBAF (0.19 mL, 0.1889 mmol) dropwise under ice-cooling, and the mixtures were stirred at the same temperature for 50 minutes. To the reaction solutions were chloroform (10 mL) and saturated brine (2 mL), and the mixtures were stirred and extracted. The organic layers were washed with saturated brine (2 mL) and then dried over sodium sulfate. The insoluble materials were removed by filtration, and the solvents were evaporated, and the resulting residues were then purified by silica gel chromatography (chloroform/methanol, 100/0 to 91/9) to obtain compound 29A (96.5 mg, containing 1.4 wt % of ethyl acetate, yield 97%).

MS (APCI): m/z=685 (M+H)$^+$ $^1$H-NMR (CDCl$_3$) δ: 9.16 (1H, s), 8.78 (1H, s), 8.33 (1H, s), 8.08-7.99 (2H, m), 7.65-7.21 (12H, m), 6.89-6.81 (4H, m), 6.05 (1H, s), 4.31 (1H, s), 3.90 (1H, s), 3.80 (6H, s), 3.59 (1H, d, J=10.8 Hz), 3.52 (1H, d, J=10.8 Hz), 3.16 (1H, d, J=10.8 Hz), 3.09 (1H, d, J=10.8 Hz)

Example 19

Preparation of guanine (1b, dpc) (compound 28G) from Thymine Compound (Compound 14)

9-{(1R,3R,4R,7S)-1-{[Bis(4-methoxyphenyl)(phenyl)methoxy]methyl}-7-[(trimethylsilyl)oxy]-2-oxa-5-azabicyclo[2.2.1]hepta-3-yl}-2-[(2-methylpropanoyl)amino]-9H-purin-6-yl diphenylcarbamate (Compound 28G)

To a suspension of compound 14 (200 mg, 0.3499 mmol) and [2-(2-methylpropanoylamino)-9H-purin-6-yl] N,N-diphenylcarbamate (437 mg, 1.050 mmol) in 1,2-dichloroethane (4 mL) was added BSA (0.856 mL, 3.499 mmol) at room temperature, and the mixtures were stirred at 60° C. as external temperature for 15 minutes. Thereto was added TMSOTf (20 μL, 0.1050 mmol) dropwise under ice-cooling, and the mixtures were stirred at 60° C. as external temperature for 15 minutes. Thereto were added saturated aqueous sodium bicarbonate solution, saturated aqueous ammonium chloride solution, saturated sodium bicarbonate solution, saturated brine, and chloroform under ice-cooling, and the mixtures were stirred for 10 minutes. The insoluble materials were removed by filtration through Celite, and the filtrates were passed through a phase separator. After the solvents were evaporated, the resulting residues were purified by silica gel chromatography (chloroform/methanol, 99/1 to 96/4) to obtain compound 28G (295 mg, containing 4.1 wt % of ethyl acetate, and 1.9 wt % of acetamide derived from BSA, yield 90%). Here compound 28G was "β form", and "α form" as an isomer could not be obtained.

MS (APCI): m/z=934 (M+H)$^+$ $^1$H-NMR (CDCl$_3$) δ: 8.37 (1H, s), 7.95 (1H, s), 7.52-7.20 (19H, m), 6.88-6.82 (m, 4H), 5.99 (1H, s), 4.29 (1H, s), 3.84 (1H, s), 3.79 (6H, s), 3.46 (1H, d, J=10.8 Hz), 3.29 (1H, d, J=10.8 Hz), 3.14-3.00 (1H, m), 3.08 (1H, d, J=10.2 Hz), 2.97 (1H, d, J=10.2 Hz), 1.28 (3H, d, J=6.7 Hz), 1.27 (3H, d, J=6.7 Hz)

Example 20

Desilylation of Guanine (ib, dpc): (Compound 29G)

9-[(1R,3R,4R,7S)-1-{[Bis(4-methoxyphenyl)(phenyl)methoxy]methyl]-7-hydroxy-2-oxa-5-azabicyclo[2.2.1]hepta-3-yl]-2-[(2-methylpropanoyl)amino]-9H-purin-6-yl diphenylcarbamate (Compound 29G)

Similarly to Example 18 from compound 28G (210 mg, 0.2182 mmol), compound 29G (163 mg, yield 87%) was prepared.

MS (APCI): m/z=862 (M+H)$^+$ $^1$H-NMR (CDCl$_3$) δ: 8.20 (1H, s), 8.08 (15, s), 7.49-7.18 (19H, m), 6.85-6.80 (m, 4H), 5.93 (1H, s), 4.48 (1H, s), 4.01 (1H, s), 3.77 (6H, s), 3.49 (1H, d, J=10.8 Hz), 3.45 (1H, d, J=10.8 Hz), 3.19 (1H, d, J=10.8 Hz), 3.13 (1H, d, J=10.8 Hz), 2.80 (1H, brs), 1.24 (3H, d, J=6.7 Hz), 1.23 (3H, d, J=6.7 Hz)

Example 21

Preparation of Methylcytosine (bz) (Compound 28$^{Me}$C) from Thymine Compound (Compound 14)

N-(1-{(1R,3R,4R,7S)-1-{[Bis(4-methoxyphenyl)(phenyl)methoxy]methyl]-7-[(trimethylsilyl)oxy]-2-oxa-5-azabicyclo[2.2.1]hepta-3-yl}-5-methyl-2-oxo-1,2-dihydropyrimidin-4-yl)benzamide (Compound 28$^{Me}$C)

To a suspension of compound 14 (200 mg, 0.3499 mmol) and N-(5-methyl-2-oxo-1H-pyrimidin-4-yl)benzamide (241 mg, 1.050 mmol) in 1,2-dichloroethane (3.5 mL) was added BSA (0.77 mL, 3.149 mmol), and the mixtures were stirred at 40° C. as external temperature for 15 minutes. Thereto was added TMSOTf (10 µL, 0.05248 mmol) under ice-cooling, and the mixtures were stirred at 40° C. as external temperature again for 15 minutes. To the reaction solutions were added ethyl acetate (10 mL) and saturated aqueous sodium bicarbonate solution (2 mL) under ice-cooling, and the mixtures were stirred and extracted. The organic layers were washed with saturated brine (2 mL) and dried over sodium sulfate. The insoluble materials were removed by filtration, and the solvents were evaporated from the filtrates, and the resulting residues were then purified by silica gel chromatography (chloroform/methanol, 100/0 to 95/5) to obtain compound 28$^{Me}$C (176 mg, yield 67%).

Here compound 28$^{Me}$C was "β form", and "α form" as an isomer could not be obtained.

MS (APCI): m/z=747 (M+H)$^+$ $^1$H-NMR (CDCl$_3$) δ: 13.44 (1H, brs), 8.36-8.29 (2H, m), 8.05 (1H, s), 7.58-7.21 (12H, m), 6.90-6.80 (4H, m), 5.58 (1H, s), 4.27 (1H, s), 3.81 (6H, s), 3.59 (1H, s), 3.53 (1H, d, J=10.8 Hz), 3.23 (1H, d, J=10.8 Hz), 2.97 (1H, d, J=9.8 Hz), 2.78 (1H, d, J=9.8 Hz), 1.87 (3H, s), 0.06 (9H, s)

Example 22

Desilylation of Methylcytosine (bz): (Compound 29$^{Me}$C)

N-(1-{(1R,3R,4R,7S)-1-{[Bis(4-methoxyphenyl)(phenyl)methoxy]methyl}-7-hydroxy-2-oxa-5-azabicyclo[2.2.1]hepta-3-yl}-5-methyl-2-oxo-1,2-dihydropyrimidin-4-yl)benzamide (compound 29$^{Me}$C)

Similarly to Example 18 from compound 28$^{Me}$C (1124 mg, 1.5049 mmol), compound 29$^{Me}$C (1001 mg, yield 99%) was prepared.

MS (APCI): m/z=675 (M+H)$^+$ $^1$H-NMR (CDCl$_3$) δ: 13.40 (1H, brs), 8.36-8.24 (2H, m), 7.91-7.86 (1H, m), 7.56-7.20 (12H, m), 6.92-6.79 (4H, m), 5.56 (1H, s), 4.22 (1H, s), 3.85-3.77 (6H, m), 3.68 (1H, s), 3.56 (1H, d, J=10.8 Hz), 3.46 (1H, d, J=10.8 Hz), 2.97 (1H, d, J=10.3 Hz), 2.93 (1H, d, J=10.3 Hz), 1.87-1.84 (3H, m)

Example 23

Preparation of Cytosine (bz) (Compound 28C) from Thymine Compound (Compound 14)

N-(1-{(1R,3R,4R,7S)-1-{[Bis(4-methoxyphenyl)(phenyl)methoxy]methyl}-7-[(trimethylsilyloxy]-2-oxa-5-azabicyclo[2.2.1]hepta-3-yl}-2-oxo-1,2-dihydropyrimidin-4-yl)benzamide (Compound 28C)

Similarly to Example 21 from compound 14 (200 mg, 0.350 mmol) and N-(2-oxo-1H-pyrimidin-4-yl)benzamide (226 mg, 1.05 mmol), compound 28C (101 mg, yield 39%) was prepared. Here compound 28C was "β form", and "α form" as an isomer could not be obtained.

MS (APCI): m/z=733 (M+H)$^+$ $^1$H-NMR (CDCl$_3$) δ: 8.61 (1H, d, J=7.7 Hz), 7.94-7.89 (2H, m), 7.66-7.25 (13H, m), 6.92-6.86 (4H, m), 5.70 (1H, s), 4.22 (1H, s), 3.85 (6H, s), 3.70 (1H, s), 3.53 (1H, d, J=10.8 Hz), 3.32 (1H, d, J=10.8 Hz), 3.00 (1H, d, J=9.8 Hz), 2.82 (1H, d, J=9.8 Hz), 0.02 (9H, s)

Example 24

Desilylation of Cytosine (bz): (Compound 29C)

N-(1-{(1R,3R,4R,7S)-1-{[Bis(4-methoxyphenyl)(phenyl)methoxy]methyl}-7-hydroxy-2-oxa-5-azabicyclo[2.2.1]hepta-3-yl}-2-oxo-1,2-dihydropyrimidin-4-yl)benzamide (Compound 29C)

Similarly to Example 18 from compound 28C (101 mg, 0.133 mmol), compound 29C (86.0 mg, yield 98%) was prepared.

MS (APCI): m/z=661 (M+H)$^+$ $^1$H-NMR (CDCl$_3$) δ: 8.48 (1H, d, J=7.7 Hz), 7.82-7.76 (2H, m), 7.60-7.19 (13H, m), 6.93-6.82 (4H, m), 5.63 (1H, s), 4.24 (1H, s), 3.87 (1H, s), 3.81 (6H, s), 3.53 (1H, d, J=10.8 Hz), 3.44 (1H, d, J=10.8 Hz), 3.01 (1H, d, J=10.3 Hz), 2.88 (1H, d, J=10.3 Hz)

[chem. 112]

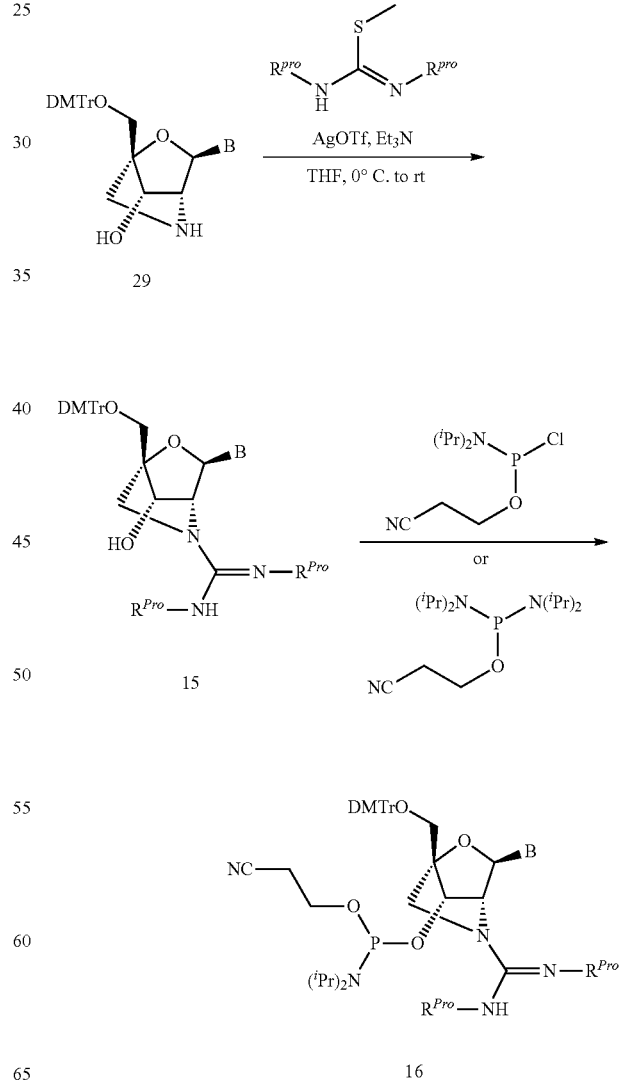

| Ring B | | 29 DMTrO-[sugar]-B HO NH | 15 DMTrO-[sugar]-B HO N=N-R^pro, R^pro-NH | | 16 DMTrO-[sugar]-B, NC-CH₂CH₂-O-P((iPr)₂N)-O-[sugar] N=N-R^pro, R^pro-NH | |
|---|---|---|---|---|---|---|
| | | | $R^{pro}$ = Teoc | $R^{pro}$ = Boc | $R^{pro}$ = Teoc | $R^{pro}$ = Boc |
| A | NHBz-adenine | 29A | 15Aa | 15Ab | 16Aa | 16Ab |
| G | OCONPh₂ / NHCO^iPr-guanine | 29G | 15Ga | 15Gb | 16Ga | 16Gb |
| $^{Me}$C | 5-methyl-N-Bz-cytosine | 29$^{Me}$C | 15$^{Me}$Ca | 15$^{Me}$Cb | 16$^{Me}$Ca | 16$^{Me}$Cb |
| C | NHBz-cytosine | 29C | 15Ca | 15Cb | 16Ca | 16Cb |

Example 25

Guanidination (teoc) of Adenine (bz): (Compound 15Aa)

Bis[2-(trimethylsilyl)ethyl] {[(1R,3R,4R,7S)-1-{[bis(4-methoxyphenyl)(phenyl)methoxy]methyl}-7-hydroxy-3-{6-[(phenylcarbonyl)amino]-9H-purin-9-yl}-2-oxa-5-azabicyclo[2.2.1] hepta-5-yl]methylidene}biscarbamate (Compound 15Aa)

Similarly to Example 8 from compound 29A (91.5 mg, 0.134 mmol), compound 15Aa (111 mg, containing 1.1 wt % of ethyl acetate, yield 82%) was prepared.

MS(APCI): m/z=1015 (M+H)$^+$ $^1$H-NMR (CDCl$_3$) δ: 10.66 (1H, brs), 9.01 (1H, s), 8.77 (1H, s), 8.25 (1H, s), 8.08-7.98 (2H, m), 7.67-7.40 (5H, m), 7.39-7.17 (7H, m), 6.90-6.78 (4H, m), 6.28 (1H, s), 5.13 (1H, brs), 4.63-4.54 (1H, m), 4.32-4.15 (4H, m), 3.96 (1H, d, J=11.3 Hz), 3.87-3.74 (7H, m), 3.62-3.50 (2H, m), 3.31-3.09 (1H, m), 1.16-0.98 (4H, m), 0.04 (18H, s)

Example 26

Phosphorylation (teoc) of Adenine (bz) (Compound 16Aa)

Bis[2-(trimethylsilyl)ethyl] {[(1R,3R,4R,7S)-1-{[bis(4-methoxyphenyl)(phenyl)methoxy]methyl}-7-{[(2-cyanoethoxy)(dipropan-2-ylamino)phosphanyl]oxy}-3-{6-[(phenylcarbonyl)amino]-9H-purin-9-yl}-2-oxa-5-azabicyclo[2.2.1]hepta-5-yl]methylidene}biscarbamate (Compound 16Aa)

Similarly to Example 9 from compound 15Aa (104.8 mg, 0.1032 mmol), compound 16Aa (66.8 mg, yield 53%) was prepared.

MS (APCI): m/z=1215 (M+H)$^+$ $^{31}$P-NMR (CDCl$_3$) δ: 149.67, 149.39, 149.34, 148.01

Example 27

Guanidination (teoc) of Guanine (ib, dpc): (Compound 15Ga)

Bis[2-(trimethylsilyl)ethyl] {[(1R,3R,4R,7S)-1-{[bis(4-methoxyphenyl)(phenyl)methoxy]methyl}-3-{6-[(diphenylcarbamoyl)oxy]-2-[(2-methylpropanoyl)amino]-9H-purin-9-yl}-7-hydroxy-2-oxa-5-azabicyclo[2.2.1]hepta-5-yl]methylidene}biscarbamate (Compound 15Ga)

Similarly to Example 8 from compound 29G (94.4 mg, 0.110 mmol), compound 15Ga (114 mg, yield 84%) was prepared.

MS (APCI): m/z=1192 (M+H)$^+$ $^1$H-NMR (CDCl$_3$) δ: 10.87 (1H, brs), 8.12 (1H, s), 8.03 (1H, s), 7.52-7.33 (11H, m), 7.32-7.13 (8H, m), 6.81-6.75 (4H, m), 6.24 (1H, brs), 5.18 (1H, s), 4.99 (1H, brs), 4.26-4.03 (6H, m), 3.93-3.81 (1H, m), 3.76 (3H, s), 3.76 (3H, s), 3.45 (1H, d, J=10.8 Hz), 3.38 (1H, d, J=10.8 Hz), 2.65-2.52 (1H, m), 1.22 (3H, d, J=7.2 Hz), 1.17 (3H, d, J=6.7 Hz), 1.13-0.87 (4H, m), 0.03 (9H, brs), −0.01 (9H, brs)

Example 28

Phosphorylation (teoc) of guanine (ib, dpc): (Compound 16Ga)

Bis [2-(trimethylsilyl)ethyl]{[(1R,3R,4R,7S)-1-{[bis(4-methoxyphenyl)(phenyl)methoxy]methyl}-7-{[(2-cyanoethoxy)(dipropan-2-ylamino)phosphanyl]oxy}-3-{6-[(diphenylcarbamoyl)oxy]-2-[(2-methylpropanoyl)amino]-9H-purin-9-yl}-2-oxa-5-azabicyclo[2.2.1]hepta-5-yl]methylidene}biscarbamate (Compound 16Ga)

;e'3qTo a solution of compound 15Ga (50.5 mg, 0.0423 mmol) in acetonitrile (1 mL) were added diisopropyl ammonium tetrazolide (10.9 mg, 0.0635 mmol), 2-cyanoethyl N,N,N',N'-tetraisopropylphosphorodiamidite (19.1 mg, 0.0635 mmol) and 2-cyanoethyl N,N,N',N'-tetraisopropylphosphorodiamidite (19.1 mg, 0.0635 mmol) at room temperature, and the mixtures were stirred at room temperature for 1 hour. Thereto were added further diisopropyl ammonium tetrazolide (21.8 mg, 0.127 mmol) and 2-cyanoethyl N,N,N',N'-tetraisopropylphosphorodiamidite (38.3 mg, 0.127 mmol), and the mixtures were stirred at room temperature for 3 hours. Thereto was added further 2-cyanoethyl N,N,N',N'-tetraisopropylphosphorodiamidite (6.4 mg, 0.0212 mmol), and the mixtures were stirred at room temperature for 20 minutes. Thereto were added chloroform (5 mL) and saturated brine (2 mL) under ice-cooling, and the mixtures were stirred and passed through a phase separator. After the solvents were evaporated, the mixtures were purified by silica gel chromatography (hexane/ethyl acetate, 80/20 to 60/40) to obtain compound 16Ga (61.4 mg, yield 83%).

MS (APCI): m/z=1392 (M+H)$^+$ $^{31}$P-NMR (CDCl$_3$) δ: 149.16, 148.68

Example 29

Guanidination (teoc) of Methylcytosine (bz): (Compound 15$^{Me}$Ca)

Bis[2-(trimethylsilyl)ethyl] {[(1R,3R,4R,7S)-1-{[bis(4-methoxyphenyl)(phenyl)methoxy]methyl}-7-hydroxy-3-{5-methyl-2-oxo-4-[(phenylcarbonyl)amino]pyrimidin-1(2H)-yl}-2-oxa-5-azabicyclo[2.2.1]hepta-5-yl]methylidene}biscarbamate (compound 15$^{Me}$Ca) 2-Trimethylsilylethyl N-(((1R,4R,6R,7S)-6-(4-benzamide-5-methyl-2-oxo-pyrimidin-1-yl)-4-((bis(4-methoxyphenyl)-phenylmethoxy)methyl)-7-hydroxy-5-oxa-2-azabicyclo(2.2.1)hepta-2-yl)-(2-trimethylsilylethoxycarbonylamino)methylene)carbamate (Compound 15$^{Me}$Ca)

Similarly to Example 8 from compound 29$^{Me}$C (890 mg, 1.319 mmol), compound 15$^{Me}$Ca (870 mg, yield 66%) was prepared.

MS (APCI): m/z=1005 (M+H)$^+$ $^1$H-NMR (CDCl$_3$) δ: 13.41 (1H, brs), 10.37 (1H, brs), 8.37-8.25 (2H, m), 7.75 (1H, s), 7.58-7.21 (12H, m), 6.93-6.81 (4H, m), 5.67 (1H, s), 4.76 (1H, s), 4.36-4.12 (5H, m), 3.86-3.73 (7H, m), 3.63 (1H, d, J=11.7 Hz), 3.56 (1H, d, J=11.3 Hz), 3.52 (1H, d, J=11.3 Hz), 1.87 (3H, s), 1.11-1.00 (4H, m), 0.04 (18H, s)

Example 30

Phosphorylation (teoc) of methylcytosine (bz): (Compound 16$^{Me}$Ca)

Bis[2-(trimethylsilyl)ethyl] {[(1R,3R,4R,7S)-1-{[bis(4-methoxyphenyl)(phenyl)methoxy]methyl}-7-{[(2-cyanoethoxy)(dipropan-2-ylamino)phosphanyl]oxy}-3-{5-methyl-2-oxo-4-[(phenylcarbonyl)amino]pyrimidin-1(2H)-yl}-2-oxa-5-azabicyclo[2.2.1]hepta-5-yl]methylidene}biscarbamate (Compound 16$^{Me}$Ca)

Similarly to Example 9 from compound 15$^{Me}$Ca (50 mg, 0.0497 mmol), compound 16$^{Me}$Ca (31 mg, yield 52%) was prepared.

MS (APCI): m/z=1205 (M+H)$^+$ $^{31}$P-NMR (CDCl$_3$) δ: 149.66, 149.44, 149.03. 148.87

Example 31

Guanidination (boc) of Adenine (bz): (Compound 15Ab)

Di-tert-butyl {[(1R,3R,4R,7S)-1-{[bis(4-methoxyphenyl)(phenyl)methoxy]methyl}-7-hydroxy-3-{6-[(phenylcarbonyl)amino]-9H-purin-9-yl}-2-oxa-5-azabicyclo[2.2.1]hepta-5-yl]methylidene}biscarbamate (Compound 15Ab)

Similarly to Example 10 from compound 29A (1.74 g, 2.54 mmol), compound 15Ab (1.735 g, containing 2.0 wt % of hexane, yield 74%) was prepared.

MS(APCI): m/z=927 (M+H)$^+$ $^1$H-NMR (CDCl$_3$) δ: 10.46 (1H, brs), 9.08 (1H, s), 8.76 (1H, s), 8.26 (1H, s), 8.06-7.99 (2H, m), 7.66-7.18 (12H, m), 6.88-6.80 (4H, m), 6.22 (1H, s), 5.21 (1H, s), 4.50 (1H, s), 3.95-3.81 (2H, m), 3.79 (6H, s), 3.58-3.49 (2H, m), 3.47-3.37 (1H, m), 1.65 (9H, s), 1.59-1.40 (9H, m)

Example 32

Phosphorylation (boc) of Adenine (bz): (Compound 16Ab)

Di-tert-butyl {[(1R,3R,4R,7S)-1-{[bis(4-methoxy-phenyl)(phenyl)methoxy]methyl}-7-{[(2-cyanoethoxy)(dipropan-2-ylamino)phosphanyl]oxy}-3-{6-[(phenylcarbonyl)amino]-9H-purin-9-yl}-2-oxa-5-azabicyclo[2.2.1]hepta-5-yl]methylidene}biscarbamate (Compound 16Ab)

Similarly to Example 9 from compound 15Ab (100 mg, 0.1079 mmol), compound 16Ab (105 mg, yield 86%) was prepared.

MS (APCI): m/z=1127 (M+H)$^+$ $^{31}$P-NMR (CDCl$_3$) δ: 149.39, 149.23

Example 33

Guanidination (boc) of Guanine (ib, dpc): (Compound 15Gb)

Di-tert-butyl {[(1R,3R,4R,7S)-1-{[bis(4-methoxy-phenyl)(phenyl)methoxy]methyl}-3-{6-[(diphenyl-carbamoyl)oxy]-2-[(2-methylpropanoyl)amino]-9H-purin-9-yl}-7-hydroxy-2-oxa-5-azabicyclo[2.2.1]hepta-5-yl]methylidene}biscarbamate (Compound 15Gb)

Similarly to Example 10 from compound 29G (77.8 mg, 0.0903 mol), compound 15Gb (83.2 mg, yield 82%) was prepared.

MS (APCI): m/z=1104 (M+H)$^+$ $^1$H-NMR (CDCl$_3$) δ: 10.56 (1H, s), 8.13 (1H, s), 8.01 (1H, s), 7.49-7.33 (11H, m), 7.32-7.14 (8H, m), 6.77-6.80 (4H, m), 6.17 (1H, brs), 5.10 (1H, brs), 4.14-4.00 (2H, m), 3.89-3.81 (1H, m), 3.76 (3H, s), 3.76 (3H, s), 3.50-3.36 (2H, m), 2.73-2.58 (1H, m), 1.55-1.32 (18H, m), 1.22 (3H, d, J=7.2 Hz), 1.17 (3H, d, J=7.2 Hz)

Example 34

Phosphorylation (boc) of Guanine (ib, dpc): (Compound 16Gb)

Di-tert-butyl {[(1R,3R,4R,7S)-1-{[bis(4-methoxy-phenyl)(phenyl)methoxy]methyl}-7-{[(2-cyanoethoxy)(dipropan-2-ylamino)phosphanyl]oxy}-3-{6-[(diphenylcarbamoyl)oxy]-2-[(2-methylpropanoyl)amino]-9H-purin-9-yl}-2-oxa-5-azabicyclo[2.2.1]hepta-5-yl]methylidene}biscarbamate (Compound 16Gb)

Similarly to Example 28 from compound 15Gb (41.8 mg, 0.0379 mmol), compound 16Gb (43.8 mg, yield 84%) was prepared.

MS (APCI): m/z=1304 (M+H)$^+$ $^{31}$P-NMR (CDCl$_3$) δ: 148.92, 148.80, 148.36

Example 35

Guanidination (boc) of Methylcytosine (bz): (Compound 15$^{Me}$Cb)

Di-tert-butyl {[(1R,3R,4R,7S)-1-{[bis(4-methoxy-phenyl)(phenyl)methoxy]methyl}-7-hydroxy-3-{5-methyl-2-oxo-4-[(phenylcarbonyl)amino]pyrimidin-1(2H)-yl}-2-oxa-5-azabicyclo[2.2.1]hepta-5-yl]methylidene}biscarbamate (Compound 15$^{Me}$Cb)

Similarly to Example 10 from compound 29$^{Me}$C (1762 mg, 2.612 mmol), compound 15$^{Me}$Cb (1467 mg, yield 61%) was prepared.

MS (APCI): m/z=917 (M+H)$^+$ $^1$H-NMR (CDCl$_3$) δ: 13.39 (1H, brs), 10.11 (1H, brs), 8.38-8.26 (2H, m), 7.77 (1H, s), 7.57-7.21 (12H, m), 6.91-6.80 (4H, m), 5.62 (1H, s), 4.71 (1H, s), 4.34 (1H, s), 3.85-3.75 (7H, m), 3.58 (1H, d, J=11.3 Hz), 3.54 (1H, d, J=11.3 Hz), 3.49 (1H, d, J=11.3 Hz), 1.88 (3H, s), 1.53-1.45 (18H, m)

Example 36

Phosphorylation (boc) of Methylcytosine (bz): (Compound 16$^{Me}$Cb)

Di-tert-butyl {[(1R,3R,4R,7S)-1-{[bis(4-methoxy-phenyl)(phenyl)methoxy]methyl}-7-{[(2-cyanoethoxy)(dipropan-2-ylamino)phosphanyl]oxy}-3-{5-methyl-2-oxo-4-[(phenylcarbonyl)amino]pyrimidin-1(2H)-yl}-2-oxa-5-azabicyclo[2.2.1]hepta-5-yl]methylidyne}biscarbamate (Compound 16$^{Me}$Cb)

Similarly to Example 9 from compound 15$^{Me}$Cb (142 mg, 0.1549 mmol), compound 16$^{Me}$Cb (85.0 mg, yield 49%) was prepared.

MS (APCI): m/z=1117 (M+H)$^+$ $^{31}$P-NMR (CDCl$_3$) δ: 149.48, 149.08, 148.56

Example 37

Guanidination (boc) of Cytosine (bz): (Compound 15Cb)

Di-tert-butyl {[(1R,3R,4R,7S)-1-{[bis(4-methoxy-phenyl)(phenyl)methoxy]methyl}-7-hydroxy-3-{2-oxo-4-[(phenylcarbonyl)amino]pyrimidin-1(2H)-yl}-2-oxa-5-azabicyclo[2.2.1]hepta-5-yl]methylidene}biscarbamate (Compound 15Cb)

Similarly to Example 10 from compound 29C (86 mg, 0.130 mmol), compound 15Cb (91 mg, yield 77%) was prepared.

MS (APCI): m/z=903 (M+H)$^+$ $^1$H-NMR (CDCl$_3$) δ: 10.06 (1H, brs), 8.66 (1H, brs), 8.33 (1H, d, J=7.7 Hz), 7.92-7.85 (2H, m), 7.65-7.23 (13H, m), 6.92-6.85 (4H, m), 5.71 (1H, s), 4.86 (1H, s), 4.30 (1H, s), 4.26-4.07 (1H, m), 3.87-3.74 (7H, m), 3.62-3.53 (2H, m), 3.45 (1H, d, J=10.8 Hz), 1.49 (18H, s)

Example 38

Phosphorylation (boc) of Cytosine (bz): (Compound 16Cb)

Di-tert-butyl {[(1R,3R,4R,7S)-1-{[bis(4-methoxy-phenyl)(phenyl)methoxy]methyl}-7-{[(2-cyanoethoxy)(dipropan-2-ylamino)phosphanyl]oxy}-3-{2-oxo-4-[(phenylcarbonyl)amino]pyrimidin-1(2H)-yl}-2-oxa-5-azabicyclo[2.2.1]hepta-5-yl]methylidyne}biscarbamate (Compound 16Cb)

Similarly to Example 9 from compound 15Cb (91 mg, 0.100 mmol), compound 16Cb (61 mg, yield 55%) was prepared.

MS (APCI): m/z=1103 (M+H)$^+$ $^{31}$P-NMR (CDCl$_3$) δ: 149.58, 149.25, 148.86

Preparation Method of Uracil Product (Compound 26A) and Guanine Product (Compound 26G) (Hereinafter, Sometimes Referred to Uracil Route) is Described.
[chem.113]
Uracil route
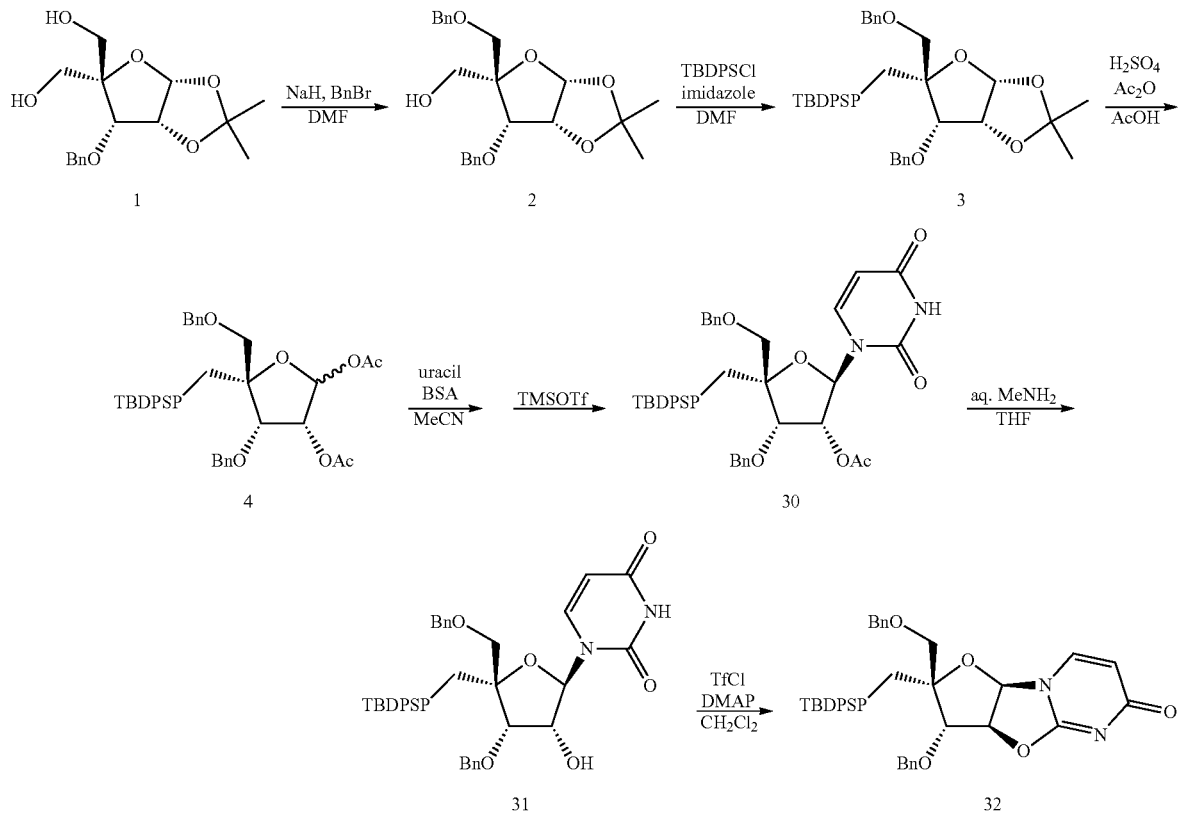
[chem. 114]
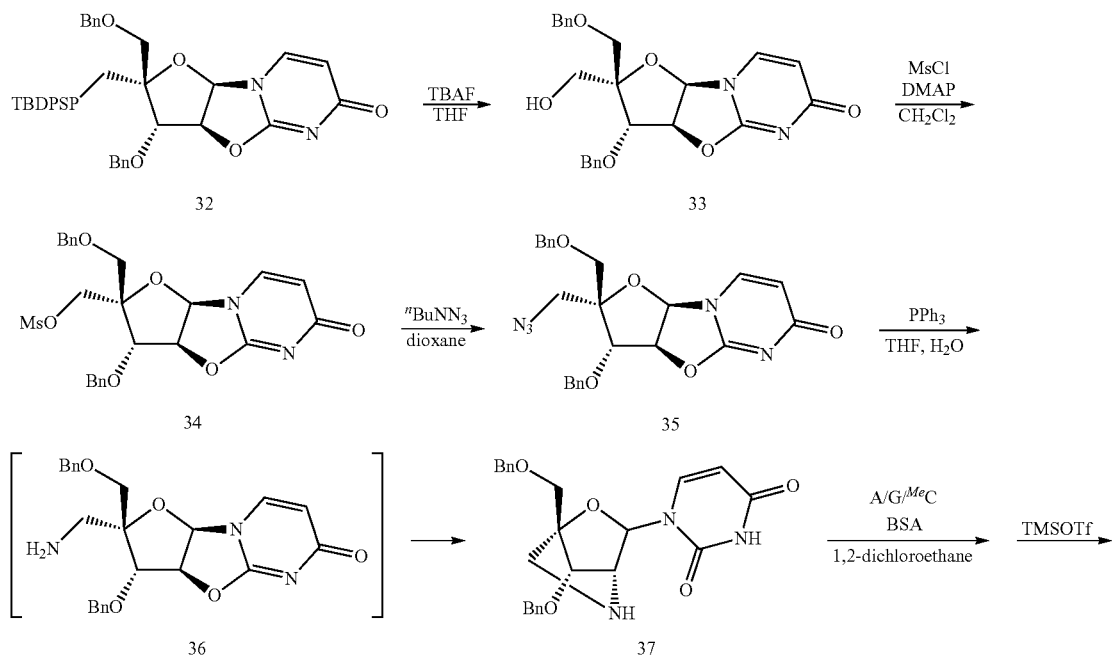

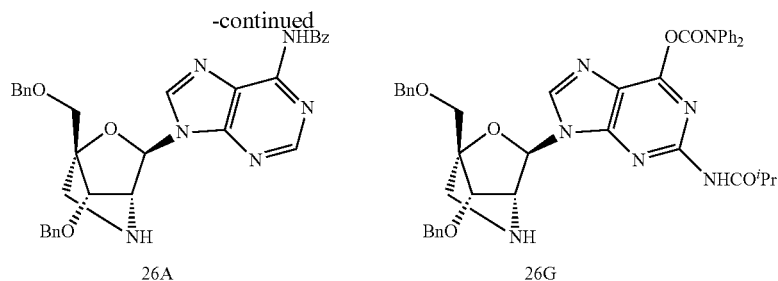

26A            26G

Example 39

1-{2-O-Acetyl-3-O-benzyl-4-[(benzyloxy)methyl]-5-O-[tert-butyl(diphenyl)silyl]-α-L-lyxofuranosyl}pyrimidine-2,4(1H,3H)-dione (Compound 30)

Acetonitrile (100 mL) and uracil (5.668 g, 50.57 mmol) were mixed with compound 4 (25.58 g, 37.46 mmol) (which was prepared via 2 steps according to the method described in the literature (J. Org. Chem. 2011, 76, 9891-9899) from 3,5-di-O-benzyl-4-C-hydroxymethyl-1,2-O-isopropylidene-α-D-ribofuranose (compound 2) (15.0 g, 37.45 mmol)), and thereto was added BSA (21.02 mL, 85.97 mmol) dropwise over 10 minutes. After the reaction system was heated at 50° C. for 13 minutes until the reaction system became homogeneous, the mixtures were cooled to 0° C. Thereto was added TMSOTf (7.7 mL, 40.08 mmol) dropwise at 0° C. After the mixtures were stirred at room temperature for 5 minutes, the mixtures were stirred at 50° C. under heating for 2 hours. After saturated aqueous sodium bicarbonate solution (200 mL) was added thereto at 0° C., the reaction solutions were concentrated. After the residues were extracted with ethyl acetate, the extracts were washed with saturated brine, dried over anhydrous sodium sulfate, and the insoluble materials were removed by filtration, and the solvents were evaporated. The crude product was subjected to column chromatography (n-hexane/ethyl acetate=65/35 to 50/50) to obtain compound 30 (23.84 g, yield 87%, via 3 steps from 2).

MS (APCI): m/z=735 (M+H)$^+$ $^1$H-NMR (CDCl$_3$) δ: 8.00-7.95 (1H, m), 7.72 (1H, d, J=8.2 Hz), 7.64-7.56 (4H, m) 7.46-7.27 (14H, m), 7.22-7.16 (2H, m), 6.07 (1H, d, J=5.7 Hz), 5.35-5.27 (2H, m), 4.58-4.47 (4H, m), 4.35 (1H, d, J=5.7 Hz), 3.92 (1H, d, J=10.8 Hz), 3.82-3.63 (3H, m), 1.94 (3H, s), 1.04 (9H, s)

Example 40

1-{3-O-Benzyl-4-[(benzyloxy)methyl]-5-O-[tert-butyl(diphenyl)silyl]-α-L-lyxofuranosyl}pyrimidine-2,4(1H,3H)-dione (Compound 31)

((2R,3R,4S,5S)-4-Benzyloxy-5-(benzyloxymethyl)-5-((tert-butyl(diphenyl)silyl)oxymethyl)-2-(2,4-dioxopyrimidin-1-yl)tetrahydrofuran-3-yl)acetate (compound 30, 11 g, 14.97 mmol) and tetrahydrofuran (55 mL) were mixed, and thereto was added methylamine (34 mL, 306.5 mmol) dropwise with a dropping funnel at room temperature, and the mixtures were stirred at room temperature for 1 hour. After ethyl acetate was added thereto, the mixtures were extracted with ethyl acetate. The mixtures were washed with saturated brine, dried over anhydrous sodium sulfate, and the insoluble materials were then removed by filtration, and the solvents were evaporated. The crude product was subjected to column chromatography (n-hexane/ethyl acetate=50/50 to 40/60) to obtain compound 31 (9.23 g, yield 89%).

MS (APCI): m/z=693 (M+H)$^+$ $^1$H-NMR (CDCl$_3$) δ: 8.08 (1H, brs), 7.68-7.59 (5H, m) 7.48-7.26 (14H, m), 7.24-7.19 (2H, m), 5.95 (1H, d, J=4.1 Hz), 5.40-5.33 (1H, m), 4.73 (1H, d, J=11.1 Hz), 4.63 (1H, d, J=11.1 Hz), 4.49-4.40 (2H, m), 4.37-4.26 (2H, m), 3.82-3.69 (3H, m), 3.59 (1H, d, J=10.1 Hz), 3.54 (1H, d, J=10.1 Hz), 1.06 (9H, s)

Example 41

(2S,3S,3aS,9aR)-3-(Benzyloxy)-2-[(benzyloxy)methyl]-2-({[tert-butyl(diphenyl)silyl]oxy}methyl)-2,3,3a,9a-tetrahydro-6H-furo[2',3':4,5][1,3]oxazolo[3,2-a]pyrimidine-6-one (Compound 32)

Compound 31 (9.23 g, 13.3 mmol), methylene chloride (66.6 mL) and DMAP (5.70 g, 46.6 mmol) were mixed, and the mixtures were cooled to 0° C. Thereto was added TfCl (5.61 g, 33.3 mmol) dropwise at 0° C. The mixtures were stirred at room temperature for 1 hour. Thereto was added water at 0° C., and the mixtures were extracted with chloroform. The mixtures were washed with saturated brine, and dried over anhydrous sodium sulfate, and the insoluble materials were removed by filtration, and the solvents were evaporated. The crude product was subjected to column chromatography (chloroform/methanol=100/0 to 90/10) to obtain compound 32 (8.58 g, yield 95%).

MS (APCI): m/z=675 (M+H)$^+$ $^1$H-NMR (CDCl$_3$) δ: 7.67-7.58 (4H, m), 7.48-7.19 (15H, m), 7.13-7.07 (2H, m), 6.21 (1H, d, J=6.1 Hz), 6.09 (1H, d, J=7.2 Hz), 5.51 (1H, dd, J=6.1, 4.1 Hz), 4.80 (1H, d, J=11.3 Hz), 4.60 (1H, d, J=11.3 Hz), 4.41-4.28 (3H, m), 3.82 (1H, d, J=10.8 Hz), 3.68 (1H, d, J=10.8 Hz), 3.36-3.27 (2H, m), 1.03 (9H, s)

Example 42

(2R,3S,3aS,9aR)-3-(Benzyloxy)-2-[(benzyloxy)methyl]-2-(hydroxymethyl)-2,3,3a,9a-tetrahydro-6H-furo[2',3':4,5][1,3]oxazolo[3,2-a]pyrimidine-6-one (Compound 33)

Compound 32 (8.58 g, 12.7 mmol) and THF (63.6 mL) were mixed, and thereto was added 1 M TBAF (16.5 mL, 16.5 mmol) dropwise with a dropping funnel under cooling at 0° C. The mixtures were stirred at room temperature for 2.5 hours. After the solvents were evaporated, the crude product was subjected to column chromatography (chloroform/methanol=100/0 to 85/15) to obtain compound 33 (5.54 g, yield quant.).

MS (APCI): m/z=437 (M+H)$^+$ $^1$H-NMR (CDCl$_3$) δ: 7.41-7.26 (9H, m), 7.20-7.13 (2H, m), 6.27 (1H, d, J=6.2 Hz), 6.06 (1H, d, J=7.7 Hz), 5.35 (1H, dd, J=6.2, 2.6 Hz), 4.78 (1H, d, J=11.8 Hz), 4.60 (1H, d, J=11.8 Hz), 4.43-4.31 (3H, m), 3.88-3.80 (1H, m), 3.72-3.63 (1H, m), 3.40-3.26 (2H, m), 2.35-2.21 (1H, m)

Example 43

{(2S,3S,3aS,9aR)-3-(Benzyloxy)-2-[(benzyloxy)methyl]-6-oxo-2,3,3a,9a-tetrahydro-6H-furo[2',3':4,5][1,3]oxazolo[3,2-a]pyrimidin-2-yl}methyl methanesulfonate (Compound 34)

Compound 33 (5.54 g, 12.7 mmol) and methylene chloride (127 mL) were mixed, and thereto were added MsCl (1.68 mL, 21.6 mmol) and DMAP (4.65 g, 38.1 mmol) at 0° C. The mixtures were stirred at room temperature for 1 hour. After water was added thereto at 0° C., the mixtures were extracted with chloroform. The extracts were washed with saturated brine, and dried over anhydrous sodium sulfate, and the insoluble materials were removed by filtration, and the solvents were evaporated. The crude product was subjected to column chromatography (ethyl acetate/methanol=100:0 to 90/10) to obtain compound 34 (5.47 g, yield 84%).

MS (APCI): m/z=515 (M+H)$^+$ $^1$H-NMR (CDCl$_3$) δ: 7.41-7.25 (9H, m), 7.21-7.15 (2H, m), 6.23 (1H, d, J=6.2 Hz), 6.08 (1H, d, J=7.7 Hz), 5.30 (1H, dd, J=6.2, 2.6 Hz), 4.76 (1H, d, J=11.6 Hz), 4.60 (1H, d, J=11.6 Hz), 4.46-4.29 (5H, m), 3.39 (1H, d, J=10.3 Hz), 3.31 (1H, d, J=10.3 Hz), 2.92 (3H, s)

Example 44

(2R,3S,3aS,9aR)-2-(Azidomethyl)-3-(benzyloxy)-2-[(benzyloxy)methyl]-2,3,3a,9a-tetrahydro-6H-furo[2',3':4,5][1,3]oxazolo[3,2-a]pyrimidine-6-one (Compound 35)

Compound 34 (3.00 g, 5.830 mmol) and 1,4-dioxane (58.3 mL) were mixed, and thereto was added tetrabutylammonium azide (4.976 g, 17.49 mmol). The mixtures were stirred at 120° C. under heating for 4.5 hours. After the mixtures were cooled to room temperature, thereto was added saturated aqueous sodium bicarbonate solution at 0° C., and the mixtures were extracted with ethyl acetate. The extracts were washed with saturated brine, and dried over anhydrous sodium sulfate, and the insoluble materials were removed by filtration, and the solvents were evaporated. The crude product was subjected to column chromatography (ethyl acetate/methanol=100/0 to 90/10) to obtain compound 35 (2.264 g, yield 84%).

MS (APCI): m/z=462 (M+H)$^+$ $^1$H-NMR (CDCl$_3$) δ: 7.41-7.24 (9H, m), 7.20-7.13 (2H, m), 6.21 (1H, d, J=6.1 Hz), 6.07 (1H, d, J=7.7 Hz), 5.32 (1H, dd, J=6.1, 2.1 Hz), 4.76 (1H, d, J=11.8 Hz), 4.60 (1H, d, J=11.8 Hz), 4.40 (1H, d, J=12.1 Hz), 4.34 (1H, d, J=12.1 Hz), 4.29 (1H, d, J=2.1 Hz), 3.62 (1H, d, J=12.8 Hz), 3.47 (1H, d, J=12.8 Hz), 3.32 (1H, d, J=10.2 Hz), 3.27 (1H, d, J=10.2 Hz)

Example 45

1-{(1R,3R,4R,7S)-7-(Benzyloxy)-1-[(benzyloxy)methyl]-2-oxa-5-azabicyclo[2.2.1]hepta-3-yl}-pyrimidine-2,4(1H,3H)-dione (Compound 37)

Compound 35 (2.2 g, 4.8 mmol), THF (32 mL) and H$_2$O (6.4 mL, 360 mmol) were mixed, and thereto was added Ph$_3$P (1.90 g, 7.20 mmol), and the mixtures were stirred for 21.5 hours at 70° C. under heating. After the solvents were evaporated, the crude product was subjected to column chromatography (ethyl acetate/methanol=100/0 to 17/2) to obtain compound 37 (2.067 g, yield quant.).

MS (APCI): m/z=436 (M+H)$^+$ $^1$-NMR (CDCl$_3$) δ: 8.30 (1H, brs), 7.80 (1H, d, J=8.2 Hz), 7.40-7.21 (10H, m), 5.53 (1H, s), 5.46 (1H, d, J=8.2 Hz), 4.65-4.49 (4H, m), 3.87 (1H, s), 3.83 (1H, d, J=10.9 Hz), 3.78 (1H, d, J=10.9 Hz), 3.64 (1H, s), 3.14 (1H, d, J=10.0 Hz), 2.89 (1H, d, J=10.0 Hz)

Example 46

N-(9-{(1R,3R,4R,7S)-7-(Benzyloxy)-1-[(benzyloxy)methyl]-2-oxa-5-azabicyclo[2.2.1]hepta-3-yl)}-9H-purin-6-yl)benzamide (Compound 26A)

To a solution of compound 37 (100 mg, 0.2296 mmol), N-(9H-purin-6-yl)benzamide (164.8 mg, 0.6889 mmol) in 1,2-dichloromethane (2.296 mL) was added BSA (0.5053 mL, 2.067 mmol), and the reaction solutions were stirred at 60° C. for 15 minutes. The mixtures were allowed to cool to room temperature, and stirred, and thereto was added TMSOTf (0.01331 mL, 0.06889 mmol) and the mixtures were stirred at 50° C. under heating for 15 minutes. After the mixtures were diluted with chloroform, thereto was added saturated aqueous sodium bicarbonate solution at 0° C., and the mixtures were extracted with chloroform. The mixtures were washed with saturated brine, and dried over anhydrous sodium sulfate, and the insoluble products were removed by filtration, and the solvents were evaporated. The crude product was subjected to column chromatography (chloroform/methanol=100/0 to 95/5) and reverse phase preparative chromatography (10 mM aqueous ammonium carbonate solution/acetonitrile=90/10 to 60/40) to obtain compound 26A (129.2 mg, yield 84%). Here compound 26A was "β form", and "α form" as an isomer could not be obtained.

MS (APCI): m/z=563 (M+H)$^+$

The date of $^1$H-NMR was identical to that of compound 26A of Example 13.

Example 47

Preparation of Guanine Product from Uracil Product: (Compound 26G)

9-{(1R,3R,4R,7S)-7-(Benzyloxy)-1-[(benzyloxy)methyl]-2-oxa-5-azabicyclo[2.2.1]hepta-3-yl}-2-[(2-methylpropanoyl)amino]-9H-purin-6-yl diphenylcarbamate (Compound 26G)

Similarly to Example 13 from compound 37 (300 mg, 0.689 mmol) and (2-(2-methylpropanoylamino)-9-purin-1-yl) N,N-diphenylcarbamate (861 mg, 2.07 mmol) (the preparation method follows the method described in J. Org. Chem. 1996, 61, 9207), compound 26G (412 mg, yield 81%). Here compound 26G was "β form", and "α form" as an isomer could not be obtained.

MS (APCI): m/z=740 (M+H)$^+$

The data of $^1$H-NMR was identical to that of compound 26G of Example 14.

Next, preparation method of pyrimidine derivatives (compound 38a and compound 38b) is described.

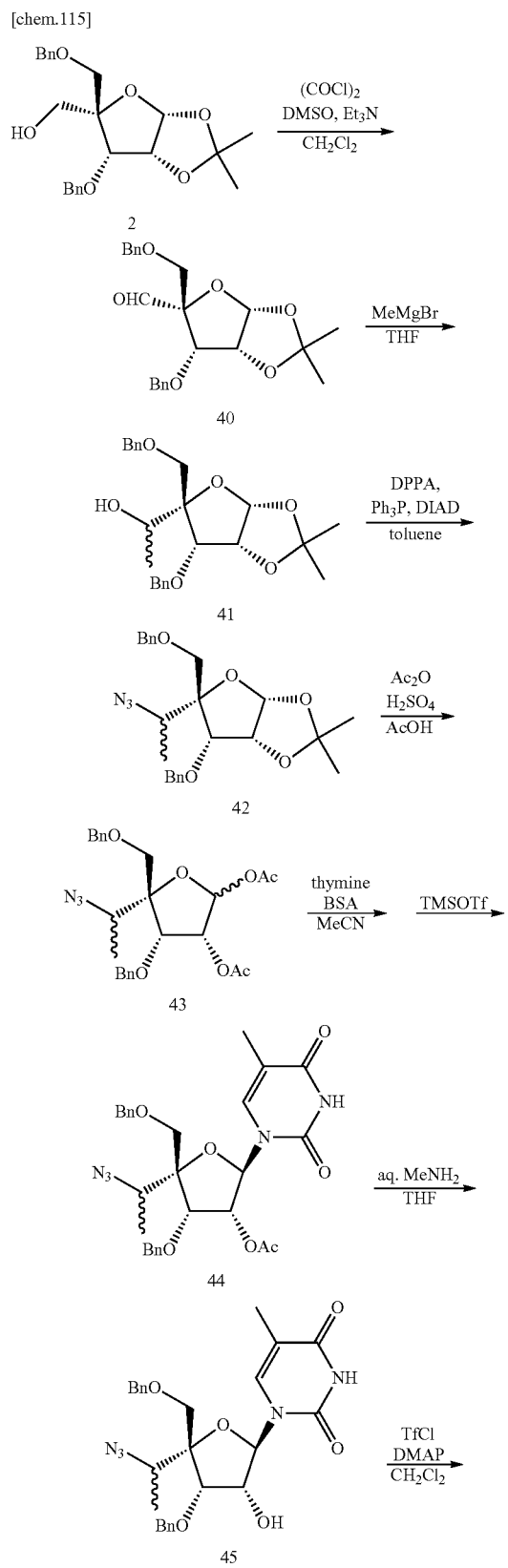

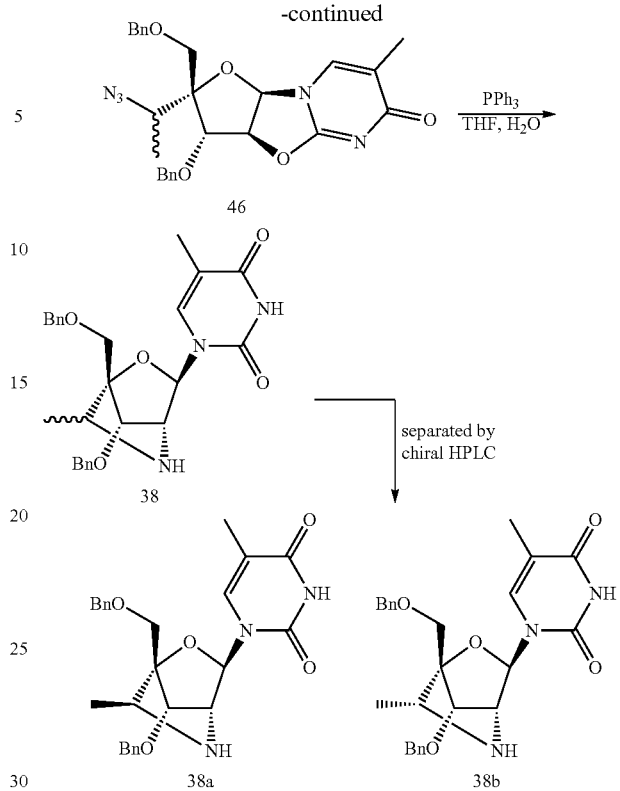

Example 48

(5xi)-3-O-Benzyl-4-[(benzyloxy)methyl]-6-deoxy-1,2-O-(1-methylethylidene)-β-L-lyxo-hexofuranose (Compound 41)

Compound 40 (prepared from compound 2 according to the method described in J. Med. Chem. 2000, 43, 4516-4525) (2.00 g, 5.02 mmol) and THF (25.1 mL) were mixed, and the mixtures were cooled to −78° C. Thereto was added methyl magnesium bromide (0.91 M, 8.3 mL, 7.53 mmol) dropwise at the same temperature, and the mixtures were stirred at −78° C. for 1 hour. After saturated aqueous ammonium chloride solution was added thereto, the mixtures were extracted with ethyl acetate. The mixtures were washed with saturated brine, and dried over anhydrous sodium sulfate, and the solvents were evaporated. The crude product was purified by silica gel chromatography (n-hexane/ethyl acetate, 80/20 to 75/25) to obtain compound 41 (1.62 g) as a mixture.

(5xi)-5-Azido-3-O-benzyl-4-[(benzyloxy)methyl]-5,6-dideoxy-1,2-O-(1-methylethylidene)-β-L-lyxo-hexofuranose (Compound 42)

Compound 41 (1.44 g) and toluene (17.4 mL) were mixed, and thereto were added Ph₃P (2.73 g, 10.4 mmol) and DIAD (2.15 mL, 10.9 mmol) under cooling at 0° C., and thereto was added DPPA (2.24 mL, 10.4 mmol) dropwise. The mixtures were stirred at room temperature for 1 hour, and stirred at 50° C. under heating for 2 hours, and the solvents were evaporated. The crude product was purified by silica gel chromatography (n-hexane/ethyl acetate, 85/15 to 80/20) to obtain compound 42 (1.53 g) as a mixture.

(5xi)-1,2-Di-O-acetyl-5-azido-3-O-benzyl-4-[(benzyloxy)methyl]-5,6-dideoxy-L-lyxo-hexofuranose (Compound 43)

Compound 42 (1.47 g), acetic anhydride (4 mL) and acetic acid (2.31 mL) were mixed, and thereto was added concentrated sulfuric acid (17.9 μL) at 0° C., and the mixtures were stirred at room temperature for 2 hours. Thereto was added saturated aqueous sodium carbonate solution (8.8 mL) dropwise at 0° C. to make the mixtures pH=6, and thereto was added saturated aqueous sodium hydrogen carbonate solution, and the mixtures were extracted with ethyl acetate. The organic layers were washed with saturated aqueous sodium hydrogen carbonate solution, water, and saturated brine successively, and the mixtures were dried over anhydrous sodium sulfate. The solvents were evaporated, and then azeotroped with toluene three times to obtain compound 43 (1.60 g). The obtained compound was used without purification in next step.

1-{(5xi)-2-O-Acetyl-5-azido-3-O-benzyl-4-[(benzyloxy)methyl]-5,6-dideoxy-α-L-lyxo-hexofuranosyl}-5-methylpyrimidine-2,4(1H,3H)-dione (Compound 44)

Compound 43 (1.60 g), acetonitrile (11.0 mL) and thymine (563 mg, 4.467 mmol) were mixed, and thereto was added BSA (1.86 mL, 7.60 mmol) dropwise. The reaction system was heated at 50° C. for 10 minutes until the reaction system became homogeneous, the mixtures were cooled to 0° C. Thereto was added TMSOTf (0.684 mL, 3.54 mmol) dropwise at the same temperature. The mixtures were stirred at room temperature for 5 minutes, and then stirred at 50° C. under heating for 2 hours. Thereto was added saturated aqueous sodium hydrogen carbonate solution dropwise at 0° C., and the reaction solutions were concentrated. The residues were extracted with ethyl acetate, and the organic layers were washed with saturated brine, and dried over anhydrous sodium sulfate, and the solvents were evaporated. The crude product was purified by silica gel chromatography (n-hexane: ethyl acetate, 67/33 to 50/50) to obtain compound 44 (628 mg, yield 35%: on the basis of compound 41) as a mixture.

1-{(5xi)-5-Azido-3-O-benzyl-4-[(benzyloxy)methyl]-5,6-dideoxy-α-L-lyxo-hexofuranosyl}-5-methylpyrimidine-2,4(1H,3H)-dione (Compound 45)

Compound 44 (620 mg, 1.13 mmol) and THF (4.5 mL) were mixed, and thereto was added 40% aqueous methyl amine solution (2.56 mL) dropwise at room temperature, and the mixtures were stirred at room temperature for 40 minutes. The reaction solutions were extracted with ethyl acetate. The organic layers were washed with saturated brine, and dried over anhydrous sodium sulfate, and the solvents were evaporated. The crude product was purified by silica gel chromatography (n-hexane/ethyl acetate, 60/40 to 40/60) to obtain compound 45 (556 mg, yield 97%) as a mixture.

(2R,3S,3aS,9aR)-2-(1-Azidoethyl)-3-(benzyloxy)-2-[(benzyloxy)methyl]-7-methyl-2,3,3a,9a-tetrahydro-6H-furo[2′,3′:4,5][1,3]oxazolo[3,2-a]pyrimidine-6-one (compound 46)

Compound 45 (541 mg, 1.07 mmol), methylene chloride (5.3 mL), and DMAP (456 mg, 3.73 mmol) were mixed, and the mixtures were cooled to 0° C. After TfCl (0.282 mL, 2.67 mmol) was added dropwise thereto at the same temperature, the mixtures were stirred at room temperature for 90 minutes. After water was added to the reaction solutions at 0° C., the mixtures were extracted with chloroform. The organic layers were washed with saturated brine, and dried over anhydrous sodium sulfate, and the solvents were evaporated. The crude product was purified by silica gel chromatography (chloroform/methanol, 100/0 to 89/11) to obtain compound 46 (458 mg, yield 88%) as a mixture.

1-{(1R,3R,4R,6S,7S)-7-(Benzyloxy)-1-[(benzyloxy)methyl]-6-methyl-2-oxa-5-azabicyclo[2.2.1]hepta-3-yl}-5-methylpyrimidine-2,4(1H,3H)-dione (compound 38a)

1-{(1R,3R,4R,6R,7S)-7-(Benzyloxy)-1-[(benzyloxy)methyl]-6-methyl-2-oxa-5-azabicyclo[2.2.1]hepta-3-yl}-5-methylpyrimidine-2,4(1H,3H)-dione (Compound 38b)

Compound 46 (450 mg, 0.919 mmol), THF (6.1 mL) and water (1.22 mL) were mixed, and thereto was added Ph$_3$P (362 mg, 1.38 mmol), and the mixtures were stirred at 70° C. under heating for 16 hours. After the solvents were evaporated, the crude product was purified by silica gel chromatography (ethyl acetate/methanol, 100/0 to 85/15) to obtain compound 38 (406 mg, yield 95%) as a mixture. Compound 38 (287 mg) was purified by chiral HPLC (DAICEL, CHIRALPAK IC, φ 30×250 mm, methanol/THF/diethylamine, 65/35/0/1, flow rate 20 mL/min.) to obtain crude 38a (138 mg) and crude 38b (139 mg), which contain BHT as a stabilizer of THF. Each of the products was purified by silica gel chromatography (ethyl acetate/methanol, 100/0 to 85/15) to obtain compound 38a (132 mg) and compound 38b (123 mg).

Compound 38a:
MS (APCI): m/z=464 (M+H)$^+$
$^1$H-NMR (CDCl$_3$) δ: 8.21 (1H, brs), 7.55-7.50 (1H, m), 7.39-7.22 (10H, m), 5.48 (1H, s), 4.66-4.56 (3H, m), 4.49 (1H, d, J=11.8 Hz), 3.91-3.83 (3H, m), 3.70 (1H, s), 3.25 (1H, q, J=6.7 Hz), 1.62-1.57 (3H, m), 1.20 (3H, d, J=6.7 Hz)

Compound 38b:
MS (APCI): m/z=464 (M+H)$^+$
$^1$H-NMR (CDCl$_3$) δ: 8.18 (1H, brs), 7.67-7.62 (1H, m), 7.39-7.22 (10H, m), 5.47 (1H, s), 4.66-4.50 (4H, m), 4.02 (1H, s), 3.77 (1H, d, J=11.0 Hz), 3.72 (1H, d, J=11.0 Hz), 3.55 (1H, s), 3.49 (1H, q, J=6.7 Hz), 1.58-1.54 (3H, m), 1.14 (3H, d, J=6.7 Hz)

Preparation of Adenine Product from Thymine Product: (Compound 39Aa)

[chem. 116]

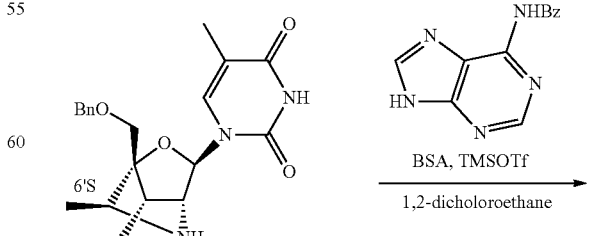

38

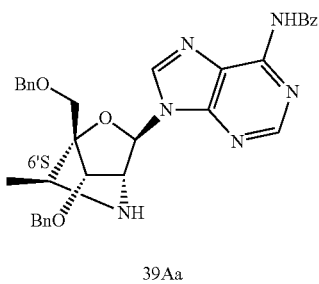

39Aa

Example 49

N-(9-{(1R,3R,4R,6S,7S)-7-(Benzyloxy)-1-[(benzy-loxy)methyl]-6-methyl-2-oxa-5-azabicyclo[2.2.1]hepta-3-yl)}-9H-purin-6-yl)benzamide (Compound 39Aa)

Similarly to Example 13 from compound 38a (50 mg, 0.108 mmol) and (N-(9H-purin-6-yl)benzamide (77.4 mg, 0.324 mmol), compound 39Aa (50.9 mg, yield 82) was prepared. Here compound 39Aa was "β form", and "α form" as an isomer could not be obtained.

MS (APCI): m/z=577 (M+H)$^+$ $^1$H-NMR (CDCl$_3$) δ: 9.03 (1H, s), 8.78 (1H, s), 8.28 (1H, s), 8.08-8.00 (2H, m), 7.65-7.50 (3H, m), 7.40-7.16 (10H, m), 5.99 (1H, s), 4.70-4.62 (2H, m), 4.53-4.44 (2H, m), 4.14 (1H, s), 3.96 (1H, s), 3.91-3.82 (2H, m), 3.37 (1H, q, J=6.7 Hz), 1.25 (3H, d, J=6.7 Hz)

Preparation of Adenine Product from Thymine Product: (Compound 39Ab)

[chem. 117]

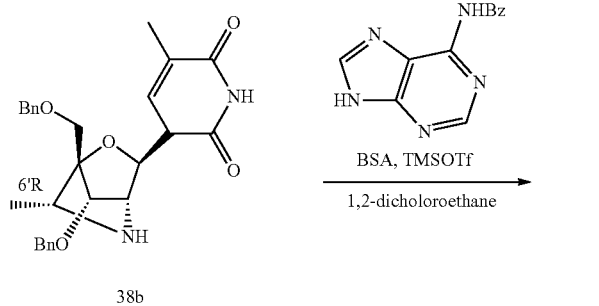

38b

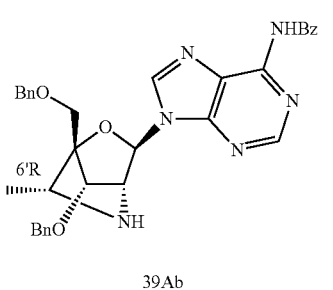

39Ab

Example 50

N-(9-{(1R,3R,4R,6R,7S)-7-(Benzyloxy)-1-[(benzy-loxy)methyl]-6-methyl-2-oxa-5-azabicyclo[2.2.1]hepta-3-yl)}-9H-purin-6-yl)benzamide (Compound 39Ab)

Similarly to Example 13 from compound 38b (50 mg, 0.108 mmol) and (N-(9H-purin-6-yl)benzamide (77.4 mg, 0.324 mmol), compound 39Ab (48.1 mg, yield 77%) was prepared. Here compound 39Ab was "β form", and "α form" as an isomer could not be obtained.

MS (APCI): m/z=577 (M+H)$^+$ $^1$H-NMR (CDCl$_3$) δ: 9.03 (1H, s), 8.77 (1H, s), 8.41 (1H, s), 8.08-8.00 (2H, m), 7.66-7.49 (3H, m), 7.41-7.14 (10H, m), 5.99 (1H, s), 4.70 (1H, d, J=12.3 Hz), 4.60 (1H, d, J=12.3 Hz), 4.56-4.46 (2H, m), 4.29 (1H, s), 3.78-3.68 (3H, m), 3.54 (1H, q, J=6.7 Hz), 1.20 (3H, d, J=6.7 Hz)

Preparation of Guanine Product from Thymine Product: (Compound 39Ga)

[chem.118]

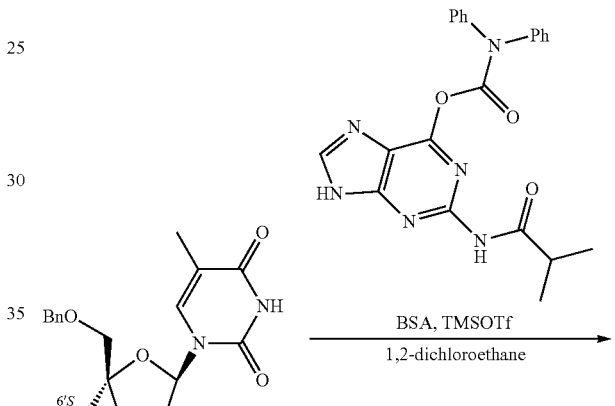

38a

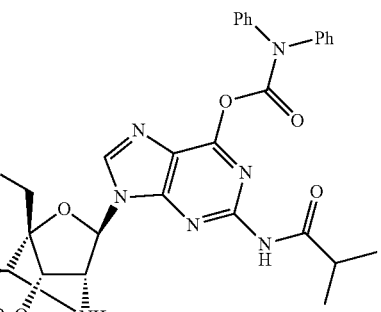

39Ga

Example 51

9-{(1R,3R,4R,6S,7S)-7-(Benzyloxy)-1-[(benzyloxy)methyl]-6-methyl-2-oxa-5-azabicyclo[2.2.1]hepta-3-yl}-2-[(2-methylpropanoyl)amino]-9H-purin-6-yl diphenylcarbamate (Compound 39Ga)

Similarly to Example 13 from compound 38a (33 mg, 0.0712 mmol) and (2-(2-methylpropanoylamino)-9-purin-1- yl) N,N-diphenylcarbamate (130 mg, 0.641 mmol) (the preparation method follows the method described in J. Org. Chem. 1996, 61, 9207), compound 39Ga (37.6 mg, yield 70%) was prepared. Here compound 39Ga was "β form", and "α form" as an isomer could not be obtained.

MS (APCI): m/z=754 (M+H)$^+$ $^1$H-NMR (CDCl$_3$) δ: 8.21 (1H, s), 7.88 (1H, s), 7.49-7.41 (2H, m), 7.40-7.15 (19H, m), 5.87 (1H, s), 4.64 (2H, s), 4.49 (1H, d, J=11.8 Hz), 4.45 (1H, d, J=11.8 Hz), 4.07 (1H, s), 3.95 (1H, s), 3.87-3.80 (2H, m), 3.33 (1H, q, J=6.7 Hz), 3.07 (1H, brs), 1.26 (6H, d, J=6.7 Hz), 1.22 (3H, d, J=6.7 Hz)

Preparation of Guanine Product from Thymine Product: (Compound 39Gb)

[chem.119]

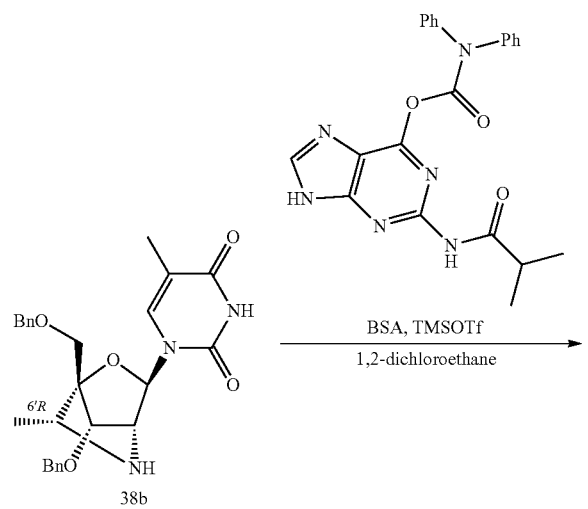

Example 52

9-{(1R,3R,4R,6R,7S)-7-(Benzyloxy)-1-[(benzyloxy) methyl]-6-methyl-2-oxa-5-azabicyclo[2.2.1]hepta-3-yl}-2-[(2-methylpropanoyl)amino]-9H-purin-6-yl diphenylcarbamate (Compound 39Gb)

Similarly to Example 13 from compound 38b (20 mg, 0.0432 mmol) and (2-(2-methylpropanoylamino)-9-purin-1-yl N,N-diphenylcarbamate (79.0 mg, 0.388 mmol) (the preparation method follows the method described in J. Org. Chem. 1996, 61, 9207), compound 39Gb (27.9 mg, yield 80). Here compound 39Gb was "β form", and "α form" as an isomer could not be obtained.

MS (APCI): m/z=754 (M+H)$^+$ $^1$H-NMR (CDCl$_3$) δ: 8.33 (1H, s), 7.88 (1H, s), 7.48-7.41 (2H, m), 7.41-7.14 (19H, m), 5.88 (1H, s), 4.69 (1H, d, J=12.3 Hz), 4.58 (1H, d, J=12.3 Hz), 4.52-4.45 (2H, m), 4.24 (1H, s), 3.74-3.65 (3H, m), 3.50 (1H, q, J=6.7 Hz), 3.04 (1H, brs), 1.26 (3H, d, J=7.2 Hz), 1.25 (3H, d, J=7.2 Hz), 1.16 (3H, d, J=6.7 Hz)

Preparation of Adenine Product from 3',5'-hydroxy Thymine Product: (Compound 47)

[chem. 120]

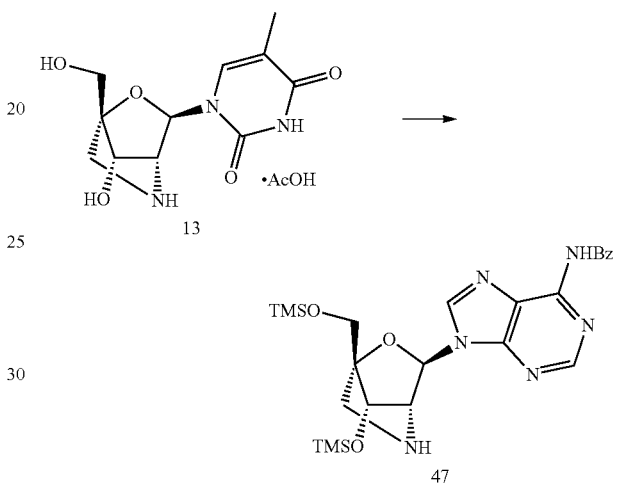

Example 51

N-(9-{(1R,3R,4R,7S)-7-[(Trimethylsilyl)oxy]-1-{[(trimethylsilyl)oxy]methyl}-2-oxa-5-azabicyclo [2.2.1]hepta-3-yl)}-9H-purin-6-yl)benzamide (Compound 47)

Similarly to Example 13 from compound 13 (50 mg, 0.132 mmol) and BSA (0.36 mL, 1.45 mmol), compound 47 (56.6 mg, containing 2.9 wt % of ethyl acetate, yield 79%) was prepared. Here compound 47 was "β form", and "α form" as an isomer could not be obtained.

MS (APCI): m/z 527 (M+H)$^+$ $^1$H-NMR (CDCl$_3$) δ: 9.07 (1H, s), 8.80 (1H, s), 8.36 (1H, s), 8.08-8.02 (2H, m), 7.65-7.59 (1H, m), 7.57-7.51 (2H, m), 6.04 (1H, s), 4.29 (1H, s), 3.90 (1H, d, J=11.8 Hz), 3.84 (1H, d, J=11.8 Hz), 3.76 (1H, s), 3.16 (1H, d, J=9.7 Hz), 3.90 (1H, d, J=9.7 Hz), 0.19 (9H, s), 0.09 (9H, s)

Preparation of GuNA Nucleotide Monomer having Different Ring Size of Bridged Chain by Transglycosylation By modifying the number of carbon in a carbon chain that is composed of a bridged chain to ribose backbone, GuNA monomer having different ring size can be prepared. One example of the preparation thereof is described below, in which transglycosylation can be carried out using compound 61 obtained by the below-mentioned scheme to prepare GuNA monomer having different ring size containing various nucleic acid base(s).

[chem. 121]
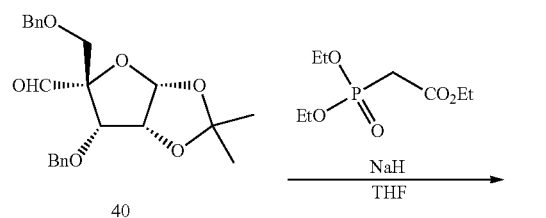
40
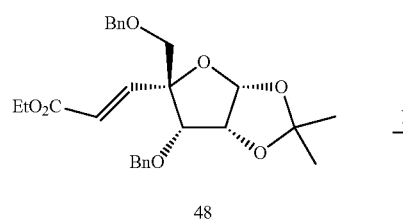
48
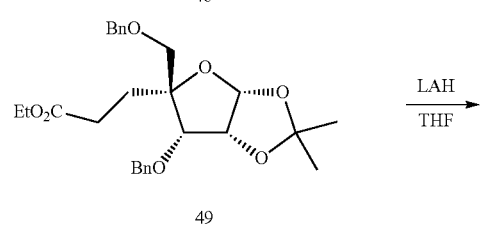
49
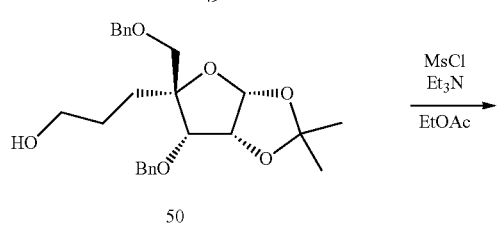
50
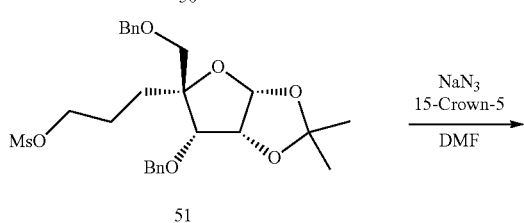
51
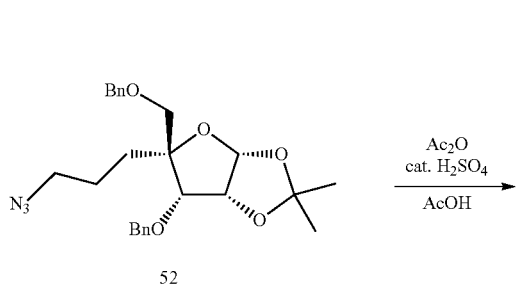
52
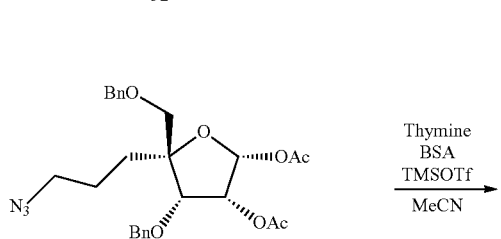
53
-continued
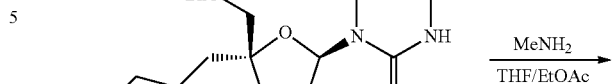
54
55
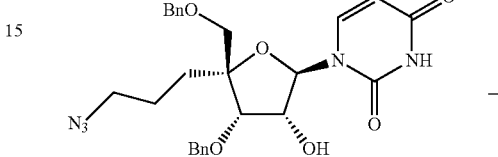
56
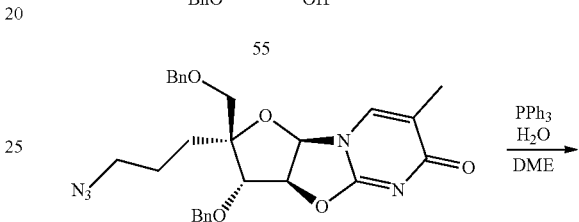
57
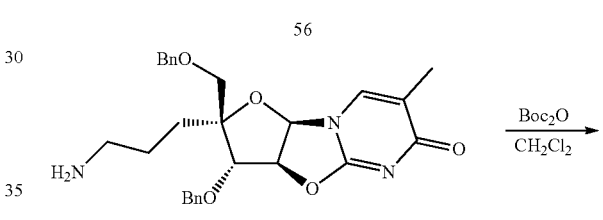
58
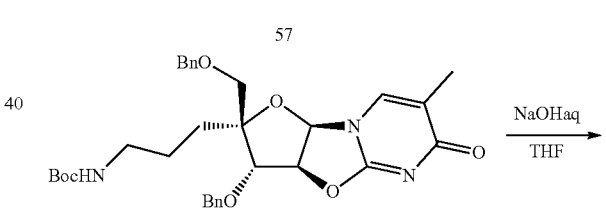
59
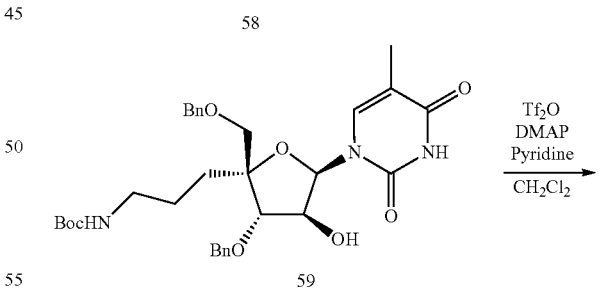
60

-continued

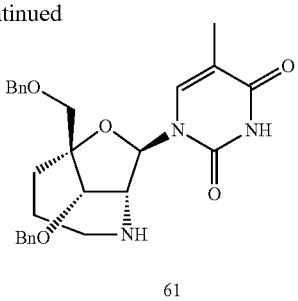

61

Hereinafter, each step of the above-mentioned preparation method is described.

[chem.122]

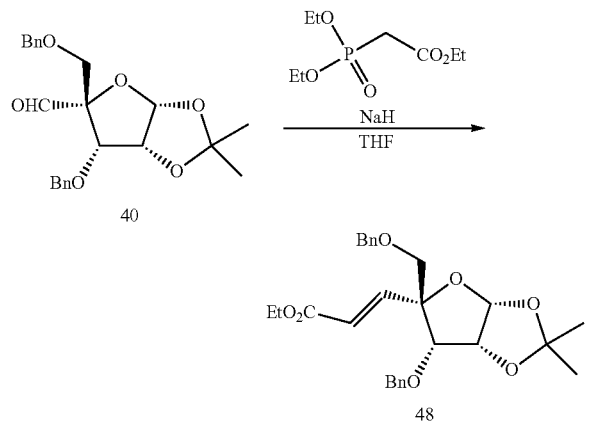

Example 52

Ethyl (5E)-3-O-benzyl-4-[(benzyloxy)methyl]-5,6-dideoxy-1,2-O-(1-methylethylidene)-β-L-lyxo-hepta-5-enofuranuronate (Compound 48)

To a solution of ethyl diethylphosphonoacetate (6.83 mL, 34.43 mmol) in THF (163 mL) was added sodium hydride (1.38 g, 34.43 mmol, 60% contents) under ice-cooling, and the mixtures were stirred at room temperature for 30 minutes. The reaction solutions were cooled under ice-cooling, and thereto was added a solution of compound 40 (10.96 g, 26.48 mmol) in THF (54 mL) dropwise. The ice-water bath was removed, and the reaction mixtures were stirred at room temperature for 1 hour. To the reaction solutions were added ethyl acetate (300 mL) and cold water (500 mL), and the mixtures were stirred for a while, and the organic layers were then separated by a separatory funnel. The aqueous layers were extracted with ethyl acetate (100 mL) using a separatory funnel, and the combined organic layers were washed with water and saturated brine, and then dried over anhydrous sodium sulfate. The solvents were evaporated under reduced pressure, and the resulting residues were purified by silica gel chromatography (hexane/ethyl acetate, 95/5 to 60/40) to obtain compound 48 (12.18 g, yield 97%).

MS (APCI): m/z 486 (M+NH$_4$)$^+$ $^1$H-NMR (CDCl$_3$) δ: 7.38-7.19(11H, m), 6.24 (1H, d, J=15.9 Hz), 5.76 (1H, d, J=4.1 Hz), 4.77 (1H, d, J=12.3 Hz), 4.60 (1H, d, J=12.3 Hz), 4.57 (1H, dd, J=4.6, 4.1 Hz), 4.50 (1H, d, J=11.8 Hz), 4.41 (1H, d, J=11.8 Hz), 4.27 (1H, t, J=4.6 Hz), 4.23-4.13 (2H, m), 3.38-3.30 (2H, m), 1.47 (3H, s), 1.30-1.24 (6H, m)

[chem.123]

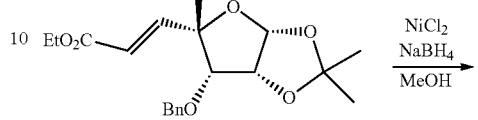

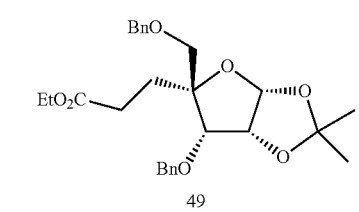

Example 53

Ethyl 3-O-benzyl-4-[(benzyloxy)methyl]-5,6-dideoxy-1,2-O-(1-methylethylidene)-β-L-lyxo-heptofuranuronate (Compound 49)

To a solution of compound 48 (12.06 g, 25.50 mmol) in methanol (241 mL) was added nickel(II) chloride hexahydrate (1212 mg, 5.100 mmol). The reaction solutions were cooled in ice-cooling, and thereto was added sodium borohydride (1930 mg, 51.00 mmol) over 40 minutes. The ice-water bath was removed, and the mixtures were stirred at room temperature for 2 hours. The reaction solutions were filtered through Celite, washed with ethyl acetate (300 mL) and water (300 mL), and the organic layers of the filtrates were separated by a separatory funnel. The aqueous layers were extracted with ethyl acetate (150 mL portions were carried out twice) by a separatory funnel, and the combined organic layers were washed with water (300 mL) and saturated brine (300 mL), and then dried over anhydrous sodium sulfate. The solvents were evaporated under reduced pressure to obtain compound 49 (11.90 g, yield 98%).

MS (APCI): m/z 488 (M+NH$_4$)$^+$ $^1$H-NMR (CDCl$_3$) δ: 7.38-7.21 (10H m), 5.75 (1H, d, J=4.1 Hz), 4.76 (1H, d, J=12.3 Hz), 4.61 (1H, dd, J=5.1, 4.1 Hz), 4.55 (1H, d, J=12.3 Hz), 4.49 (1H, d, J=12.3 Hz), 4.40 (1H, d, J=12.3 Hz), 4.14-4.06 (3H, m), 3.40 (1H, d, J=10.3 Hz), 3.26 (1H, d, J=10.3 Hz), 2.66-2.50 (2H, m), 2.37-2.26 (1H, m), 1.92-1.81 (1H, m), 1.62 (3H, s), 1.32 (3H, s), 1.23 (3H, t, J=7.2 Hz)

[chem.124]

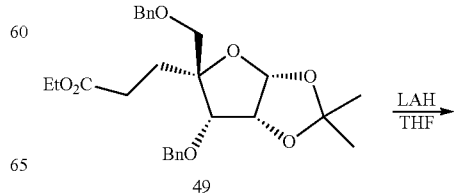

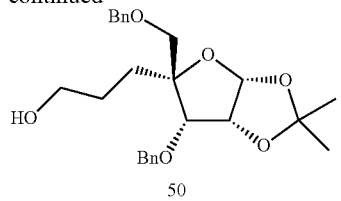

Example 54

3-O-Benzyl-4-[(benzyloxy)methyl]-5,6-dideoxy-1,2-O-(1-methylethylidene)-β-L-lyxo-heptofuranose (Compound 50)

To a suspension of lithium aluminum hydride (1904 mg, 50.17 mmol) in THF (155 mL) was added a solution of compound 49 (11.90 g, 25.08 mmol) in THF (83 mL) dropwise over 15 minutes under ice-cooling, and the mixtures were stirred at room temperature for 1 hour. The reaction solutions were cooled under ice-cooling, and thereto was added saturated aqueous sodium sulfate solution (10 mL) dropwise, and followed by adding water (3 mL) successively, and the mixtures were stirred at room temperature for a whole day and night. The reaction solutions were filtered through Celite, washed with ethyl acetate (100 mL portions were carried out three times), and the filtrates were dried over anhydrous sodium sulfate. The solvents were evaporated under reduced pressure to obtain compound 50 (10.98 g, 25.04 mmol, yield 100%).

MS (APCI): m/z 446 (M+NH4)$^+$ $^1$H-NMR (CDCl$_3$) δ: 7.37-7.21 (10H, m), 5.76 (1H, d, J=4.1 Hz), 4.76 (1H, d, J=12.3 Hz), 4.62 (1H, dd, J=5.7, 4.1 Hz), 4.56 (1H, d, J=12.3 Hz), 4.51 (1H, d, J=12.3 Hz), 4.41 (1H, d, J=12.3 Hz), 4.16 (1H, d, J=5.7 Hz), 3.76-3.58 (2H, m), 3.50 (1H, d, J=10.3 Hz), 3.32 (1H, d, J=10.3 Hz), 2.28-2.15 (1H, m), 2.06-2.01 (1H, m), 1.79-1.67 (2H, m), 1.65-1.55 (4H, m), 1.33 (3H, s)

[chem. 125]

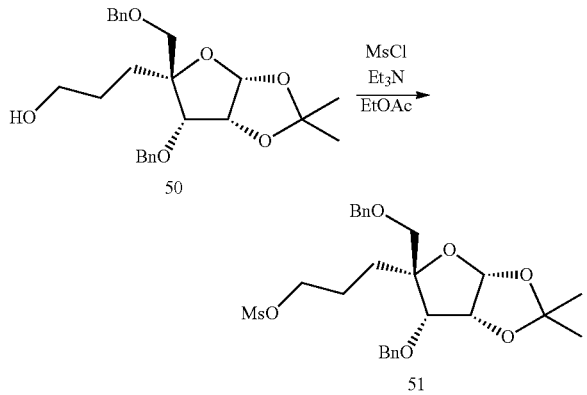

Example 55

3-O-Benzyl-4-[(benzyloxy)methyl]-5,6-dideoxy-1,2-O-(1-methylethylidene)-7-O-(methylsulfonyl)-β-L-lyxo-heptofuranose (Compound 51)

To a solution of compound 50 (10.45 g, 23.83 mmol) in ethyl acetate (209 mL) was added triethylamine (4.64 mL, 33.36 mmol) under ice-cooling, and followed by adding methanesulfonyl chloride (2.22 mL, 28.6 mmol) dropwise successively. The mixtures were stirred at the same temperature for 1 hour. To the reaction solutions was added methanol (0.5 mL) and the mixtures were stirred for 30 minutes. The reaction solutions were poured into water (200 mL), and the organic layers were separated by a separatory funnel. After the organic layers were washed with saturated brine (100 mL), the mixtures were dried over anhydrous sodium sulfate. The solvents were evaporated under reduced pressure and the resulting residues were purified by silica gel chromatography (hexane/ethyl acetate, 90/10 to 30/70) to obtain compound 51 (11.72 g, containing 3.3 wt % of ethyl acetate, yield 97%).

MS (APCI): m/z 524 (M+NH$_4$)$^+$ $^1$H-NMR (CDCl$_3$) δ: 7.37-7.22 (10H, m), 5.74 (1H, d, J=4.1 Hz), 4.76 (1H, d, J=12.3 Hz), 4.61 (1H, dd, J=5.7, 4.1 Hz), 4.55 (1H, d, J=12.3 Hz), 4.51 (1H, d, J=12.3 Hz), 4.41 (1H, d, J=12.3 Hz), 4.30-4.12 (2H, m), 4.11 (1H, d, J=5.7 Hz), 3.41 (1H, d, J=10.3 Hz), 3.28 (1H, d, J=10.3 Hz), 2.95 (3H, s), 2.25-2.15 (1H, m), 2.07-1.94 (1H, m), 1.83-1.65 (2H, m), 1.59 (3H, s), 1.33 (3H, s)

[chem. 126]

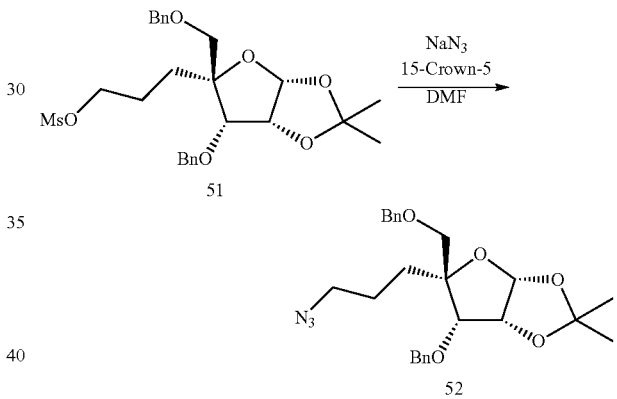

Example 56

7-Azido-3-O-benzyl-4-[(benzyloxy)methyl]-5,6,7-trideoxy-1,2-O-(1-methylethylidene)-β-L-lyxo-heptofuranose (Compound 52)

To a solution of compound 51 (11.72 g, 22.38 mmol) and 15-crown-5 (4.43 mL, 22.38 mmol) in DMF (117 mL) was injected sodium azide (4365 mg, 67.15 mmol), and the mixtures were stirred at 50° C. for 16 hours. To the reaction solutions was added water, and the mixtures were extracted with ethyl acetate by a separatory funnel. The combined organic layers were washed with water and saturated brine, and then dried over anhydrous sodium sulfate. The solvents were evaporated under reduced pressure and the resulting residues were purified by silica gel chromatography (hexane/ethyl acetate, 95/5 to 70/30) to obtain compound 52 (9.94 g, yield 98%).

MS (APCI): m/z 471 (M+NH4)$^+$ $^1$H-NMR (CDCl$_3$) δ: 7.36-7.22 (10H, m), 5.74 (1H, d, J=4.1 Hz), 4.76 (1H, d, J=12.3 Hz), 4.60 (1H, dd, J=5.1, 4.1 Hz), 4.55 (1H, d, J=12.3 Hz), 4.51 (1H, d, J=12.3 Hz), 4.41 (1H, d, J=12.3 Hz), 4.11 (1H, d, J=5.1 Hz), 3.42 (1H, d,

J=10.3 Hz), 3.34-3.19 (3H, m), 2.22-2.11 (1H, m), 1.92-1.80 (1H, m), 1.69-1.51 (2H, m), 1.60 (3H, s), 1.33 (3H, s)

[chem. 127]

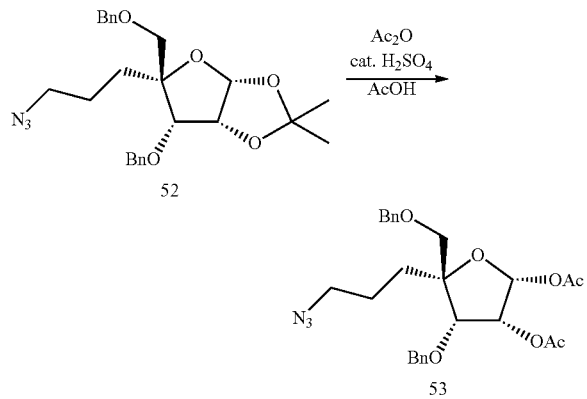

Example 57

1,2-Di-O-acetyl-7-azido-3-O-benzyl-4-[(benzyloxy)methyl]-5,6,7-trideoxyL-lyxo-heptofuranose (Compound 53)

To a solution of compound 52 (9.94 g, 21.9 mmol) in acetic acid (19.9 mL) were added acetic anhydride (9.94 mL, 105 mmol) and concentrated sulfuric acid (0.0497 mL, 0.932 mmol), and the mixtures were stirred at room temperature for 4 hours. To the reaction solutions was added ethyl acetate (200 mL). Thereto was added 10% aqueous sodium carbonate solution (200 mL) dropwise over 40 minutes while stirring vigorously, and the mixtures were stirred vigorously insitu for 1 hour. The organic layers were separated by a separatory funnel and the aqueous layers were extracted with ethyl acetate (50 mL) by a separatory funnel. The combined organic layers were washed with 5% aqueous sodium bicarbonate solution (200 mL) and saturated brine (100 mL), and dried over anhydrous sodium sulfate. The solvents were evaporated under reduced pressure, and the residues were azeotroped with toluene (150 mL portions were carried out twice) and then dried under reduced pressure to obtain compound 53 (11.40 g, containing 4.9 wt % of toluene, yield 100%).

MS (APCI): m/z 515 (M+NH$_4$)$^+$ $^1$H-NMR (CDCl$_3$) δ: 7.38-7.13 (10H, m), 6.10 (1H, s), 5.33 (1H, d, J=5.1 Hz), 4.60 (1H, d, J=11.8 Hz), 4.55-4.42 (3H, m), 4.29 (1H, d, J=5.1 Hz), 3.40 (1H, d, J=9.8 Hz), 3.35 (1H, d, J=9.8 Hz), 3.31-3.18 (2H, m), 2.11 (3H, s), 1.89 (3H, s), 1.89-1.56 (4H, m)

[chem. 128]

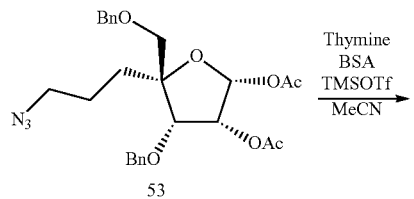

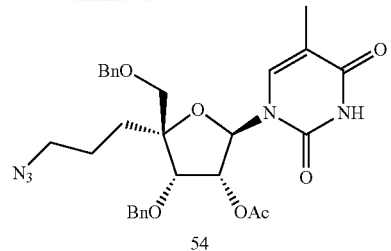

Example 58

1-{2-O-Acetyl-7-azido-3-O-benzyl-4-[(benzyloxy)methyl]-5,6,7-trideoxy-α-L-lyxo-heptofuranosyl}-5-methylpyrimidine-2,4(1H,3H)-dione (Compound 54)

To a solution of compound 53 (11.40 g, 21.78 mmol) in acetonitrile (57 mL) was inserted thymine (3022 mg, 23.96 mmol) at room temperature, followed by adding BSA (16 mL, 47.93 mmol) dropwise slowly successively. The mixtures were stirred at 60° C. as external temperature for 1 hour. Thereto was added TMSOTf (4.337 mL, 23.96 mmol) dropwise slowly at the same temperature, and the mixtures were stirred at 80° C. as external temperature for 3 hours. The reaction solutions were cooled under ice-cooling, and thereto was added 5% aqueous sodium carbonate solution (50 mL) over 30 minutes, and the reactions were quenched. Thereto were added ethyl acetate (100 mL) and water (100 mL), and the mixtures were stirred for a while, and the organic layers were separated by a separatory funnel. The aqueous layers were extracted with ethyl acetate (50 mL) by a separatory funnel, and the combined organic layers were washed with 5% aqueous sodium hydrogen carbonate solution (100 mL) and saturated brine (100 mL), and dried over anhydrous sodium sulfate. The solvents were evaporated under reduced pressure, and the resulting residues were purified by silica gel chromatography (hexane/ethyl acetate, 95/5 to 50/50) to obtain compound 54 (10.62 g, yield 83%).

MS (ESI): m/z 564 (M+H)$^+$ $^1$H-NMR (CDCl$_3$) δ: 8.14 (1H, s), 7.44-7.42 (1H, m), 7.39-7.27 (10H, m), 6.19 (1H, d, J=5.7 Hz), 5.39 (1H, t, J=5.7 Hz), 4.64 (1H, d, J=11.3 Hz), 4.55-4.42 (3H, m), 4.37 (1H, d, J=5.7 Hz), 3.66 (1H, d, J=10.3 Hz), 3.37 (1H, d, J=10.3 Hz), 3.34-3.17 (2H, m), 2.10 (3H, s), 1.95-1.70 (2H, m), 1.63-1.51 (5H, m)

[chem. 129]

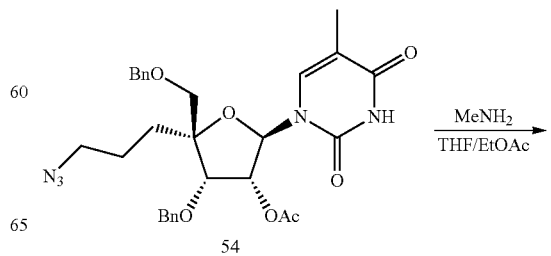

Example 59

1-{7-Azido-3-O-benzyl-4-[(benzyloxy)methyl]-5,6,7-trideoxy-α-L-lyxo-heptofuranosyl}-5-methylpyrimidine-2,4(1H,3H)-dione (Compound 55)

To a solution of compound 54 (10.62 g, 18.10 mmol) in THF (32 mL) and ethyl acetate (11 mL) was added methyl amine (10.62 mL, 120 mmol, 40% aqueous solution) under ice-cooling, and the mixtures were stirred for 2 hours. To the reaction solutions was added 1N-hydrochloric acid (105 mL) to make pH=8. The mixtures were extracted with ethyl acetate (200 mL, and 50 mL) by a separatory funnel. The combined organic layers were washed with saturated brine (100 mL), and then dried over anhydrous sodium sulfate. The solvents were evaporated under reduced pressure, and the resulting residues were azeotroped with toluene twice, and dried under reduced pressure to obtain compound 55 (10.74 g, yield 100%).

MS (ESI): m/z 522 (M+H)$^+$ $^1$H-NMR (CDCl$_3$) δ: 8.23 (1H, brs), 7.41-7.23 (9H, m), 7.19-7.12 (2H, m), 5.89 (1H, d, J=6.2 Hz), 4.71 (1H, d, J=11.3 Hz), 4.65 (1H, d, J=11.3 Hz), 4.56 (1H, d, J=11.3 Hz), 4.52 (1H, d, J=11.3 Hz), 4.38-4.30 (1H, m), 4.17 (1H, d, J=6.2 Hz), 3.63 (1H, d, J=9.8 Hz), 3.41 (1H, d, J=9.8 Hz), 3.37-3.28 (1H, m), 3.27-3.18 (1H, m), 2.94 (1H, d, J=8.2 Hz), 1.98-1.71 (2H, m), 1.64-1.50 (5H, m)

[chem. 130]

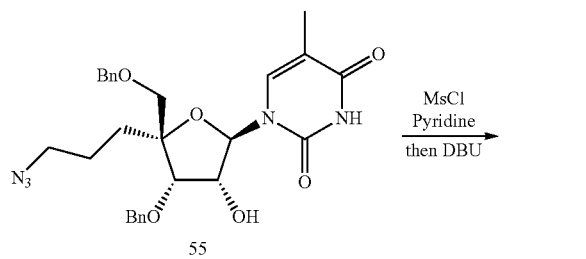

Example 60

(2R,3S,3aS,9aR)-2-(3-Azidopropyl)-3-(benzyloxy)-2-[(benzyloxy)methyl]-7-methyl-2,3,3a,9a-tetrahydro-6H-furo[2',3':4,5][1,3]oxazolo[3,2-a]pyrimidine-6-one (Compound 56)

To a solution of compound 55 (10.74 g, 18.14 mol) in pyridine (32 mL) was added methanesulfonyl chloride (1.83 mL, 23.59 mmol) dropwise under ice-cooling, and the mixtures were stirred at room temperature for 3.5 hours. The reaction solutions were cooled under ice-cooling, and thereto was added 1,8-diazabicyclo[5.4.0]-7-undecene (8.21 mL, 54.43 mmol) dropwise, and the mixtures were stirred at room temperature for 4 hours. The reaction solutions were diluted with ethyl acetate (400 mL), and were poured into 10% aqueous citric acid solution (500 mL), and the mixtures were stirred for a while. The organic layers were separated by a separatory funnel, and the aqueous layers were extracted with ethyl acetate (100 mL) by a separatory funnel. The combined organic layers were washed with water (500 mL) and saturated brine (300 mL). To the organic layers (brown color) was added activated carbon (1.00 g), and after the mixtures were stirred for 20 minutes, the mixtures were filtered through Celite. The filtrates were concentrated under reduced pressure, and then azeotroped with toluene. To the resulting concentrated residues was added ethyl acetate (40 mL) to prepare a suspension, and thereto was added hexane (300 mL), and the precipitates were collected by filtration. The precipitates were air-dried under nitrogen atmosphere and then dried under reduced pressure to obtain compound 56 (8.61 g, yield 94%).

MS (ESI): m/z 504 (M+H)$^+$ $^1$H-NMR (CDCl$_3$) δ: 7.41-7.27 (8H, m), 7.18 (1H, d, J=1.5 Hz), 7.16-7.12 (2H, m), 6.09 (1H, d, J=6.2 Hz,), 5.21 (1H, dd, J=6.2, 1.0 Hz), 4.72 (1H, d, J=11.8 Hz), 4.57 (1H, d, J=11.8 Hz), 4.37 (1H, d, J=11.8 Hz), 4.29 (1H, s), 4.26 (1H, d, J=11.8 Hz), 3.24 (2H, t, J=6.2 Hz), 3.18 (1H, d, J=9.8 Hz), 3.13 (1H, d, J=9.8 Hz), 1.97 (3H, d, J=1.0 Hz), 1.88-1.45 (4H, m)

[chem. 131]

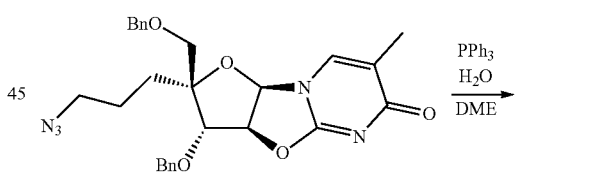

Example 61

(2R,3S,3aS,9aR)-2-(3-Aminopropyl)-3-(benzyloxy)-2-[(benzyloxy)methyl]-7-methyl-2,3,3a,9a-tetrahydro-6H-furo[2',3':4,5][1,3]oxazolo[3,2-a]pyrimidine-6-one (Compound 57)

To a solution of compound 56 (8.61 g, 17.1 mmol) in 1,2-dimethoxyethane (198 mL) was added water (17.2 mL), and thereto was added triphenylphosphine (4930 mg, 18.8 mmol) portion wise at 60° C. (external temperature) while observing a forming phenomenon. The mixtures were stirred at the same temperature for 20 minutes, and then stirred at 80° C. as external temperature for 2 hours. The reaction solutions were concentrated under reduced pressure and the resulting residues were purified by silica gel chromatography (chloroform/methanol, 100/0 to 70/30) to obtain compound 57 (8.25 g, containing 6.1 wt % of ethyl acetate, yield 100%).

MS (ESI): m/z 478 (M+H)$^+$ $^1$H-NMR (CDCl$_3$) δ: 7.39-7.23 (8H, m), 7.18 (1H, d, J=1.0 Hz), 7.15-7.10 (2H, m), 6.11 (1H, d, J=6.2 Hz,), 5.23 (1H, dd, J=6.2, 1.5 Hz), 4.72 (1H, d, J=11.8 Hz,), 4.56 (1H, d, J=11.8 Hz), 4.35 (1H, d, J=11.8 Hz), 4.29 (1H, d, J=1.5 Hz), 4.26 (1H, d, J=11.8 Hz), 3.20 (1H, d, J=10.3 Hz), 3.18 (1H, d, J=10.3 Hz,), 2.65 (2H, t, J=7.2 Hz), 1.95 (3H, d, J=1.0 Hz,), 1.80-1.29 (6H, m)

[chem. 132]

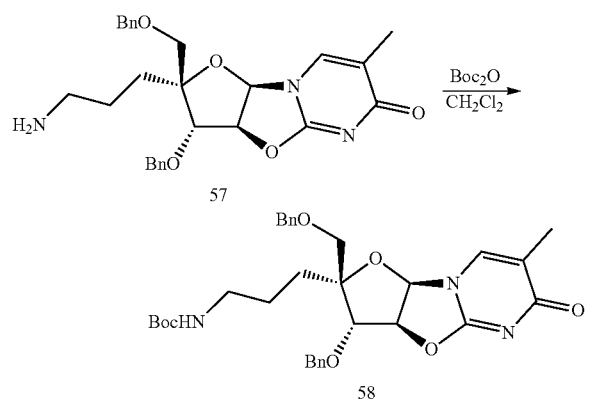

Example 62

Tert-butyl (3-{(2R,3S,3aS,9aR)-3-(benzyloxy)-2-[(benzyloxy)methyl]-7-methyl-6-oxo-2,3,3a,9a-tetrahydro-6H-furo[2',3':4,5][1,3]oxazolo[3,2-a]pyrimidin-2-yl}propyl)carbamate (Compound 58)

To a solution of compound 57 (7.54 g, 14.8 mmol) in dichloromethane (98 mL) was added di-tert-butyl bicarbonate (3560 mg, 16.3 mmol), and the mixtures were stirred at room temperature for 3 hours. The reaction solutions were concentrated under reduced pressure and the resulting residues were purified by silica gel chromatography (ethyl acetate/methanol, 100/0 to 97/3) to obtain compound 58 (7.67 g, containing 1.1 wt % of ethyl acetate, yield 89%).

MS (ESI): m/z 578 (M+H)$^+$ $^1$H-NMR (CDCl$_3$) δ: 7.40-7.27 (8H, m), 7.17 (1H, d, J=1.5 Hz), 7.15-7.09 (2H, m), 6.09 (1H, d, J=6.2 Hz), 5.20 (1H, dd, J=6.4, 1.5 Hz), 4.71 (1H, d, J=11.8 Hz), 4.56 (1H, d, J=11.8 Hz), 4.48 (1H, brs), 4.35 (1H, d, J=12.3 Hz), 4.28 (1H, d, J=1.5 Hz), 4.24 (1H, d, J=12.3 Hz), 3.17 (1H, d, J=9.8 Hz), 3.14 (1H, d, J=9.8 Hz), 3.11-3.03 (2H, m), 1.97 (3H, d, J=1.0 Hz), 1.78-1.62 (2H, m), 1.55-1.48 (1H, m), 1.43 (9H, s), 1.42-1.33 (1H, m)

[chem. 133]

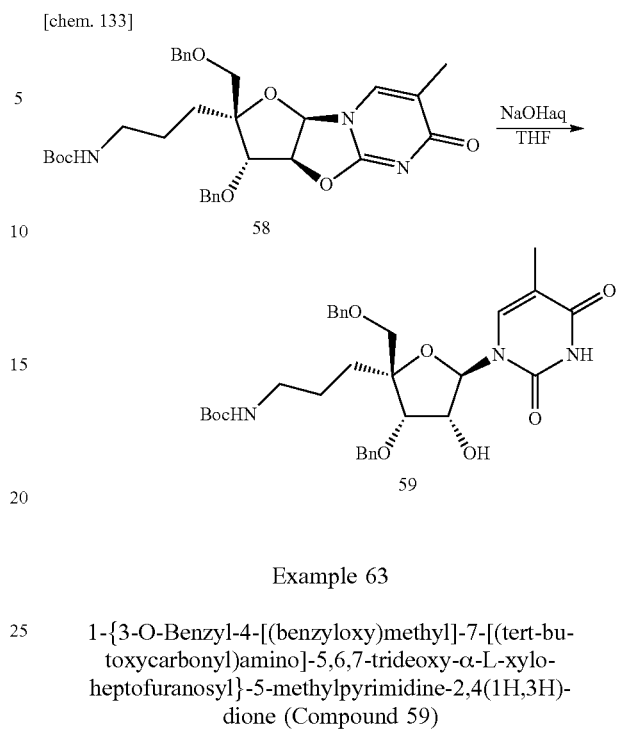

Example 63

1-{3-O-Benzyl-4-[(benzyloxy)methyl]-7-[(tert-butoxycarbonyl)amino]-5,6,7-trideoxy-α-L-xyloheptofuranosyl}-5-methylpyrimidine-2,4(1H,3H)-dione (Compound 59)

To a solution of compound 58 (7.67 g, 13.1 mmol) in THF (153 mL) was added 1 M aqueous sodium hydroxide solution (32.8 mL, 32.8 mmol) dropwise under ice-cooling, and the ice bath was removed, and the mixtures were stirred at room temperature for 6 hours. To the reaction solutions were added ethyl acetate (200 mL) and 5% aqueous citric acid solution (120 mL), and the mixtures were stirred for a while, and the organic layers were then separated by a separatory funnel. The aqueous layers were extracted with ethyl acetate (100 mL) by a separatory funnel, and the combined organic layers were washed with water (200 mL) and saturated brine (100 mL), and dried over anhydrous sodium sulfate. The solvents were evaporated under reduced pressure and the resulting residues were purified by silica gel chromatography (hexane/ethyl acetate, 90/10 to 0/100) to obtain compound 59 (7.82 g, containing 2.4 wt % of ethyl acetate, yield 100%).

MS (ESI): 496 [M−Boc+H]$^+$ $^1$H-NMR (CDCl$_3$) δ: 8.46 (1H, brs), 7.52 (1H, d, J=1.0 Hz), 7.40-7.25 (10H, m), 6.07 (1H, d, J=4.6 Hz), 4.77 (1H, d, J=11.8 Hz), 4.61-4.46 (4H, m), 4.42 (1H, brs), 4.17-3.86 (2H, m), 3.73 (1H, d, J=10.3 Hz), 3.47 (1H, d, J=10.3 Hz), 3.17-2.98 (2H, m), 1.77-1.45 (7H, m), 1.43 (9H, s)

[chem. 134]

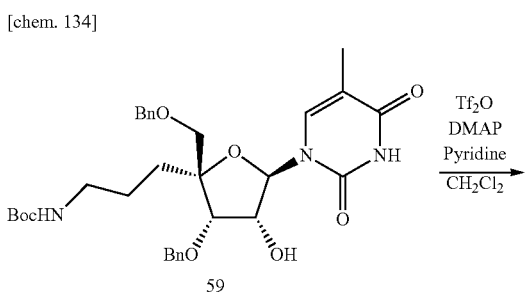

161

-continued

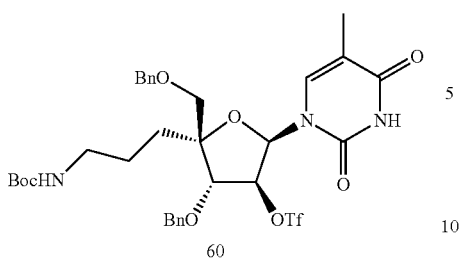

60

Example 64

1-{3-O-Benzyl-4-[(benzyloxy)methyl]-7-[(tert-butoxycarbonyl)amino]-5,6,7-trideoxy-2-O-[(trifluoromethyl)sulfonyl]-α-L-xylo-heptofuranosyl}-5-methylpyrimidine-2,4(1H,3H)-dione (Compound 60)

To a solution of compound 59 (7.82 g, 12.8 mmol) in dichloromethane (63 mL) were added pyridine (15.6 mL, 193 mmol) and DMAP (3130 mg, 25.6 mmol), and thereto was added trifluoromethanesulfonic anhydride (5.39 mL, 32.0 mmol) dropwise over 30 minutes under ice-cooling, and the mixtures were stirred at the same temperature for 1 hour. Thereto was added additionally trifluoromethanesulfonic anhydride (2.16 mL, 12.8 mmol), and the mixtures were stirred at the same temperature for 3 hours. To the reaction solutions was added saturated aqueous sodium bicarbonate solution (200 mL) under ice-cooling, and the mixtures were stirred for a while. The organic layers were separated by a separatory funnel, and the aqueous layers were extracted with dichloromethane (100 mL) by a separatory funnel. The combined organic layers were washed with saturated brine, and dried over anhydrous sodium sulfate. The solvents were evaporated under reduced pressure and azeotroped with toluene three times. The resulting residues were purified by silica gel chromatography (hexane/ethyl acetate, 90/10 to 50/50) to obtain compound 60 (8.24 g, containing 4.2 wt % of ethyl acetate, yield 88%).

MS (ESI): 628 [M−Boc+H]$^+$ $^1$H-NMR (CDCl$_3$) δ: 8.36 (1H, brs), 7.41-7.27 (9H, m), 7.25-7.21 (2H, m), 6.31 (1H, d, J=5.1 Hz), 5.44-5.38 (1H, m,), 4.75 (1H, d, J=11.8 Hz,), 4.59-4.40 (5H, m), 3.52 (1H, d, J=9.8 Hz), 3.40 (1H, d, J=9.8 Hz), 3.22-3.01 (2H, m), 1.79-1.51 (7H, m,), 1.44 (9H, s)

[chem. 135]

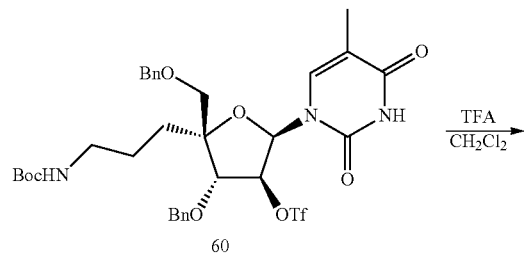

60

162

-continued

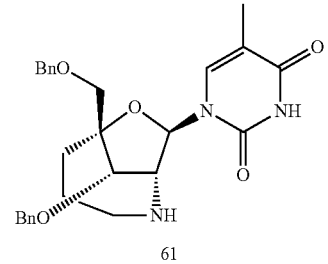

61

Example 65

1-{(1R,6R,8R,9S)-9-(Benzyloxy)-6-[(benzyloxy)methyl]-7-oxa-2-azabicyclo[4.2.1]non-8-yl}-5-methylpyrimidine-2,4(1H,3H)-dione (Compound 61)

To a solution of compound 60 (8.24 g, 10.9 mmol) in dichloromethane (124 mL) was added trifluoroacetic acid (41.2 mL, 535 mmol) under ice-cooling, and the ice bath was removed, and the mixtures were stirred at room temperature for 2 hours. The reaction solutions were concentrated under reduced pressure, and then azeotroped with toluene. The resulting residues were dissolved in dichloromethane (200 mL), and thereto was added saturated aqueous sodium bicarbonate solution (100 mL) under ice-cooling while stirring vigorously, and the mixtures were stirred at room temperature for 13 hours. The organic layers of the reaction solutions were separated by a separatory funnel, and the aqueous layers were extracted with chloroform (50 mL portions were carried out twice) by a separatory funnel. The combined organic layers were dried over anhydrous sodium sulfate. The solvents were evaporated and the resulting residues were purified by silica gel chromatography (chloroform/methanol, 100/0 to 95/5) to obtain compound 61 (4.96 g, yield 96%).

MS (ESI): 478 [M+H]$^+$ $^1$H-NMR (CDCl$_3$) δ: 8.24 (1H, brs), 7.97 (1H, d, J=1.5 Hz), 7.40-7.26 (8H, m), 7.25-7.20 (2H, m), 5.86 (1H, s), 4.76 (1H, d, J=11.8 Hz), 4.56 (1H d, J=11.8 Hz), 4.53-4.46 (2H, m), 4.40 (1H, d, J=7.2 Hz), 3.72 (1H, d, J=10.8 Hz), 3.58 (1H, d, J=7.2 Hz), 3.54 (1H, d, J=10.8 Hz), 3.34-3.21 (1H, m), 3.14-3.03 (1H, m), 1.90-1.55 (4H, m), 1.41 (3H, d, J=1.5 Hz)

[chem. 136]

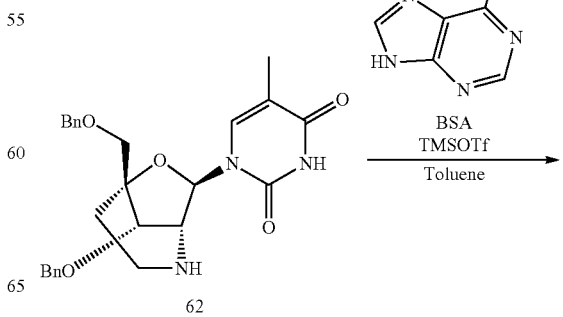

62

-continued

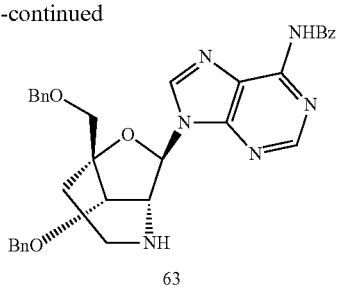

63

Example 66

N-(9-{(1R,5R,7R,8S)-8-(Benzyloxy)-5-[(benzyloxy)methyl]-6-oxa-2-azabicyclo[3.2.1]oct-7-yl}-9H-purin-6-yl)benzamide (Compound 63)

Compound 62 (1-{(1R,5R,7R,8S)-8-(benzyloxy)-5-[(benzyloxy)methyl]-6-oxa-2-azabicyclo[3.2.1]oct-7-yl}-5-methylpyrimidine-2,4(1H,3H)-dione (prepared from 3,5-di-O-benzyl-4-C-hydroxymethyl-1,2-O-isopropylidene-α-D-ribofuranose 2 according to the method described in J. Am. Chem. Soc. 2006, 128, 15173) (49.8 mg, 0.107 mmol) and N-(9H-purin-6-yl)benzamide (77.1 mg, 0.322 mmol) were placed in a 10 mL egg-plant shaped flask, and thereto were added toluene (1 mL) and BSA (0.235 mL, 0.961 mmol). The mixtures were stirred at 60° C. as external temperature for 15 minutes, and then warmed to 100° C. as external temperature, and thereto was added TMSOTf (0.005 mL, 0.026 mmol). The mixtures were stirred at the same temperature for 30 minutes, and warmed to room temperature, and thereto were added 3% aqueous sodium bicarbonate solution (10 mL) and chloroform (10 mL), and the mixtures were stirred. The organic layers were separated, and the aqueous layers were extracted with chloroform (10 mL). The organic layers were mixed, and washed with water (10 mL). The aqueous layers were extracted with chloroform (5 mL), and the extracts were mixed with the organic layers. The mixed organic layers were filtered through a cotton plug to remove solids. The solvents were evaporated from the filtrates, and the residues were subjected to reverse phase HPLC preparative chromatography (10 mM aqueous ammonium carbonate solution/acetonitrile=60/40 to 30/70) and thin layer chromatography (the development using chloroform/methanol=12/1 was carried out twice) to obtain compound 63 (4.9 mg, yield 8%).

MS (ESI): 577 [M+H]⁺

¹H-NMR (CDCl₃) δ: 9.08 (1H, brs), 8.77 (1H, s), 8.72 (1H, s), 8.05 (2H, d, J=7.7 Hz), 7.65-7.59 (1H, m), 7.57-7.51 (2H, m), 7.39-7.21 (10H, m), 6.45 (1H, s), 4.64 (1H, d, J=12.3 Hz), 4.58 (1H, d, J=12.3 Hz), 4.55 (1H, d, J=11.8 Hz), 4.47 (1H, d, J=11.8 Hz), 4.23 (1H, d, J=3.6 Hz), 3.71 (1H, d, J=3.6 Hz), 3.66 (1H, d, J=10.8 Hz), 3.52 (1H, d, J=10.8 Hz), 3.26-3.16 (1H, m), 3.07 (1H, dd, J=13.9, 6.7 Hz), 2.07-1.97 (1H, m), 1.86 (1H, brs), 1.37 (1H, dd, J=12.8, 4.6 Hz)

[chem. 137]

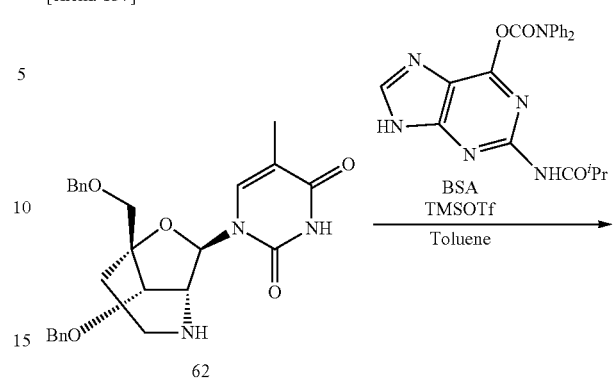

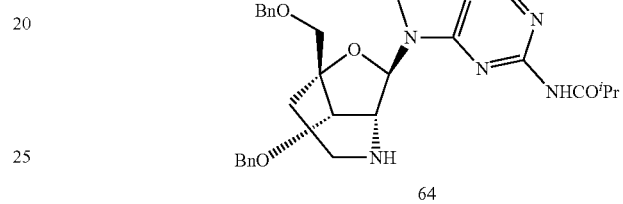

Example 67

9-{(1R,5R,7R,8S)-8-(Benzyloxy)-5-[(benzyloxy)methyl]-6-oxa-2-azabicyclo[3.2.1]oct-7-yl}-2-[(2-methylpropanoyl)amino]-9H-purin-6-yl diphenylcarbamate (Compound 64)

Similarly to Example 66 from compound 62 (49.8 mg, 0.107 mmol) and [2-(2-methylpropanoylamino)-9H-purin-6-yl] N,N-diphenylcarbamate (133.9 mg, 0.3216 mmol) (the preparation method follows the method described in J. Org. Chem. 1996, 61, 9207), compound 64 (24.4 mg, yield 30%) was prepared.

MS (ESI): 754 [M+H]⁺

¹H-NMR (CDCl₃) δ: 8.65 (1H, s), 8.04 (1H, s), 7.49-7.42 (2H, m), 7.40-7.21 (18H, m), 6.37 (1H, s), 4.64 (1H, d, J=12.3 Hz), 4.56 (1H, d, J=12.3 Hz), 4.53 (1H, d, J=11.8 Hz), 4.44 (1H, d, J=11.8 Hz), 4.24 (1H, d, J=3.6 Hz), 3.66 (1H, d, J=3.6 Hz), 3.63 (1H, d, J=10.8 Hz), 3.50 (1H, d, J=10.8 Hz), 3.21-3.12 (1H, m), 3.04 (1H, dd, J=13.9, 6.7 Hz), 2.90 (1H, brs), 2.07 (1H, brs), 2.06-1.93 (1H, m), 1.35 (1H, dd, J=12.8, 4.6 Hz), 1.27 (3H, d, J=1.5 Hz), 1.25 (3H, d, J=1.5 Hz)

[chem. 136]

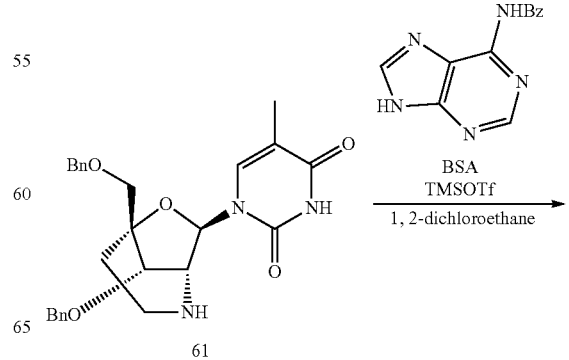

61

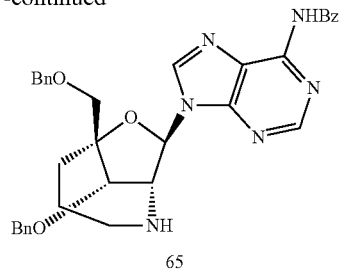

65

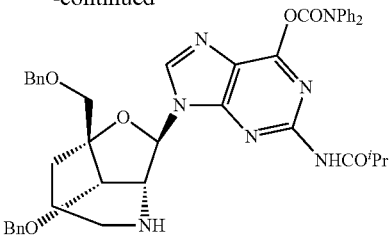

66

Example 68

N-(9-{(1R,6R,8R,9S)-9-(Benzyloxy)-6-[(benzyloxy)methyl]-7-oxa-2-azabicyclo[4.2.1]non-8-yl}-9H-purin-6-yl)benzamide (Compound 65)

Compound 61 (49.7 mg, 0.104 mmol) and N-(9H-purin-6-yl)benzamide (74.7 mg, 0.312 mmol) were placed in an egg-plant shaped flask, and thereto were added 1,2-dichloroethane (1 mL) and BSA (0.230 mL, 0.941 mmol). After the mixtures were stirred at 60° C. as external temperature for 15 minutes, thereto was added TMSOTf (0.0050 mL, 0.026 mmol), and the mixtures were stirred at 60° C. as external temperature for 3.5 hours. The mixtures were cooled to room temperature, and thereto were added 3% aqueous sodium bicarbonate solution (10 mL) and chloroform (15 mL), and the mixtures were stirred. The organic layers were separated, and the aqueous layers were extracted with CHCl₃ (10 mL). The organic layers were mixed, and washed with tap water (10 mL). The aqueous layers were extracted with CHCl₃ (5 mL), and the extracts were mixed with the organic layers. The aqueous layers were extracted with chloroform (5 mL). The organic layers were mixed again, concentrated under reduced pressure at 50° C., and then subjected to reverse phase HPLC preparative chromatography (10 mM aqueous ammonium carbonate solution/acetonitrile=50/50 to 20/80) to obtain compound 65 (19.2 mg, yield 31%).

MS (ESI): 591 [M+H]⁺

¹H-NMR (CDCl₃) δ: 9.00 (1H, brs), 8.80 (1H, s), 8.70 (1H, s), 8.04 (2H, d, J=7.2 Hz), 7.64-7.59 (1H, m), 7.56-7.51 (2H, m), 7.37-7.24 (10H, m), 6.28 (1H, s), 4.65 (1H, d, J=6.7 Hz), 4.60 (1H, d, J=11.3 Hz), 4.59 (1H, d, J=12.3 Hz), 4.52 (1H, d, J=12.3 Hz), 4.47 (1H, d, J=11.3 Hz), 3.86 (1H, d, J=6.7 Hz), 3.65 (1H, d, J=10.8 Hz), 3.51-3.47 (2H, m), 3.36-3.28 (1H, m), 3.17-3.08 (1H, m), 1.98-1.89 (2H, m), 1.83-1.67 (2H, m)

[chem. 139]

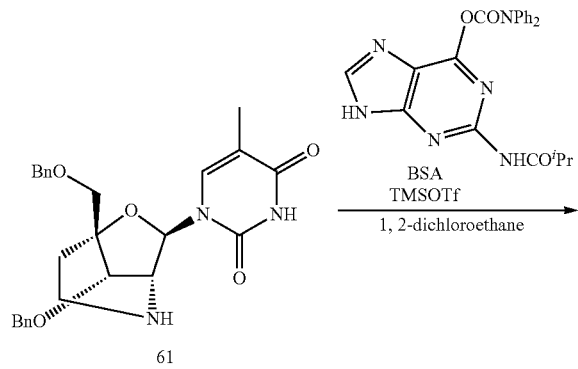

61

$\xrightarrow{\text{BSA} \atop \text{TMSOTf}}_{\text{1, 2-dichloroethane}}$

Example 69

9-{(1R,6R,8R,9S)-9-(Benzyloxy)-6-[(benzyloxy)methyl]-7-oxa-2-azabicyclo[4.2.1]non-8-yl}-2-[(2-methylpropanoyl)amino]-9H-purin-6-yl diphenylcarbamate (Compound 66)

Similarly to Example 66 from compound 61 (50.1 mg, 0.105 mmol) and [2-(2-methylpropanolylamino)-9H-purin-6-yl] N,N-diphenylcarbamate (131.1 mg, 0.3148 mmol) (the preparation method follows the method described in J. Org. Chem. 1996, 61, 9207), compound 66 (42.4 mg, yield 53%) was prepared.

MS (ESI): 768 [M+H]⁺

¹H-NMR (CDCl₃) δ: 8.60 (1H, s), 8.01 (1H, s), 7.47-7.42 (2H, m), 7.40-7.21 (18H, m), 6.18 (1H, s), 4.68 (1H, d, J=6.7 Hz), 4.62 (1H, d, J=11.3 Hz), 4.60 (1H, d, J=12.3 Hz), 4.51 (1H, d, J=12.3 Hz), 4.47 (1H, d, J=11.3 Hz), 3.84 (1H, d, J=6.7 Hz), 3.63 (1H, d, J=10.8 Hz), 3.49 (1H, d, J=10.8 Hz), 3.36-3.25 (1H, m), 3.13-3.04 (1H, m), 2.92 (1H, brs), 1.97 (1H, s), 1.94-1.84 (1H, m), 1.80-1.65 (3H, m), 1.26 (6H, d, J=7.2 Hz)

Example 70

Preparation and Purification of Oligonucleotide Analogues

Using compound 16Ab prepared by Example 32, compound 16$^{Me}$Ca prepared by Example 30, compound 16Ga prepared by Example 28, and various commercially available phosphoramidites, oligonucleotide analogues having various nucleic acid base(s) were prepared by DNA/RNA oligonucleotide automatic synthesizer nS-8 or nS-8II (the both are manufactured by GeneDesign, Inc.) with 5' terminal DMTr ON or OFF mode using 0.2 μmol scale of CPG or polystyrene support. When GuNA monomer was subjected to a coupling reaction, the coupling time of a solution of the GuNA monomer in acetonitrile (0.1 M) was 8 minutes, and the other steps were carried out under usual oligonucleotide synthesis condition of nS-8 or nS-8II. 5-Ethylthio-1H-tetrazole (0.25 M) was used as an activating agent.

The purification and confirmation of purity of the synthesized oligonucleotide analogues were carried out by reverse phase HPLC chromatography under the following conditions.

Mobile Phase

A solution: 0.1 M triethylammonium acetate buffer, pH 7.0

B solution: 0.1 M triethylammonium acetate (water:acetonitrile=1:1) solution

Gradient: A:B=95:5→70:30 (23 min.) or A:B=95:5→50:50 (22.5 min.)

Used column:
 Analysis: Waters XBridge™ OST C18 2.5 µm (4.6×50 mm)
 Preparation: Waters XBridge™ OST C18 2.5 µm (10×50 mm)
Flow rate:
 Analysis: 1 mL/min.
 Preparation: 4 mL/min.
 Column temperature: 50° C.
 Detection: UV (254 nm)

The molecular weight of the synthesized oligonucleotide analogues was determined by a time-of-flight mass spectrometry (MALDI-TOF-MS).

Preparation of 5'-d(TTTTATTTTT)-3' (SEQ ID No. 1) (A: guanidine bridged nucleic acid, compound 48)

Boc-protected oligonucleotide was prepared using compound 16Ab prepared by Example 32 on 0.2 µmol of polystyrene support (LV-PS dT 0.2 µmol, manufactured by Glen Research), and the column after the synthesis was charged by a solution of 20% trifluoroacetic acid in methylene chloride and allowed to stand at room temperature for 1 hour. Methylene chloride and acetonitrile were passed through the column successively to wash the support, and the support was dried under nitrogen stream, and further dried under reduced pressure.

Next, the column was filled with a solution of ammonia in methanol (7N), and the column was allowed to stand at room temperature for 1 hour, and the support was then cleaved, and the support was washed with 28% aqueous ammonia. The cleavage solution and the washing solution were combined in a snap vial, and heated at 65° C. as external temperature for 6 hours. The mixtures were concentrated under reduced pressure to about 80% volume, and purified by reverse phase HPLC chromatography (gradient: A:B=95:5→70:30 (23 min.)).

Yield 27%.

MALDI-TOF-MS: m/z Theoretical value (M–H⁻) 3057.06,

Measured value (M–H⁻) 3053.00

Preparation Method 2 of 5'-d(TTTTATTTTT)-3'(SEQ ID No. 1)

(A: Guanidine Bridged Nucleic Acid, Compound 48)

Boc-protected oligonucleotide was prepared using compound 16Ab prepared by Example 32 on CPG support (CPG 500 Å dT 0.2 µmol, manufactured by Proligo LLC), and the column after the synthesis was charged by a Boc-deprotecting solution (a mixture of trimethylsilyl triflate 940 µL, 2,6-dimethylpyridine 1,260 µL, and methylene chloride 10 mL), and allowed to stand at room temperature for 3 hours. The Boc-deprotecting solution was removed, and 10 v/v % of 2,6-dimethylpyridine/methylene chloride solution and methylene chloride were passed through the column successively to wash the support.

Next, 28% aqueous ammonia was added thereto, and the column was allowed to stand for 12 hours, and the cleavage solution was transferred into a snap vial, and heated at 65° C. as external temperature for 5 hours. The solution was concentrated under reduced pressure to half volume, and purified by reverse phase simple column (Sep-Pak (trademark) Plus C18 Cartridges, manufactured by Waters Inc.) and subjected to reverse phase HPLC purification (gradient: A:B=95:5→70:30 (23 min.)).

Yield 12%.

MALDI-TOF-MS: m/z Theoretical value (M–H⁻) 3057.06,

Measured value (M–H⁻) 3058.82

Preparation Method of 5'-d(TTTT$^{m}$C TTTTT)-3' (SEQ ID No. 2) ($^{m}$C: Guanidine Bridged Nucleic Acid, Compound 49)

Teoc-protected oligonucleotide was prepared using compound 16$^{Me}$Ca prepared by Example 30 on 0.2 µmol of polystyrene support (LV-PS dT 0.2 µmol, manufactured by Glen Research), and the support was transferred from the column to a snap vial. A solution of tetrabutylammonium fluoride in tetrahydrofuran (0.2 M) was added thereto, and the mixtures were heated at 65° C. as external temperature for 8 hours, and then 28% aqueous ammonia was added thereto, and the mixtures were heated at 65° C. as external temperature for 8 hours. The mixtures were concentrated under reduced pressure to about half volume, and the residues were purified by a gel filtration column (Illustra™ NAP™-10 Column Sephadex™ G-25 DNA Grade, manufactured by GE Healthcare Inc.) and successively reverse-phase simple column (Sep-Pak (trademark) Plus C18 Cartridges, manufactured by Waters Inc.), and further subjected to reverse phase HPC purification (gradient: A:B=95:5→450:50 (22.5 min.)).

Yield 19%.

MALDI-TOF-MS: m/z Theoretical value (M–H⁻) 3047.06,

Measured value (M–H⁻) 3046.06

Preparation method of 5'-d(TTTTGTTTTT)-3' (SEQ ID No. 3) (G: Guanidine Bridged Nucleic Acid, Compound 50)

Teoc-protected oligonucleotide was prepared using compound 16Ga prepared by Example 28 on CPG support (CPG 500 Å dT 0.2 µmol, manufactured by Proligo LLC) according to the above-mentioned preparation method 2 of compound 48, and the workup treatments from the deprotection procedures to the purification procedures were carried out similarly to compound 48.

Yield 23%.

MALDI-TOF-MS: m/z Theoretical value (M–H⁻) 3073.06,

Measured value (M–H⁻) 3071.24

Since the result of a molecular weight measurement by a time-of-flight mass spectrometry (MALDI-TOF-MS) showed good match with the theoretical value, it was confirmed that each of the desirable oligonucleotides was obtained.

Compounds 51 to 58 were prepared similarly. The results are shown in Table 1.

TABLE 1

Oligonucleotide containing guanidine bridged nucleic acid

| Oligonucleotide (the underlined part indicates guanidine bridged nucleic acid) | Time-of-flight mass spectrometry calculated value (M-H⁻) | Measured value (M-H⁻) |
|---|---|---|
| 5'-d(GCGTT<u>T</u>TTTGCT)-3' (compound 51)(SEQ ID No. 4) | 3701.45 | 3702.52 |
| 5'-d(GCGTT<u>A</u>TTTGCT)-3' (compound 52)(SEQ ID No. 5) | 3710.48 | 3711.41 |
| 5'-d(GCGTT<u>ᵐC</u>TTTGCT)-3' (compound 53)(SEQ ID No. 6) | 3700.47 | 3702.23 |
| 5'-d(GCGTT<u>G</u>TTTGCT)-3' (compound 54)(SEQ ID No. 7) | 3726.47 | 3728.41 |
| 5'-d(TTTT<u>T</u>TTTT)-3' (compound 55)(SEQ ID No. 8) | 3186.18 | 3184.70 |
| 5'-d(AAAA<u>A</u>AAAA)-3' (compound 56)(SEQ ID No. 9) | 3276.33 | 3276.52 |
| 5'-d(TTT<u>ᵐCᵐCᵐC</u>CTTTT)-3' (compound 57)(SEQ ID No. 10) | 3183.23 | 3186.41 |
| 5'-d(TTT<u>GGG</u>TTTT)-3' (compound 58)(SEQ ID No. 11) | 3261.22 | 3263.47 |

As a comparison and contrast, oligonucleotides in which the base sequences are identical to those of compounds 51 to 58, and guanidine bridged nucleic acid is not contained, and only naturally occurring nucleotides are contained) (compounds 59 to 66 respectively) were prepared according to the usual synthesis condition of oligonucleotide, and then purified. Also, as complementary strands that can form a double strand with the above-mentioned oligonucleotide, oligonucleotides in which the base sequences are complementary sequences against compounds 51 to 58, and guanidine bridged nucleic acid is not contained, and only naturally occurring nucleotides are contained (compounds 67 to 74 respectively), and oligonucleotides being RNA in which the base sequences are complementary sequences against compounds 51 to 54, and guanidine bridged nucleic acid is not contained, and only naturally occurring nucleotides are contained (compounds 75 to 78 respectively) were prepared according to the usual synthesis condition of oligonucleotide, and then purified.

Example 71

Measurement of Melting Temperature (Tm)

Each of various oligonucleotides prepared by Example 70 (compounds 48 to 66) and the complementary oligonucleotides (compounds 67 to 74, or compounds 75 to 78) were annealed to form a double strand, and then Tm value that is a temperature at which 50%, of the double strand is deviated, was measured, and the double strand-forming capacity of oligonucleotide was examined.

Specifically, regarding a sample solution (130 µL) which contains sodium chloride 100 mM, sodium phosphate buffer (pH 6.99) 10 mM, oligonucleotide 4 µM and the complementary strands 4 µM, the compounds indicated in Table 2 were warmed from room temperature to 95° C. at a rate of 5° C. per minute and then cooled to 5° C. at a rate of 0.5° C. per minute, while the compounds indicated in Table 3 were heated using the boiling water bath and allowed to stand to cool to room temperature. Nitrogen stream was passed into a cell chamber of spectrophotometer (Shimadzu, UV-1650PC or UV-1800) so as to prevent a condensation phenomenon, and the sample solution was cooled to 5° C. gradually, and kept at 5° C. for 1 minute, and the measurement was then started. The temperature was warmed moderately to 90° C. at a rate of 0.5° C. per minute, and the ultraviolet absorption at 260 nm was measured at every timing of 0.5° C. rise. Here in order to prevent a concentration change due to a temperature rise, the cell with a lid was used. The measurement results are shown in Table 2 as a Tm value and the difference in Tm value per a modified unit. It shows that the higher Tm value was, the higher the capacity of forming double strand was.

TABLE 2

Effect on Tm value by introduction of one residue of guanidine bridged nucleic acid

| Oligonucleotide (the underlined part indicates guanidine bridged nucleic acid) | Tm (ΔTm/modified unit) (° C.) DNA* | RNA* |
|---|---|---|
| 5'-d(GCGTTTTTTGCT)-3' (compound 59) (SEQ ID No. 4) | 53 | 47 |
| 5'-d(GCGTT<u>T</u>TTTGCT)-3' (compound 51) | 56 (+3) | 53 (+6) |
| 5'-d(GCGTTATTTGCT)-3' (compound 60) (SEQ ID No. 5) | 50 | 46 |
| 5'-d(GCGTT<u>A</u>TTTGCT)-3' (compound 52) | 52 (+2) | 50 (+4) |
| 5'-d(GCGTTCTTTGCT)-3' (compound 61) (SEQ ID No. 6) | 53 | 53 |
| 5'-d(GCGTT<u>ᵐC</u>TTTGCT)-3' (compound 53) | 60 (+7) | 60 (+7) |

TABLE 2-continued

Effect on Tm value by introduction of one residue of guanidine bridged nucleic acid

| Oligonucleotide (the underlined part indicates guanidine bridged nucleic acid) | Tm (ΔTm/modified unit) (° C.) | |
|---|---|---|
| | DNA* | RNA* |
| 5'-d(GCGTTGTTTGCT)-3' (compound 62) (SEQ ID No. 7) | 55 | 52 |
| 5'-d(GCGTT<u>G</u>TTTGCT)-3' (compound 54) | 60(+5) | 57(+5) |

*: base sequences of complementary strand oligonucleotides:
Complementary strands of compounds 51 and 59:
DNA/5'-d(AGCAAAAAACGC)-3' (compound 67) (SEQ ID No. 12),
RNA/5'-r(AGCAAAAAACGC)-3' (compound 75) (SEQ ID No. 13),
Complementary strand of compounds 52 and 60:
DNA/5'-d(AGCAAATAACGC)-3' (compound 68) (SEQ ID No. 14),
RNA/5'-r(AGCAAATAACGC)-3' (compound 76) (SEQ ID No. 15),
Complementary strand of compounds 53 and 61:
DNA/5'-d(AGCAAAGAACGC)-3' (compound 69) (SEQ ID No. 16),
RNA/5'-r(AGCAAAGAACGC)-3' (compound 77) (SEQ ID No. 17),
Complementary strand of compounds 54 and 62:
DNA/5'-d(AGCAAACAACGC)-3' (compound 70) (SEQ ID No. 18),
RNA/5'-r(AGCAAACAACGC)-3' (compound 78) (SEQ ID No. 19).

TABLE 3

Effect on Tm value by introduction of three residues of guanidine bridged nucleic acid

| Oligonucleotide (the underlined part indicates guanidine bridged nucleic acid) | Complementary strand (DNA) | Tm (ΔTm/modified unit) (° C.) |
|---|---|---|
| 5'-d(TTTTTTTTTT)-3' (compound 63)(SEQ ID No. 8) | 5'-d(AAAAAAAAAA)-3' (compound 71) (SEQ ID No.20) | 23 |
| 5'-d(TTT<u>TTT</u>TTTT)-3' (compound 55) | 5'-d(AAAAAAAAAA)-3' (compound 71) | 50(+9.0) |
| 5'-d(AAAAAAAAAA)-3' (compound 64)(SEQ ID No. 9) | 5'-d(TTTTTTTTTT)-3' (compound 72) (SEQ ID No. 21) | 23 |
| 5'-d(AAA<u>AAA</u>AAAA)-3' (compound 56) | 5'-d(TTTTTTTTTT)-3' (compound 72) | 37(+4.7) |
| 5'-d(TTTCCCTTTT)-3' (compound 65)(SEQ ID No. 10) | 5'-d(AAAAGGGAAA)-3' (compound 73) (SEQ ID No. 22) | 31 |
| 5'-d(TTT<u><sup>m</sup>C<sup>m</sup>C<sup>m</sup>C</u>CTTTT)-3' (compound 57) | 5'-d(AAAAGGGAAA)-3' (compound 73) | 52(+7.0) |
| 5'-d(TTTGGGTTTT)-3' (compound 66)(SEQ ID No. 11) | 5'-d(AAAACCCAAA)-3' (compound74) (SEQ ID No. 23) | 36 |
| 5'-d(TTT<u>GGG</u>TTTT)-3' (compound 58) | 5'-d(AAAACCC2AA)-3' (compound74) | 56(+6.7) |

As evident from Tables 2 and 3, oligonucleotides containing guanidine bridged artificial nucleic acid showed excellent capacity of forming double strand for all bases in the cases of not only RNA but also DNA. Also, it was found that for any base, the higher the introduction ratio of guanidine bridged artificial nucleic acid into oligonucleotide was, the higher the rise of Tm value was. Accordingly, oligonucleotide of the present invention in which guanidine bridged artificial nucleic acid is introduced is considered an oligonucleotide suitable for an antisense method.

INDUSTRIAL APPLICABILITY

According to the novel preparation method of bridged nucleic acid GuNA of the present invention, the number of steps for preparing bridged nucleic acid GuNA can be shorten, and the yields of bridged nucleic acid GuNA can be improved. Also, using the compound as a novel intermediate of the present invention, bridged artificial nucleic acid GuNA containing various kinds of nucleic acid base can be prepared. The preparation method of the present invention and the intermediate compound of the present invention are useful for efficient preparation of guanidine bridged nucleic acid GuNA, and the guanidine bridged artificial nucleic acid GuNA oligomer can be used for various pharmaceuticals, diagnosis, and experiment and research.

[Sequence Listing Free Text]

SEQ ID Nos. 1 to 12, 14, 16, 18, and 20 to 23 show DNA oligonucleotides.

SEQ ID Nos. 13, 15, 17, and 19 show RNA oligonucleotides.

The invention claimed is:

1. A method for preparing a compound represented by general formula I:

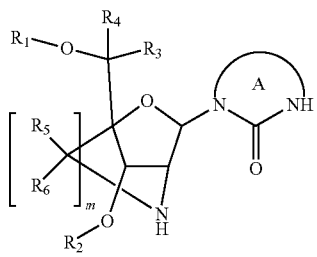

wherein, $R_1$ and $R_2$ represent independently of each other a protecting group for hydroxy group, $R_3$ and $R_4$ represent independently of each other a hydrogen atom or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and a cycle A represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, or salts thereof, said method comprising a step of reacting a compound represented by formula II:

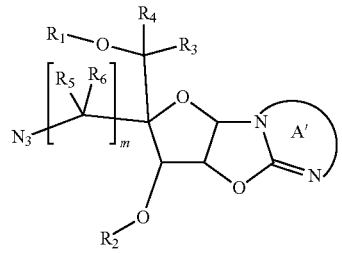

wherein, each of $R_1$, $R_2$, $R_3$, $R_4$, $R_5$, $R_6$ and m is the same as defined in the above-mentioned general formula I, a cycle A' represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring with a reducing agent to cleave an oxazolidine ring fused to a cycle A', wherein the reducing agent comprises at least one of phosphines, metal hydrides, or transition metal catalysts in the presence of hydrogen gas.

2. The method according to claim 1 wherein each of $R_1$ and $R_2$ represents a benzyl group, each of $R_3$, $R_4$, $R_5$, and $R_6$ represents a hydrogen atom, cycle A represents a 1-thyminyl group or a 1-uracilyl group, and cycle A' represents the following structural formula II-1 or II-2:

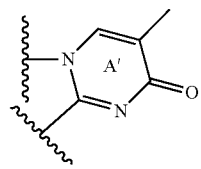
(II-1)

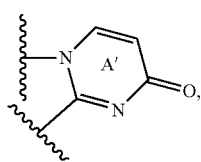
(II-2)

and the reducing agent is Ph$_3$P.

3. A compound represented by general formula II:

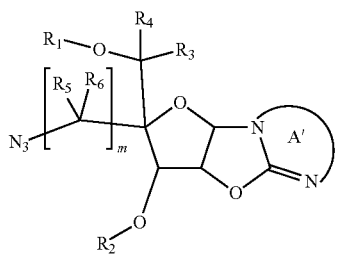

wherein,

R$_1$ and R$_2$ represent independently of each other a protecting group for hydroxy group, R$_3$ and R$_4$ represent independently of each other a hydrogen atom or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, m is an integer of 1 to 3, and a cycle A' represents a mono or di-one ring derived from uracil, cytosine or thymine, which may be optionally substituted with one or more substituents selected from the group consisting of a C$_{1-6}$ alkyl group which may be optionally substituted with one or more substituents, a C$_{2-6}$ alkenyl group which may be optionally substituted with one or more substituents, a C$_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, or salts thereof.

4. The compound according to claim 3 or salts thereof wherein R$_1$ and R$_2$ represent a benzyl group, each of R$_3$, R$_4$, R$_5$, and R$_6$ represents a hydrogen atom, and cycle A' represents the following structural formula II-1 or II-2:

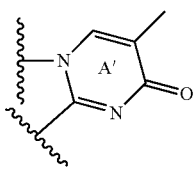
(II-1)

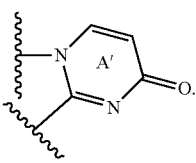
(II-2)

5. A method for preparing a compound represented by general formula II:

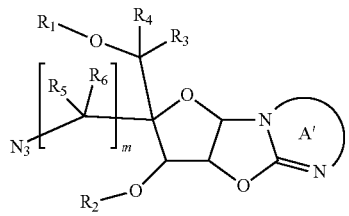

wherein,

R$_1$ and R$_2$ represent independently of each other a protecting group for hydroxy group, R$_3$ and R$_4$ represent independently of each other a hydrogen atom, or a C$_{1-6}$ alkyl group which may be optionally substituted with one or more substituents, each R$_5$ represents independently a hydrogen atom, or a C$_{1-6}$ alkyl group which may be optionally substituted with one or more substituents, each R$_6$ represents independently a hydrogen atom, or a C$_{1-6}$ alkyl group which may be optionally substituted with one or more substituents, m is an integer of 1 to 3, and cycle A' represents a mono or di-one ring derived from uracil, cytosine or thymine, which may be optionally substituted with one or more substituents selected from the group consisting of a C$_{1-6}$ alkyl group which may be optionally substituted with one or more substituents, a C$_{2-6}$ alkenyl group which may be optionally substituted with one or more substituents, a C$_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, or salts thereof, said method comprising a step of reacting a compound represented by general formula III:

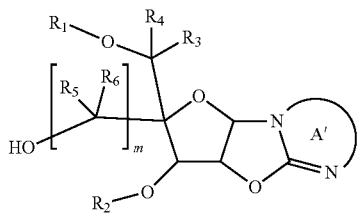

wherein, each of $R_1$, $R_2$, $R_3$, $R_4$, $R_5$, $R_6$, m and cycle A' is the same as defined in the above-mentioned general formula II, with an azide agent, wherein the azide agent comprises at least one of hydrazoic acid, sodium azide, lithium azide, tetrabutylammonium azide, trimethylsilyl azide, diphenylphosphoryl azide, nicotinyl azide, or zinc azide.

6. The method according to claim 5 wherein each of $R_1$ and $R_2$ represents a benzyl group, each of $R_3$, $R_4$, $R_5$, and $R_6$ is a hydrogen atom, cycle A' represents the following structural formula II-1 or II-2:

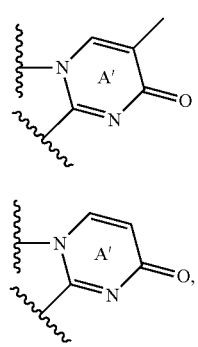

(II-1)

(II-2)

and the azide agent is diphenylphosphoryl azide.

7. A compound represented by general formula III:

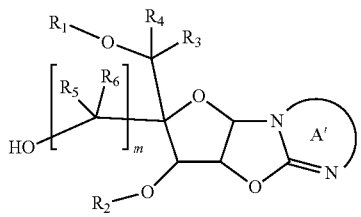

wherein, $R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A' represents a mono or di-one ring derived from uracil, cytosine or thymine, which may be optionally substituted with one or more substituent selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, or salts thereof.

8. The compound according to claim 7 or salts thereof wherein each of $R_1$ and $R_2$ represents a benzyl group, each of $R_3$, $R_4$, $R_5$, and $R_6$ represents a hydrogen atom, and cycle A' represents the following structural formula II-1 or II-2:

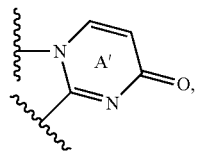

(II-1)

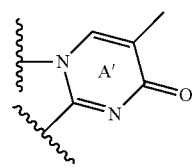

(II-2)

9. A method for preparing a compound represented by general formula IV:

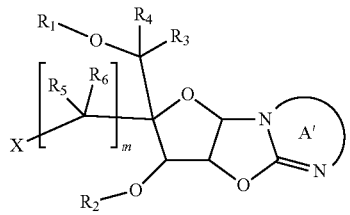

wherein, $R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and cycle A' represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, or salts thereof, the method comprising a step of reacting a compound represented by general formula V:

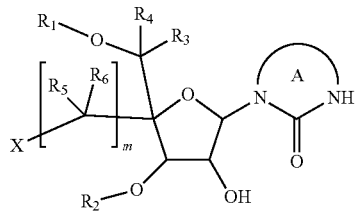

wherein, each of $R_1$, $R_2$, $R_3$, $R_4$, $R_5$, $R_6$, X and m is the same as defined in the above-mentioned general formula IV, and cycle A represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, with an activating agent for hydroxy group to activate an unprotected hydroxy group which is substituted on a tetrahydrofuran ring in the general formula V, wherein the activating agent comprises at least one of methanesulfonylating agent, trifluoromethansulfonylating agent, ethanesulfonylating agent, 2,2,2-trifluoroethanesulfonylating agent, propanesulfonylating agent, isopropanesulfonylating agent, butanesulfonylating agent, nonafluorobutanesulfonylating agent, heptafluoropropane-1-sulfonylating agent, pentanesulfonylating agent, pentafluoroethanesulfonylating agent, cyclopentanesulfonylating agent, hexanesulfonylating agent, cyclohexanesulfonylating agent, o-toluenesulfonylating agent, m-toluenesulfonylating agent, p-toluenesulfonylating agent, benzenesulfonylating agent, o-bromobenzenesulfonylating agent, m-bromobenzenesulfonylating agent, p-bromobenzenesulfonylating agent, o-nitrobenzenesulfonylating agent, m-nitrobenzenesulfonylating agent, or p-nitrobenzenesulfonylating agent.

10. The method according to claim 9 wherein each of $R_1$ and $R_2$ represents a benzyl group, each of $R_3$, $R_4$, $R_5$ and $R_6$ represents a hydrogen atom, X represents a mesyloxy group (Ms-O—), cycle A represents a 1-thyminyl group or a 1-uracilyl group, cycle A' represents the following structural formula II-1 or II-2:

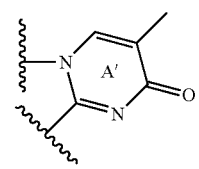

(II-1)

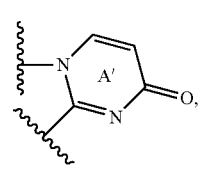

(II-2)

and the activating agent for hydroxy group represents a trifluoromethanesulfonyl chloride.

11. A compound represented by general formula IV:

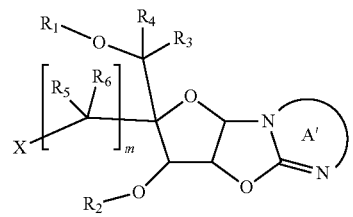

wherein, $R_1$ and $R^2$ represents independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and cycle A' represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, or salts thereof.

12. The compound according to claim 11 or salts thereof wherein each of $R_1$ and $R_2$ represents a benzyl group, and each of $R_3$, $R_4$, $R_5$, and $R_6$ represents a hydrogen atom, X represents a mesyloxy group (Ms-O—), and cycle A' represents the following structural formula II-1 or II-2:

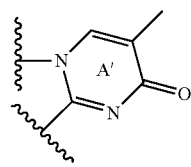
(II-1)

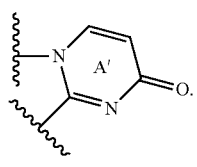
(II-2)

13. A compound represented by general formula V:

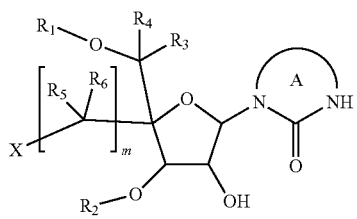

wherein, $R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, X represents a leaving group, m is an integer of 1 to 3, and cycle A represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, or salts thereof.

14. The compound according to claim 13 or salts thereof wherein each of $R_1$ and $R_2$ represents a benzyl group, each of $R_3$, $R_4$, $R_5$ and $R_6$ represents a hydrogen atom, X represents a mesyloxy group (Ms-O—), and cycle A represents a 1-thyminyl group or a 1-uracilyl group.

15. A method for preparing a compound represented by general formula II:

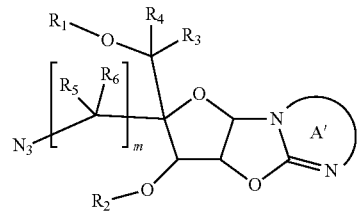

wherein, $R_1$ and $R_2$ represents independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A' represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, or salts thereof, the method comprising a step of reacting a compound represented by formula IV:

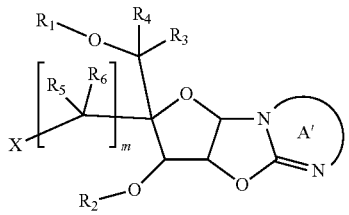

wherein,

X represents a leaving group, and each of $R_1$, $R_2$, $R_3$, $R_4$, $R_5$, $R_6$, m and cycle A' is the same as defined in the above-mentioned general formula II, with an azide agent, wherein the azide agent comprises at least one of hydrazoic acid, sodium azide, lithium azide, tetrabutylammonium azide, trimethylsilyl azide, diphenylphosphoryl azide, nicotinyl azide, or zinc azide, in order to produce the compound represented by general formula II.

16. The method according to claim 15 wherein each of $R_1$ and $R_2$ represent a benzyl group, each of $R_3$, $R_4$, $R_5$, and $R_6$ represents a hydrogen atom, and X represents a mesyloxy group (Ms-O—), cycle A' represents the following structural formula II-1 or II-2:

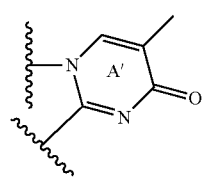

(II-1)

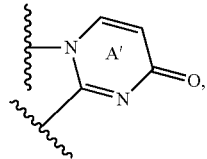

(II-2)

and the azide agent represents $nBu_4NN_3$ or sodium azide.

17. A method for preparing a compound represented by general formula II:

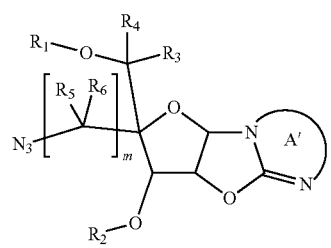

wherein, $R_1$ and $R_2$ represent independently of each other a protecting group for hydroxy group, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, m is an integer of 1 to 3, and cycle A' represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, or salts thereof, the method comprising a step of reacting a compound represented by general formula VI:

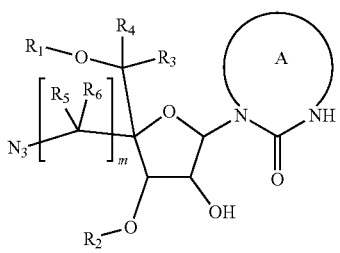

wherein, each of $R_1$, $R_2$, $R_3$, $R_4$, $R_5$, $R_6$ and m is the same as defined in the above-mentioned general formula II, and cycle A represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, with an activating agent for hydroxy group to activate an unprotected hydroxy group which is substituted on a tetrahydrofuran ring in the general formula VI, wherein the activating agent comprises at least one of methanesulfonylating agent, trifluoromethansulfonylating agent, ethanesulfonylating agent, 2,2,2-trifluoroethanesulfonylating agent, propanesulfonylating agent, isopropanesulfonylating agent, butanesulfonylating agent, nonafluorobutanesulfonylating agent, heptafluoropropane-1-sulfonylating agent, pentanesulfonylating agent, pentafluoroethanesulfonylating agent, cyclopentanesulfonylating agent, hexanesulfonylating agent, cyclohexanesulfonylating agent, o-toluenesulfonylating agent, m-toluenesulfonylating agent, p-toluenesulfonylating agent, benzenesulfonylating agent, o-bromobenzenesulfonylating agent, m-bromobenzenesulfonylating agent, p-bromobenzenesulfonylating agent, o-nitrobenzenesulfonylating agent, m-nitrobenzenesulfonylating agent, or p-nitrobenzenesulfonylating agent.

18. The method according to claim 17 wherein each of $R_1$ and $R_2$ represents a benzyl group, each of $R_3$, $R_4$, $R_5$ and $R_6$ represents a hydrogen atom, cycle A represents a 1-thyminyl group or a 1-uracilyl group, cycle A' represents the following structural formula II-1 or the II-2:

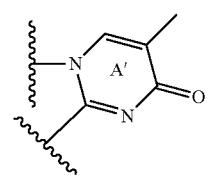

(II-1)

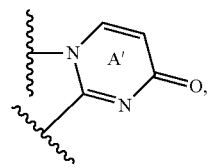

(II-2)

and the activating agent for hydroxy group represents a trifluoromethanesulfonyl chloride.

19. A method for preparing a compound represented by general formula VIII:

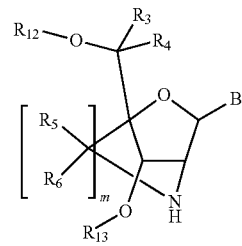

wherein,

B represents a base moiety of a nucleic acid wherein said base moiety may be optionally substituted with one or more substituents, $R_3$ and $R_4$ represents independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, and Rig and Ria represents independently of each other a hydrogen atom or a protecting group for hydroxy group, and m is an integer of 1 to 3, or salts thereof, the method comprising a step of substituting a cycle A in a compound represented by a general formula IX:

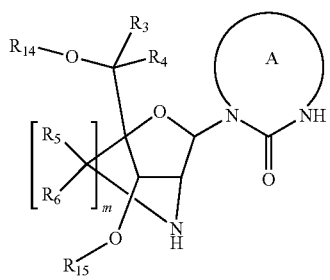

wherein, each of $R_3$, $R_4$, $R_5$, $R_6$, and m is the same as defined in the above-mentioned general formula VIII, each of $R_{14}$ and $R_{15}$ represents independently of each other a hydrogen atom, or a protecting group for hydroxy group, and cycle A represents a mono or di-one ring derived from uracil, cytosine or thymine, which may be optionally substituted with one or more substituents selected from the group consisting of a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, an amino group which may be optionally substituted with one or more substituents, a hydroxy group which may be optionally substituted with one or more substituents, an oxo group, a thioxo group, and a halogen atom, wherein the mono ring may be further fused with another cycle selected from the group consisting of azetidine, pyrrolidine, pyrazolidine, piperidine, piperazine, morpholine, thiomorpholine, homopiperidine, oxazolidine, isoxazolidine, thiazolidine, isothiazolidine, imidazolidine, imidazoline, tetrahydrofuran, dihydrofuran, tetrahydrothien, dihydrothien, dihydropyran, tetrahydropyran, indoline, isoindoline, chroman, isochroman, dihydrobenzofuran, dihydrofuropyridine, and dihydrobenzothien to form the di-one ring, with a B.

20. The method according to claim 19 wherein B represents a 9-adeninyl group which may optionally have one or more protecting groups, a 9-guaninyl group which may optionally have one or more protecting groups, a 1-cytosinyl group which may optionally have one or more protecting groups, a 5-methyl-1-cytosinyl group which may optionally have one or more protecting groups, a 1-thyminyl group which may optionally have one or more protecting groups, or a 1-uracilyl group which may optionally have one or more protecting groups, each of $R_{12}$, $R_{13}$, $R_{14}$, and $R_{15}$ represents a benzyl group, and cycle A represents a 1-thyminyl group or a 1-uracilyl group.

21. The method according to claim 19 wherein B represents a 9-adeninyl group which may optionally have one or more protecting groups, a 9-guaninyl group which may optionally have one or more protecting groups, a 1-cytosinyl group which may optionally have one or more protecting groups, a 5-methyl-1-cytosinyl group which may optionally have one or more protecting groups, a 1-thyminyl group which may optionally have one or more protecting groups, or a 1-uracilyl group which may optionally have one or more protecting groups, $R_{12}$ represents a DMTr group, $R_{13}$ represents a TMS group, $R_{14}$ represents a DMTr group, $R_{15}$ represents a hydrogen atom, and cycle A represents a 1-thyminyl group or a 1-uracilyl group.

22. The method according to claim 19 wherein B represents a 9-adeninyl group which may optionally have one or more protecting groups, a 9-guaninyl group which may optionally have one or more protecting groups, a 1-cytosinyl group which may optionally have one or more protecting groups, a 5-methyl-1-cytosinyl group which may optionally have one or more protecting groups, a 1-thyminyl group which may optionally have one or more protecting groups, or a 1-uracilyl group which may optionally have one or more protecting groups, $R_{12}$ represents a TMS group, $R_{13}$ represents a TMS group, $R_{14}$ represents a hydrogen atom, $R_{15}$ represents a hydrogen atom, and the cycle A represents a 1-thyminyl group or a 1-uracilyl group.

23. A compound represented by general formula VIII:

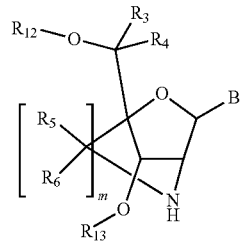

wherein,

B represents a base moiety of a nucleic acid wherein said base moiety may be optionally substituted with one or more substituents, $R_3$ and $R_4$ represent independently of each other a hydrogen atom, or a $C_{1-6}$ alkyl group which may be optionally substituted with one or more substituents, each $R_5$ represents independently a hydrogen atom, or a $C_{1-6}$ alkyl group which may be optionally substituted with one or more substituents, each $R_6$ represents independently a hydrogen atom, or a $C_{1-6}$ alkyl group which may be optionally substituted with one or more substituents, $R_{12}$ represents a benzyl group, a DMTr group, or a TMS group, and Ria represents a benzyl group, a hydrogen atom, or a TMS group, and m is an integer of 1 to 3, or salts thereof.

24. The compound according to claim 23 or salts thereof wherein B represents a 9-adeninyl group which may optionally have one or more protecting groups, a 9-guaninyl group which may optionally have one or more protecting groups, a 1-cytosinyl group which may optionally have one or more protecting groups, a 5-methyl-1-cytosinyl group which may optionally have one or more protecting groups, a 1-thyminyl group which may optionally have one or more protecting groups, or a 1-uracilyl group which may optionally have one or more protecting groups, each of $R_3$, $R_4$, $R_5$, and $R_6$ represents a hydrogen atom, and each of $R_{12}$ and $R_{13}$ represents a benzyl group.

25. The compound according to claim 23 or salts thereof wherein B represents a 9-adeninyl group which may optionally have one or more protecting groups, a 9-guaninyl group which may optionally have one or more protecting groups, a 1-cytosinyl group which may optionally have one or more protecting groups, a 5-methyl-1-cytosinyl group which may optionally have one or more protecting groups, a 1-thyminyl group which may optionally have one or more protecting groups, or a 1-uracilyl group which may optionally have one or more protecting groups, and each of $R_3$, $R_4$, $R_5$ and $R_6$ represents a hydrogen atom, $R_{12}$ represents a DMTr group, and $R_{13}$ represents a hydrogen atom.

* * * * *

UNITED STATES PATENT AND TRADEMARK OFFICE
CERTIFICATE OF CORRECTION

| | |
|---|---|
| PATENT NO. | : 10,961,269 B2 |
| APPLICATION NO. | : 15/760513 |
| DATED | : March 30, 2021 |
| INVENTOR(S) | : Satoshi Obika et al. |

It is certified that error appears in the above-identified patent and that said Letters Patent is hereby corrected as shown below:

On the Title Page

In Item (72), Inventors:
Change:
"Yuuki Aral, Osaka (JP);"
To:
-- Yuuki Arai, Osaka (JP); --

Signed and Sealed this
Twenty-seventh Day of July, 2021

Drew Hirshfeld
*Performing the Functions and Duties of the
Under Secretary of Commerce for Intellectual Property and
Director of the United States Patent and Trademark Office*

```
                        SEQUENCE LISTING

<160> NUMBER OF SEQ ID NOS: 23

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
ttttattttt                                                             10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: modified_base
<222> LOCATION: (5)..(5)
<223> OTHER INFORMATION: m5c

<400> SEQUENCE: 2 ttttnttttt                                                             10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
ttttgttttt                                                             10

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
gcgttttttg ct                                                          12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
```
gcgttatttg ct                                                    12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: modified_base
<222> LOCATION: (6)..(6)
<223> OTHER INFORMATION: m5c

<400> SEQUENCE: 6
gcgttntttg ct                                                    12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gcgttgtttg ct                                                    12

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
tttttttttt                                                       10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
aaaaaaaaaa                                                       10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (6)..(6)
<223> OTHER INFORMATION: m5c

```
<400> SEQUENCE: 10 tttnnntttt                                                            10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
tttgggtttt                                                            10

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
agcaaaaaac gc                                                         12

<210> SEQ ID NO 13
<211> LENGTH: 12
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 13
agcaaaaaac gc                                                         12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
agcaaataac gc                                                         12

<210> SEQ ID NO 15
<211> LENGTH: 12
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 15
agcaaauaac gc                                                         12

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
```
agcaaagaac gc                                                   12

<210> SEQ ID NO 17
<211> LENGTH: 12
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 17
agcaaagaac gc                                                   12

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
agcaaacaac gc                                                   12

<210> SEQ ID NO 19
<211> LENGTH: 12
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 19
agcaaacaac gc                                                   12

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
aaaaaaaaaa                                                      10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
tttttttttt                                                      10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22

```
aaaagggaaa                                                            10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
aaaacccaaa                                                            10
```